United States Patent
Lou et al.

(10) Patent No.: US 12,378,204 B2
(45) Date of Patent: Aug. 5, 2025

(54) TRIAZOLE COMPOUNDS AND PREPARATION METHOD THEREFOR AND USE THEREOF

(71) Applicant: WUHAN LL SCIENCE AND TECHNOLOGY DEVELOPMENT CO., LTD., Hubei (CN)

(72) Inventors: Jun Lou, Hubei (CN); Yongkai Chen, Hubei (CN); Wei Peng, Hubei (CN); Yihan Zhang, Hubei (CN); Xiaodan Guo, Hubei (CN); Li Liu, Hubei (CN); Junhua Liu, Hubei (CN); Lina Qian, Hubei (CN); Chaodong Wang, Hubei (CN)

(73) Assignee: WUHAN LL SCIENCE AND TECHNOLOGY DEVELOPMENT CO., LTD., Hubei (CN)

( * ) Notice: Subject to any disclaimer, the term of this patent is extended or adjusted under 35 U.S.C. 154(b) by 1038 days.

(21) Appl. No.: 17/310,091

(22) PCT Filed: Jan. 15, 2020

(86) PCT No.: PCT/CN2020/072187
§ 371 (c)(1),
(2) Date: Jul. 15, 2021

(87) PCT Pub. No.: WO2020/147740
PCT Pub. Date: Jul. 23, 2020

(65) Prior Publication Data
US 2022/0073476 A1 Mar. 10, 2022

(30) Foreign Application Priority Data
Jan. 15, 2019 (CN) .......................... 201910037049.7

(51) Int. Cl.
| | | |
|---|---|---|
| *C07D 249/06* | (2006.01) | |
| *C07D 213/65* | (2006.01) | |
| *C07D 263/22* | (2006.01) | |
| *C07D 401/04* | (2006.01) | |
| *C07D 403/06* | (2006.01) | |
| *C07D 403/12* | (2006.01) | |
| *C07D 413/04* | (2006.01) | |
| *C07D 413/12* | (2006.01) | |
| *C07D 413/14* | (2006.01) | |

(52) U.S. Cl.
CPC ......... *C07D 249/06* (2013.01); *C07D 213/65* (2013.01); *C07D 263/22* (2013.01); *C07D 401/04* (2013.01); *C07D 403/06* (2013.01); *C07D 403/12* (2013.01); *C07D 413/04* (2013.01); *C07D 413/12* (2013.01); *C07D 413/14* (2013.01)

(58) Field of Classification Search
CPC .. C07D 249/06; C07D 213/65; C07D 263/22; C07D 401/04; C07D 403/06; C07D 403/12; C07D 413/04; C07D 413/12; C07D 413/14
See application file for complete search history.

(56) References Cited

U.S. PATENT DOCUMENTS

2017/0360759 A1* 12/2017 Cheng ................. C07D 401/14
2018/0333395 A1 11/2018 Cheng et al.

FOREIGN PATENT DOCUMENTS

| CN | 104066729 A | 9/2014 |
|---|---|---|
| CN | 109963843 A | 7/2019 |
| CN | 112055711 A | 12/2020 |
| CN | 112189010 A | 1/2021 |
| WO | 2012138648 A1 | 10/2012 |
| WO | 2013025733 A1 | 2/2013 |
| WO | 2013189865 A1 | 12/2013 |
| WO | 2017223016 A1 | 12/2017 |
| WO | 2019126090 A1 | 6/2019 |
| WO | 2019126093 A1 | 6/2019 |
| WO | 2019126094 A1 | 6/2019 |
| WO | 2020081410 A2 | 4/2020 |

OTHER PUBLICATIONS

Qian, Yimin et al.; "Discovery of Highly Selective and Orally Active Lysophosphatidic Acid Receptor-1 Antagonists with Potent Activity on Human Lung Fibroblasts"; Journal of Medicinal Chemistry; Sep. 13, 2012; vol. 55, No. 17; ISSN: 0022-2623; pp. 7920-7939.

Sidduri, Achyutharao et al.; "Discovery of novel non-carboxylic acid 5-amino-4-cyanopyrazole derivatives as potent and highly selective LPA1R antagonists"; Bioorganic & Medicinal Chemistry Letters; Aug. 8, 2014; vol. 24; No. 18; ISSN: 0960-894X; pp. 4450-4454.

Yang, Xu; CN201910037049.7 First Office Action; The State Intellectual Property Office of People's Republic of China; Oct. 26, 2022; pp. 1-9.

Yang, Xu; CN202080004789.1 First Office Action; The State Intellectual Property Office of People's Republic of China; Jan. 20, 2023; pp. 1-8.

* cited by examiner

*Primary Examiner* — Timothy R Rozof
(74) *Attorney, Agent, or Firm* — NKL Law; Allen Xue

(57) ABSTRACT

Certain triazole compounds have good LPAR1 antagonistic activity and selectivity, low toxicity, and good metabolic stability, and can be used for preventing or treating the LPAR1-related disease or disorder. The $IC_{50}$ value of some triazole compounds can be below 300 nM, even 50 nM. The range of $CC_{50}$ of the triazole compounds can be greater than 200 μM. They also show good metabolic stability in human, fancy rats, and house mice.

8 Claims, No Drawings

TRIAZOLE COMPOUNDS AND PREPARATION METHOD THEREFOR AND USE THEREOF

CROSS REFERENCES TO RELATED APPLICATIONS

The present application is a U.S. national stage entry of International Application No. PCT/CN2020/072187, filed Jan. 15, 2020, which claims priority to Chinese Patent Application No. 201910037049.7 filed to China National Intellectual Property Administration on Jan. 15, 2019 and entitled "TRIAZOLE COMPOUNDS AND PREPARATION METHOD THEREFOR AND USE THEREOF", which is incorporated herein by reference in its entirety.

TECHNICAL FIELD

The present invention relates to the technical field of pharmaceutical chemistry, and in particular to triazole compounds, a preparation method therefor and use thereof.

BACKGROUND

To date, six types of LPA receptors (LPARs), LPAR1 to LPAR6, have been discovered. Lysophosphatidic acid receptor 1 (LPAR1) is a G protein-coupled receptor that mediates the growth factor-like activity of lysophosphatidic acid (LPA), and plays an important role in the progression of cancers, especially breast cancer and ovarian cancer. siRNA silencing of LPA1 or the use of LPA1 antagonists leads to the reduction of tumor burden in bone tissues and soft tissues; in addition, LPA signaling can protect individuals from infection-induced inflammation; LPA receptor agonists may be effective in protecting individuals with acute radiation syndrome; the up-regulation of LPA activity is associated with the fibrosis observed in systemic scleroderma.

No drug is available on the market that, as an LPAR1 inhibitor, treats numerous disorders, including idiopathic pulmonary fibrosis. Therefore, the development of novel compounds capable of inhibiting the activity of LPAR1 is of great significance for treating diseases.

SUMMARY

To solve the technical problem of the insufficiency of LPAR1 antagonist in the prior art, the present invention provides a triazole compound, an intermediate thereof, a preparation method therefor and a use thereof. The triazole compound disclosed herein features high antagonistic activity against and good selectivity for LPAR1, low toxicity, and good metabolic stability.

The present invention solves the above-mentioned problems by the following technical solutions. The present invention provides a triazole compound of formula (I) or a stereoisomer, a tautomer, an isotopically labeled compound, a nitrogen oxide, a solvate, a polymorph, a metabolite, an ester, a pharmaceutically acceptable salt or a prodrug thereof,

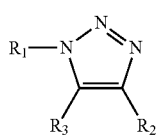

Formula (I)

wherein, $R_1$ is selected from H and the following groups unsubstituted or optionally substituted with one, two or more $R_a$: $C_{1-40}$ alkyl, $—C_{6-20}$ aryl-O—$C_{3-20}$ cycloalkyl and $C_{3-20}$ cycloalkyl; preferably, $R_1$ is selected from $C_{1-40}$ alkyl unsubstituted or optionally substituted with one, two or more $R_a$, e.g., methyl;

$R_2$ is selected from CN, $NO_2$, halogen and the following groups unsubstituted or optionally substituted with one, two or more $R_b$: $C_{1-40}$ alkyl, $C_{1-40}$ alkoxy, $C_{1-40}$ haloalkyl,

$—C_{6-20}$ aryl-X—$R_4$, -5-20 membered heteroaryl-X—$R_4$, $—C_{3-20}$ cycloalkyl-X—$R_4$, $—C_{1-40}$ alkyl-X—$R_4$, $—C_{2-40}$ alkenyl-X—$R_4$ and $—C_{2-40}$ alkynyl-X—$R_4$; X is selected from NH and O; $R_4$ is selected from $C_{1-40}$ alkyl, $C_{2-40}$ alkenyl, $C_{3-20}$ cycloalkyl and $C_{6-20}$ aryl; $R_5'$ is selected from $C_{1-40}$ alkyl; $R_6'$ is selected from $C_{1-40}$ alkyl; $R_7'$ is selected from $C_{3-20}$ cycloalkyl and $C_{1-40}$ alkyl-$C_{6-20}$ aryl; or, $R_6'$ and $R_7'$ may, together with an N atom connected thereto, form 3-20 membered heterocyclyl unsubstituted or optionally substituted with one, two or more $R_e$; $R_3$ is selected from H, CN, $NO_2$, halogen and the following groups unsubstituted or optionally substituted with one, two or more $R_e$: $C_{1-40}$ alkyl, $C_{1-40}$ alkoxy, $C_{1-40}$ haloalkyl,

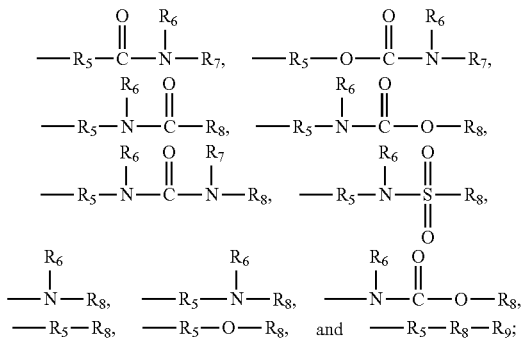

$R_5$ is selected from $C_{1-40}$ alkyl, $C_{2-40}$ alkenyl, 3-20 membered heterocyclyl, 5-20 membered heteroaryl and $C_{6-20}$ aryl; preferably, $R_5$ is selected from $C_{1-40}$ alkyl, $C_{2-40}$ alkenyl, 3-20 membered heterocyclyl and 5-20 membered heteroaryl, e.g., methyl, ethyl, vinyl,

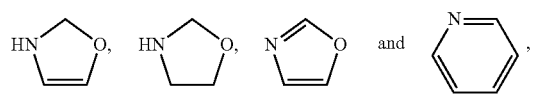

further preferably methyl and ethyl; $R_6$ is selected from H, $C_{1-40}$ alkyl and $C_{3-20}$ cycloalkyl; preferably, $R_6$ is selected from H and $C_{1-40}$ alkyl, e.g., H and methyl; $R_7$ is selected from $C_{1-40}$ alkyl, $—C_{1-40}$ alkyl-$C_{6-20}$ aryl, $C_{1-40}$ alkyl-$C_{6-20}$ aryl- and $C_{3-20}$ cycloalkyl; e.g., $R_7$ is selected from methyl, -methyl-phenyl and cyclopentyl, preferably methyl and cyclopentyl; $R_8$ is selected from $C_{1-40}$ alkyl-$C_{6-20}$ aryl-, $—C_{1-40}$ alkyl-$C_{6-20}$ aryl, $C_{2-40}$ alkenyl-$C_{6-20}$ aryl-, —$C_{2-40}$ alkenyl-$C_{6-20}$ aryl, $C_{6-20}$ aryl, $C_{3-20}$ cycloalkyl, —$C_{1-40}$ alkyl-$C_{3-20}$ cycloalkyl, $C_{1-40}$ alkyl, 3-20 membered heterocyclyl, 5-20 membered heteroaryl, 5-20 membered heteroaryl-$C_{3-20}$ cycloalkyl- and -5-20 membered heteroaryl-$C_{3-20}$ cycloalkyl; preferably, $R_8$ is selected from —$C_{1-40}$ alkyl-$C_{6-20}$ aryl, —$C_{2-40}$ alkenyl-$C_{6-20}$ aryl, $C_{1-40}$ alkyl, 3-20 membered heterocyclyl, $C_{6-20}$ aryl and $C_{3-20}$ cycloalkyl, e.g., -methyl-phenyl, -vinyl-phenyl, methyl, isopropyl,

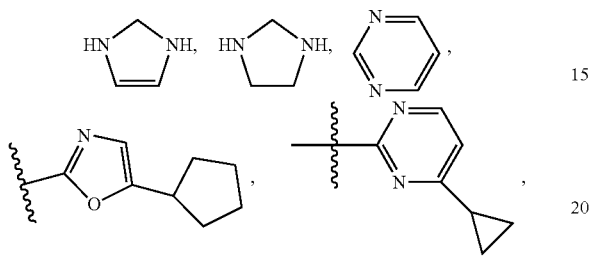

oxazole, phenyl, cyclopentyl, cyclohexyl and methyl-cyclopentyl, further preferably methyl and cyclopentyl; $R_9$ is selected from $C_{1-40}$ alkyl-$C_{6-20}$ aryl and $C_{6-20}$ aryl; preferably, $R_9$ is selected from $C_{1-40}$ alkyl-$C_{6-20}$ aryl, e.g., methyl-phenyl; or, any two of $R_6$, $R_7$ and $R_8$ may, together with an N atom connected thereto, form 3-20 membered heterocyclyl unsubstituted or optionally substituted with one, two or more $R_d$;

$R_a$ is selected from halogen, COOH, $NH_2$ and OH; preferably, when selected from halogen, $NH_2$, and OH, $R_a$ is not directly connected to position $C_1$ of alkyl;

$R_b$ and $R_e$ are the same or different, and are independently selected from COOH, CN, $NO_2$, halogen, $C_{1-40}$ alkyl and $C_{1-40}$ haloalkyl; preferably, $R_b$ and $R_e$ are the same or different, and are independently selected from =O, COOH and $C_{1-40}$ haloalkyl, wherein the $C_{1-40}$ haloalkyl, e.g., is selected from $C_{1-40}$ fluoroalkyl, e.g., $CF_3$;

$R_c$ is selected from =O, COOH, CN, $NO_2$, $C_{1-40}$ alkyl and $C_{1-40}$ haloalkyl, and preferably selected from =O, COOH and $C_{1-40}$ haloalkyl, wherein the $C_{1-40}$ haloalkyl, e.g., is selected from $C_{1-40}$ fluoroalkyl, e.g., $CF_3$; and $R_d$ is selected from =O, COOH, CN, $NO_2$, $C_{1-40}$ alkyl, $C_{1-40}$ haloalkyl, halogen and $C_{3-20}$ cycloalkyl.

According to an embodiment of the present invention, $R_1$ is selected from H and the following groups unsubstituted or optionally substituted with one, two or more $R_a$: $C_{1-6}$ alkyl, —$C_{6-14}$ aryl-O—$C_{3-14}$ cycloalkyl and $C_{3-14}$ cycloalkyl; preferably, $R_1$ is selected from $C_{1-6}$ alkyl unsubstituted or optionally substituted with one, two or more $R_a$, e.g., methyl;

$R_2$ is selected from CN, $NO_2$, halogen and the following groups unsubstituted or optionally substituted with one, two or more $R_b$: $C_{1-6}$ alkyl, $C_{1-6}$ alkoxy, $C_{1-6}$ haloalkyl,

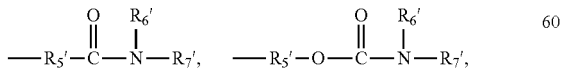

—$C_{6-14}$ aryl-X—$R_4$, -5-14 membered heteroaryl-X—$R_4$, —$C_{3-14}$ cycloalkyl-X—$R_4$, —$C_{1-6}$ alkyl-X—$R_4$, —$C_{2-10}$ alkenyl-X—$R_4$ and —$C_{2-10}$ alkynyl-X—$R_4$; X is selected from NH and O, and $R_4$ is selected from $C_{1-6}$ alkyl, $C_{2-10}$ alkenyl, $C_{3-14}$ cycloalkyl and $C_{6-14}$ aryl; $R_5'$ is selected from $C_{1-6}$ alkyl; $R_6'$ is selected from $C_{1-6}$ alkyl; $R_7'$ is selected from $C_{3-14}$ cycloalkyl and $C_{1-6}$ alkyl-$C_{6-14}$ aryl; or, $R_6'$ and $R_7'$ may, together with an N atom connected thereto, form 3-10 membered heterocyclyl unsubstituted or optionally substituted with one, two or more $R_e$; $R_3$ is selected from H, CN, $NO_2$, halogen and the following groups unsubstituted or optionally substituted with one, two or more $R_c$: $C_{1-6}$ alkyl, $C_{1-6}$ alkoxy, $C_{1-6}$ haloalkyl,

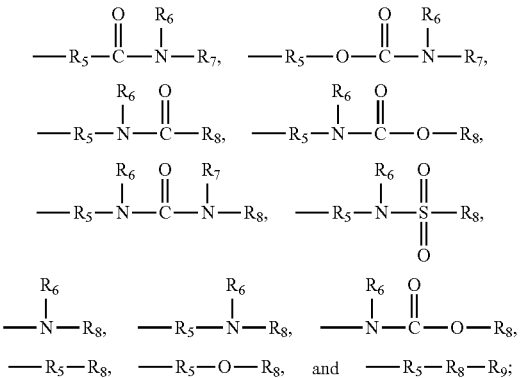

$R_5$ is selected from $C_{1-6}$ alkyl, $C_{2-10}$ alkenyl, 3-10 membered heterocyclyl, 5-14 membered heteroaryl and $C_{6-14}$ aryl; preferably, $R_5$ is selected from $C_{1-6}$ alkyl, $C_{2-10}$ alkenyl, 3-10 membered heterocyclyl and 5-14 membered heteroaryl, e.g., methyl, ethyl, vinyl,

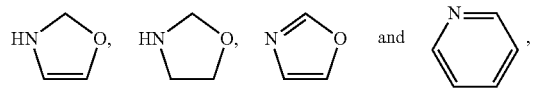

further preferably methyl and ethyl; $R_6$ is selected from H, $C_{1-6}$ alkyl and $C_{3-14}$ cycloalkyl; preferably, $R_6$ is selected from H and $C_{1-40}$ alkyl, e.g., H and methyl; $R_7$ is selected from $C_{1-6}$ alkyl, —$C_{1-6}$ alkyl-$C_{6-14}$ aryl, $C_{1-6}$ alkyl-$C_{6-14}$ aryl- and $C_{3-14}$ cycloalkyl; e.g., $R_7$ is selected from methyl, -methyl-phenyl and cyclopentyl, preferably methyl and cyclopentyl; $R_8$ is selected from $C_{1-6}$ alkyl-$C_{6-14}$ aryl-, —$C_{1-6}$ alkyl-$C_{6-14}$ aryl, $C_{2-10}$ alkenyl-$C_{6-14}$ aryl-, —$C_{2-10}$ alkenyl-$C_{6-14}$ aryl, $C_{6-14}$ aryl, $C_{3-14}$ cycloalkyl, —$C_{1-6}$ alkyl-$C_{3-14}$ cycloalkyl, $C_{1-6}$ alkyl, 3-10 membered heterocyclyl, 5-14 membered heteroaryl, 5-14 membered heteroaryl-$C_{3-14}$ cycloalkyl- and -5-14 membered heteroaryl-$C_{3-14}$ cycloalkyl; preferably, $R_8$ is selected from —$C_{1-6}$ alkyl-$C_{6-14}$ aryl, —$C_{2-10}$ alkenyl-$C_{6-14}$ aryl, $C_{1-6}$ alkyl, 3-10 membered heterocyclyl, $C_{6-14}$ aryl and $C_{3-14}$ cycloalkyl, e.g., -methyl-phenyl, -vinyl-phenyl, methyl, isopropyl,

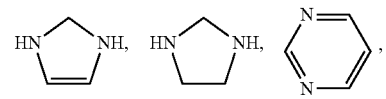

-continued

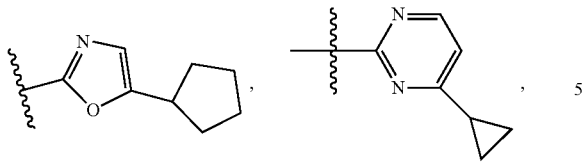

oxazole, phenyl, cyclopentyl, methylcyclopentyl and cyclohexyl, further preferably methyl and cyclopentyl; $R_9$ is selected from $C_{1-14}$ alkyl-$C_{6-14}$ aryl and $C_{6-14}$ aryl; preferably, $R_9$ is selected from $C_{1-6}$ alkyl-$C_{6-14}$ aryl, e.g., methyl-phenyl; or, any two of $R_6$, $R_7$ and $R_8$ may, together with an N atom connected thereto, form 3-10 membered heterocyclyl unsubstituted or optionally substituted with one, two or more $R_d$;

$R_a$ is selected from halogen, COOH, $NH_2$ and OH; preferably, when selected from halogen, $NH_2$, and OH, $R_a$ is not directly connected to position $C_1$ of alkyl;

$R_b$ and $R_e$ are the same or different, and are independently selected from COOH, CN, $NO_2$, halogen, $C_{1-6}$ alkyl and $C_{1-6}$ haloalkyl; preferably, $R_b$ and $R_e$ are the same or different, and are independently selected from =O, COOH and $C_{1-6}$ haloalkyl, wherein the $C_{1-6}$ haloalkyl, e.g., is selected from $C_{1-6}$ fluoroalkyl, e.g., $CF_3$;

$R_c$ is selected from =O, COOH, CN, $NO_2$, $C_{1-6}$ alkyl and $C_{1-6}$ haloalkyl, and preferably selected from =O, COOH and $C_{1-6}$ haloalkyl, wherein the $C_{1-6}$ haloalkyl, e.g., is selected from $C_{1-6}$ fluoroalkyl, e.g., $CF_3$; and $R_d$ is selected from =O, COOH, CN, $NO_2$, $C_{1-6}$ alkyl, $C_{1-6}$ haloalkyl, halogen and $C_{3-14}$ cycloalkyl.

As an example, $R_1$ is selected from H, $CH_3$,

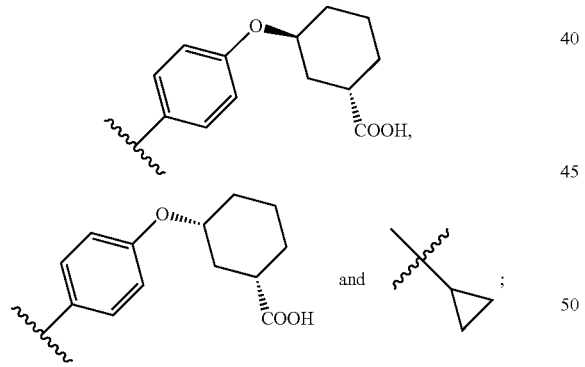

$R_2$ is selected from the following groups:

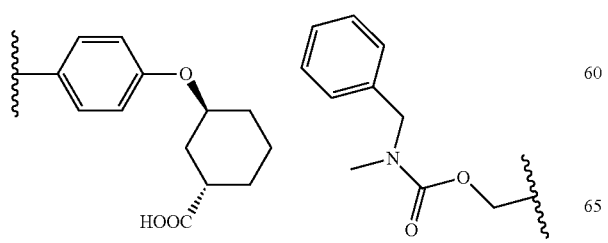

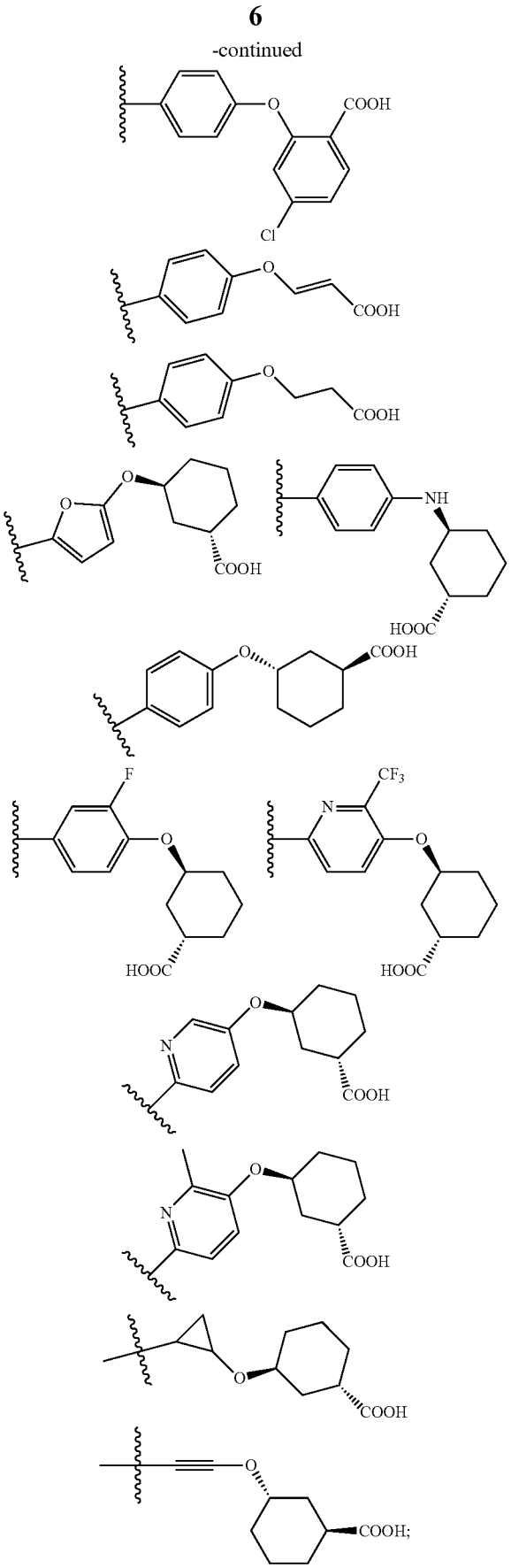

$R_3$ is selected from H and the following groups:
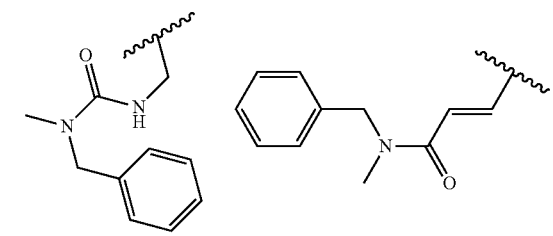
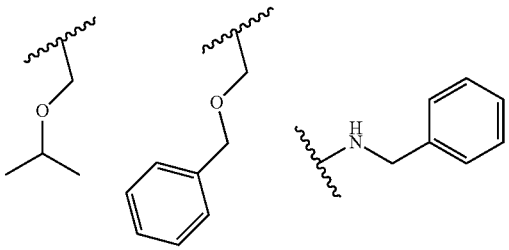
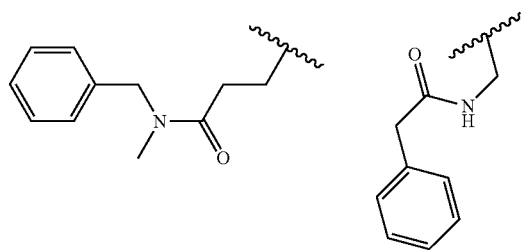
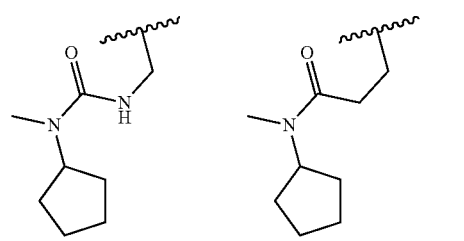
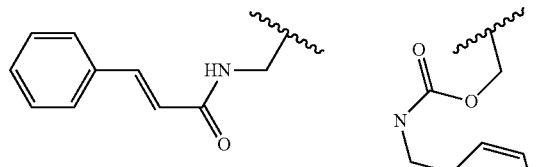
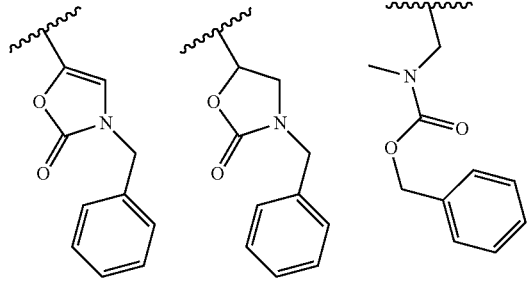
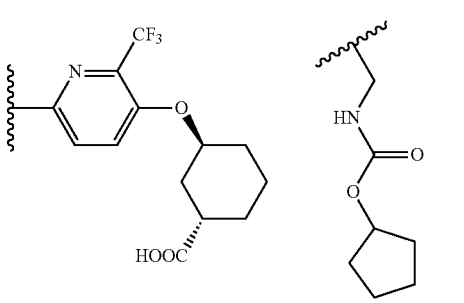
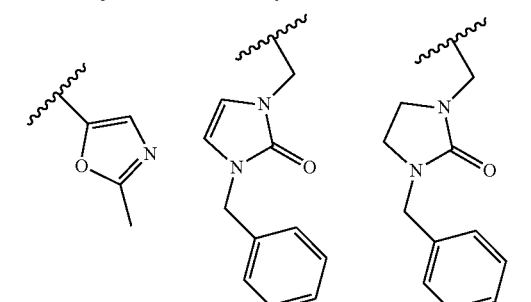
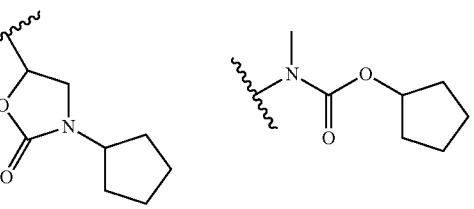
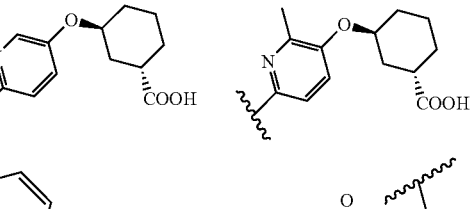
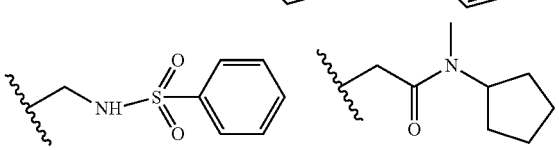
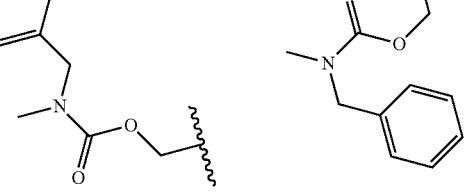
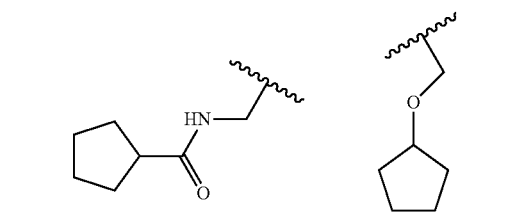
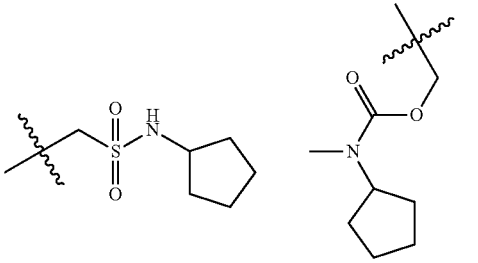

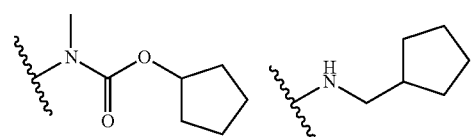
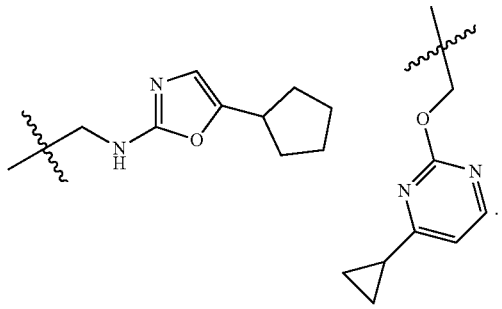
As an example, the present invention provides the following compounds:
1
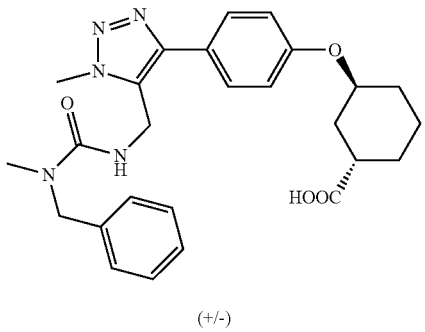
(+/-)
2
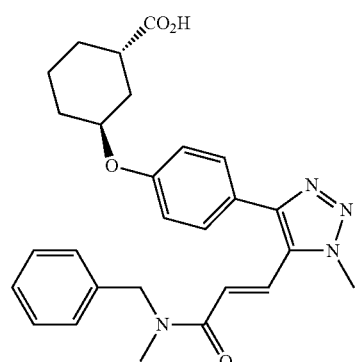
(+/-)
3
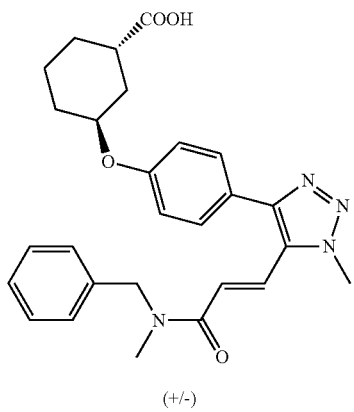
(+/-)
4
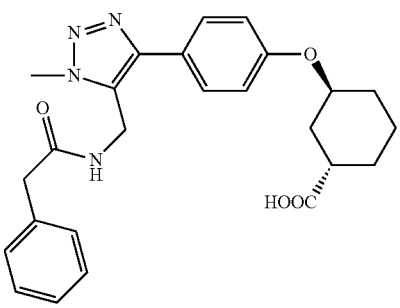
(+/-)
5
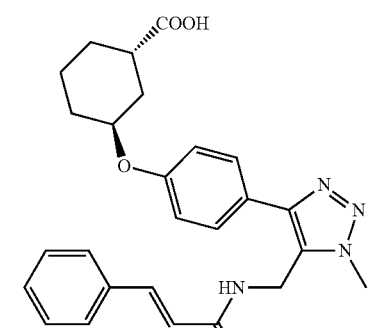
(+/-)
6
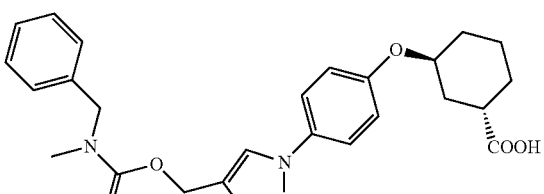
(+/-)

11
-continued
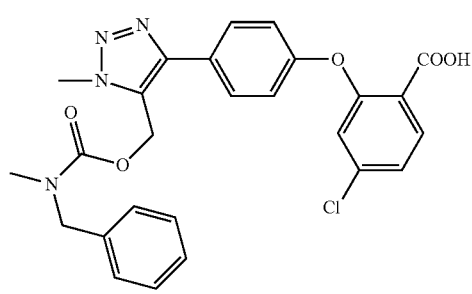
(+/-)
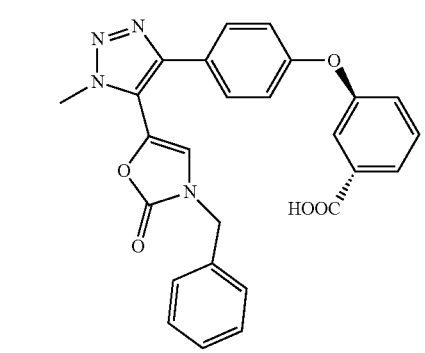
(+/-)
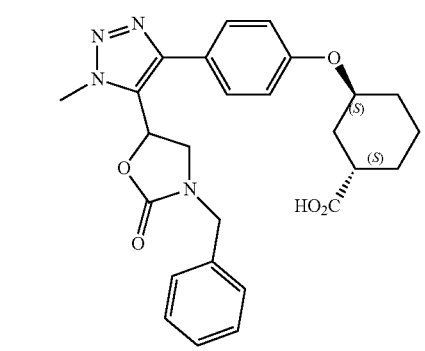
(+/-)
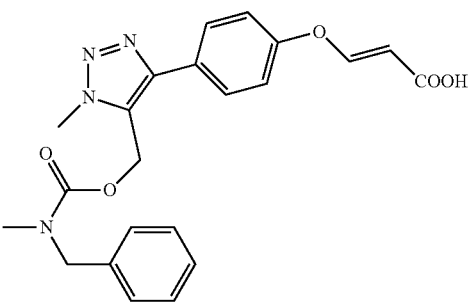
(+/-)
12
-continued
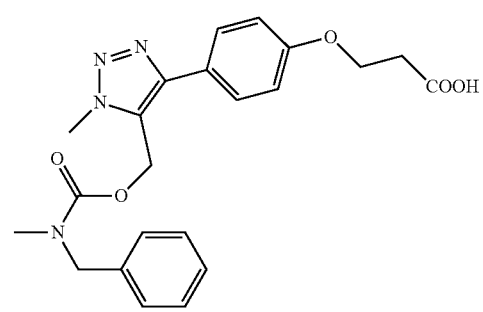
(+/-)
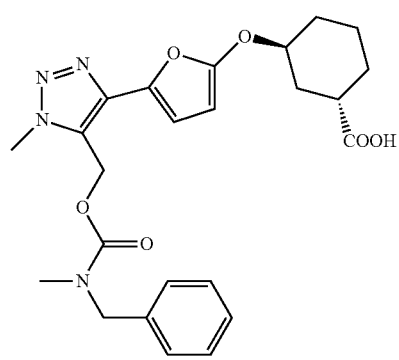
(+/-)
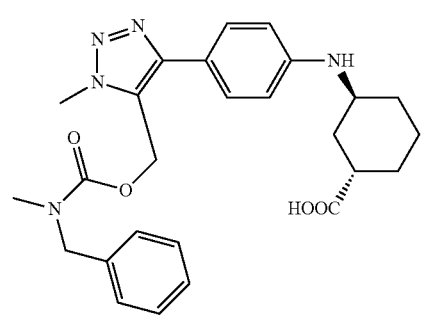
(+/-)
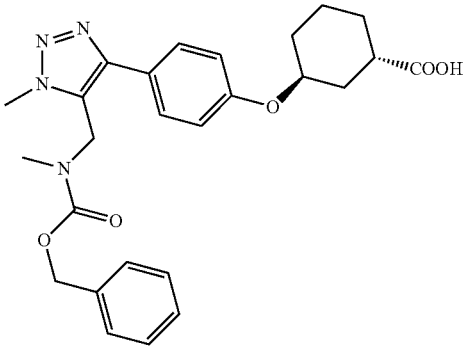
(+/-)

13
15
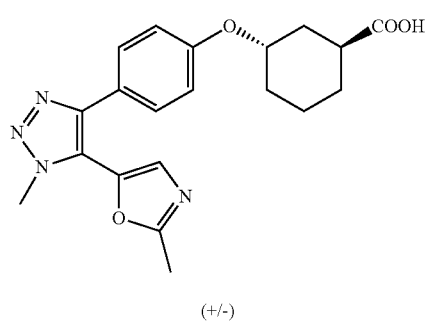
(+/-)
16
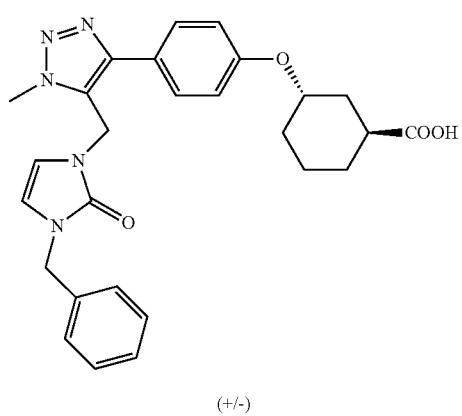
(+/-)
17
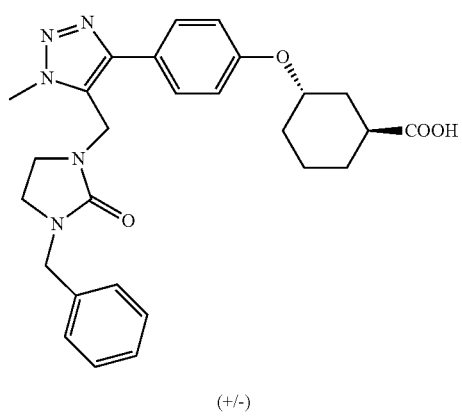
(+/-)
18
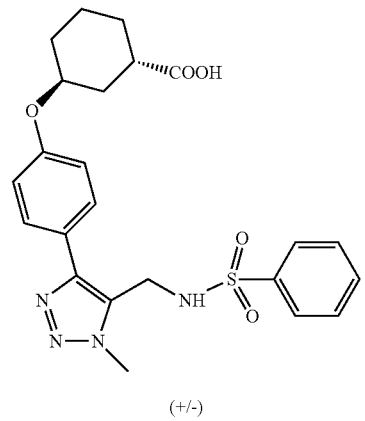
(+/-)
14
19
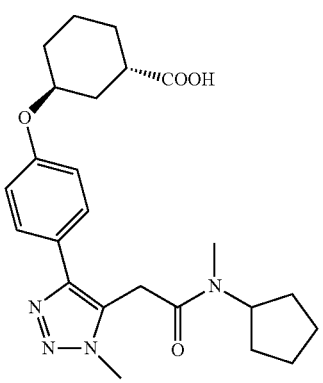
(+/-)
20
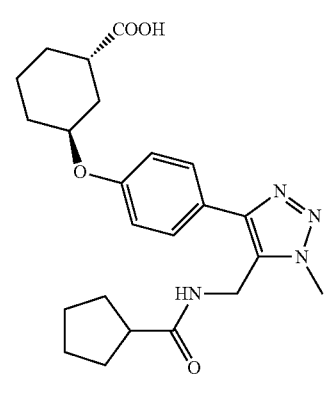
(+/-)
21
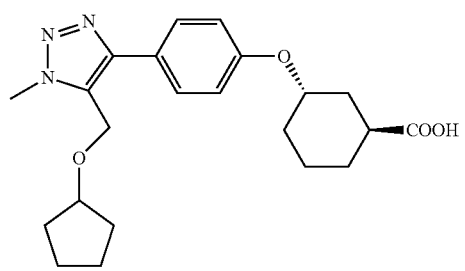
(+/-)
22
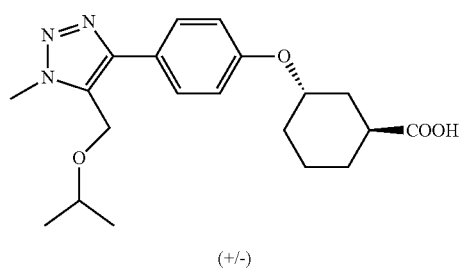
(+/-)

23
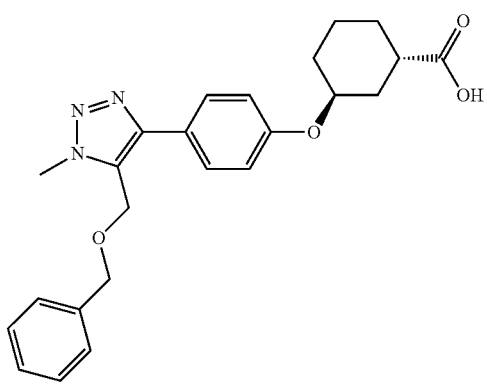
(+/-)
24
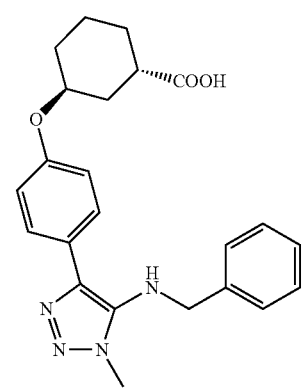
(+/-)
25
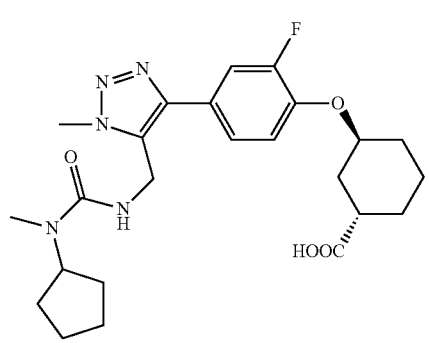
(+/-)
26
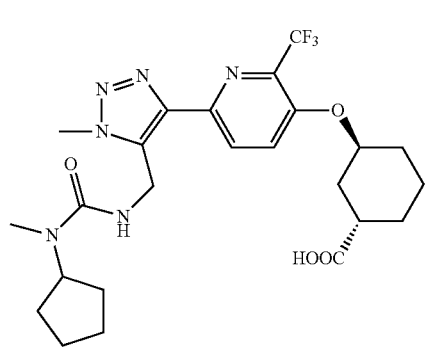
(+/-)
27-A
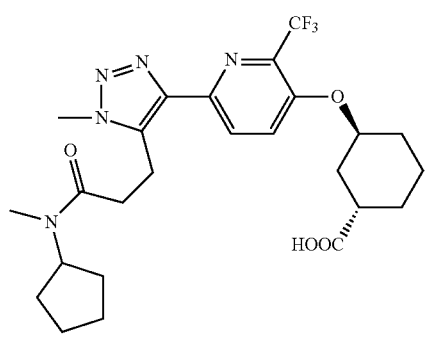
(+/-)
27-B
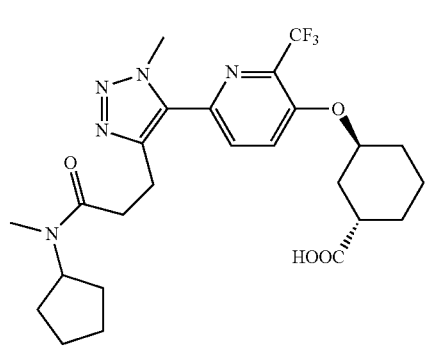
(+/-)
28
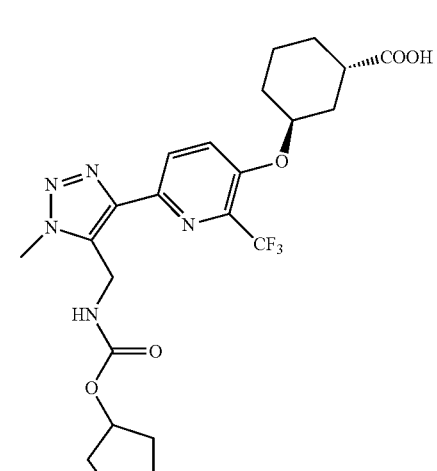
(+/-)
29
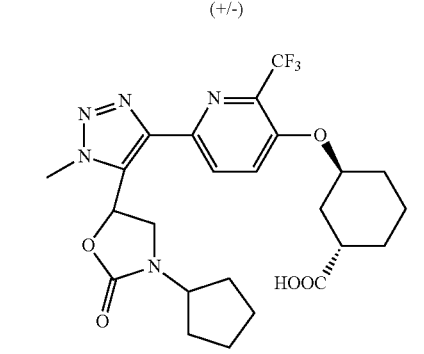
(+/-)

-continued
30
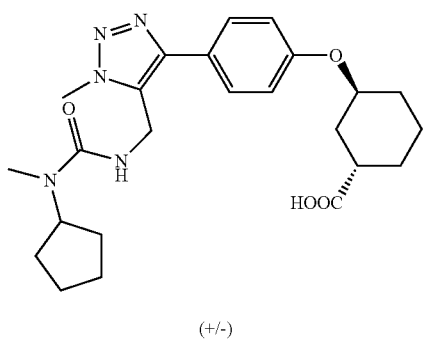
(+/-)
31
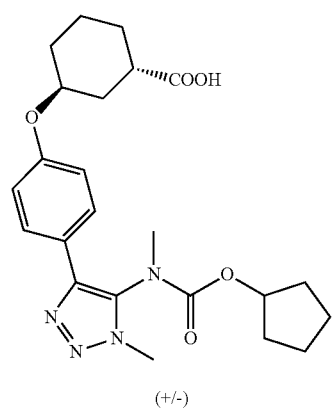
(+/-)
32
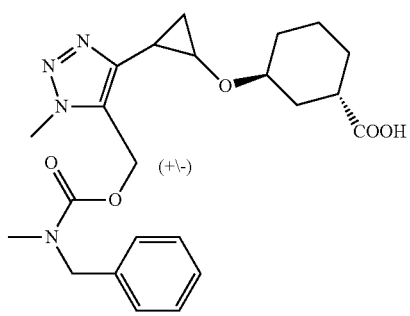
(+\-)
33
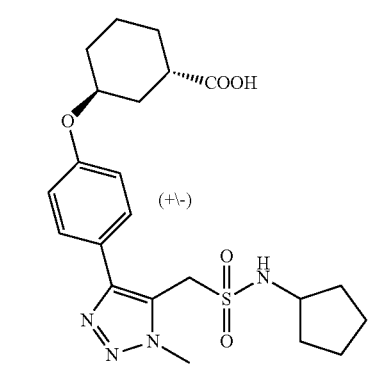
(+\-)
-continued
34
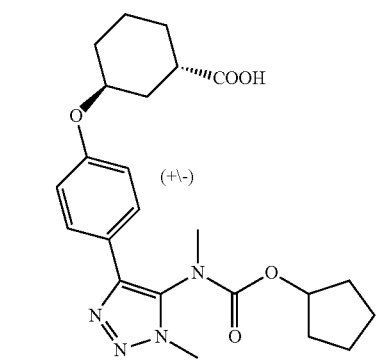
(+\-)
35
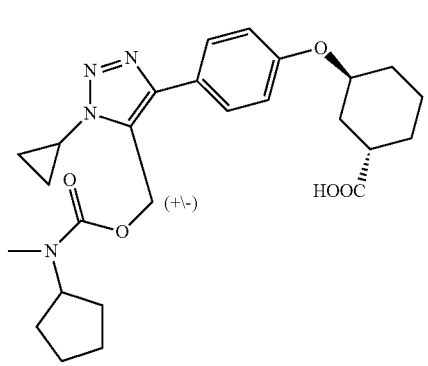
(+\-)
36
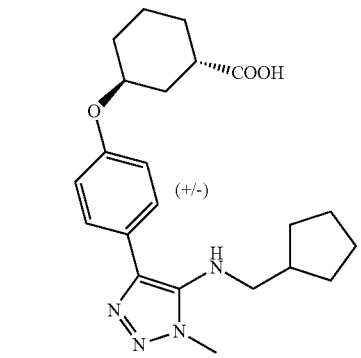
(+/-)
37
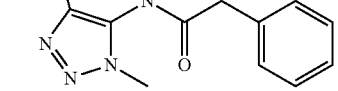
(+/-)

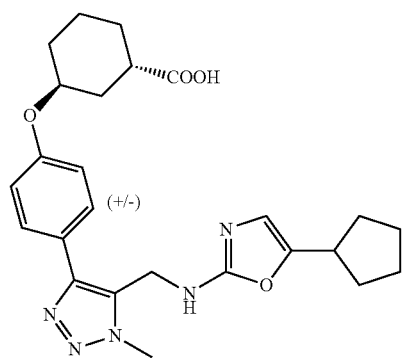

38

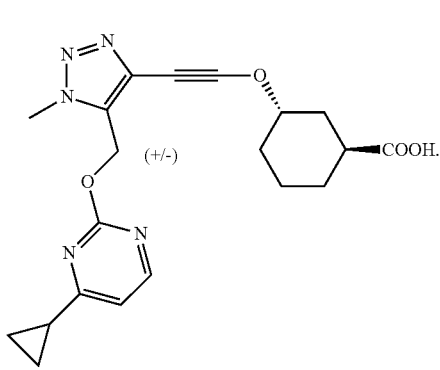

39

The present invention also provides a preparation method for the compound of formula (I), which is selected from any one of the following schemes:

Scheme 1: Compound 1a is reacted with Compound 2a in the presence of a base to give Compound M-1; Compound M-1 is reacted in the presence of an acid to give the compound of formula (I);

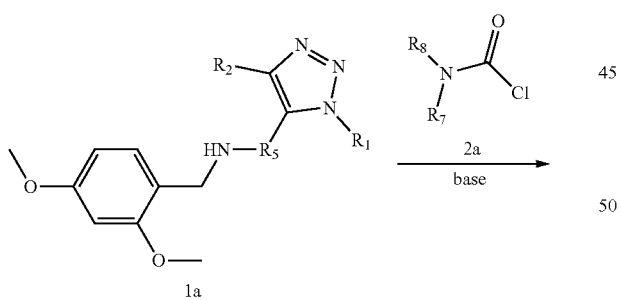

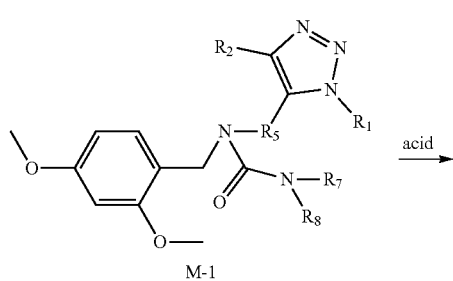 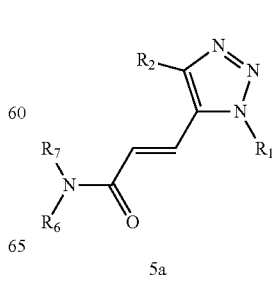

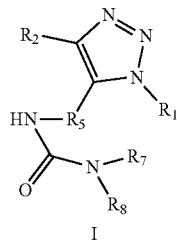

Scheme 2: Compound 3a is reacted with $I_2$ in the presence of a reductant to give Compound M-2; Compound M-2 is reacted with Compound 4a in the presence of $Pd(PPh_3)_2Cl_2$ to give the compound of formula (I);

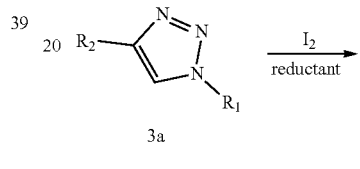

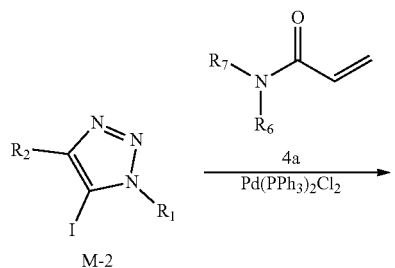

Scheme 3
Compound 5a is reacted with $H_2$ in the presence of a catalyst to give the compound of formula (I);

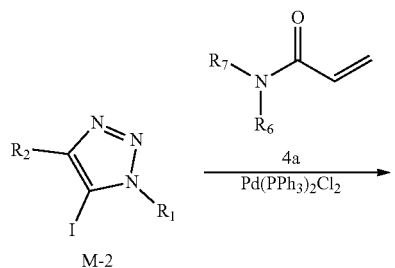

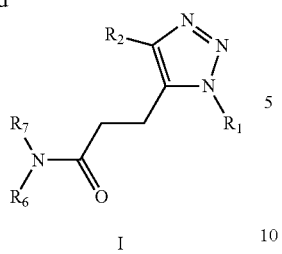

Scheme 4: Compound 6a is reacted with Compound 7a in the presence of a base to give Compound M-3; Compound M-3 is reacted in the presence of TFA to give the compound of formula (I);

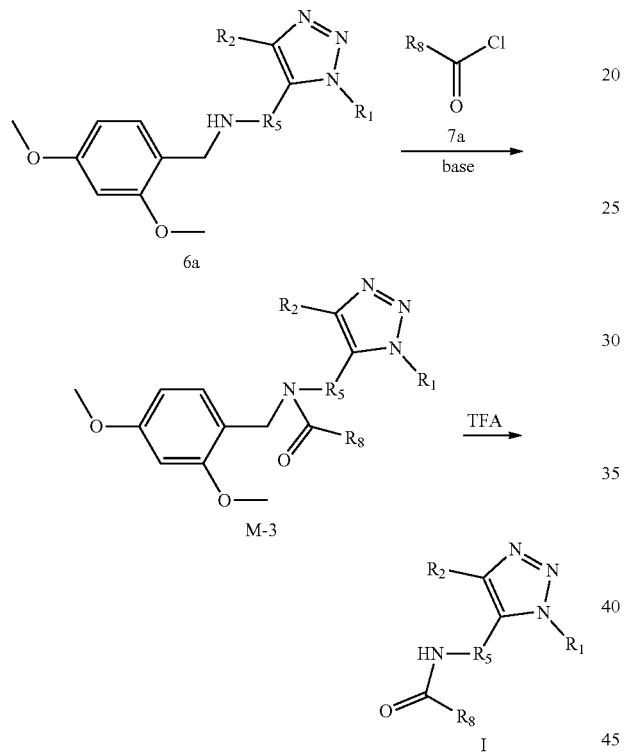

Scheme 5: Compound M-4 is reacted with Compound 6-7 and Compound 6-8A in the presence of pyridine and DIPEA to give the compound of formula (I);

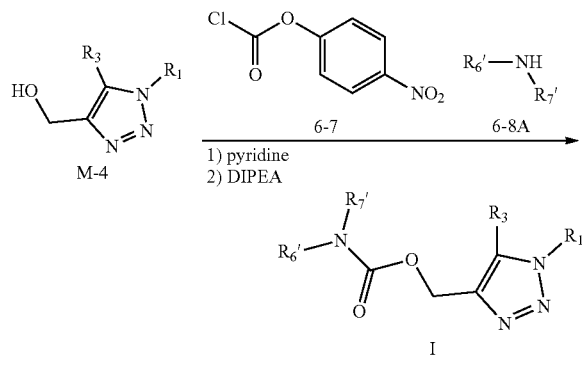

Scheme 6
Compound M-5 is reacted with trimethylsilylmethyl azide in the presence of DMF under a heating condition to give Compound M-6; Compound M-6 is reacted in the presence of TBAF to give Compound M-7; Compound M-7 is reacted in the presence of PPTS to give compound M-8; Compound M-8 is reacted with Compound 6-7 and Compound 6-8A in the presence of pyridine and DIPEA to give the compound of formula (I);

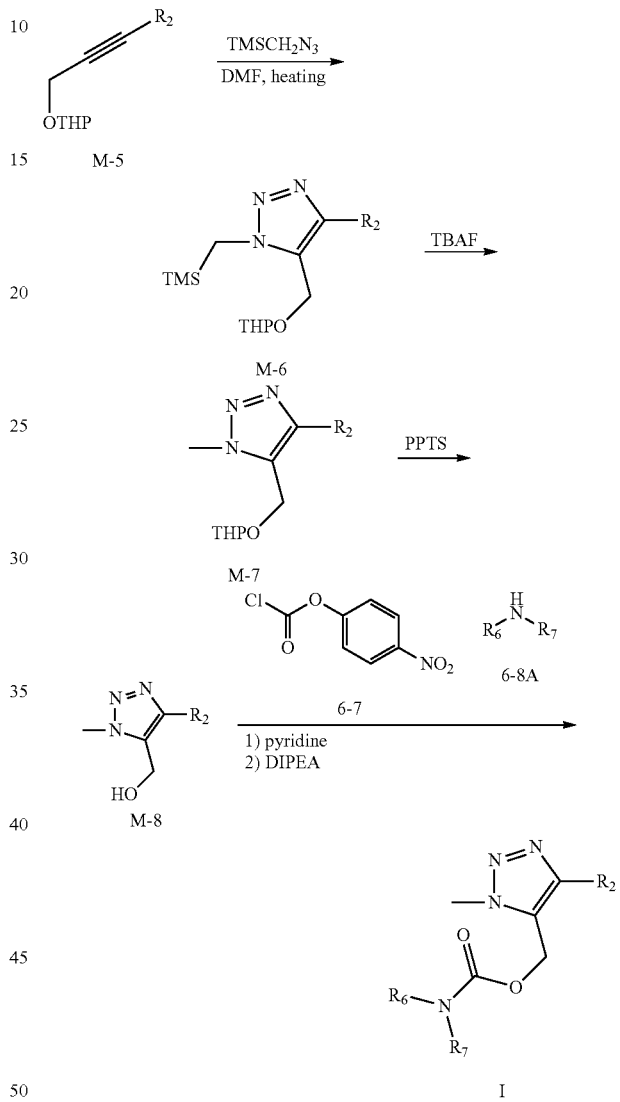

Scheme 7: Compound 8a is reacted with Compound 9a in the presence of a base and LiBH₄ to give Compound M-9; Compound M-9 is reacted with triphosgene in the presence of a base to give the compound of formula (I);

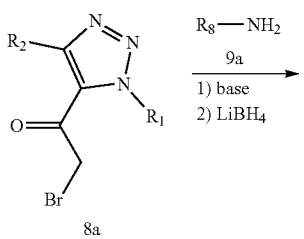

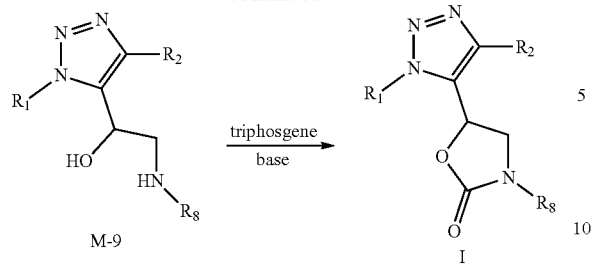

Scheme 8: Compound 10-1A is reacted in the presence of a reductant to give Compound M-10; Compound M-10 is reacted with Compound 10-3 in the presence of pyridine to give Compound M-11; Compound M-11 is reacted with Compound 10-5A in the presence of DIPEA to give the compound of formula (I);

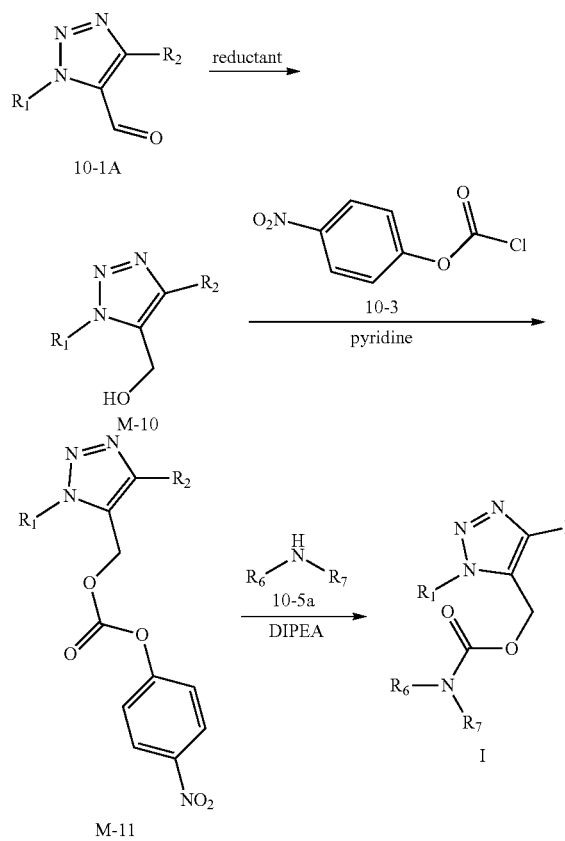

Scheme 9
Compound 10-8A is reacted with H₂ in the presence of Pd/C to give Compound M-12; Compound M-12 is reacted in the presence of a base to give the compound of formula (I);

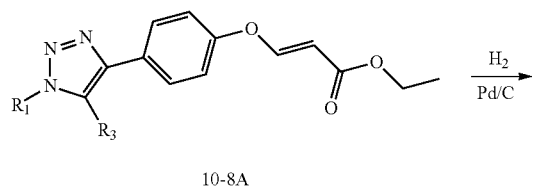

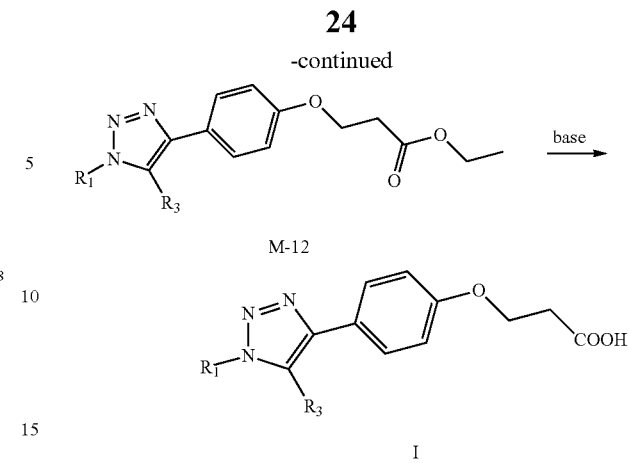

Scheme 10: Compound 13-1A is reacted with 2-(prop-2-yn-1-oxy)tetrahydro-2H-pyran in the presence of Pd(PPh₃)₂Cl₂, CuI and Et₃N to give Compound M-13; Compound M-13 is reacted with trimethylsilylmethyl azide in the presence of toluene under a heating condition to give Compound M-14; Compound M-14 is reacted in the presence of TBAF to give Compound M-15; Compound M-15 is reacted in the presence of PPTS to give Compound M-16; Compound M-16 is reacted with Compound 6-7 and Compound 6-8A in the presence of pyridine and DIPEA to give the compound of formula (I);

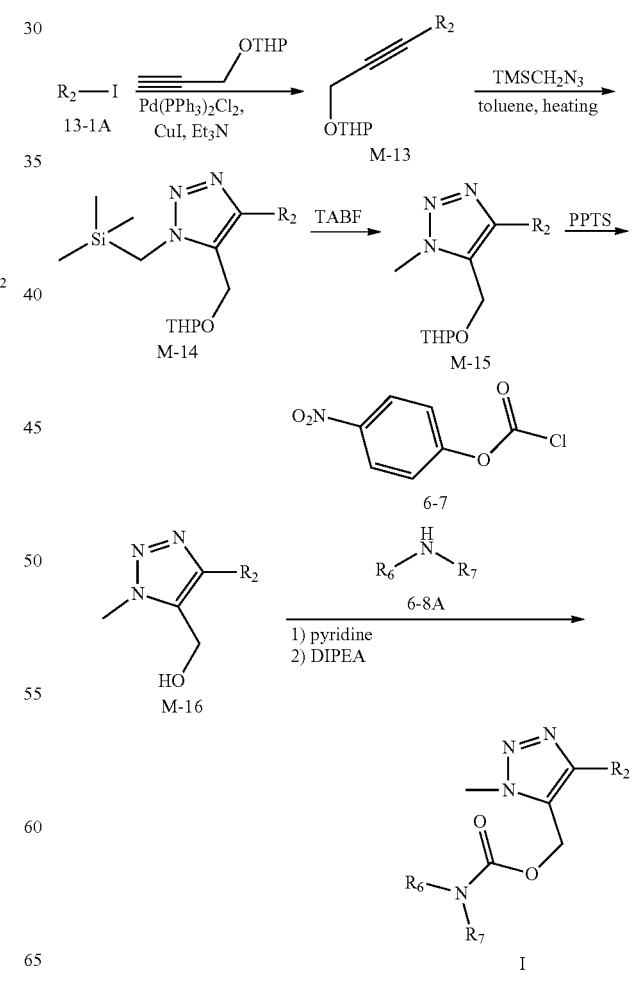

Scheme 11: Compound 14-1A is reacted with methylamine in the presence of NaBH₃CN to give Compound M-17; Compound M-17 is reacted with Compound 10a in the presence of a base to give the compound of formula (I);

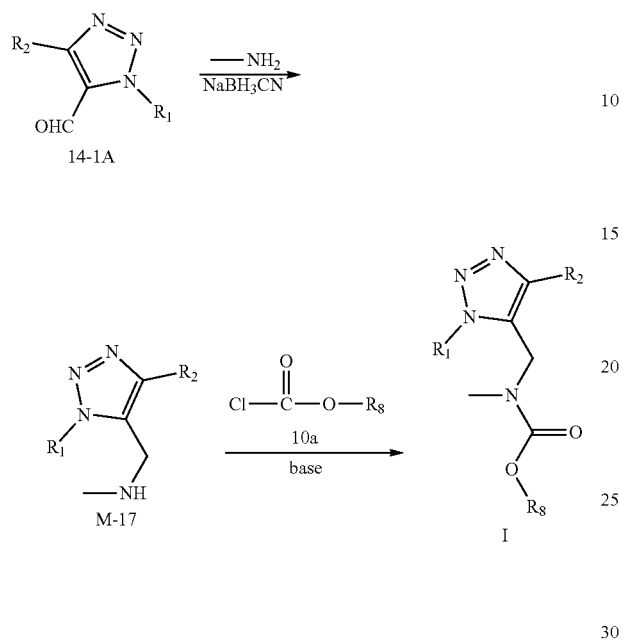

Scheme 12
Compound 15-1 is reacted with I₂ in the presence of n-butyl lithium to give Compound M-18; Compound M-18 is reacted with Compound 11a in the presence of Pd(OAc)₂ and PPh₃ to give Compound M-19; Compound M-19 is reacted with NBS to give Compound M-20; Compound M-20 is reacted with acetamide in the presence of NMP under microwave heating to give the compound of formula (I);

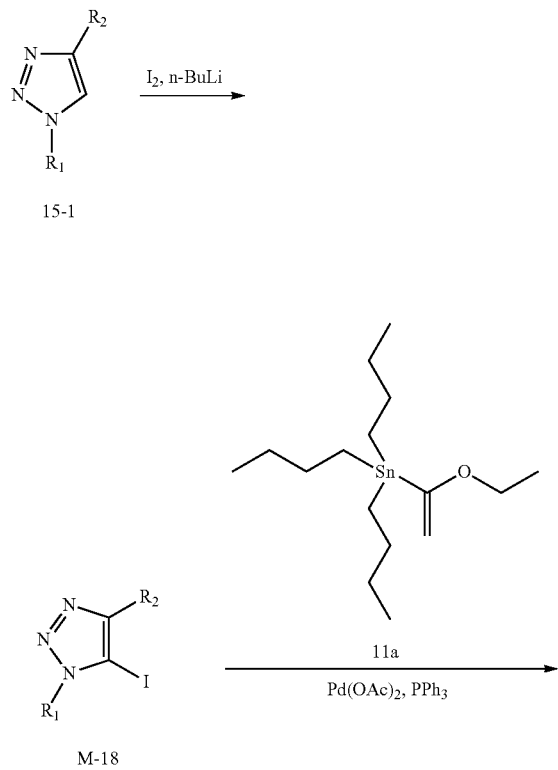

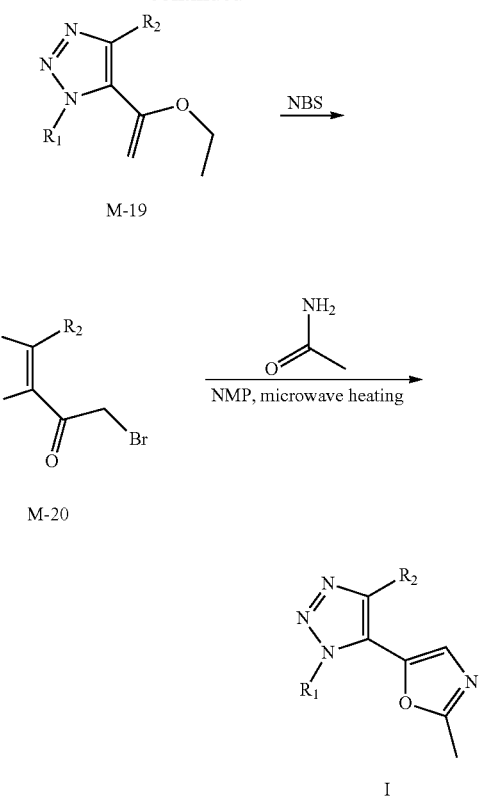

Scheme 13: Compound 16-7A is reacted with n-butyl lithium in DMF to give Compound M-21; Compound M-21 is reacted with NaBH₄ to give Compound M-22; Compound M-22 is reacted with MsCl in the presence of a base to give Compound M-23; Compound M-23 is reacted with Compound 16-3A to give the compound of formula (I);

Scheme 14
Compound 16-10A is reacted with Compound 13a in the presence of sodium hydride to give the compound of formula (I);

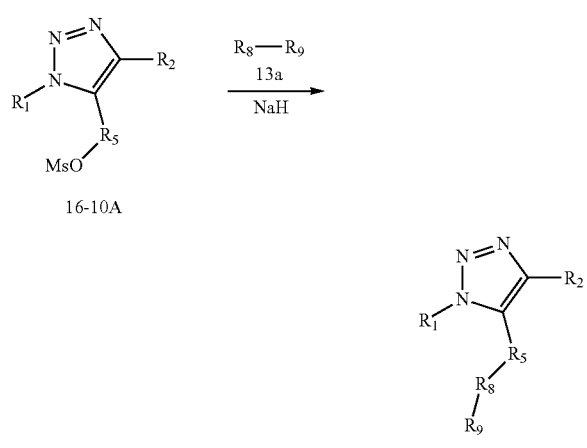

Scheme 15: Compound 1a is reacted with Compound 18-1A in the presence of DIPEA to give Compound M-24; Compound M-24 is reacted in the presence of TFA to give the compound of formula (I);

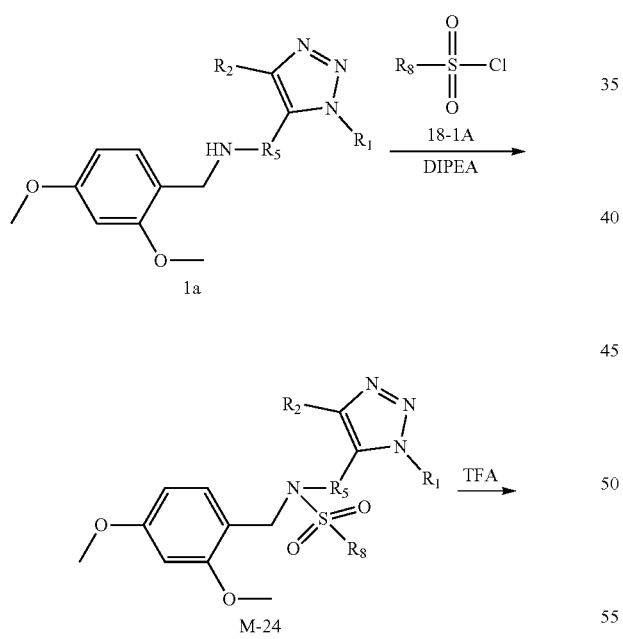

Scheme 16: Compound 1-1A is reacted with Compound 20-1A in the presence of a base to give Compound M-25; Compound M-25 is reacted with TFA to give the compound of formula (I);

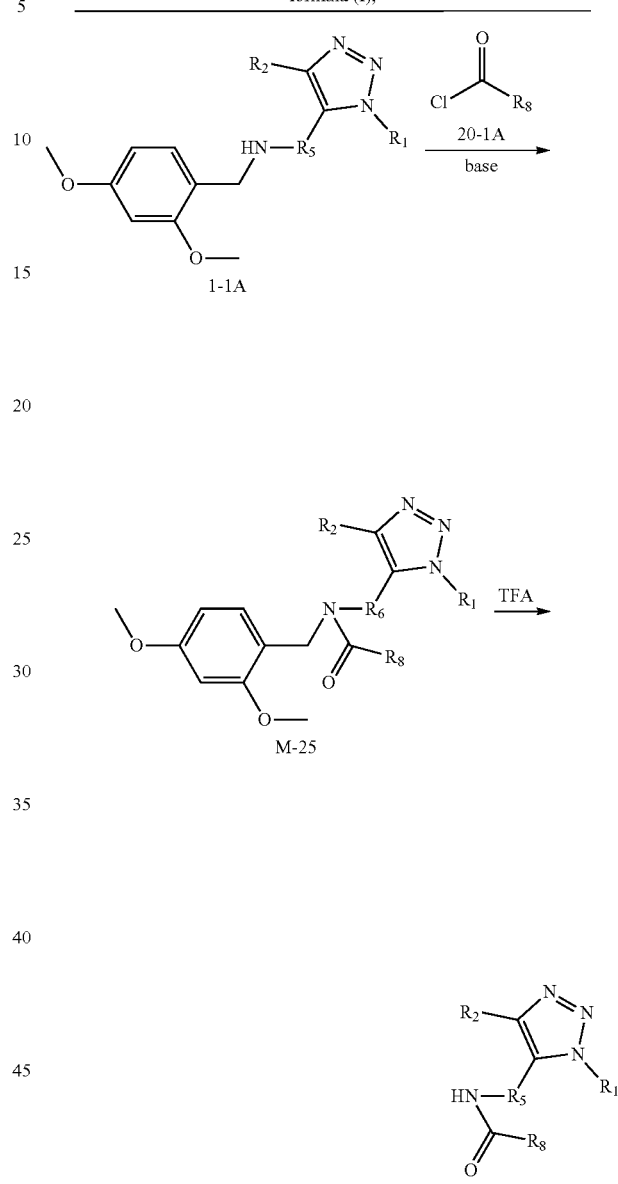

Scheme 17: Compound 16-10A is reacted with Compound 21-2A in the presence of sodium hydride to give the compound of formula (I);

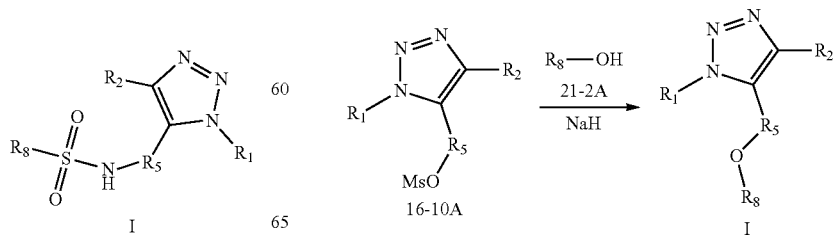

Scheme 18
Compound 16-9A is reacted with Compound 14a in the presence of sodium hydride to give the compound of formula (I);

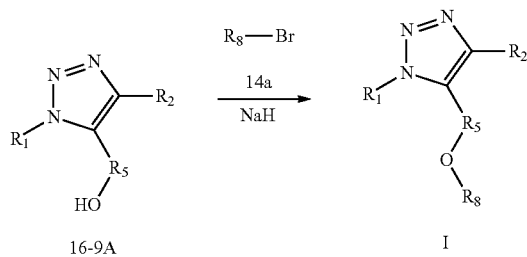

Scheme 19
Compound 24-1A is reacted in the presence of DPPA and tert-butanol to give Compound M-26; Compound M-26 is reacted with Compound 16a in the presence of sodium hydride to give Compound M-27; Compound M-27 is reacted in the presence of an acid to give the compound of formula (I);

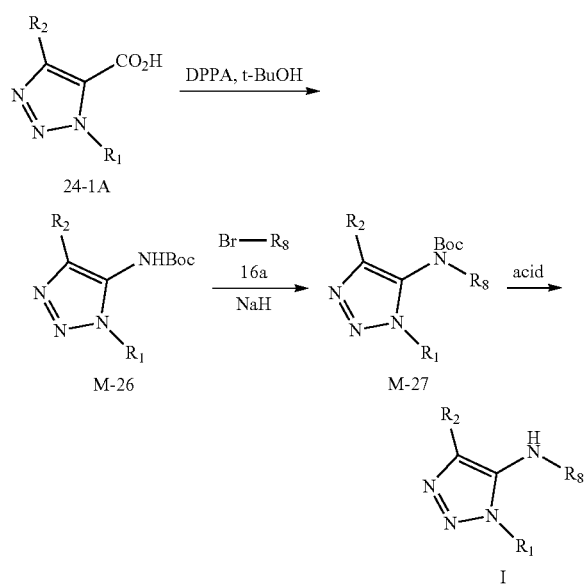

Scheme 20
Compound 26-1 is reacted with Compound 1-5 in the presence of DTAD and PPh₃ to give Compound M-28; Compound M-28 is reacted with trimethylsilylmethyl azide, and then reacted with TBAF to give Compound M-29; Compound M-29 is reacted in the presence of TFA to give Compound M-30; Compound M-30 is reacted with triphosgene and Compound 18a in the presence of a base to give the compound of formula (I);

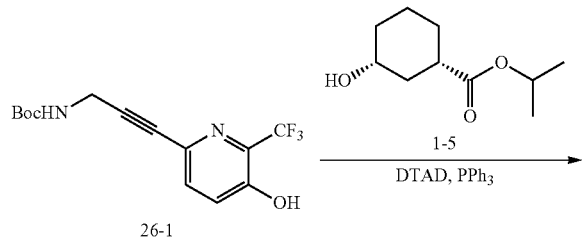

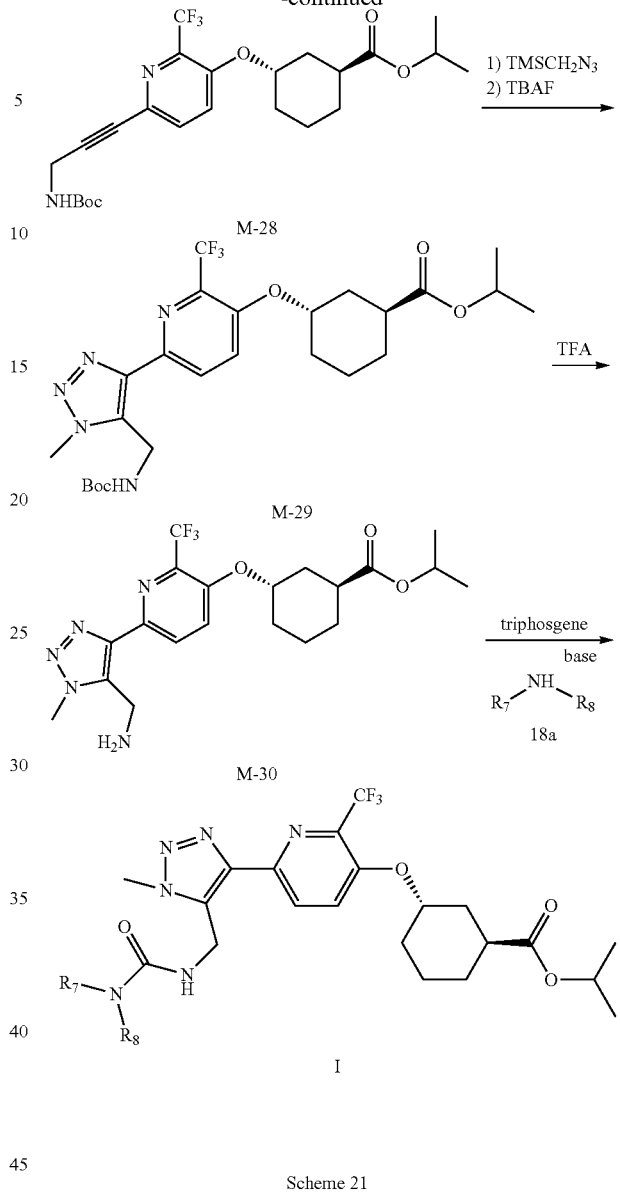

Scheme 21
Compound 27-4 is reacted with Compound 1-5 is the presence of DTAD and PPh₃ to give Compound M-31; Compound M-31 is reacted with Compound 19a in the presence of Pd(PPh₃)₂Cl₂ and CuI to give Compound M-32; Compound M-32 is reacted with trimethylsilylmethyl azide, and then reacted with TBAF to give Compound M-33 and Compound M-34; Compound M-33 and Compound M-34 are reacted in the presence of a base to give the compound of formula (I) with different structures;

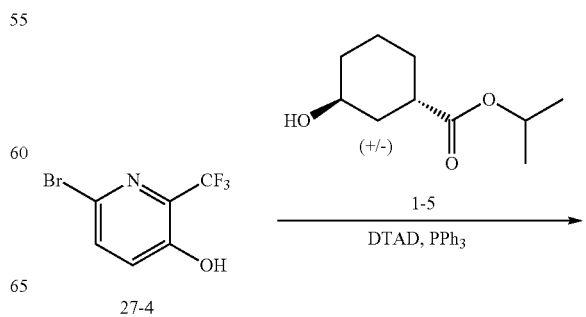

-continued
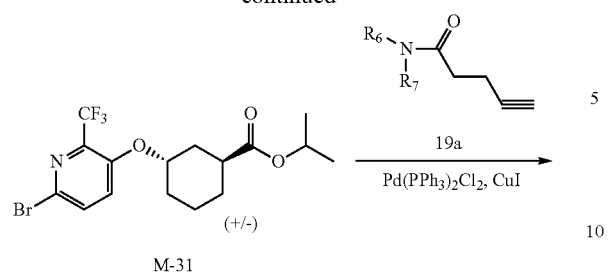
M-31
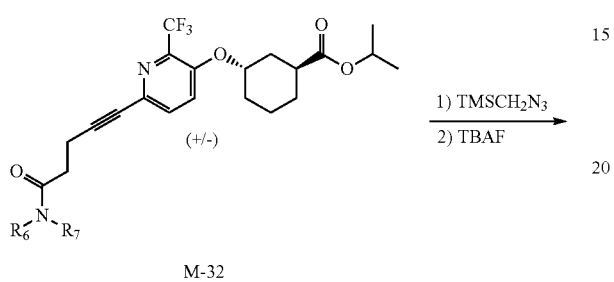
M-32
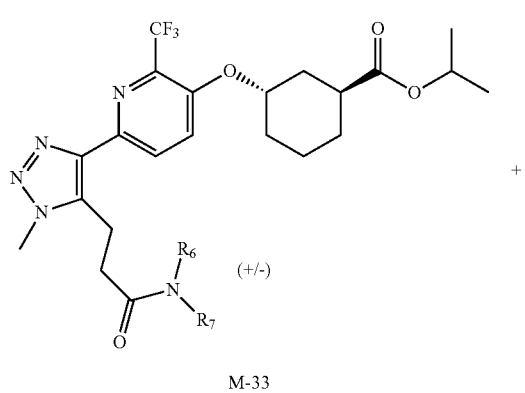
M-33
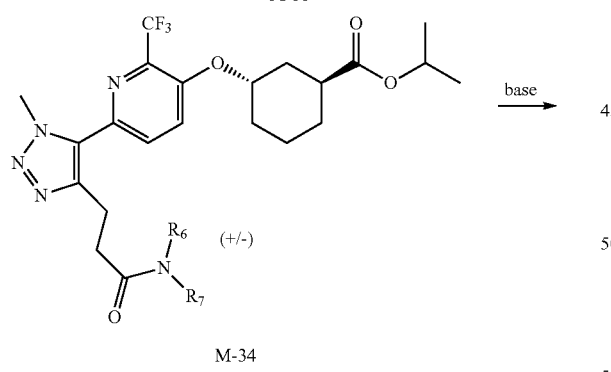
M-34
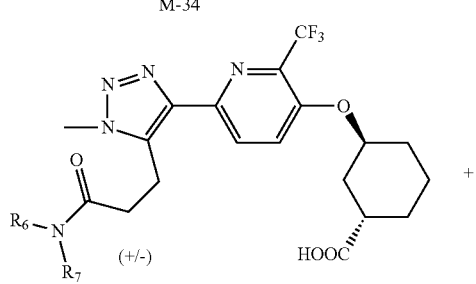
I
-continued
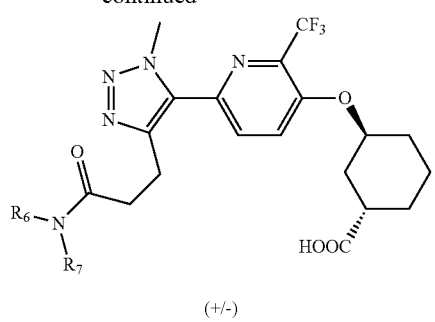
I
Scheme 22: Compound 28-1A is reacted with triphosgene and Compound 20a in the presence of a base to give the compound of formula (I);
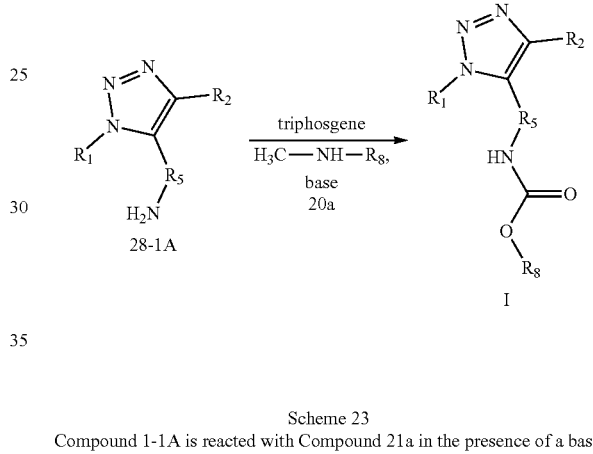
Scheme 23
Compound 1-1A is reacted with Compound 21a in the presence of a base to give Compound M-35; Compound M-35 is reacted in the presence of an acid to give the compound of formula (I);
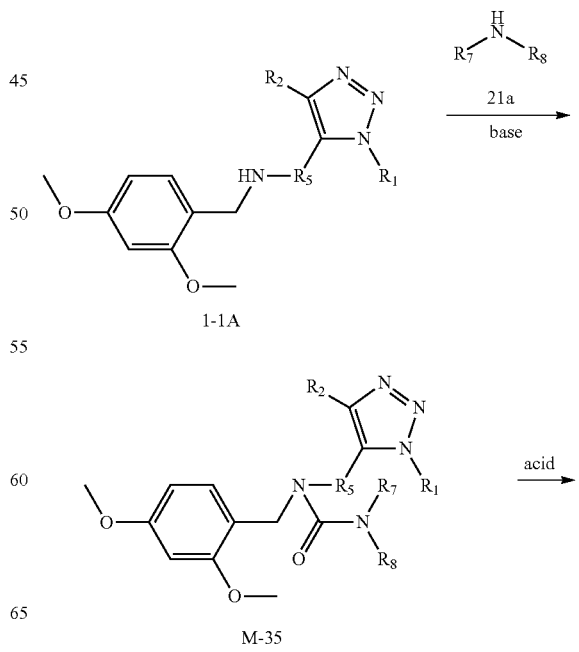
M-35

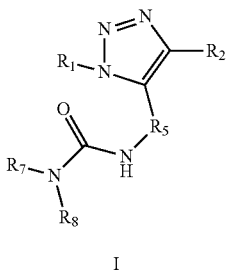

I

Scheme 24: Compound 2-4A is reacted with methyl chloroformate in the presence of n-butyl lithium to give Compound M-36; Compound M-36 is reacted in the presence of a base to give Compound M-37; Compound M-37 is reacted with Compound 22a and DPPA in the presence of a base to give Compound M-38; Compound M-38 is reacted with iodomethane in the presence of sodium hydride to give the compound of formula (I);

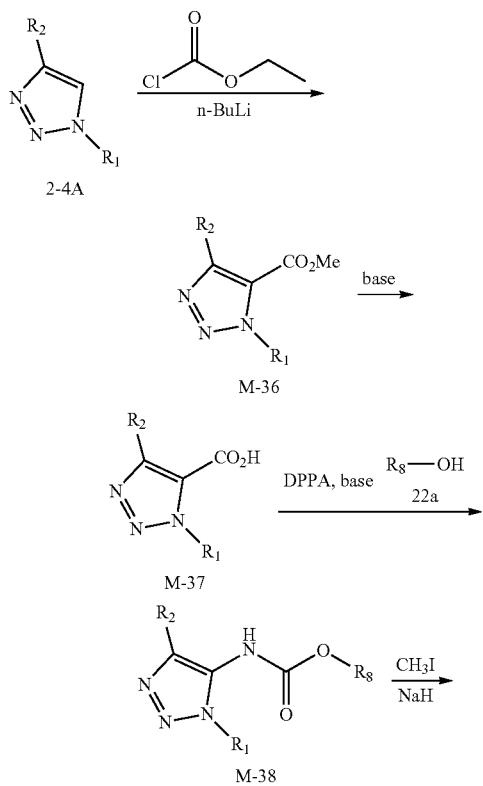

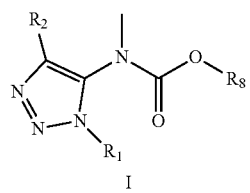

I wherein, $R_1$, $R_2$, $R_5$, $R_6$, $R_6'$, $R_7$, $R_7'$, $R_8$, and $R_9$ are defined as above.

According to an embodiment of the present invention, the preparation method for the compound of formula (I) may be selected from any one of the following schemes:

Scheme 1A
Compound 1-1A is reacted with Compound 1-2A in the presence of a base to give Compound 1-3A; Compound 1-3A is reacted in the presence of an acid to give Compound 1-4A; Compound 1-4A is reacted with Compound 1-5A in the presence of DTAD to give Compound 1-6A; Compound 1-6A is reacted in the presence of a base to give the compound of formula (I);

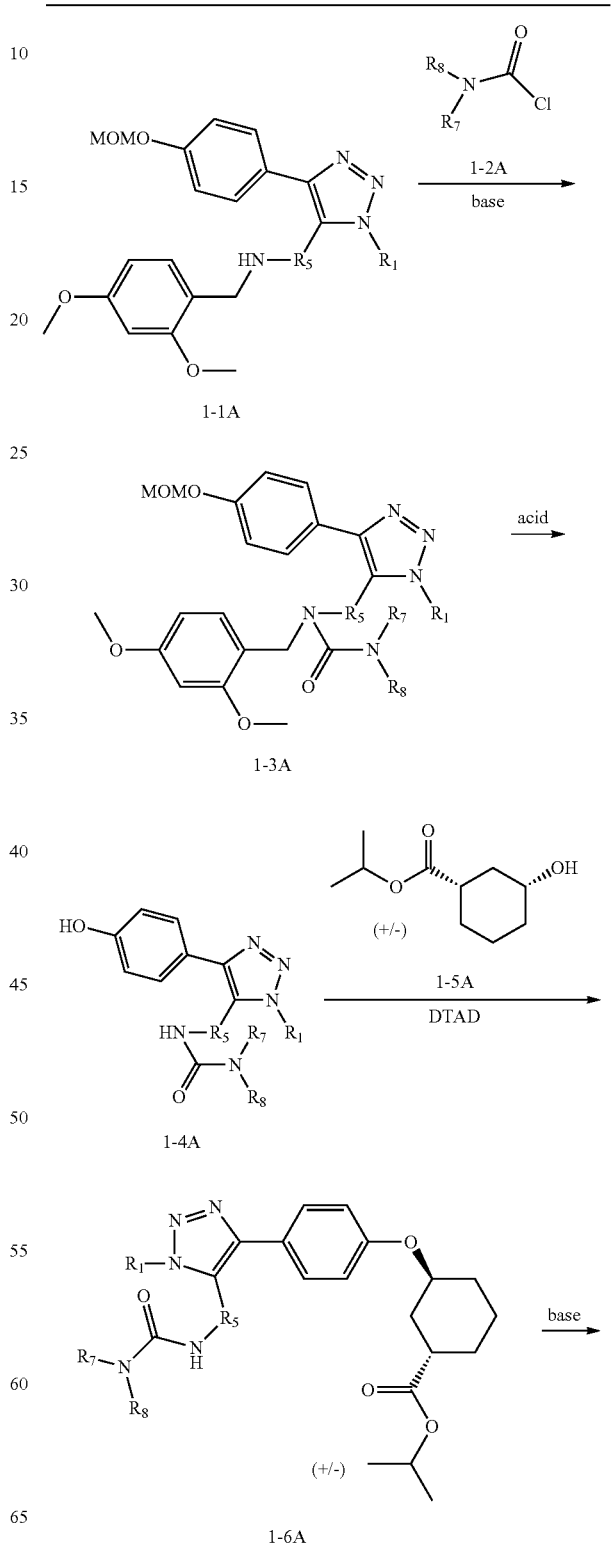

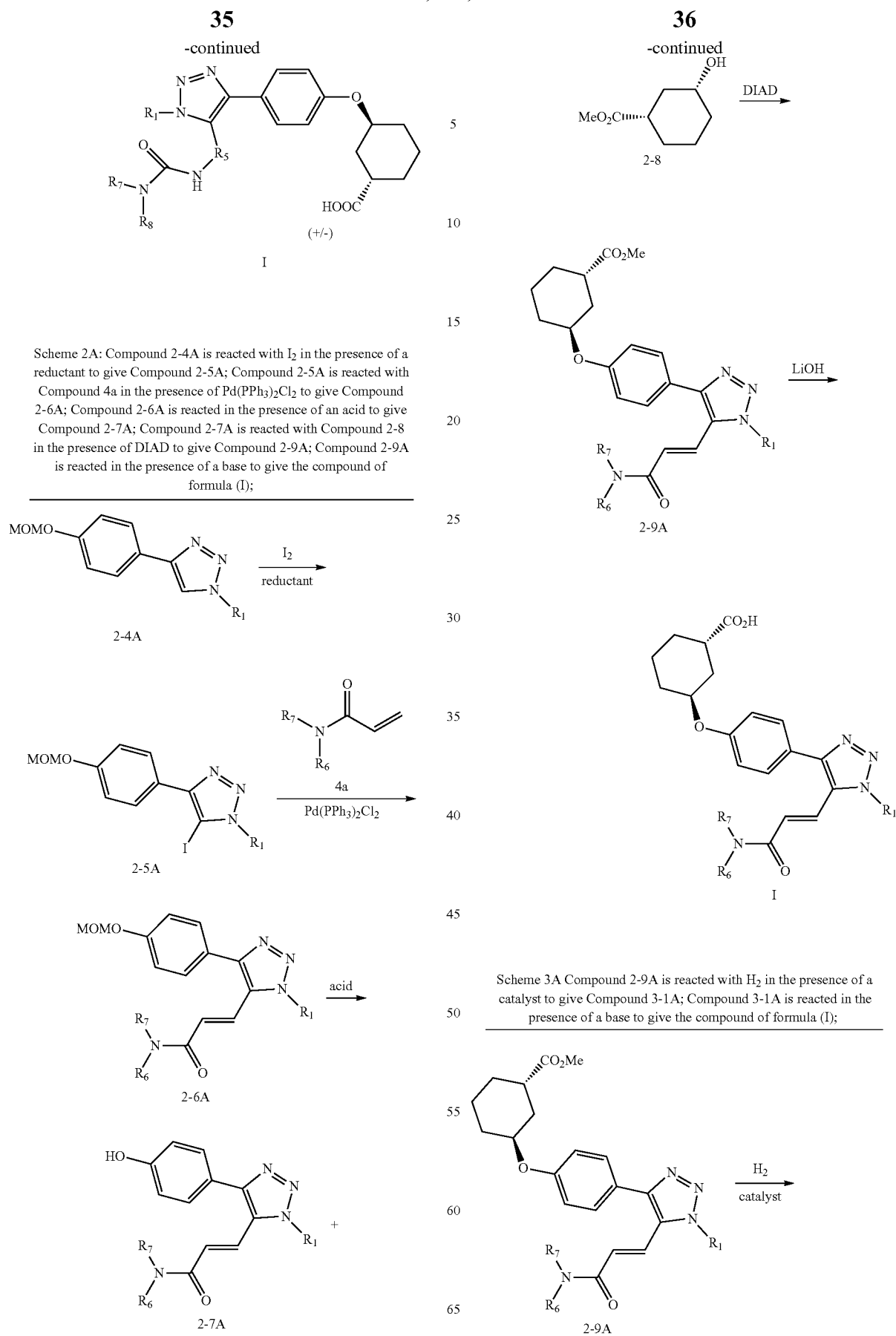

37

-continued

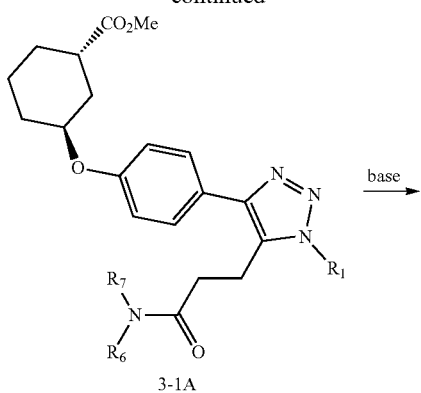

3-1A

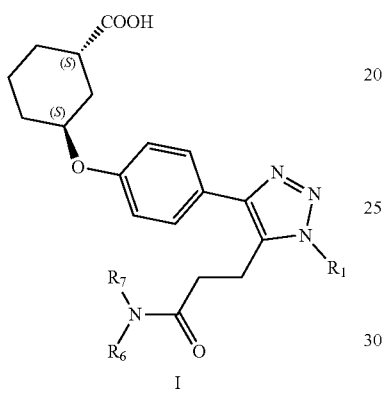

I

Scheme 4A-1: Compound 1-1A is reacted with Compound 7a in the presence of a base to give Compound 4-2A; Compound 4-2A is reacted in the presence of an acid to give Compound 4-3A; Compound 4-3A is reacted with Compound 1-5 in the presence of DTBAD to give Compound 4-4A; Compound 4-4A is reacted in the presence of TFA to give Compound 4-5A; Compound 4-5A is reacted in the presence of a base to give the compound of formula (I);

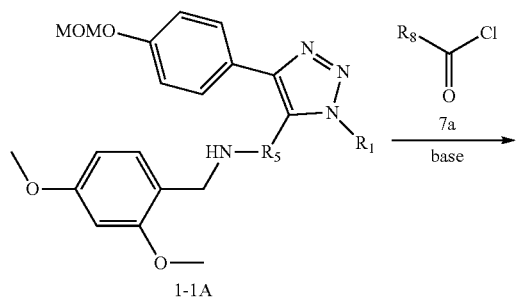

1-1A

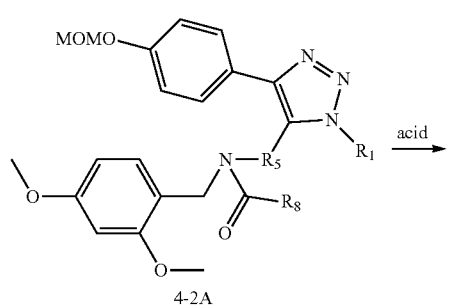

4-2A

38

-continued

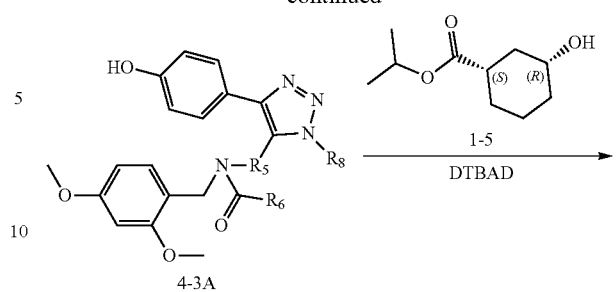

4-3A

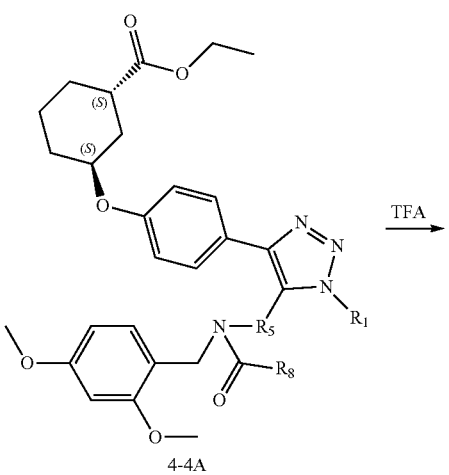

4-4A

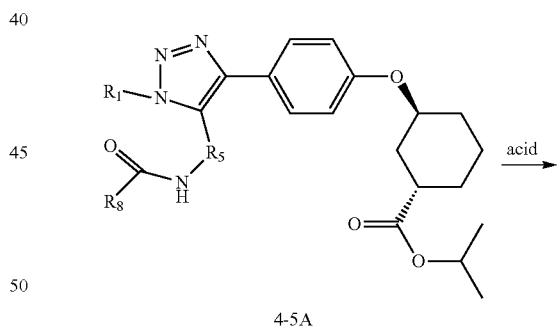

4-5A

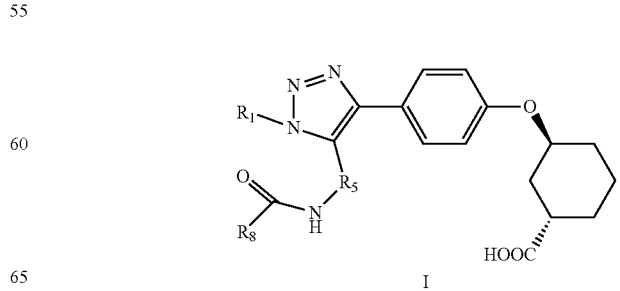

I

Scheme 4A-2 Compound 5-3A is reacted with Compound 5-4 in the presence of Cs$_2$CO$_3$ to give Compound 5-5A; Compound 5-5A is reacted in the presence of TFA to give Compound 5-6A; Compound 5-6A is reacted in the presence of a base to give the compound of formula (I);

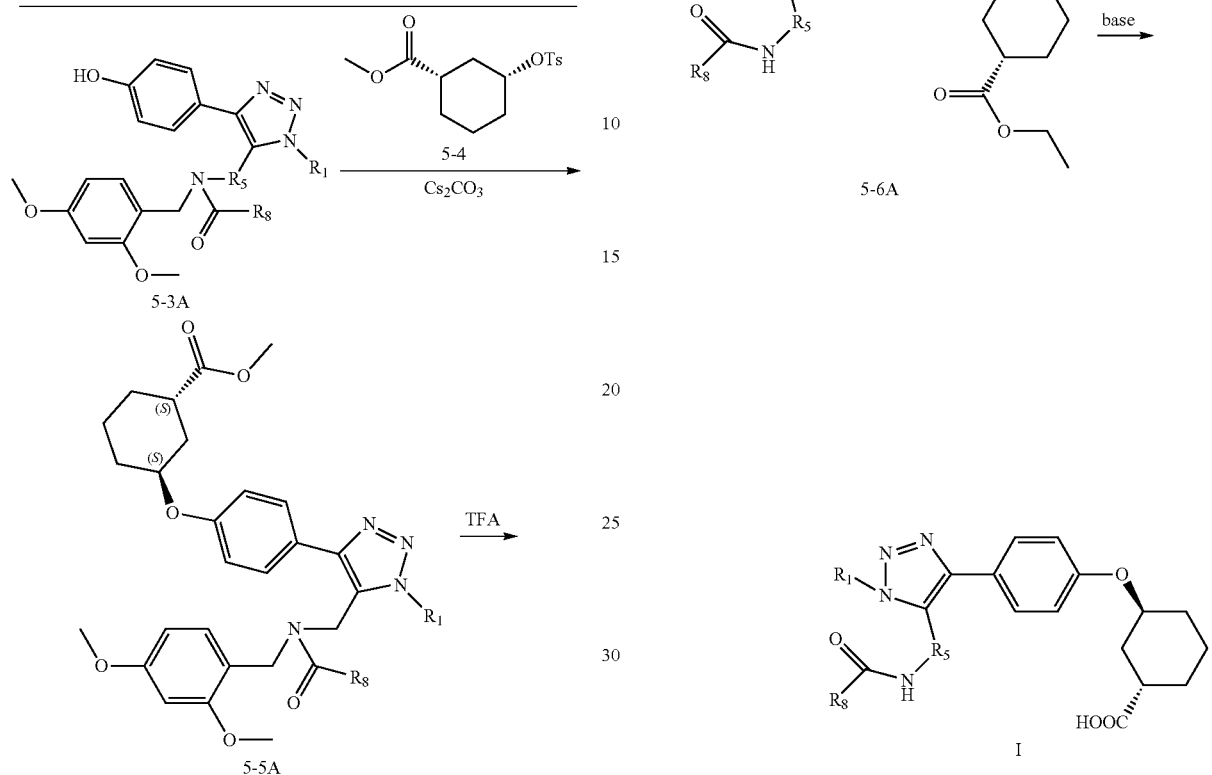

Scheme 5A: Compound 6-1 is reacted with sodium azide in the presence of Cu(AcO)$_2$ to give Compound 6-2; Compound 6-2 is reacted with 2-(prop-2-yn-1-oxy)tetrahydro-2H-pyran in the presence of CuI to give Compound 6-3; Compound 6-3 is reacted with Compound 6-4A in the presence of Cs$_2$CO$_3$ to give Compound 6-5A; Compound 6-5A is reacted in the presence of PPTS to give Compound 6-6A; Compound 6-6A is reacted with Compound 6-7 and Compound 6-8A in the presence of pyridine and DIPEA to give Compound 6-9A; Compound 6-9A is reacted in the presence of a base to give the compound of formula (I);

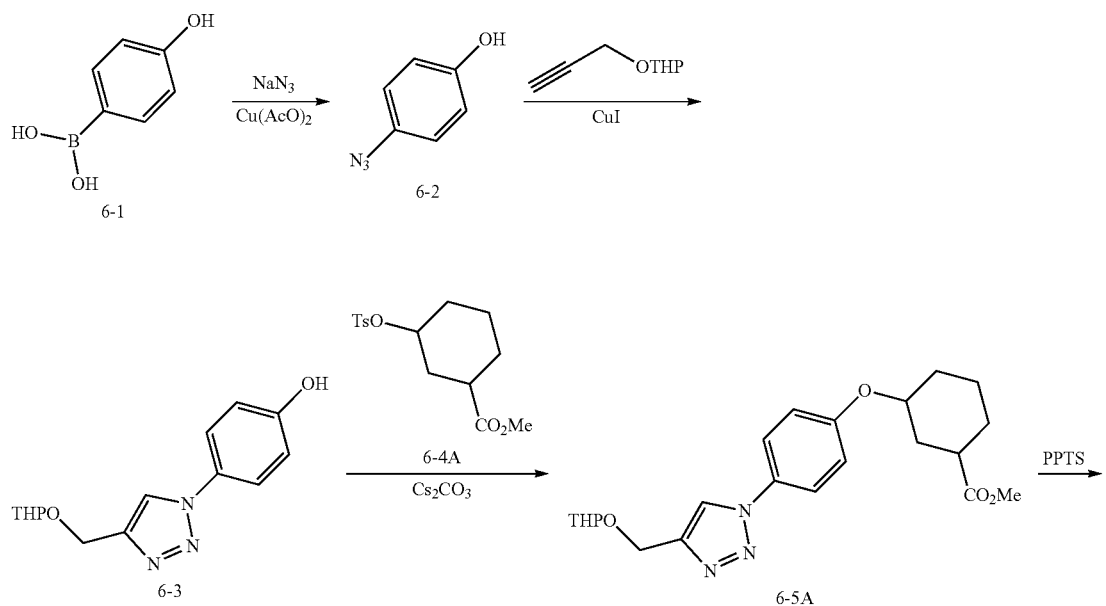

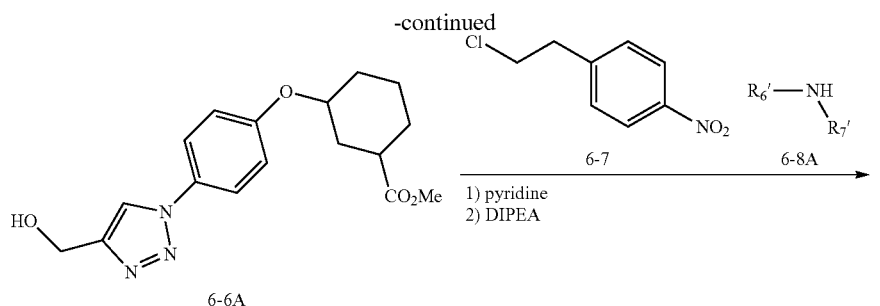

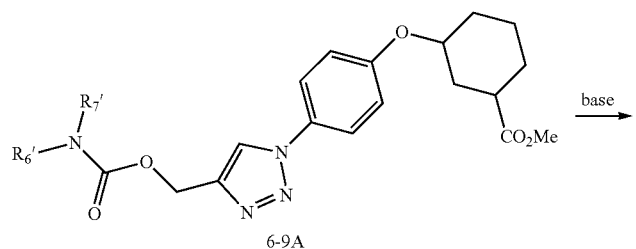

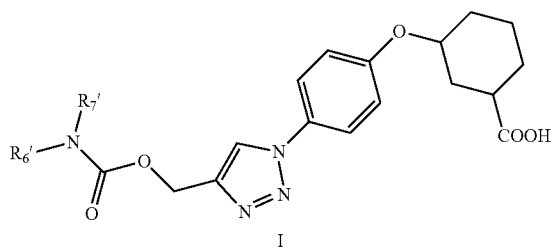

Scheme 6A Compound 7-1 is reacted with 2-(prop-2-yn-1-oxy) tetrahydro-2H-pyran in the presence of Pd(PPh3)2Cl2, CuI and Et3N to give Compound 7-2; Compound 7-2 is reacted with compound 7-3 in the presence of CuI, K2CO3 and PPh3 to give Compound 7-4; Compound 7-4 is reacted with trimethylsilylmethyl azide in the presence of DMF under a heating condition to give Compound 7-5; Compound 7-5 is reacted in the presence of TBAF to give Compound 7-6; Compound 7-6 is reacted in the presence of PPTS to give Compound 7-7; Compound 7-7 is reacted with Compound 6-7 and Compound 6-8A in the presence of pyridine and DIPEA to give Compound 7-8A; Compound 7-8A is reacted in the presence of a base to give the compound of formula (I);

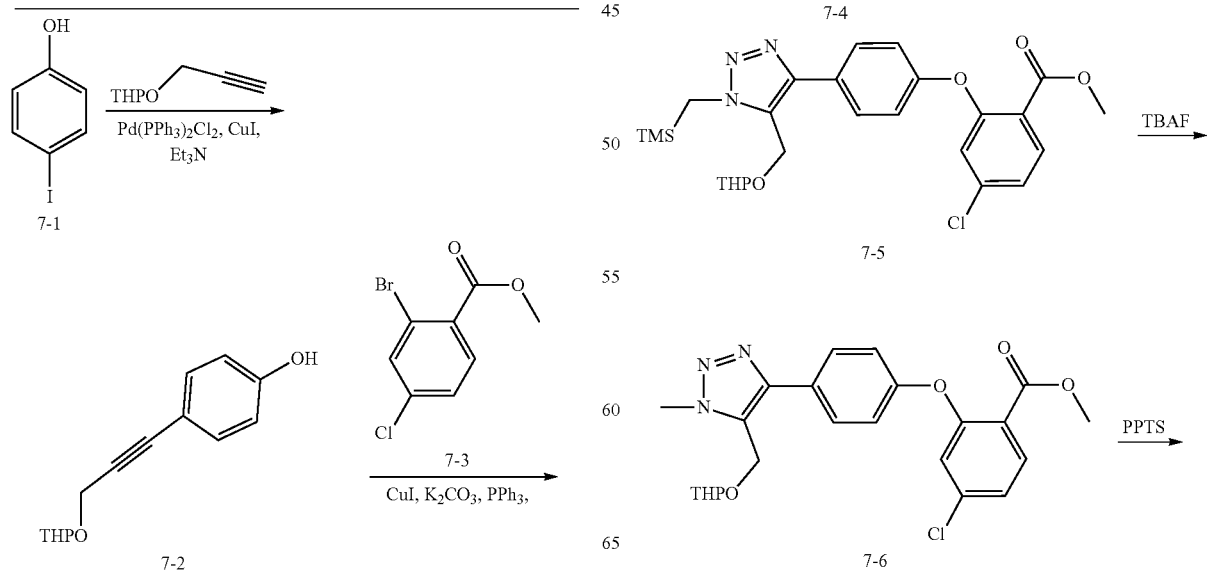

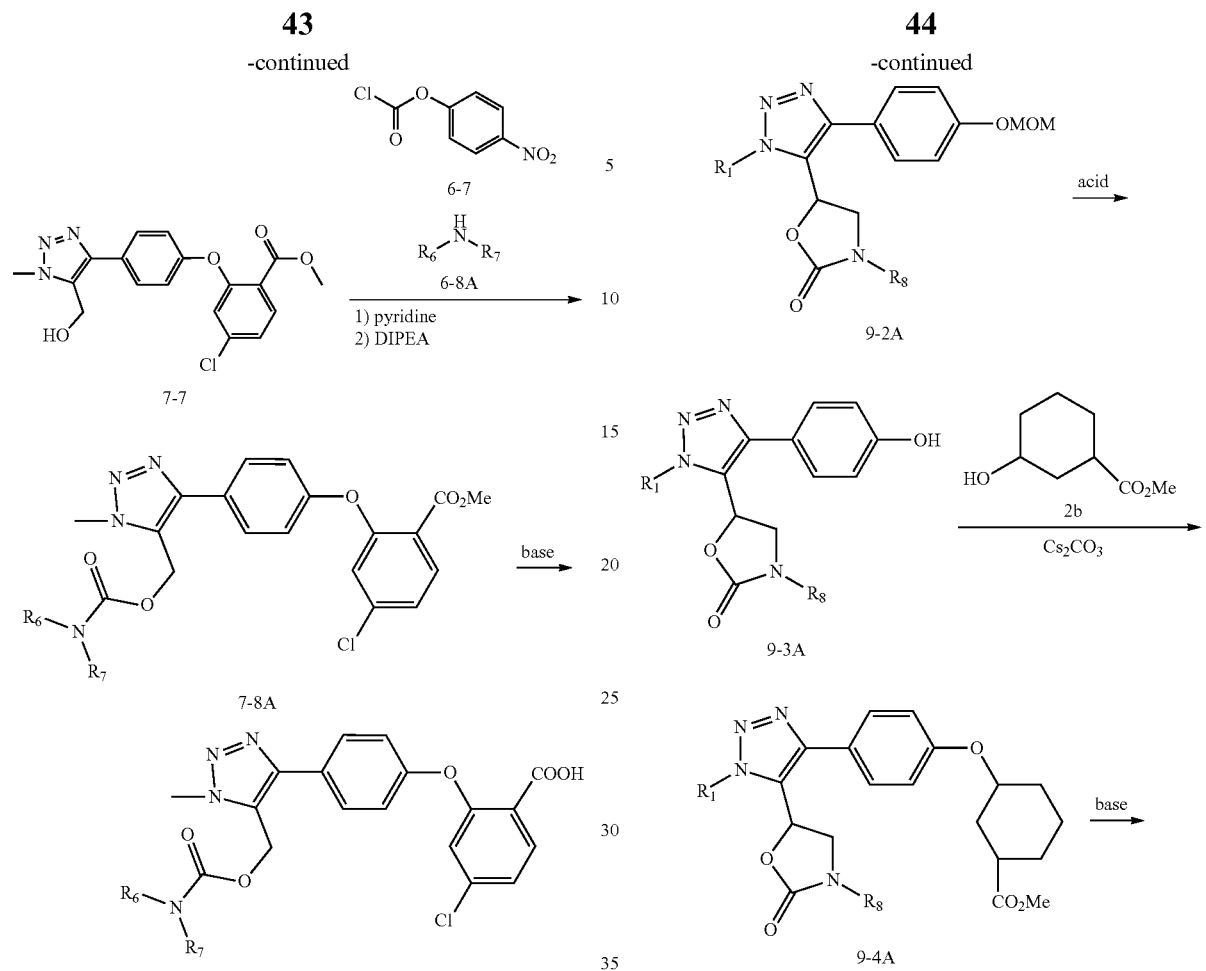

Scheme 7A Compound 1b is reacted with Compound 9a in the presence of a base and LiBH$_4$ to give Compound 9-1A; Compound 9-1A is reacted with triphosgene in the presence of a base to give Compound 9-2A; Compound 9-2A is reacted in the presence of an acid to give Compound 9-3A; Compound 9-3A is reacted with Compound 2b in the presence of Cs$_2$CO$_3$ to give Compound 9-4A; Compound 9-4A is reacted in the presence of a base to give the compound of formula (I);

Scheme 8A: Compound 10-1a is reacted in the presence of a reductant to give Compound 10-2A; Compound 10-2A is reacted with Compound 10-3 in the presence of pyridine to give Compound 10-4A; Compound 10-4A is reacted with Compound 10-5A in the presence of DIPEA to give Compound 10-6A; Compound 10-6A is reacted in the presence of an acid to give Compound 10-7A; Compund 10-7A is reacted with ethyl propiolate in the presence of DABCO to give Compound 10-8A; Compound 10-8A is reacted in the presence of a base to give the compound of formula (I);

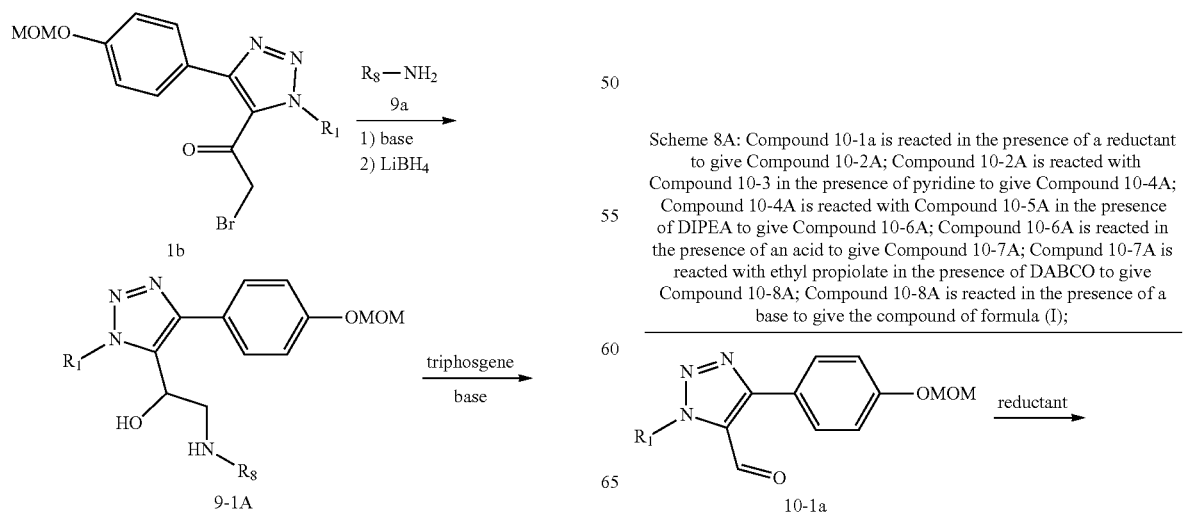

-continued

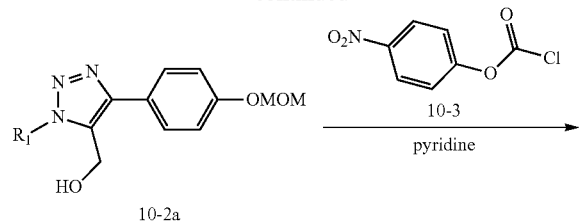
10-2a

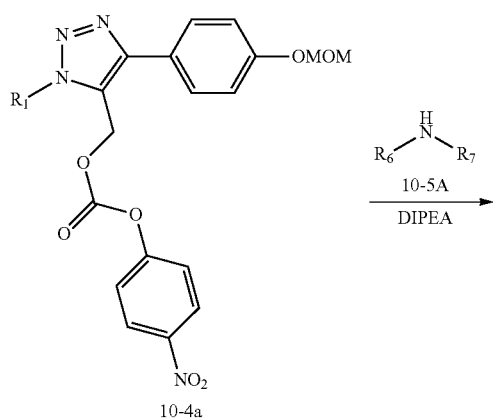
10-4a

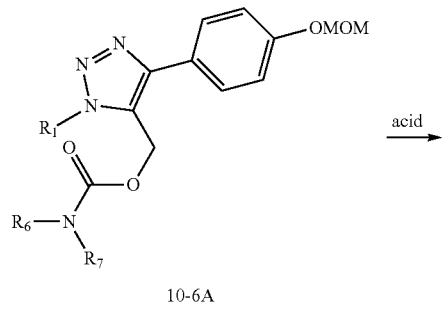
10-6A

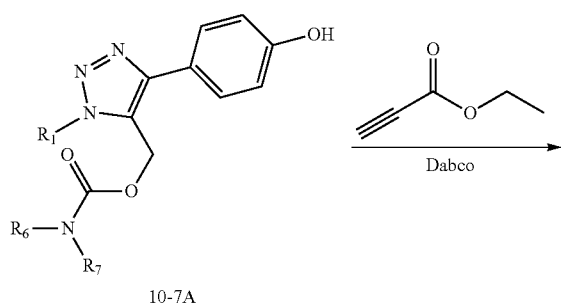
10-7A

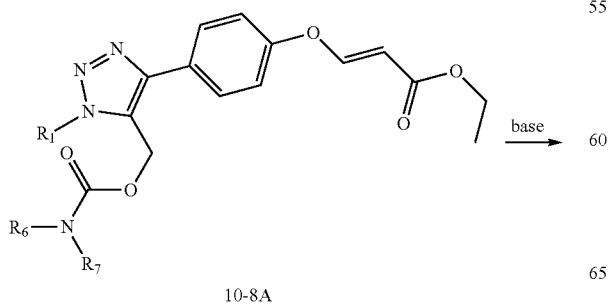
10-8A

-continued

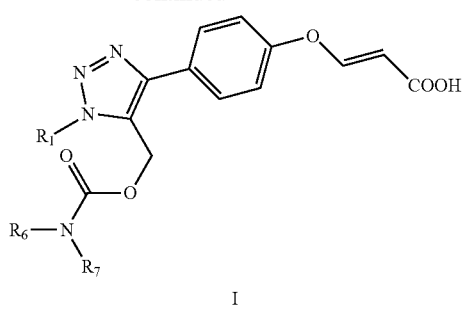
I

Scheme 10A Compound 13-1 is reacted with 2-(prop-2-yn-1-oxy)tetrahydro-2H-pyran in the presence of Pd(PPh$_3$)$_2$Cl$_2$, CuI and Et$_3$N to give Compound 13-2; Compound 13-2 is reacted with trimethylsilylmethyl azide in the presence of toluene under a heating condition to give Compound 13-3; Compound 13-3 is reacted in the presence of TBAF to give Compound 13-4; Compound 13-4 is reacted in the presence of PPTS to give Compound 13-5; Compound 13-5 is reacted with Compound 6-7 and Compound 6-8A in the presence of pyridine and DIPEA to give Compound 13-6A; Compound 13-6A is reacted in the presence of Zn and NH$_4$Cl to give Compound 13-7A; Compound 13-7A is reacted with Compound 13-8 in the presence of TMSCl and BH$_3$/THF to give Compound 13-9A; Compound 13-9A is reacted in the presence of a base to give the compound of formula (I);

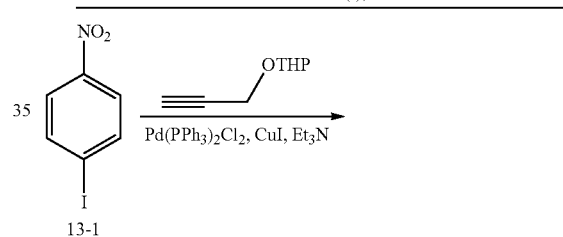
13-1

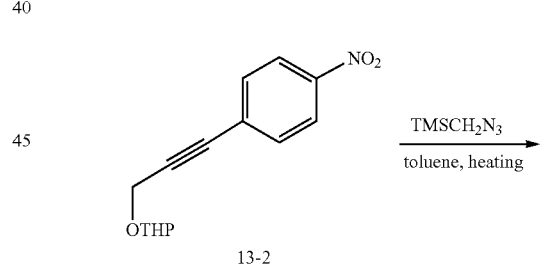
13-2

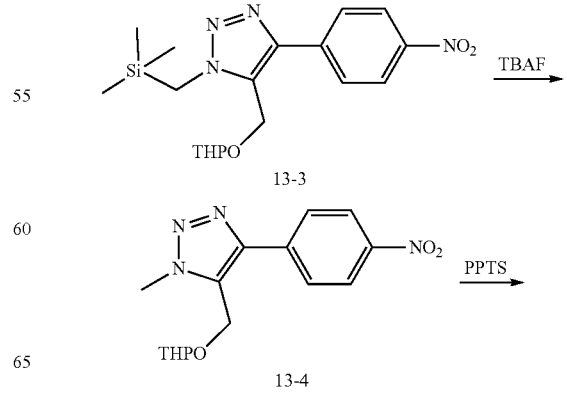
13-3

13-4

-continued

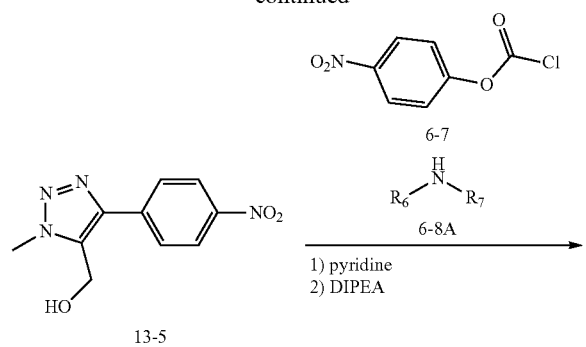

Scheme 11A Compound 14-1B is reacted with methylamine in the presence of NaBH₃CN to give Compound 14-2A; Compound 14-2A is reacted with Compound 10a in the presence of a base to give Compound 14-3A; Compound 14-3A is reacted in the presence of an acid to give Compound 14-4A; Compound 14-4A is reacted with Compound 2b in the presence of Cs₂CO₃ to give Compound 14-5A; Compound 14-5A is reacted in the presence of a base to give the compound of formula (I);

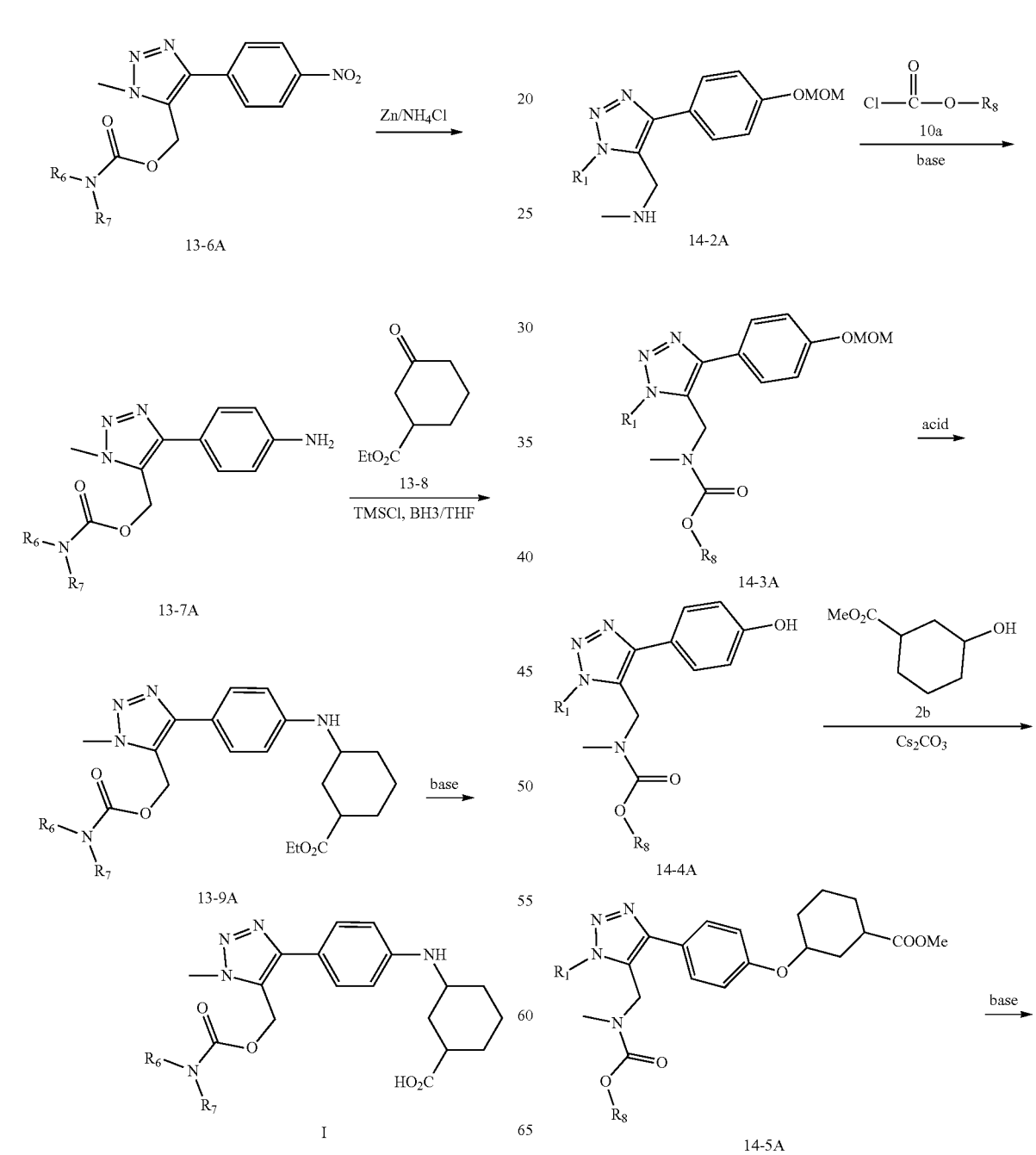

-continued

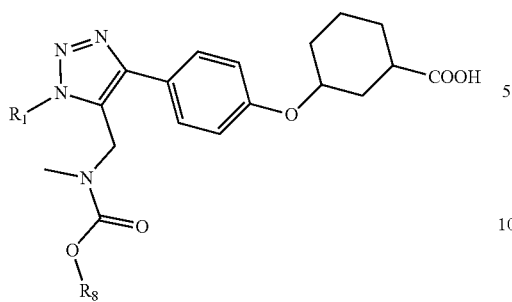

I

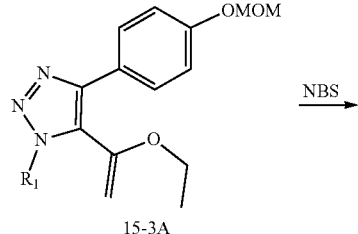

15-3A

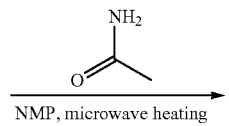

15-4A

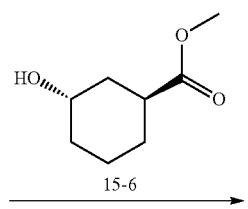

15-5A

Scheme 12A Compound 15-1a is reacted with I₂ in the presence of n-butyl lithium to give Compound 15-2A; Compound 15-2A is reacted with Compound 11a in the presence of Pd(OAc)₂ and PPh₃ to give Compound 15-3A; Compound 15-3A is reacted with NBS to give Compound 15-4A; Compound 15-4A is reacted with acetamide in the presence of NMP under microwave heating to give Compound 15-5A; Compound 15-5A is reacted with Compound 15-6 to give Compound 15-7A; Compound 15-7A is reacted in the presence of a base to give the compound of formula (I);

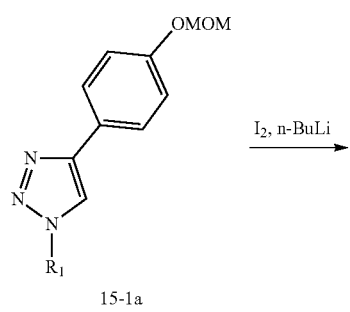

15-1a

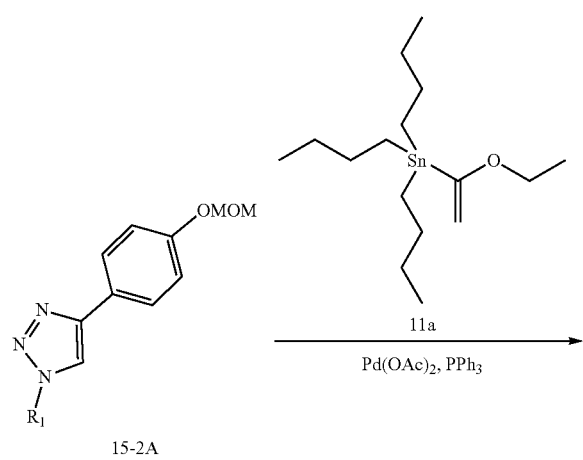

15-2A

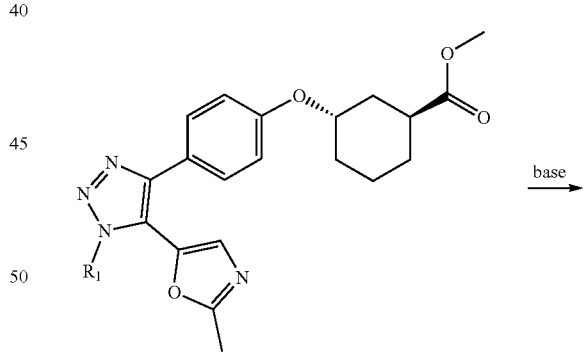

15-7A

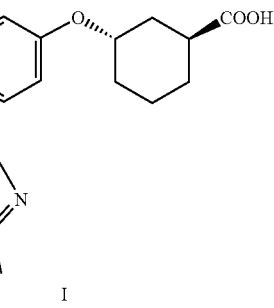

I

Scheme 13A: Compound 16-4 is reacted with MOMBr in the presence of NaH to give Compound 16-5A; Compound 16-5A is reacted with trimethylsilylacetylene in the presence of Pd(PPh$_3$)$_2$Cl$_2$, CuI and Et$_3$N, and then in the presence of K$_2$CO$_3$ and MeOH to give Compound 16-6A; Compound 16-6A is reacted with sodium azide to give Compound 16-7B; Compound 16-7B is reacted with n-butyl lithium in the presence of DMF to give Compound 16-8A; Compound 16-8A is reacted with NaBH$_4$ to give Compound 16-9A; Compound 16-9A is reacted with MsCl in the presence of a base to give Compound 16-10A; Compound 16-10A is reacted with Compound 16-3A in the presence of sodium hydride to give Compound 16-11A; Compound 16-11A is reacted in the presence of an acid to give Compound 16-12A; Compound 16-12A is reacted with Compound 12a in the presence of Cs$_2$CO$_3$ to give Compound 16-13A; Compound 16-13A is reacted in the presence of a base to give the compound of formula (I);

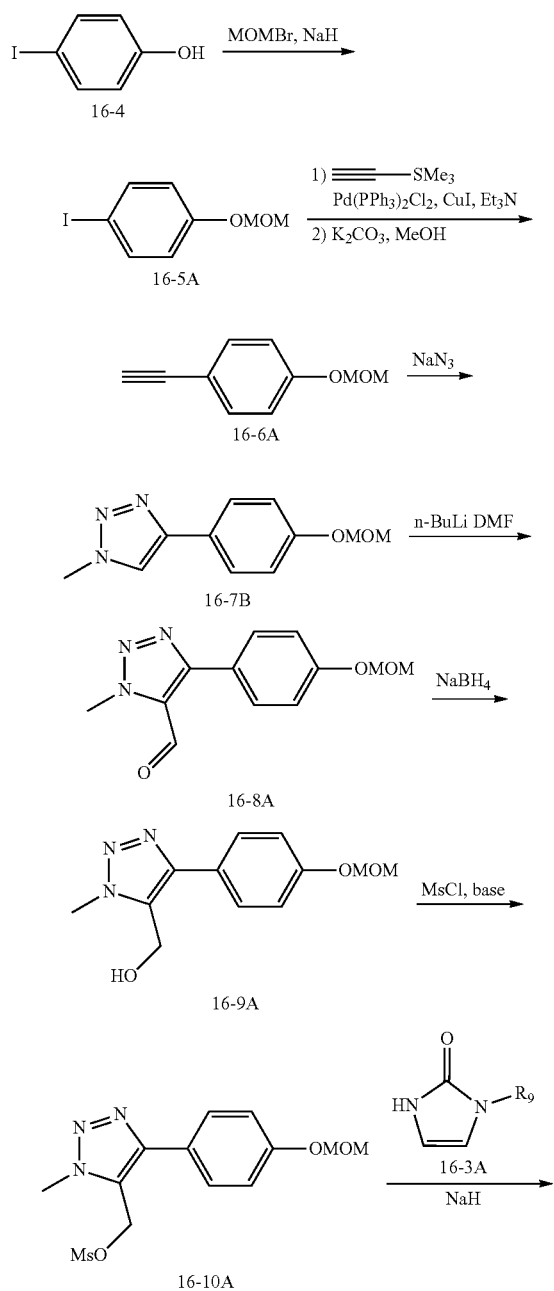

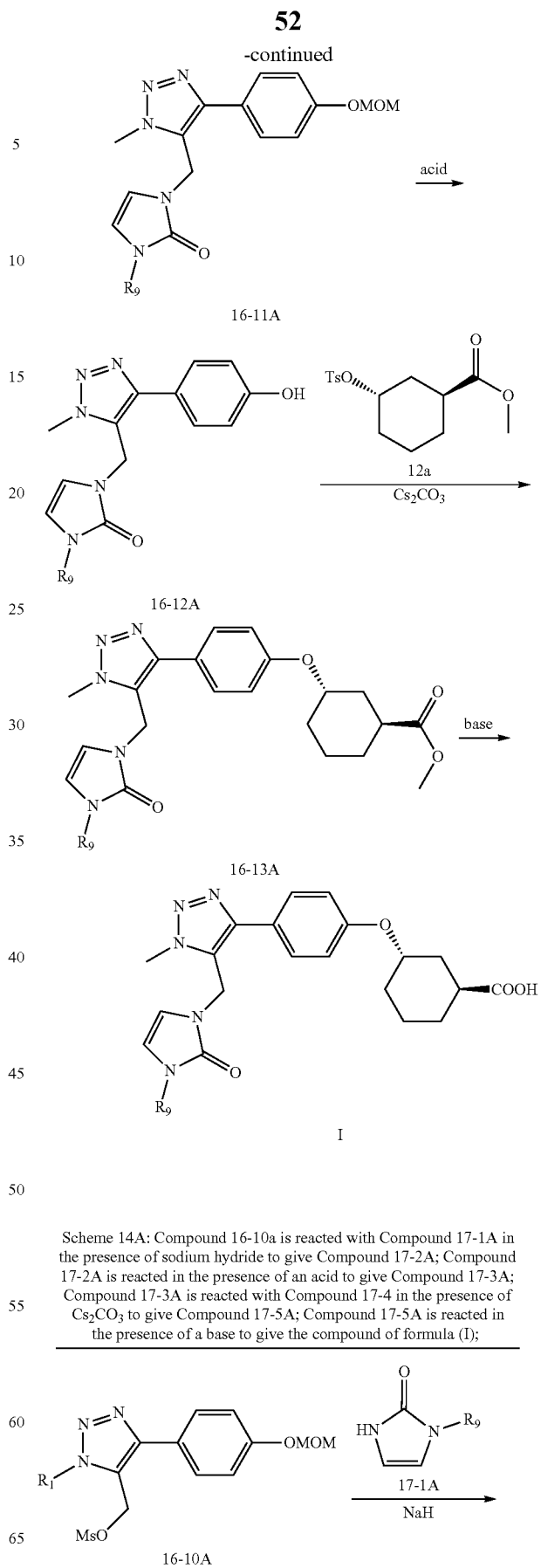

Scheme 14A: Compound 16-10a is reacted with Compound 17-1A in the presence of sodium hydride to give Compound 17-2A; Compound 17-2A is reacted in the presence of an acid to give Compound 17-3A; Compound 17-3A is reacted with Compound 17-4 in the presence of Cs$_2$CO$_3$ to give Compound 17-5A; Compound 17-5A is reacted in the presence of a base to give the compound of formula (I);

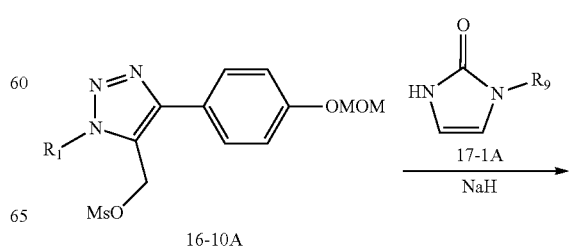

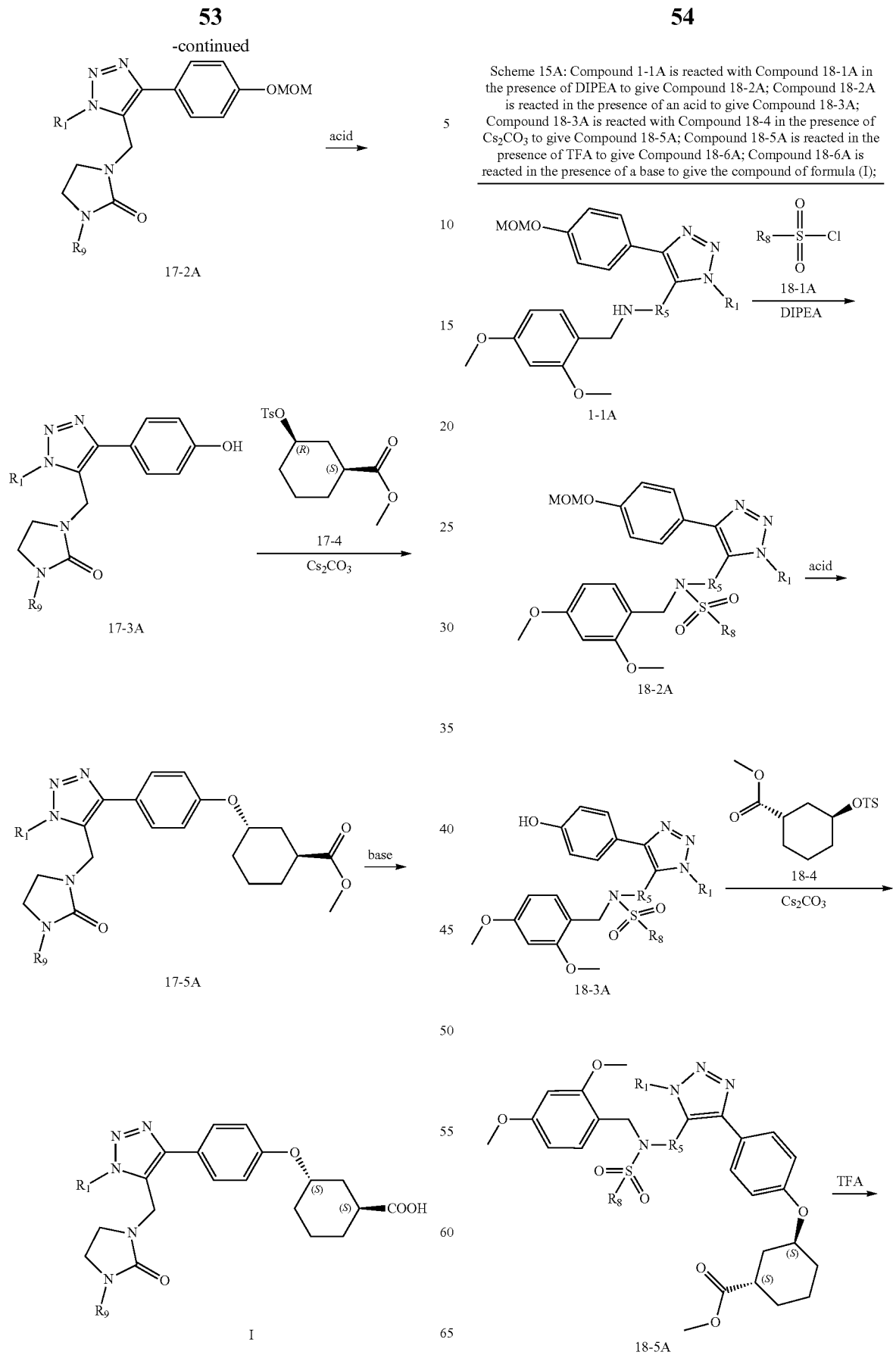

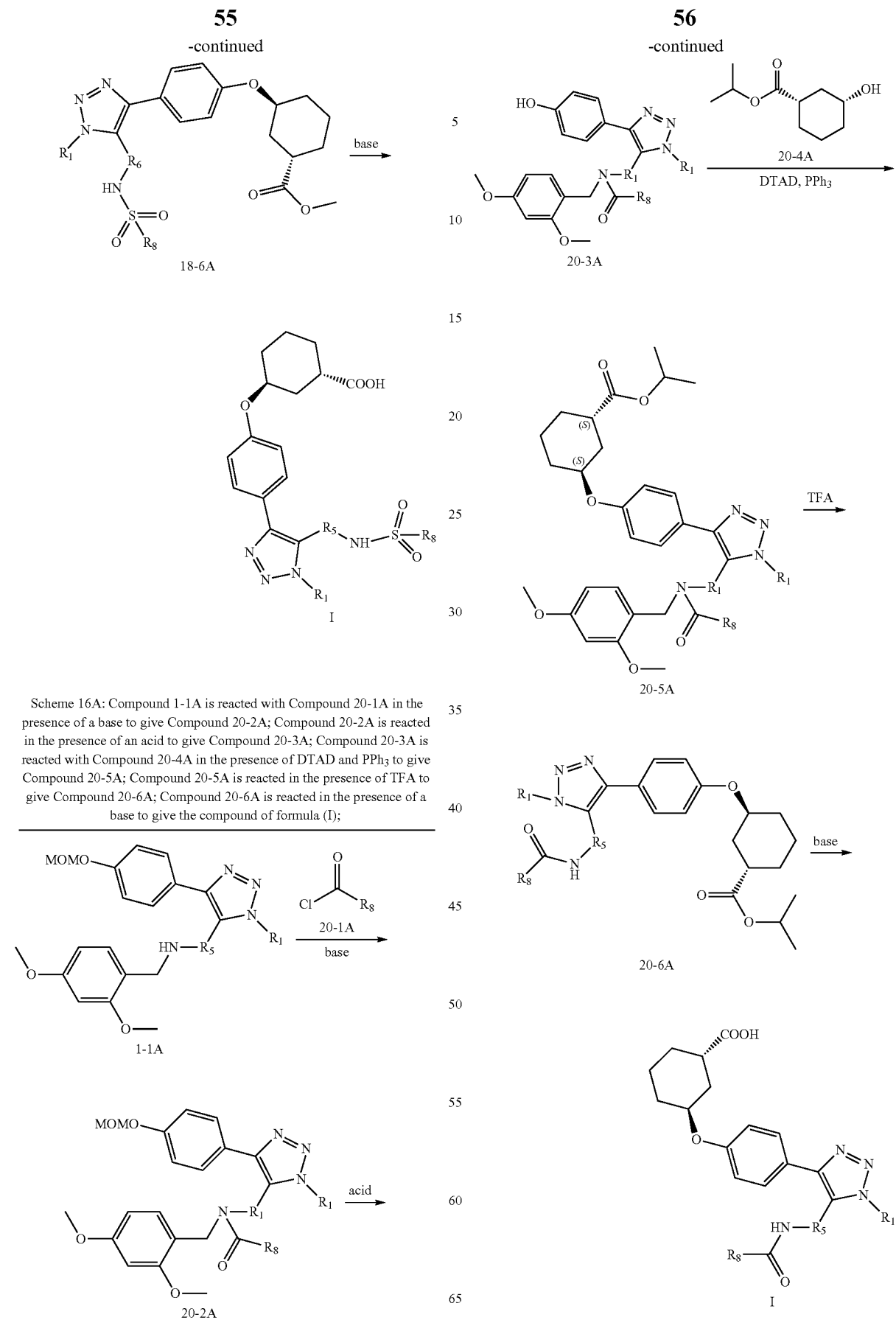

Scheme 17A: Compound 21-1A is reacted with Compound 21-2A in the presence of sodium hydride to give Compound 21-3A; Compound 21-3A is reacted in the presence of an acid to give Compound 21-4A; Compound 21-4A is reacted with Compound 21-5 in the presence of DTAD and PPh₃ to give Compound 21-6A; Compound 21-6A is reacted in the presence of a base to give the compound of formula (I);

Scheme 18A Compound 16-9B is reacted with Compound 14a in the presence of sodium hydride to give Compound 23-1A; Compound 23-1A is reacted in the presence of an acid to give Compound 23-2A; Compound 23-2A is reacted with Compound 15a in the presence of Cs₂CO₃ to give Compound 23-3A; Compound 23-3A is reacted in the presence of a base to give a compound of formula (I);

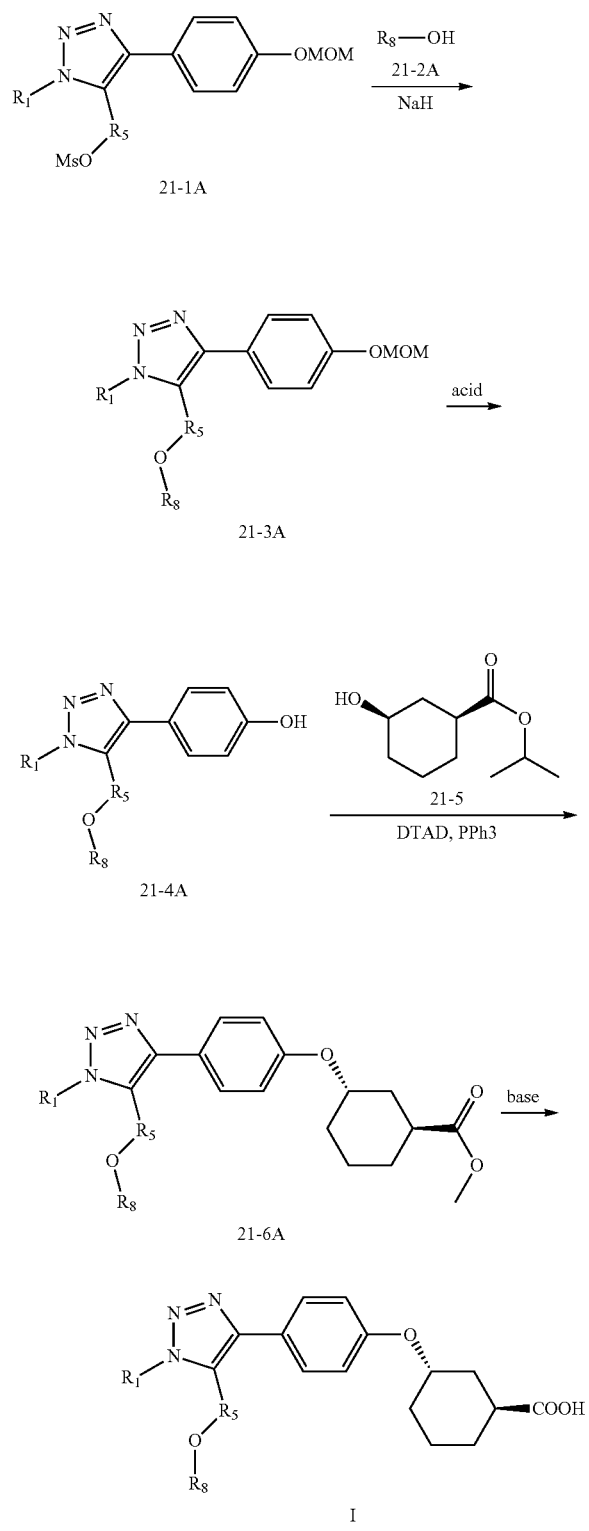

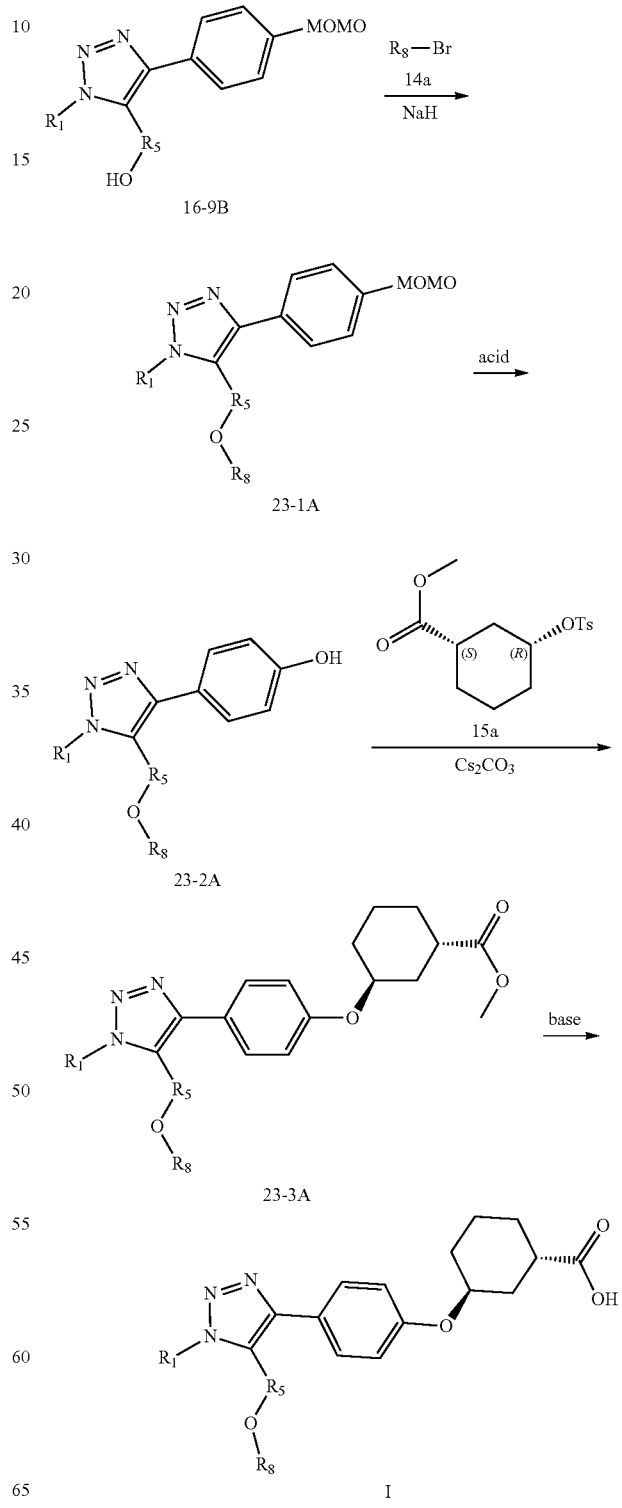

59

Scheme 19A: Compound 24-1B is reacted in the presence of DPPA and tert-butanol to give Compound 24-2A; Compound 24-2A is reacted with Compound 16a in the presence of sodium hydride to give Compound 24-3A; Compound 24-3A is reacted in the presence of an acid to give Compound 24-4A; Compound 24-4A is reacted with Compound 17a in the presence of DTAD and PPh₃ to give Compound 24-5A; Compound 24-5A is reacted in the presence of a base to give the compound of formula (I);

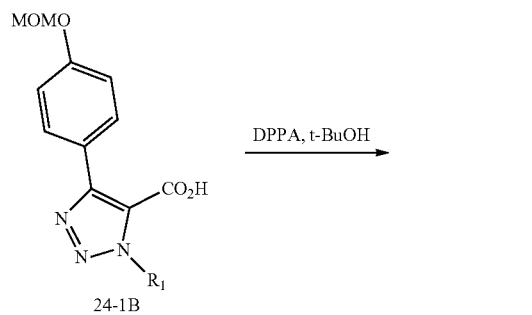

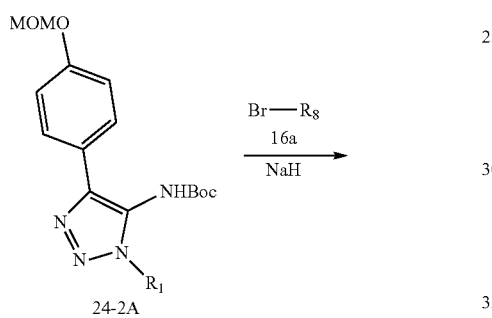

60

-continued

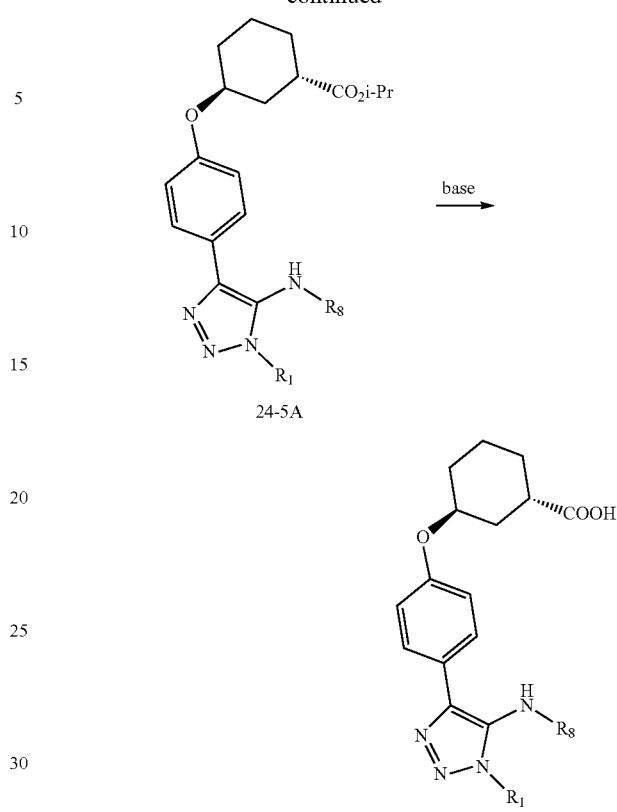

Scheme 20A: Compound 26-1 is reacted with Compound 1-5 in the presence of DTAD and PPh₃ to give Compound 26-2; Compound 26-2 is reacted with trimethylsilylmethyl azide, and then reacted with TBAF to give Compound 26-3; Compound 26-3 is reacted in the presence of TFA to give Compound 26-4; Compound 26-4 is reacted triphosgene and Compound 18a in the presence of a base to give Compound 26-5A; Compound 26-5A is reacted in the presence of a base to give the compound of formula (I);

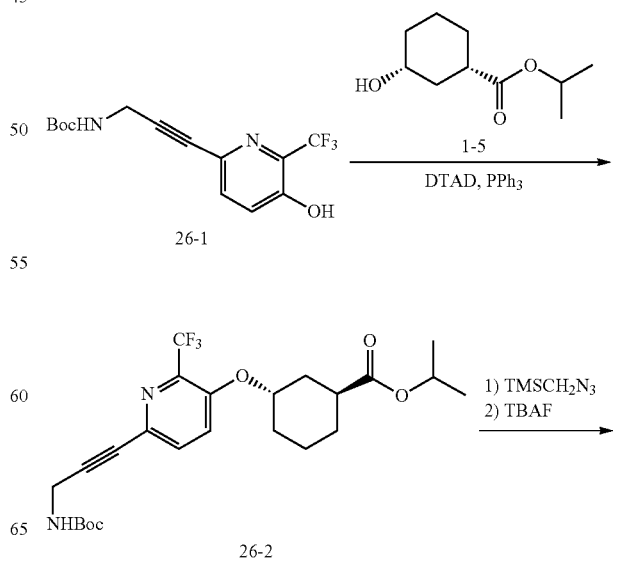

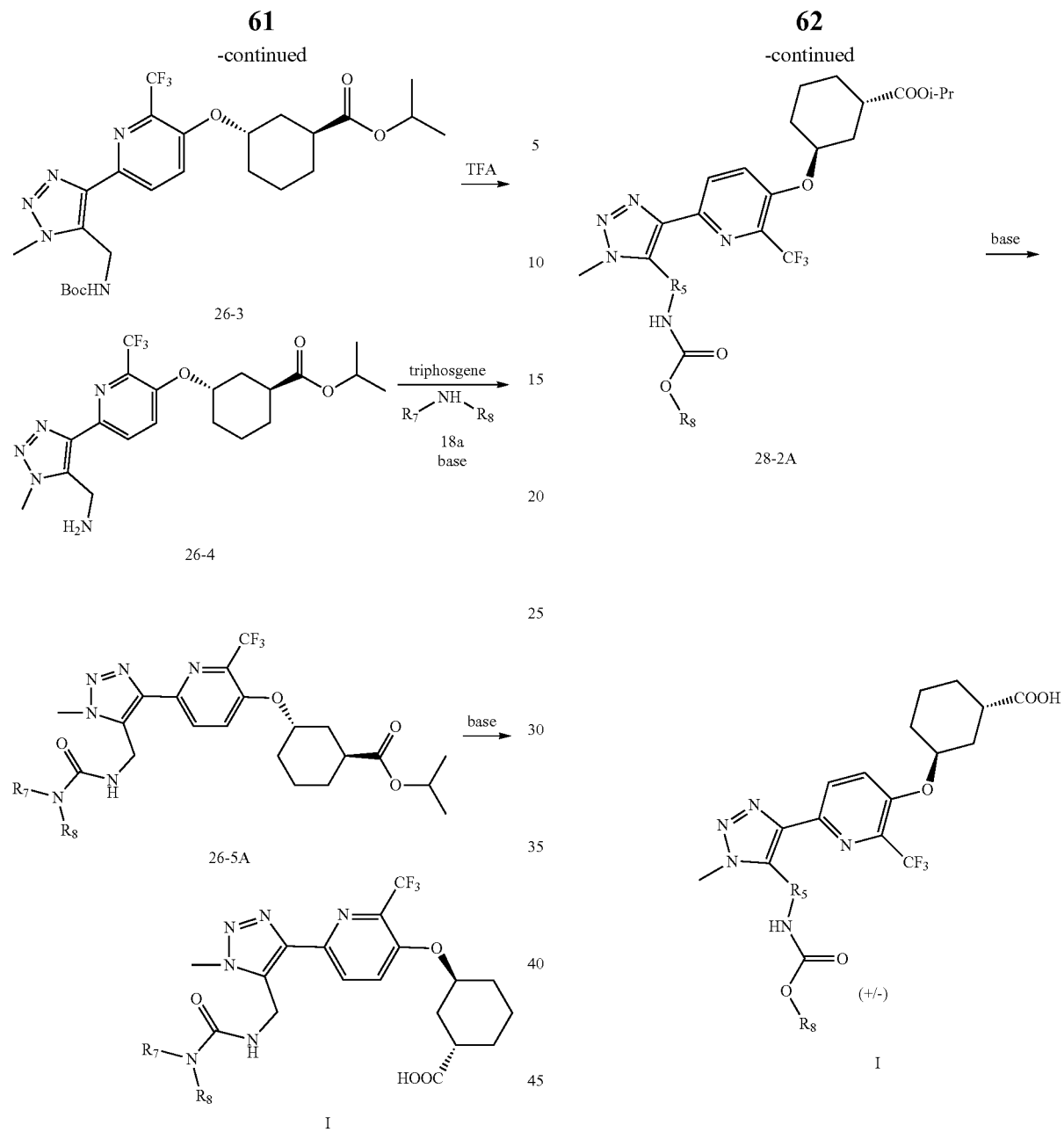

Scheme 22A: Compound 28-1B is reacted with triphosgene and Compound 20a in the presence of a base to give Compound 28-2A; Compound 28-2A is reacted in the presence of a base to give the compound of formula (I);

Scheme 23A Compound 1-1B is reacted with Compound 21a in the presence of a base to give Compound 30-1A; Compound 30-1A is reacted in the presence of an acid to give Compound 30-2A; Compound 30-2A is reacted with Compound 1-5 in the presence of DBAD and PPh₃ to give Compound 30-3A; Compound 30-3A is reacted in the presence of a base to give the compound of formula (I);

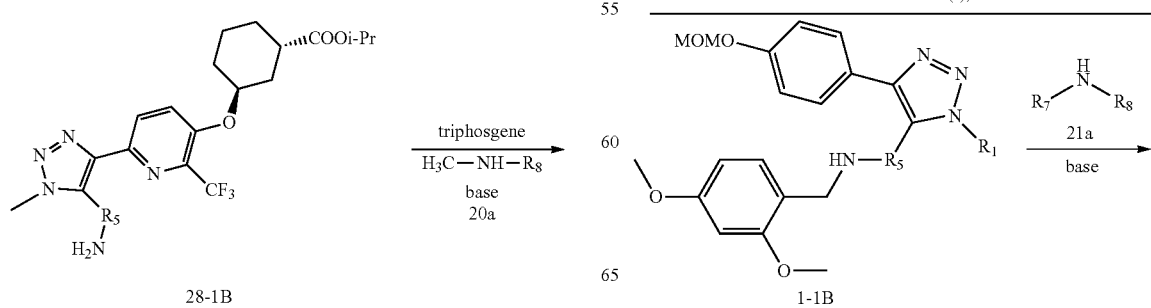

-continued

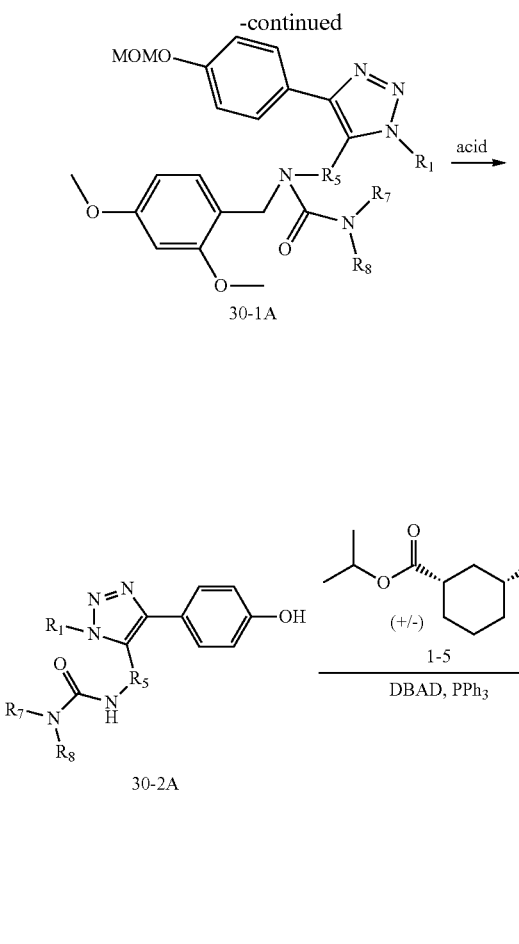

Scheme 24A Compound 2-4B is reacted with methyl chloroformate in the presence of n-butyl lithium to give Compound 31-1A; Compound 31-1A is reacted in the presence of a base to give Compound 31-2A; Compound 31-2A is reacted with Compound 22a and DPPA in the presence of a base to give Compound 31-3A; Compound 31-3A is reacted with iodomethane in the presence of sodium hydride to give Compound 31-4A; Compound 31-4A is reacted in the presence of and acid to give Compound 31-5A; Compound 31-5A is reacted with Compound 1-5 in the presence of DTAD and PPh₃ to give Compound 31-6A; Compound 31-6A is reacted in the presence of a base to give the compound of formula (I);

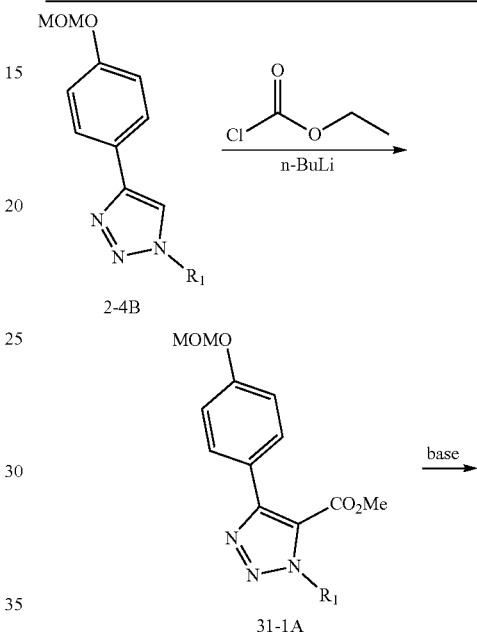

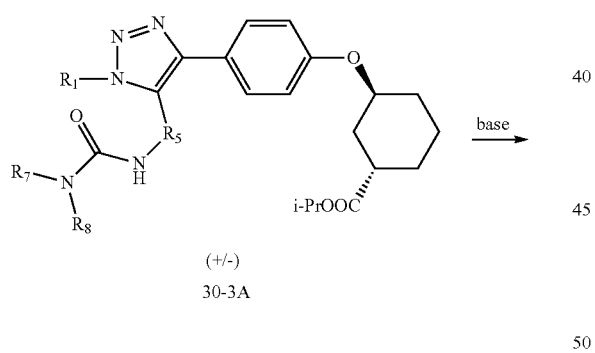

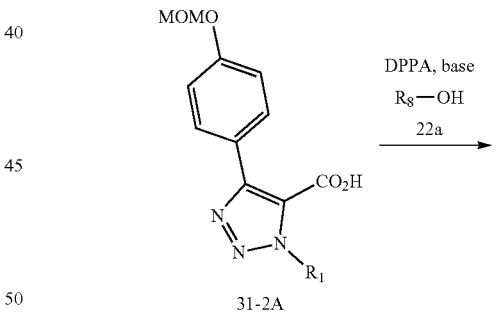

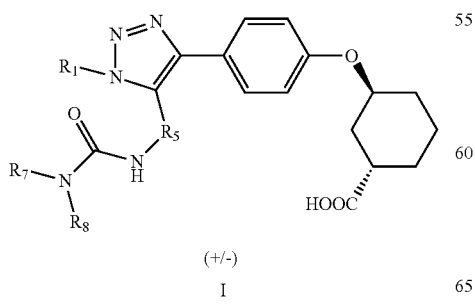

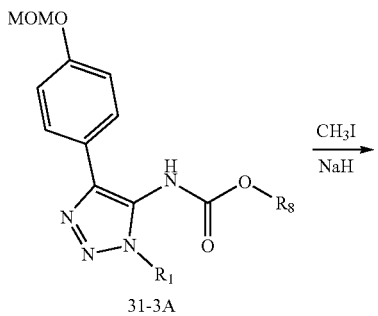

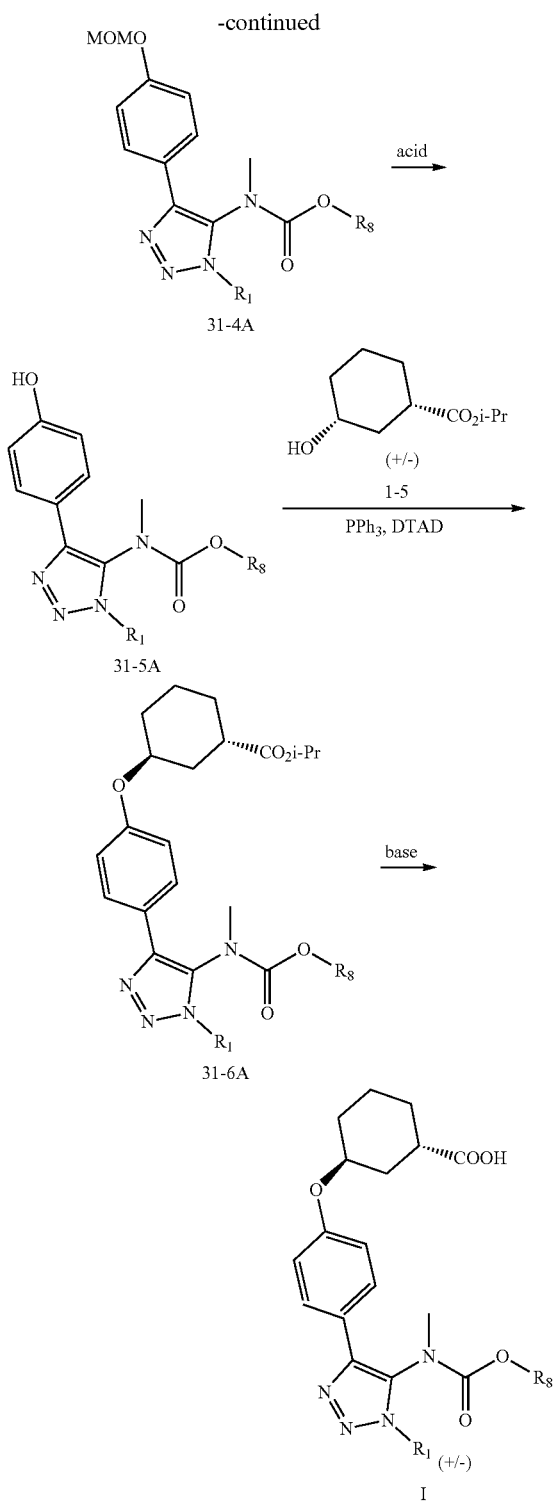

wherein, $R_1$, $R_2$, $R_5$, $R_6$, $R_6'$, $R_7$, $R_7'$, $R_8$, and $R_9$ are defined as above.

If necessary, protecting groups can be used to protect any group of the reactants or intermediates in the above schemes. After the reaction is completed, the protecting groups are removed by an appropriate method.

The starting materials for the reactants in the above schemes (such as Compound 1a and Compound 1b) can be synthesized by methods reported in the literatures, or can be purchased. The starting materials are generally from commercial sources (e.g., Aldrich) or can be readily prepared using methods well known to those skilled in the art (obtained from SciFinder and Reaxys online databases).

In the preparation method of the present invention, suitable reaction conditions and starting materials can be selected according to different situations. For example, only one substituent can be substituted with another substituent according to the present invention in a one-step reaction, or multiple substituents can be substituted with the other substituents according to the present invention in the same reaction step.

If the compounds are not available via the above routes, they can be prepared by deriving other compounds of formula (I) or by conventionally changing the synthetic routes.

The triazole compound of formula (I) or the stereoisomer, the tautomer, the isotopically labeled compound, the nitrogen oxide, the solvate, the polymorph, the metabolite, the ester, the pharmaceutically acceptable salt or the prodrug thereof described herein can be synthesized by methods similar to those known in the chemical field, with the steps and conditions that can be referred to those of similar reactions in the art, especially according to the description herein.

The other triazole compounds of formula (I) can also be obtained by peripherally modifying the triazole compound of formula (I) disclosed herein using the compounds prepared in the above schemes by conventional methods in the art.

In the present invention, after the reaction is completed, conventional post-treatment methods can be adopted. In the present invention, if the crude triazole compound of formula (I) is obtained after the treatment, conventional means such as preparative HPLC, preparative TLC or recrystallization can be adopted for separation or purification.

The present invention also provides the compounds of formulas M-1, M-2, M-3, M-4, M-5, M-6, M-7, M-8, M-9, M-10, M-11, M-12, M-13, M-14, M-15, M-16, M-17, M-18, M-19, M-20, M-21, M-22, M-23, M-24, M-25, M-26, M-27, M-28, M-29, M-30, M-31, M-32, M-33, M-34, M-35, M-36, M-37, and M-38, wherein $R_1$, $R_2$, $R_5$, $R_6$, $R_6'$, $R_7$, $R_7'$, R and $R_9$ are defined as above.

According to an embodiment of the present invention, the present invention also provides the compounds of formulas 1-3A, 1-4A, 1-6A, 2-5A, 2-6A, 2-7A, 2-9A, 3-1A, 4-1A, 4-2A, 4-3A, 4- 4A, 4-5A, 5-5A, 5-6A, 6-2, 6-3, 6-5A, 6-6A, 6-9A, 7-2, 7-4, 7-5, 7-6, 7-7, 7-8A, 9-1A, 9- 2A, 9-3A, 9-4A, 10-2A, 10-4A, 10-6A, 10-7A, 10-8A, 13-2, 13-3, 13-4, 13-5, 13-6A, 13-7A, 13-9A, 14-2A, 14-3A, 14-4A, 14-5A, 15-2A, 15-3A, 15-4A, 15-5A, 15-7A, 16-5A, 16-6A, 16-7B, 16-8A, 16-9A, 16-10A, 16-11A, 16-12A, 16-13A, 17-2A, 17-3A, 17-5A, 18-2A, 18-3A, 18-5A, 18-6A, 20-2A, 20-3A, 20-5A, 20-6A, 21-3A, 21-4A, 21-6A, 23-1A, 23-2A, 23-3A, 24-2A, 24-3A, 24-4A, 24-5A, 26-2, 26-3, 26-4, 26-5A, 28-2A, 30-1A, 30-2A, 30-3A, 31-1A, 31-2A, 31-3A, 31-4A, 31-5A and 31-6A, wherein $R_1$, $R_2$, $R_5$, $R_6$, $R_6'$, $R_7$, $R_7'$, $R_8$ and $R_9$ are defined as above.

As an example, the present invention also provides the compounds of the following formulas:

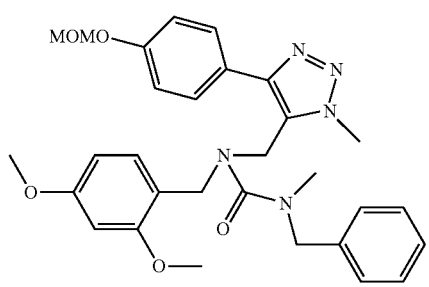
1-3
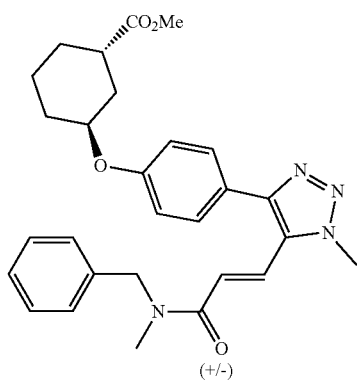
1-4
2-9
1-6
3-1
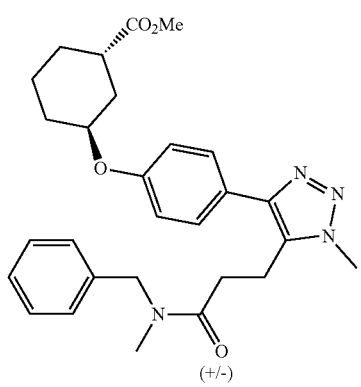
2-6
4-2
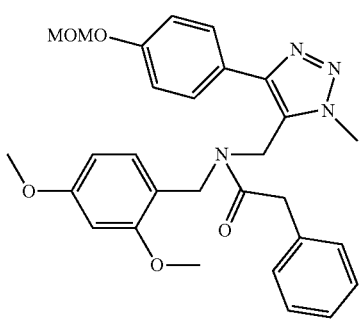
2-7
4-3
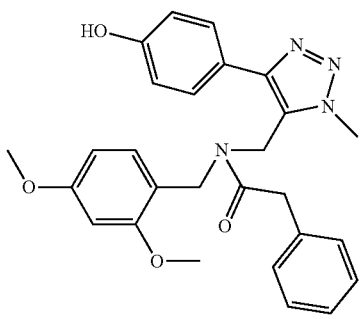

69
-continued
4-4
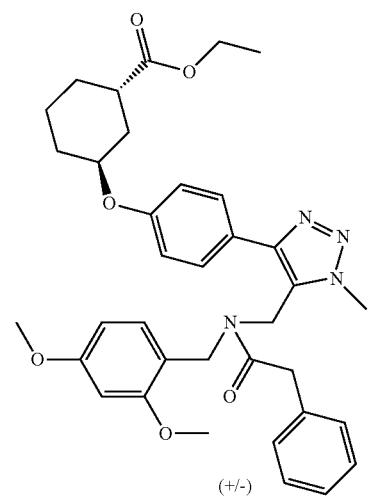
(+/-)
4-5
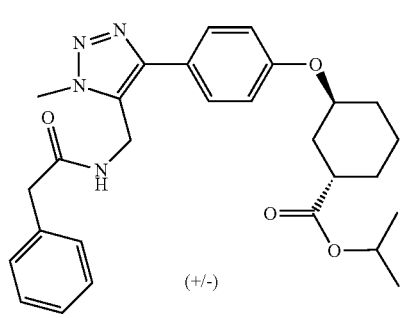
(+/-)
5-2
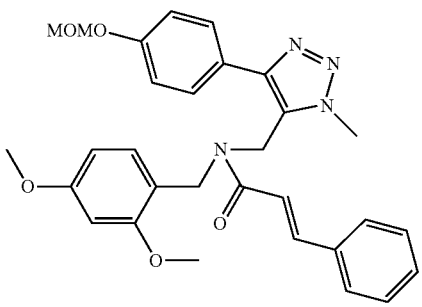
(+/-)
5-3
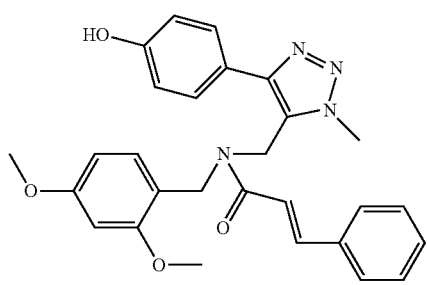
70
-continued
5-5
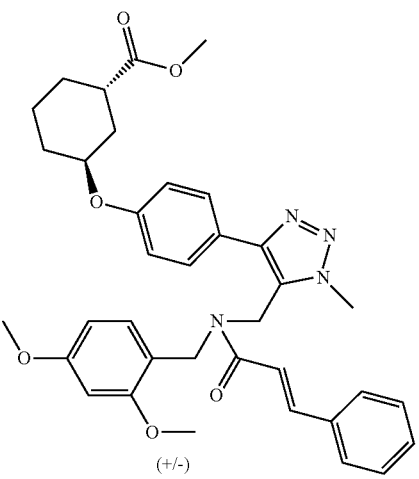
(+/-)
5-6
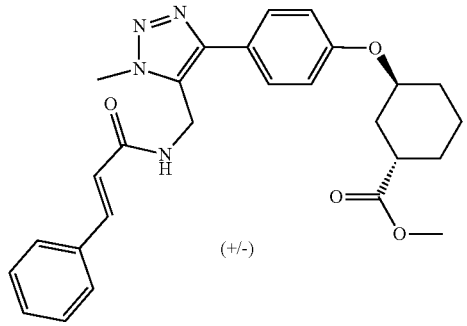
(+/-)
6-5
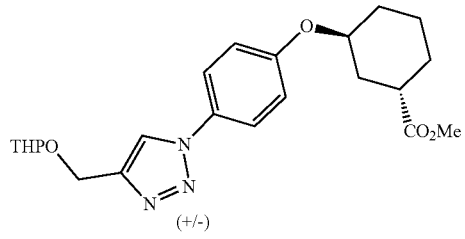
(+/-)
6-6
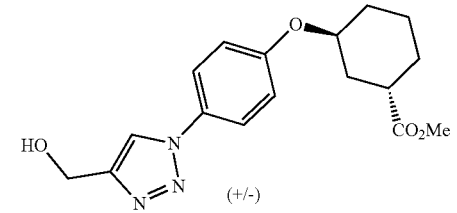
(+/-)
6-9
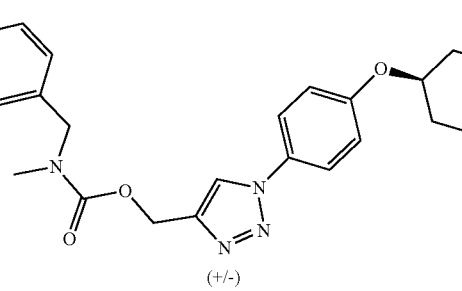
(+/-)

71
-continued
7-5
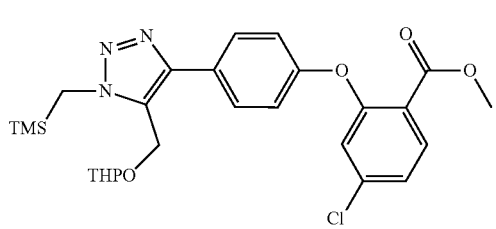
7-6
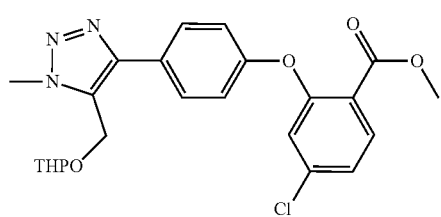
7-7
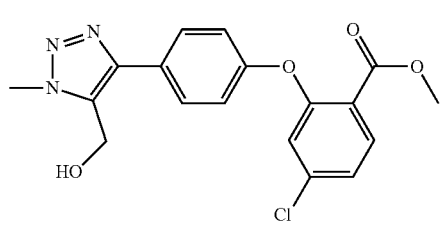
7-8
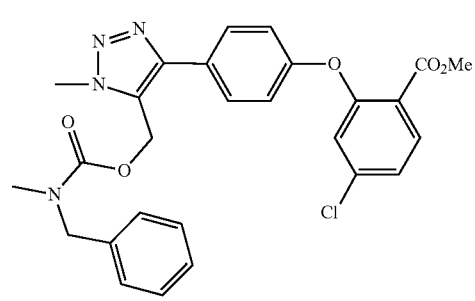
9-2
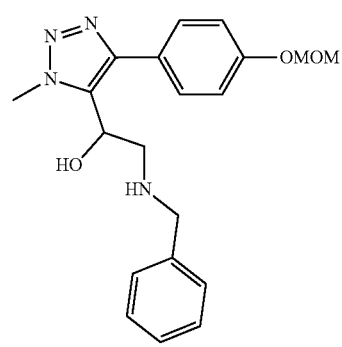
9-3
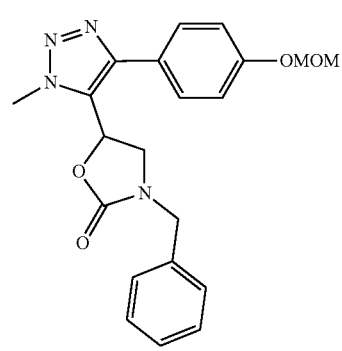
72
-continued
9-4
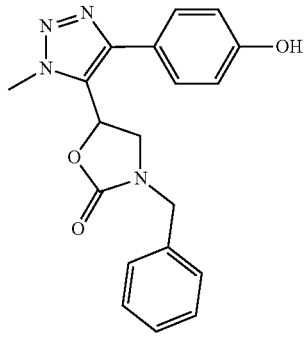
9-5
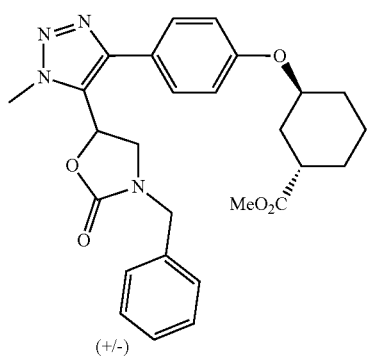
(+/−)
10-4
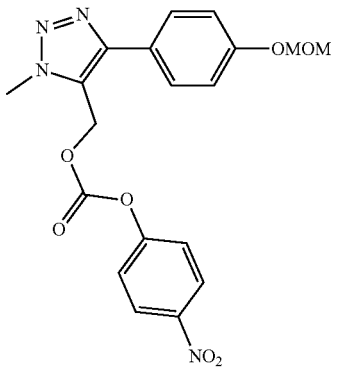
10-6
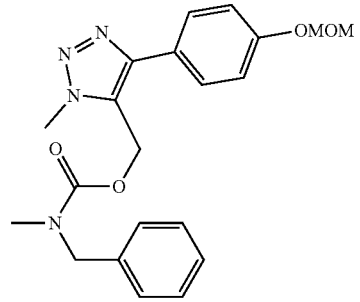

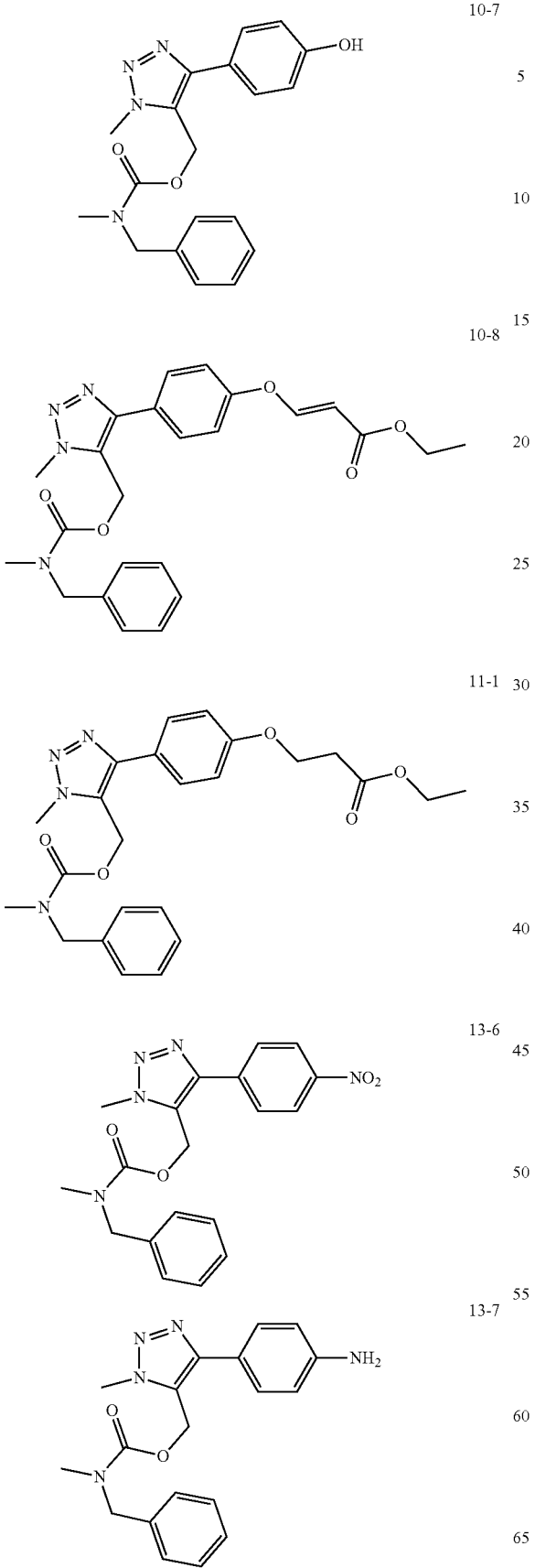
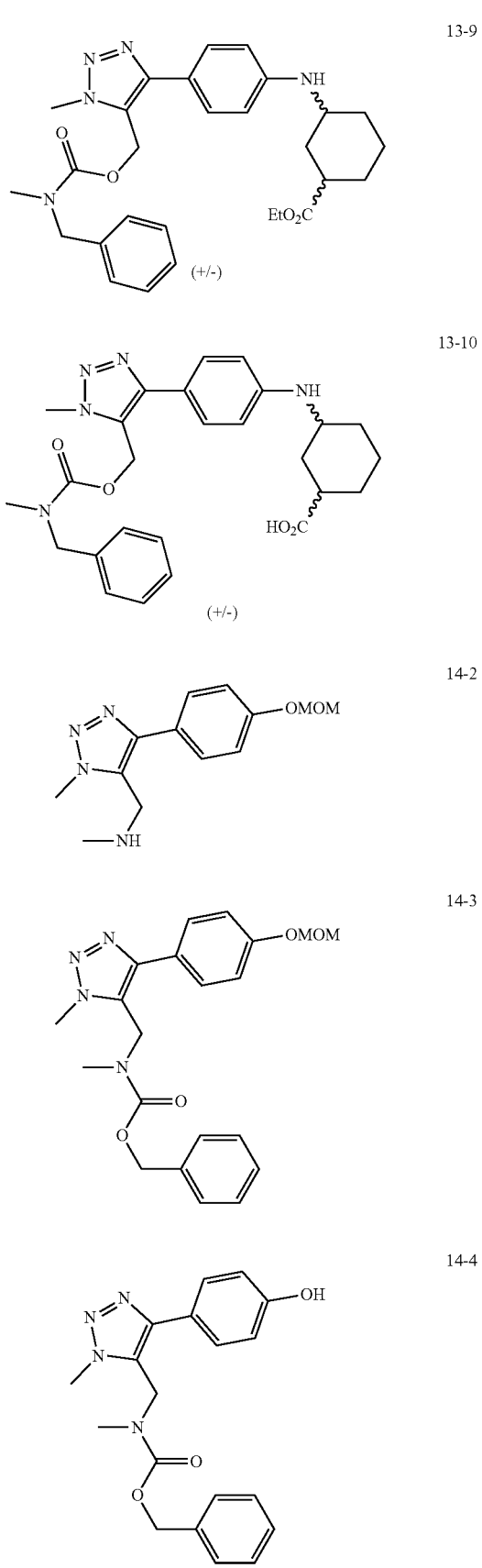

75
-continued
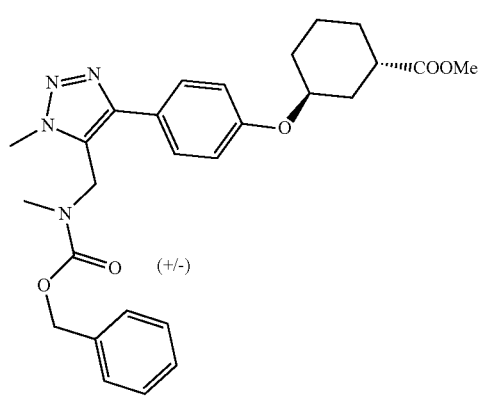
14-5
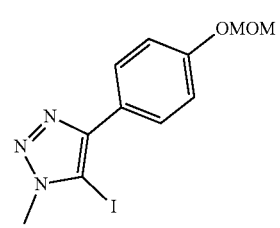
15-2
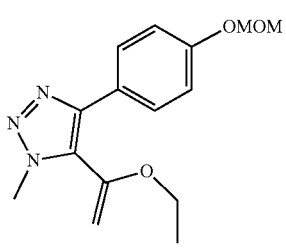
15-3
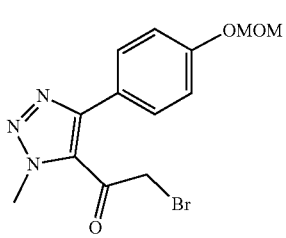
15-4
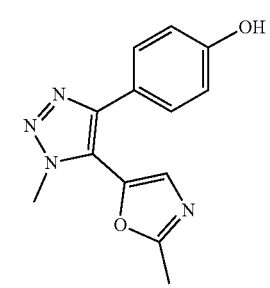
15-5
76
-continued
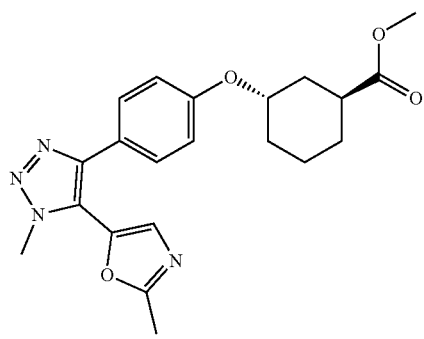
15-7
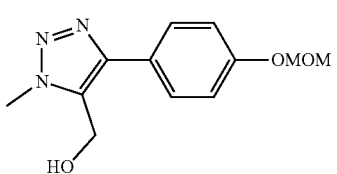
16-9
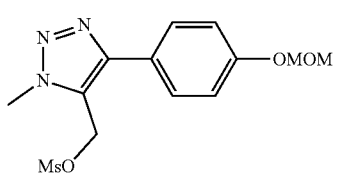
16-10
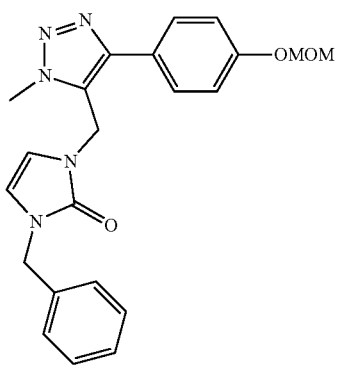
16-11
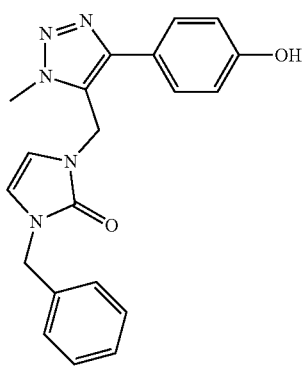
16-12

16-13
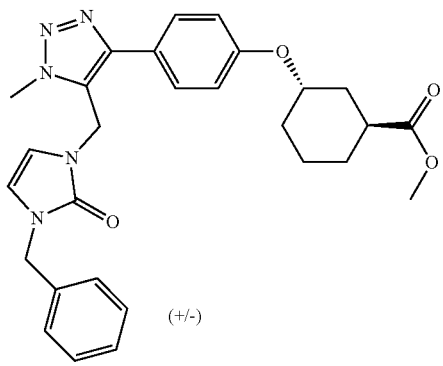
(+/-)
17-2
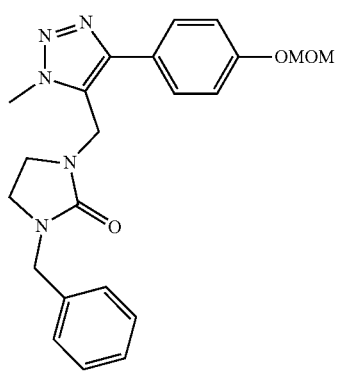
17-3
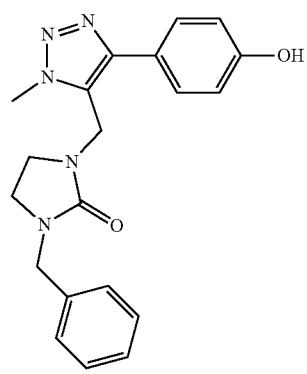
17-5
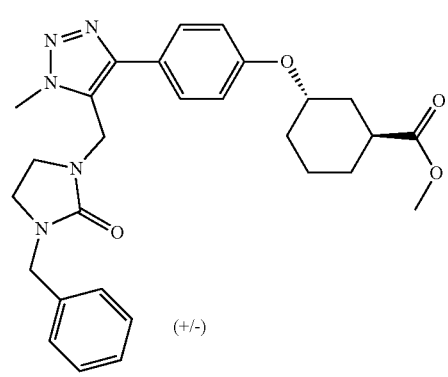
(+/-)
18-2
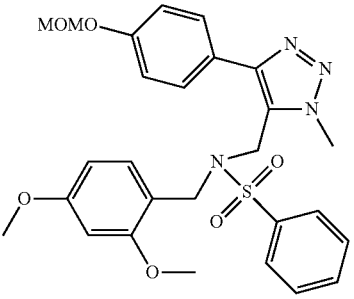
18-3
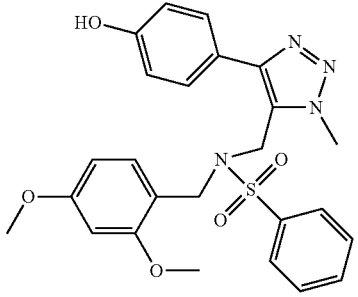
18-5
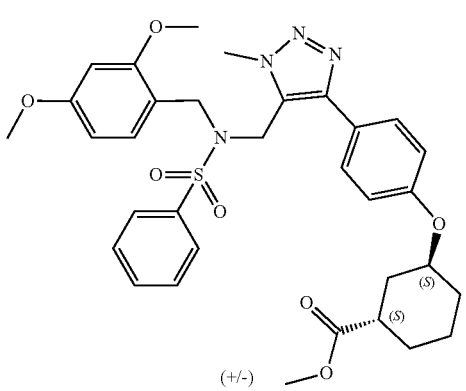
(+/-)
18-6
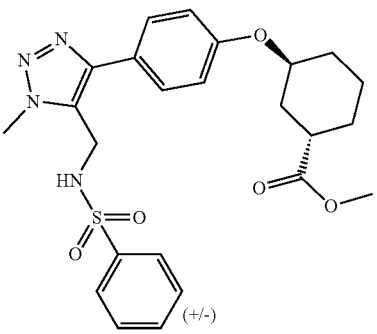
(+/-)
20-2
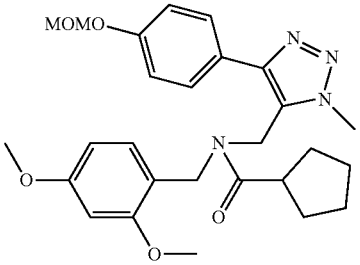

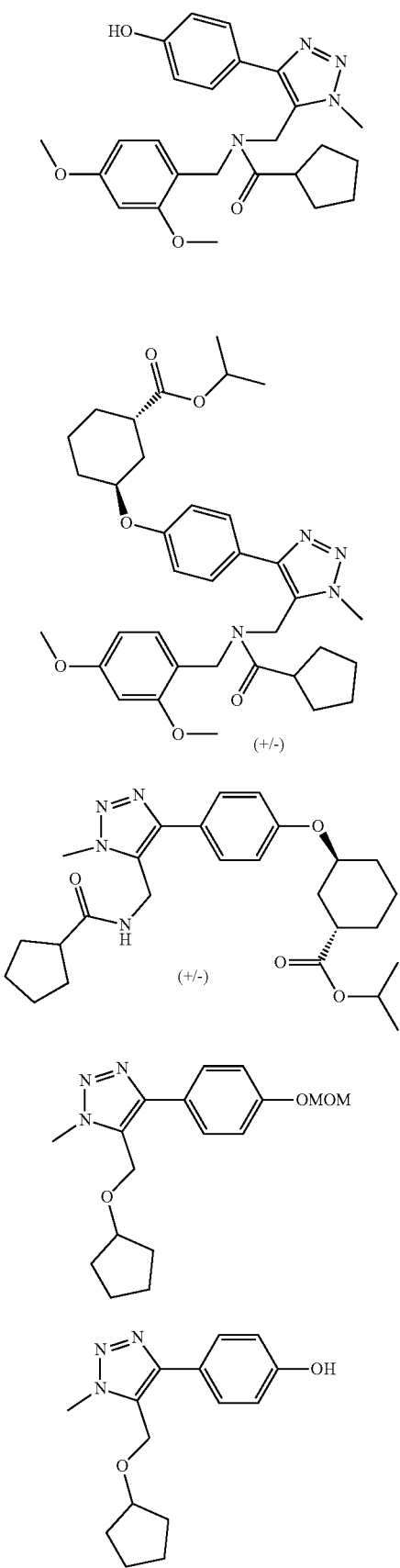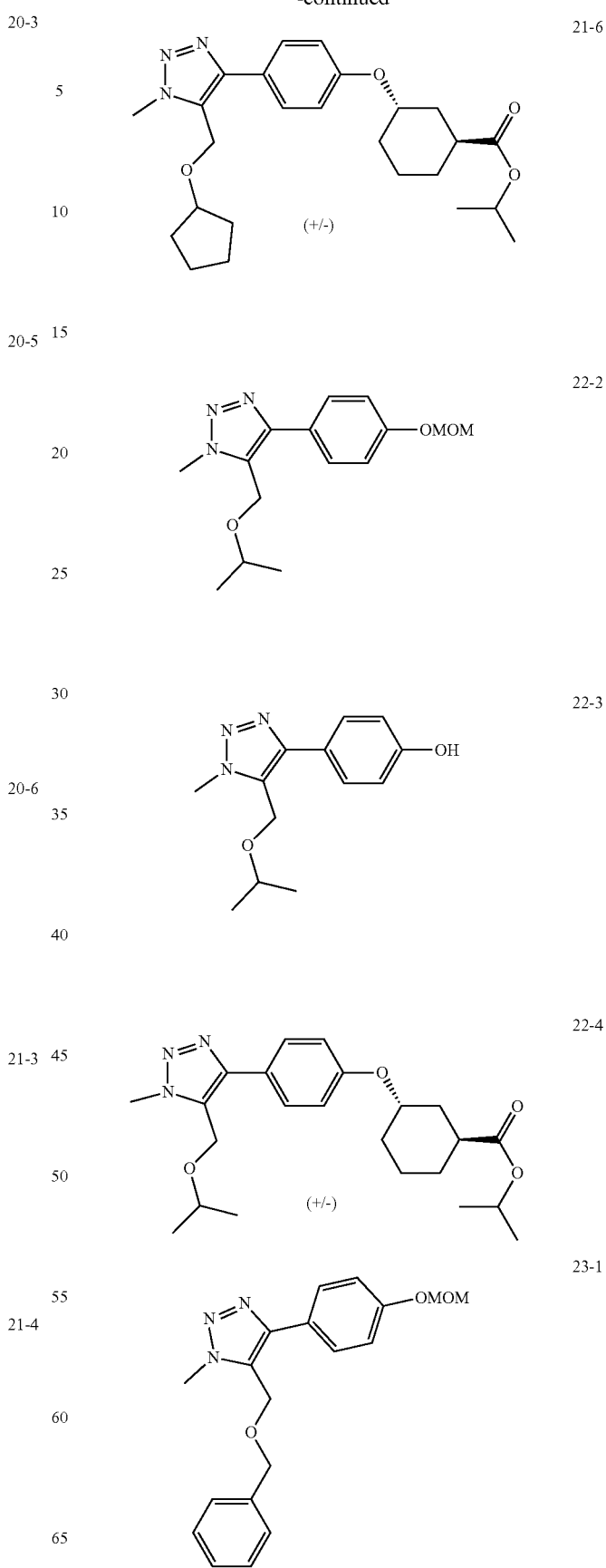

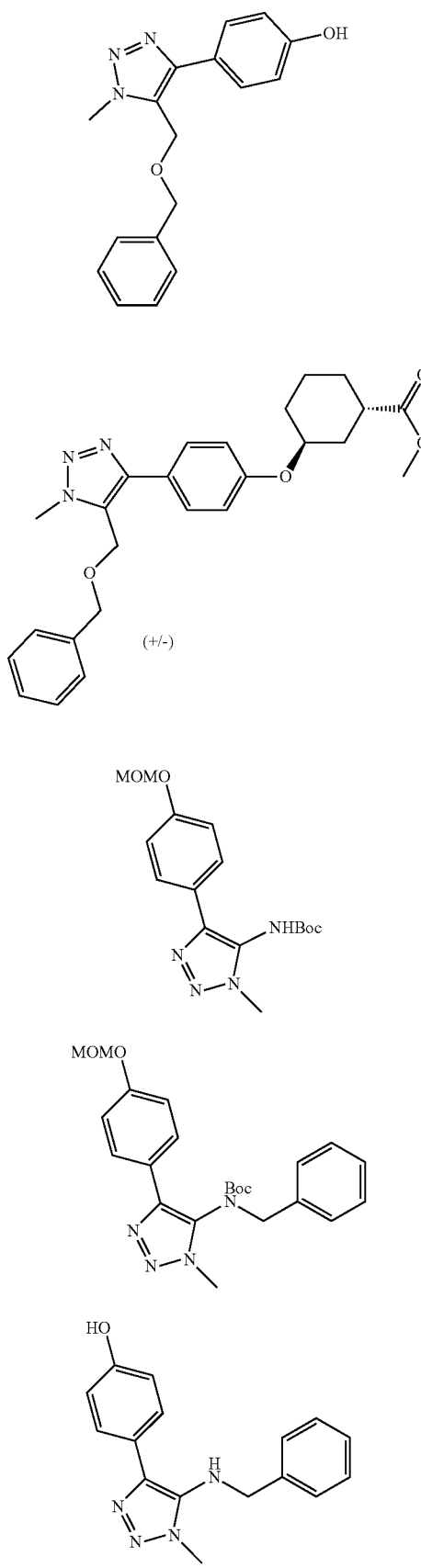
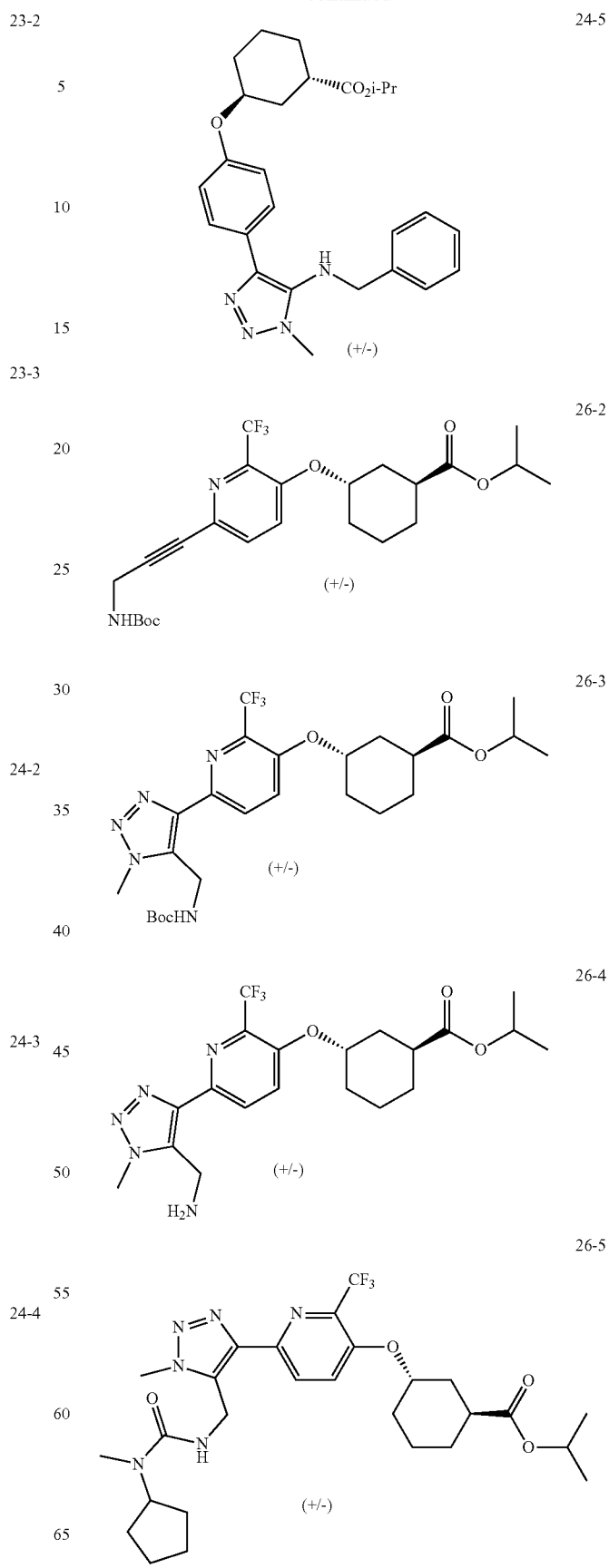

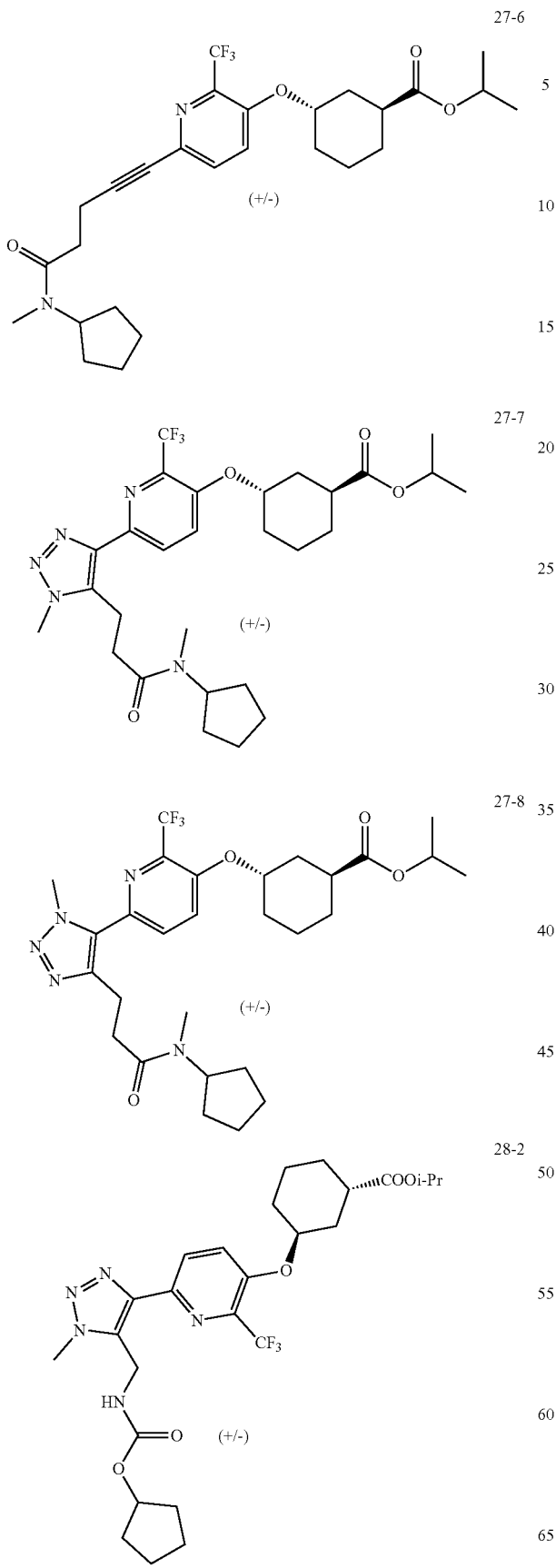
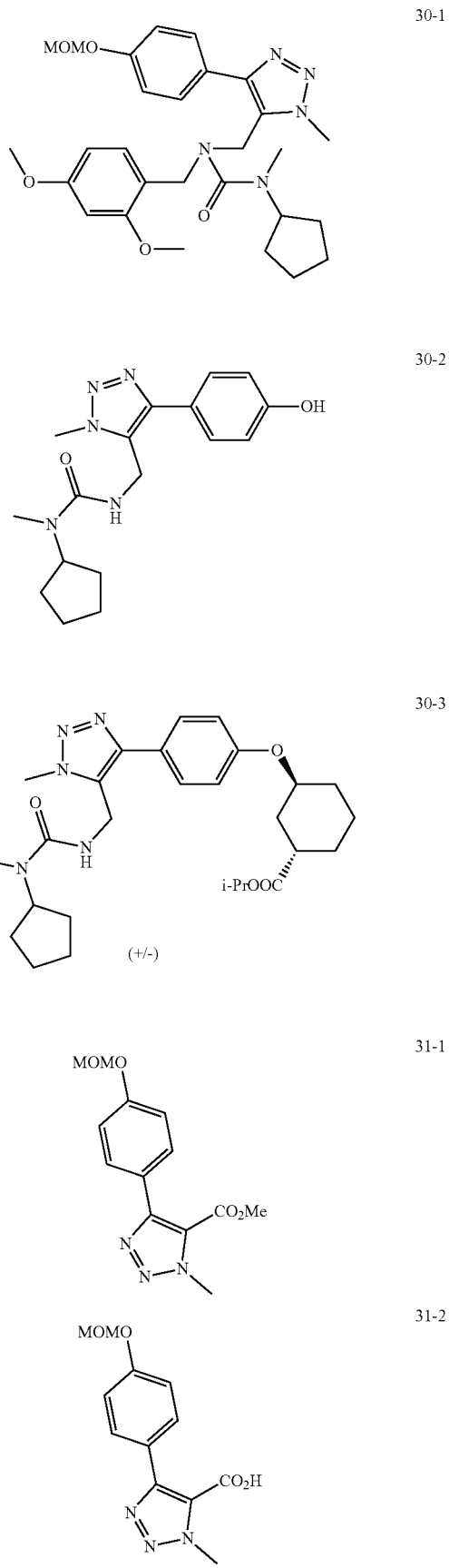

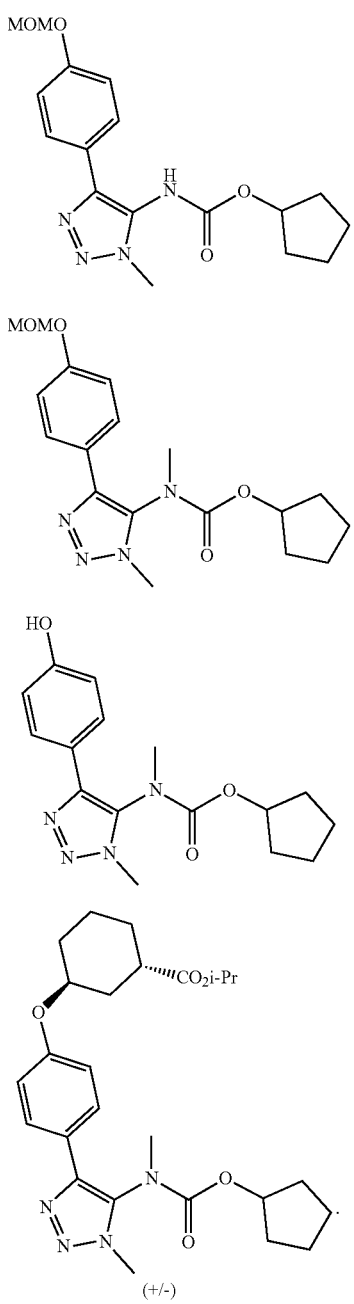

The present invention also provides a pharmaceutical composition comprising one, two or more of the triazole compound of formula (I) and the stereoisomer, the tautomer, the isotopically labeled compound, the nitrogen oxide, the solvate, the polymorph, the metabolite, the ester, the pharmaceutically acceptable salt and the prodrug thereof.

According to the present invention, the pharmaceutical composition may also optionally comprise at least one pharmaceutically acceptable excipient.

According to the present invention, the pharmaceutical composition may also optionally comprise at least one additional active ingredient; specifically, the pharmaceutical composition may also comprise one or more active ingredients besides the triazole compound of formula (I) and the stereoisomer, the tautomer, the isotopically labeled compound, the nitrogen oxide, the solvate, the polymorph, the metabolite, the ester, the pharmaceutically acceptable salt and the prodrug thereof. The pharmaceutical composition may comprise a therapeutically effective amount of the triazole compound of formula (I) and the pharmaceutically acceptable salt, the solvate, the polymorph, the metabolite, the stereoisomer, the tautomer, the isotopically labeled compound, the nitrogen oxide, the ester and the prodrug thereof.

According to the present invention, the pharmaceutical composition is an LPAR1 inhibitor.

According to the present invention, the pharmaceutical composition is used for preventing and/or treating organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers and rejection of transplanted organs.

According to the present invention, the pharmaceutical composition disclosed herein can be prepared into a dosage form suitable for administration by methods known in the art.

The present invention also provides use of one, two or more of the triazole compound of formula (I) and the pharmaceutically acceptable salt, the solvate, the polymorph, the metabolite, the ester, the stereoisomer, the tautomer, the isotopically labeled compound, the nitrogen oxide and the prodrug thereof in preparing a drug.

According to the present invention, the drug is an LPAR1 inhibitor.

According to the present invention, the drug is used for preventing and/or treating LPAR1-mediated diseases.

In some embodiments, the drug is used for preventing and/or treating organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers and rejection of transplanted organs.

The organ fibrotic diseases include, but are not limited to: pulmonary fibrosis (especially idiopathic pulmonary fibrosis), renal fibrosis, liver fibrosis, skin fibrosis, intestinal fibrosis and ocular fibrosis. The respiratory diseases include, but are not limited to: respiratory disorders, including asthma, chronic obstructive pulmonary disease (COPD), bronchospasm, cough, chronic cough and respiratory failure.

The renal diseases include, but are not limited to: acute kidney injury and chronic kidney disease.

The hepatic diseases include, but are not limited to: alcoholic steatohepatitis, non-alcoholic steatohepatitis, acute and chronic hepatitis, liver cirrhosis, hypohepatia and the like.

The inflammatory diseases include, but are not limited to: autoimmune disease, inflammation, arthritis, rheumatoid arthritis, scleroderma, Raynaud phenomenon and chronic pruritus.

The neurological diseases include, but are not limited to: Alzheimer's disease, Parkinson's disease, neurodegeneration, traumatic brain injury, epilepsy, mental disease and sleep disorder.

The cardiovascular and cerebrovascular diseases include, but are not limited to: collagen vascular diseases, myocardial infarction, cerebral stroke, thrombosis, atherosclerosis, heart failure and hypertension.

The gastrointestinal diseases include, but are not limited to: colon syndrome, inflammatory bowel disease, gastrointestinal disease and gastrointestinal dysfunction.

The pains include, but are not limited to: cancer pain, neuropathic pain, inflammatory pain, surgical pain, visceral pain, dental pain, premenstrual pain, central pain, pain caused by burns, migraine (or cluster headache) and chronic pain.

The urinary system diseases include urinary incontinence, dysuria, cystitis, prostatic hypertrophy, dysuria accompanied by prostatic hypertrophy, bladder neck sclerosis and underactive bladder. The ophthalmic diseases include macular degeneration and diabetic retinopathy.

The cancers include, but are not limited to: breast cancer, pancreatic cancer, ovarian cancer, prostate cancer, glioblastoma, bone cancer, colon cancer, intestinal cancer, head and neck cancer, melanoma, multiple myeloma, chronic lymphocytic leukemia and tumor metastasis.

The present invention also provides a method for treating and/or preventing LPAR1-mediated conditions or diseases, comprising administering a therapeutically effective amount of one, two or more of the triazole compound of formula (I) and the pharmaceutically acceptable salt, the solvate, the polymorph, the metabolite, the ester, the stereoisomer, the tautomer, the isotopically labeled compound, the nitrogen oxide and the prodrug thereof to a subject.

According to the present invention, the conditions or diseases are organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers and rejection of transplanted organs.

Definitions and General Terms

Unless otherwise stated, all technical and scientific terms used herein have the same meaning as commonly understood by those of ordinary skill in the art to which the present invention belongs. All patents and publications referred to herein are incorporated herein by reference in their entirety. Unless otherwise stated, the following definitions as used herein should be applied. For the purpose of the present invention, the chemical elements are consistent with the Periodic Table of Elements (CAS version) and the "Handbook of Chemistry and Physics" (75th Edition, 1994). In addition, general principles of organic chemistry can be found in *Organic Chemistry*, Thomas Sorrell, University Science Books, Sausalito: 1999, and *March's Advanced Organic Chemistry* by Michael B. Smith and Jerry March, John Wiley & Sons, New York: 2007, which are incorporated herein by reference in their entirety.

The term "include, includes or including" is open-ended, i.e. including what is meant by the present invention, but not excluding other aspects.

The term "stereoisomer" refers to compounds having the same chemical structure but different spatial arrangements of the atoms or groups. Stereoisomers include enantiomers, diastereomers, conformers (rotamers), geometric isomers (cis/trans-isomers), atropisomers, and the like.

The term "enantiomer" refers to two isomers of a compound that do not overlap but are mirror images of each other.

The term "diastereoisomer" refers to stereoisomers with two or more chiral centers and whose molecules are not mirror images of each other. Diastereoisomers have different physical properties, such as melting points, boiling points, spectral properties, and reactivities. Mixtures of diastereoisomers can be separated by high-resolution analytical procedures such as electrophoresis and chromatography (e.g., HPLC).

The stereochemistry definitions and rules used in the present invention generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds*, John Wiley & Sons, Inc., New York, 1994.

Any asymmetric atom (e.g., carbon, etc.) of the compounds disclosed herein may exist in a racemate or enantiomer enriched form, for example, the (R)—, (S)— or (R,S)-configuration. In certain embodiments, each asymmetric atom has at least 0% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)— or (S)-configuration.

Any resulting mixture of stereoisomers may be separated into pure or substantially pure geometric isomers, enantiomers and diastereomers depending on differences in the physicochemical properties of the components, for example, by chromatography and/or fractional crystallization.

The term "tautomer" refers to structural isomers of different energies that are interconvertible via a low energy barrier. If the tautomerization is possible (e.g., in solution), the chemical equilibrium of the tautomers can be reached. For example, proton tautomers, also known as prototropic tautomers, include interconversions by proton transfer, such as keto-enol isomerization and imine-enamine isomerization. Valence tautomers include interconversions by recombination of some bonding electrons. A specific example of keto-enol tautomerization is the interconversion of the pentan-2,4-dione and 4-hydroxypent-3-en-2-one tautomers. Another example of tautomerization is phenol-keto tautomerization. A specific example of phenol-ketone tautomerization is the interconversion of pyridine-4-ol and pyridine-4(1H)-one tautomers. Unless otherwise indicated, all tautomeric forms of the compounds disclosed herein are within the scope of the present invention. In general, the term "substituted" means that one or more hydrogen atoms in a given structure are substituted with a particular substituent. Further, when the group is substituted with one or more substituents described above, the substituents are independent of each other, that is, the one or more substituents may be different from each other or the same. Unless otherwise indicated, the substitution of a substituent may occur at various substitutable positions of the substituted group. When more than one position in a given structure can be substituted with one or more substituents selected from particular groups, the substitution of the substituents may occur at various positions, identically or differently. The substituents may be, but are not limited to, =O, hydrogen, deuterium, cyano, nitro, halogen, alkyl, haloalkyl, alkoxy, carboxyl, cycloalkyl, cycloalkyloxy, heterocyclyl, heterocyclylalkyl, aryl, arylalkyl, aryloxy, heteroaryl, heteroarylalkyl, heteroaryloxy, etc.

In each part of this specification, substituents for the disclosed compounds are disclosed according to group types or ranges. It is specifically noted that each separate subcombination of the various members of these group types and ranges is encompassed in the present invention. For example, the term "$C_{1-6}$ alkyl" refers particularly to the independently disclosed $C_1$ alkyl, $C_2$ alkyl, $C_3$ alkyl, $C_4$ alkyl, $C_5$ alkyl or $C_6$ alkyl.

In each part of the present invention, connecting substituents are described. When a connecting group is definitely required to the structure, the Markush variables listed for that group should be considered as connecting groups. For example, if a connecting group is required to the structure and the "alkyl" or "aryl" is listed for the Markush group definition of the variable, it is to be understood that the "alkyl" or "aryl" represents a connected alkylene group or arylene group, respectively.

The term "$C_{1-40}$ alkyl" used herein refers to a linear or branched saturated monovalent hydrocarbon group containing 1-40 carbon atoms, wherein the alkyl group may optionally be substituted with one or more substituents described herein. In some embodiments, the alkyl group contains 1-12 carbon atoms; in other embodiments, the alkyl group contains 1-6 carbon atoms; in still other embodiments, the alkyl group contains 1-4 carbon atoms. Examples of alkyl groups include, but are not limited to, methyl, ethyl, n-propyl and the like.

The term "$C_{2-40}$ alkenyl" refers to a linear or branched monovalent hydrocarbyl containing 2-40 carbon atoms, wherein there is at least one site of unsaturation, that is, there is a carbon-carbon $sp^2$ double bond, and the double bonds can be separated from each other or conjugated; the alkenyl group may be optionally substituted with one or more substituents described herein, which includes the positioning of "cis" and "trans", or the positioning of "E" and "Z". Examples of alkenyl groups include, but are not limited to, vinyl (—CH=CH$_2$), allyl (—CH$_2$CH=CH$_2$), and the like. In some embodiments, the alkenyl contains 2-10 carbon atoms.

The term "$C_{1-40}$ haloalkyl" means that the $C_{1-40}$ alkyl is substituted with one, two or more halogen atoms. Examples of it include, but are not limited to, trifluoromethyl and the like. The term "$C_{3-20}$ cycloalkyl" refers to a saturated monocyclic or bicyclic hydrocarbon ring containing 3-20 ring carbon atoms. In some embodiments, the cycloalkyl contains 3-14 carbon atoms. Examples of cycloalkyl groups include, but are not limited to, cyclopropyl, cyclobutyl, etc.; in other embodiments, the cycloalkyl contains 3-6 carbon atoms. The cycloalkyl group may be optionally substituted with one or more substituents described herein.

The term "3-20 membered heterocyclyl" refers to a saturated monocyclic or bicyclic hydrocarbon ring containing 3-20 ring atoms, which contains at least one heteroatom selected from nitrogen, sulfur and oxygen. In some embodiments, heterocyclyl contains 3-10 ring atoms. According to the present invention, the heterocyclyl is non-aromatic. The heterocyclyl group may be optionally substituted with one or more substituents described herein. Examples of heterocyclyl include, but are not limited to: oxiranyl, thietanyl, pyrrolidinyl and the like.

The term "halogen" or "halo" refers to fluorine (F), chlorine (Cl), bromine (Br), or iodine (I).

The term "$C_{6-20}$ aryl" refers to an aromatic or partially aromatic monocyclic, bicyclic or tricyclic monovalent hydrocarbon ring containing 6-20 carbon atoms, and is preferably "$C_{6-14}$ aryl". Examples of aryl groups may include phenyl, naphthyl or anthryl. The aryl group may be optionally substituted with one or more substituents described herein.

The term "5-20 membered heteroaryl" refers to monocyclic, bicyclic and tricyclic systems containing 5-20 ring atoms, or 5-14 ring atoms, or 5-12 ring atoms, wherein at least one ring contains one or more ring heteroatoms selected from nitrogen, oxygen, and sulfur. Unless otherwise stated, the heteroaryl group may be connected to the rest of the molecule (e.g., the host structure in the formula) via any reasonable site (which may be C in CH, or N in NH). Examples include, but are not limited to, furanyl, imidazolyl, etc., and also include, but are not limited to, bicyclic rings, such as benzimidazolyl and benzofuranyl. The heteroaryl group may be optionally substituted with one or more substituents described herein.

In addition, it should be noted that, unless otherwise explicitly indicated, the description of " . . . is independently selected from" used herein is to be understood broadly and means that each individual group described is independent from the others and may be independently selected from the same or different specific groups. In more detail, the description of " . . . is independently selected from" can mean that the specific options expressed by the same symbols in different groups do not affect each other; it can also mean that the specific options expressed by the same symbols in the same group do not affect each other.

The term "pharmaceutically acceptable" refers to molecular entities and compositions that are physiologically tolerable and generally do not produce an allergic or similar untoward reaction, such as gastrointestinal distress and dizziness, when administered to a human.

The term "carrier" refers to a diluent, adjuvant, excipient, or matrix with which the compound is administered. Such pharmaceutical carriers can be sterile liquid, such as water and oil, including those derived from petroleum, animals, plants or synthesis, such as peanut oil, soybean oil, mineral oil and sesame oil. Water or aqueous saline solutions and aqueous dextrose and glycerol solutions are preferably used as carriers, particularly injectable solutions. Suitable pharmaceutical carriers are described in *Remington's Pharmaceutical Sciences* by E. W. Martin.

The term "prodrug" used herein represents a compound that is converted in vivo to a compound of formula (I). Such conversion is affected by hydrolysis of the prodrug in the blood or by enzymatic conversion of the prodrug into the parent structure in the blood or tissue. The prodrugs disclosed herein can be esters, and in the prior art, the esters that can be used as prodrugs include phenyl esters, aliphatic ($C_{1-24}$) esters, acyloxymethyl esters, carbonates, carbamates and amino acid esters. For example, a compound disclosed herein containing hydroxyl can be acylated to give a prodrug. Other prodrugs include phosphate esters, and those phosphate esters are obtained by phosphorylating via the hydroxyl on the parent structure. For a complete discussion of prodrugs, reference can be made to the following: T. Higuchiand V. Stella, Pro-drugs as Novel Delivery Systems, Vol. 14 of the *A.C.S. Symposium Series*; Edward B. Roche, ed., Bioreversible Carriersin Drug Design, *American Pharmaceutical Association and Pergamon Press*, 1987; J. Rautioetal., Prodrugs: Design and Clinical Applications, *Nature Review Drug Discovery*, 2008, 7, 255-270; and S. J. Heckeretal., Prodrugs of Phosphates and Phosphonates, *Journal of Medicinal Chemistry*, 2008, 51, 2328-2345. The term "metabolite" used herein refers to a product obtained by the metabolism of a particular compound or salt thereof in vivo. Metabolites of a compound can be identified by techniques well known in the art, and their activities can be characterized by assays as described herein. Such products may be obtained by the oxidation, reduction, hydrolysis, amidation, deamidation, esterification, defatting, enzymatic cleavage, and the like of the administered compound. Accordingly, the present invention includes metabolites of the compound, including metabolites produced by bringing the compound disclosed herein into contact with a mammal for a sufficient period of time.

The term "pharmaceutically acceptable salt" used herein refers to both organic and inorganic salts of the compound disclosed herein. Pharmaceutically acceptable salts are well known in the art. For example, S. M. Berge et al. describe pharmaceutically acceptable salts in detail in *J. Pharmaceutical Sciences,* 1977, 66: 1-19. Pharmaceutically acceptable salts formed by non-toxic acids include, but are not limited to, inorganic acid salts such as hydrochloride, hydrobromide, phosphate, sulfate, perchlorate; organic acid salts such as acetate, oxalate, maleate, tartrate, citrate, succinate, malonate; or salts obtained by other methods described in the literature, such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentylpropionate, digluconate, dodecylsulfate, ethanesulfonate, formate, fumarate, glucoheptonate, glycerophosphate, gluconate, hemisulfate, heptanoate, hexanoate, hydriodate, 2-hydroxyethanesulfonate, lactobionate, lactate, laurate, lauryl sulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts obtained by reaction with an appropriate base include salts of alkali metals, alkaline earth metals, ammonium and $N^+(C_{1-4}$ alkyl$)_4$. The present invention also contemplates quaternary ammonium salts formed by any compound with a N-containing group. Water-soluble or oil-soluble or dispersible products can be obtained by quaternization. The alkali metals or alkaline earth metals that can form salts include sodium, lithium, potassium, calcium, magnesium, and the like. Pharmaceutically acceptable salts further include suitable and non-toxic ammonium, quaternary ammonium salts and amine cations formed by counterions, such as halides, hydroxides, carboxylates, sulfates, phosphates, nitrates, $C_{1-8}$ sulfonates and aromatic sulfonates.

"Solvate" disclosed herein refers to an association compound of one or more solvent molecules with the compound disclosed herein. Solvents that form the solvate include, but are not limited to, water, isopropanol, ethanol, methanol, dimethyl sulfoxide, ethyl acetate, acetic acid and aminoethanol. The term "hydrate" refers to an association compound in which the solvent molecules are water molecules.

"Ester" disclosed herein refers to an ester that is hydrolyzable in vivo and formed by a compound containing hydroxyl or carboxyl. Such esters are, for example, pharmaceutically acceptable esters that are hydrolyzed in human or animal to produce parent alcohols or acids. The compound of formula (I) disclosed herein contains carboxyl, which can form an ester that is hydrolyzable in vivo with appropriate groups including, but not limited to, alkyl, arylalkyl and the like.

"Nitrogen oxide" disclosed herein refers to an N-oxide formed by oxidizing one or more nitrogen atoms when the compound contains several amine functional groups. Specific examples of N-oxides are N-oxides of tertiary amines or N-oxides of a nitrogen atom of a nitrogen-containing heterocycle. The corresponding amines can be treated with an oxidizing agent such as hydrogen peroxide or peracid (e.g., peroxycarboxylic acid) to form N-oxides (see *Advanced Organic Chemistry*, Wiley Interscience, 4th Edition, Jerry March, pages). In particular, N-oxides may be prepared by the method of L. W. Deady (Syn. Comm. 1977, 7,509-514) in which an amine compound is reacted with m-chloroperoxybenzoic acid (MCPBA), for example, in an inert solvent such as dichloromethane. The term "isotopically labeled compound" includes but is not limited to compounds disclosed herein that are labeled by isotopes of hydrogen, carbon, nitrogen, oxygen, fluorine, sulfur and chlorine (e.g., $^2H$, $^3H$, $^{13}C$, $^{14}C$, $^{15}N$, $^{18}O$, $^{17}O$, $^{18}F$, $^{35}S$ and $^{36}Cl$). Isotopically-labeled compounds disclosed herein can be used for the determination of the tissue distribution of compounds and prodrugs and metabolites thereof; preferred isotopes for such determinations include $^3H$ and $^{14}C$. In addition, in some cases, substitution with heavier isotopes (e.g., deuterium ($^2H$ or D)) may result in greater metabolic stability, which provides therapeutic advantages, for example increased in vivo half-life or reduced dosage requirement. The isotopically-labeled compounds disclosed herein can generally be prepared by substituting isotopically-labeled reagents for non-isotopically-labeled reagents according to the methods described herein.

In some embodiments, the term "treat", "treating" or "treatment" used herein refers to ameliorating a disease or disorder (i.e., slowing or arresting or reducing the progression of the disease or at least one clinical symptom thereof). In other embodiments, "treat", "treating" or "treatment" refers to mitigating or improving at least one physical parameter, including physical parameters that may not be perceived by a patient. In other embodiments, "treat", "treating" or "treatment" refers to modulating a disease or disorder, either physically (e.g., stabilizing a perceptible symptom) or physiologically (e.g., stabilizing a physical parameter), or both. In other embodiments, "treat", "treating" or "treatment" refers to preventing or delaying the onset, occurrence, or deterioration of a disease or disorder.

Unless otherwise indicated, abbreviations for any of the protecting groups, amino acids and other compounds used herein are provided based on their commonly used and accepted abbreviations, or by referring to *IUPAC-IUB Commission on Biochemical Nomenclature* (see Biochem.1972, 11:942-944).

The biological activity of the compound disclosed herein can be assessed by using any conventionally known method. Appropriate detection methods are well known in the art. For example, the compound disclosed herein can be tested for inhibitory activity against LPAR1, pharmacokinetic activity, and/or liver microsomal stability, etc., by an appropriate conventional method. The detection methods provided by the present invention are presented as examples only and do not limit the present invention. The compound disclosed herein is active in at least one of the detection methods provided by the present invention.

The pharmaceutically acceptable excipients may be those widely used in the field of pharmaceutical production. The excipients are primarily used to provide a safe, stable and functional pharmaceutical composition and may also provide methods for dissolving the active ingredients at a desired rate or for promoting effective absorption of the active ingredients after administration of the composition to a subject. The pharmaceutical acceptable excipients may be inert fillers or provide a function such as stabilizing the overall pH of the composition or preventing degradation of the active ingredients of the composition. The pharmaceutical acceptable excipients may include one or more of the following excipients: binders, suspending agents, emulsifiers, diluents, fillers, granulating agents, gluing agents, disintegrants, lubricants, anti-adherents, glidants, wetting agents, gelling agents, absorption retardants, dissolution inhibitors, reinforcing agents, adsorbents, buffering agents, chelating agents, preservatives, colorants, flavoring agents and sweeteners.

Substances which may serve as pharmaceutically acceptable adjuvants include, but are not limited to, ion exchangers; aluminum; aluminum stearate; lecithin; serum proteins such as human serum protein; buffer substances such as phosphates; glycine; sorbic acid; potassium sorbate; a partial glyceride mixture of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinylpyrrolidone; polyacrylates; waxes; polyethylene-polyoxypropylene-blocking polymer; lanolin; sugars such as lactose, glucose and sucrose; starches such as corn starch and potato starch; cellulose and its derivatives such as sodium carboxymethyl cellulose, ethyl cellulose and cellulose acetate; gum powder; malt; gelatin; talc powder; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffers such as magnesium hydroxide and aluminum hydroxide; alginic acid; pyrogen-free water; isotonic salts; Ringer's solution; ethanol, phosphate buffered solution, and other non-toxic suitable lubricants such as sodium lauryl sulfate and magnesium stearate, coloring agents, releasing agents, coating agents, sweeteners, flavoring agents and perfumes, preservatives and antioxidants.

The pharmaceutical composition disclosed herein may be prepared in accordance with the disclosure using any method known to those skilled in the art, for example, conventional mixing, dissolving, granulating, emulsifying, levigating, encapsulating, embedding or lyophilizing processes.

The dosage form of the drug disclosed herein can be selected according to specific conditions. Pharmaceutical dosage forms often consist of drugs, excipients, and containers/closure systems. One or more excipients (also known as inactive ingredients) may be added to the compound disclosed herein to improve or facilitate the manufacture, stability, administration and safety of drugs, and may provide means to obtain a desired drug release profile. Thus, the type of excipient added to a drug may depend on various factors, such as physical and chemical properties of the drug, route of administration and preparation steps. There are pharmaceutical excipients in the art, including those listed in various pharmacopoeias. (See *U.S. Pharmacopeia (USP), Japanese Pharmacopoeia (JP), European Pharmacopoeia (EP) and British pharmacopoeia (BP)*; publications from the Center for Drug Evaluation and Research (CEDR) of U.S. Food and Drug Administration (www.fda.gov), for example, "*Inactive Ingredient Guide*", 1996; and "*Handbook of Pharmaceutical Additives*", 2002, edited by Ash, Synapse Information Resources, Inc., Endicott NY; etc.)

The pharmaceutical composition disclosed herein may include one or more physiologically acceptable inactive ingredients that facilitate processing of active molecules into preparations for pharmaceutical use.

Appropriate preparations will be determined according to the desired route of administration. The routes of administration include intravenous injection, transmucosal or nasal administration, oral administration and the like. For oral administration, the compound may be formulated into liquid or solid dosage forms and used as immediate release or controlled/sustained release preparations. Suitable dosage forms for oral ingestion by an individual include tablets, pills, dragees, hard and soft shell capsules, liquids, gels, syrups, ointments, suspensions and emulsions.

Oral solid dosage forms can be obtained using excipients including fillers, disintegrants, binders (dry and wet), dissolution retardants, lubricants, glidants, anti-adherents, cationic exchange resins, wetting agents, antioxidants, preservatives, colorants and flavoring agents. These excipients may be of synthetic or natural sources. Examples of such excipients include cellulose derivatives, citric acid, dicalcium phosphate, gelatin, magnesium carbonate, magnesium/sodium lauryl sulfate, mannitol, polyethylene glycol, polyvinylpyrrolidone, silicates, silica, sodium benzoate, sorbitol, starches, stearic acid or salts thereof, sugars (i.e., dextrose, sucrose, lactose, etc.), talc, tragacanth mucilage, vegetable oils (hydrogenated) and waxes. Ethanol and water may be used as adjuvants for granulation. In some cases, it is desirable to coat tablets with, for example, a taste-masking film, a gastric acid-resistant film or a sustained release film. Natural and synthetic polymers are often used to coat tablets in combination with colorants, sugars, and organic solvents or water to produce dragees. When capsules are superior to tablets, the pharmaceutical powders, suspensions or solutions may be delivered in the form of compatible hard or soft shell capsules.

The therapeutically effective dosage can first be estimated using various methods well known in the art. Initial dosage for animal studies can be based on established effective concentrations in cell culture assays. Dosage ranges suitable for humans can be determined, for example, using data obtained from animal studies and cell culture assays. In certain embodiments, the compound disclosed herein may be prepared as medicaments for oral administration.

The correct preparation, route of administration, dosage and time interval between administrations can be determined based on methods known in the art while taking the specificity of the individual into account.

In this specification, terms such as "some embodiments," "examples," or "a preferred embodiment" mean that a particular feature, structure, material or characteristic described in reference to the embodiment or example is included in at least one embodiment or example of the present invention. In this specification, the schematic descriptions of the terms described above do not necessarily refer to the same embodiment or example. Moreover, the specific features, materials, structures and other characteristics described may be combined in any one or more embodiments or examples in an appropriate manner. Moreover, various embodiments or examples and features of various embodiments or examples described in this specification can be combined by one skilled in the art to the extent that they do not contradict each other.

Beneficial Effects

Unexpectedly, it is found that the triazole compounds disclosed herein feature high antagonistic activity against LPAR1, good selectivity, low toxicity and good metabolic stability, showing a good prospect of drug development. The triazole compounds disclosed herein can be used for preventing and/or treating diseases or disorders related to LPAR1. For example, the compound of formula (I) can be used for preventing and/or treating, slowing or arresting organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers and rejection of transplanted organs. Surprisingly, it is found that $IC_{50}$ values of some of the compounds disclosed herein can be as low as 300 nM or less, or even 50 nM or less. In addition, the compounds disclosed herein have an inhibitory rate of 30-50% against A2058 cell migration, some compounds have an inhibitory rate of 50-70%, and cell migration is remarkably inhibited. Moreover, the compounds disclosed herein all have good safety, and the CC 50 values can be greater than 200 M. Furthermore, the compounds disclosed herein have relatively good metabolic stability in humans, rats and mice, wherein the $T_{1/2}$ of some compounds in human liver microsome is more than 30 min, or even more than 90 min. In view of such excellent inhibitory activity, application thereof as LPAR1 inhibitors to treat the diseases or disorders described above is promising.

In addition, the preparation method for the compounds disclosed herein features simple operation, mild reaction conditions and high product yield, and thus is suitable for industrial production.

DETAILED DESCRIPTION

The present invention is further illustrated by the following examples; however, these examples should not be construed as limiting the present invention. Experimental procedures without specified conditions in the following examples are conducted in accordance with conventional procedures and conditions, or in accordance with the manufacturer's manual.

The following abbreviations are used throughout the present invention:

DMF (N,N-dimethylformamide); DCM (dichloromethane); PE (petroleum ether); EA (ethyl acetate); DIPEA (N,N-diisopropylethylamine); THF (tetrahydrofuran); Ac (acetyl); MeOH (methanol); Boc (tert-butoxycarbonyl); B2Pin2 (bis(pinacolato)diboron); rt (room temperature); reflux (refluxing conditions); eq (equivalent); Rf (retardation factor); g (gram); mg (milligram); mol (mole); mmol (millimole); h (hour); min (minute); mL (milliliter); μL (microliter).

Overnight refers to 8-15 h, for example 12 h; the room temperature refers to 10-30° C.; solvent ratio such as PE/EA refers to the volume ratio.

Unless otherwise indicated, all temperatures in the examples described below are given in Celsius degrees. Unless otherwise indicated, reagents are purchased from commercial suppliers such as Aldrich Chemical Company, Arco Chemical Company and Alfa Chemical Company, and used without further purification. General reagents are purchased from Shantou Xilong Chemical Plant Co. Ltd., Guangdong Guanghua Sci-Tech Co., Ltd., Guangzhou Chemical Reagent Factory, Tianjin Yuyu Fine Chemical Co., Ltd., Qingdao Tenglong Chemical Reagent Co., Ltd., and Qingdao Haiyang Chemical Co., Ltd.

Anhydrous tetrahydrofuran, dioxane, toluene and diethyl ether are obtained by refluxing and drying with sodium metal. Anhydrous dichloromethane and chloroform are obtained by refluxing and drying with calcium hydride. Ethyl acetate, petroleum ether, n-hexane, N,N-dimethylacetamide and N,N-dimethylformamide are pre-dried over anhydrous sodium sulfate before use.

The following reactions are generally preformed under a positive pressure of nitrogen or argon or by placing a drying tube over an anhydrous solvent (unless otherwise indicated), the reaction flask is stoppered with a suitable rubber stopper and the substrate is driven in by syringe. Each piece of glassware is dried.

Chromatographic columns are silica gel columns. Silica gel (300-400 mesh) is purchased from Qingdao Haiyang Chemical Co., Ltd. NMR spectral data are measured on a Bruker Avance 400 NMR spectrometer or a Bruker Avance III HD 600 NMR spectrometer using CDCl$_3$, DMSO-d$_6$, CD$_3$OD or Acetone-d$_6$ as solvents (reported in ppm) and TMS (0 ppm) or chloroform (7.25 ppm) as reference standards. When multiple peaks are present, the following abbreviations will be used: s (singlet); d (doublet); t (triplet); m (multiplet); br (broadened); dd (doublet of doublets); dt (doublet of triplets); ddd (doublet of doublet of doublets); ddt (doublet of doublet of triplets); dddd (doublet of doublet of doublet of doublets). Coupling constants are expressed in hertz (Hz).

Low-resolution mass spectrometry (MS) data are determined on an Agilent 6320 series LC-MS spectrometer equipped with a G1312A binary pump and an aG1316ATCC (column temperature maintained at 30° C.), with a G1329A autosampler and a G1315BDAD detector applied to the analysis and an ESI source applied to the LC-MS spectrometer.

Example 1

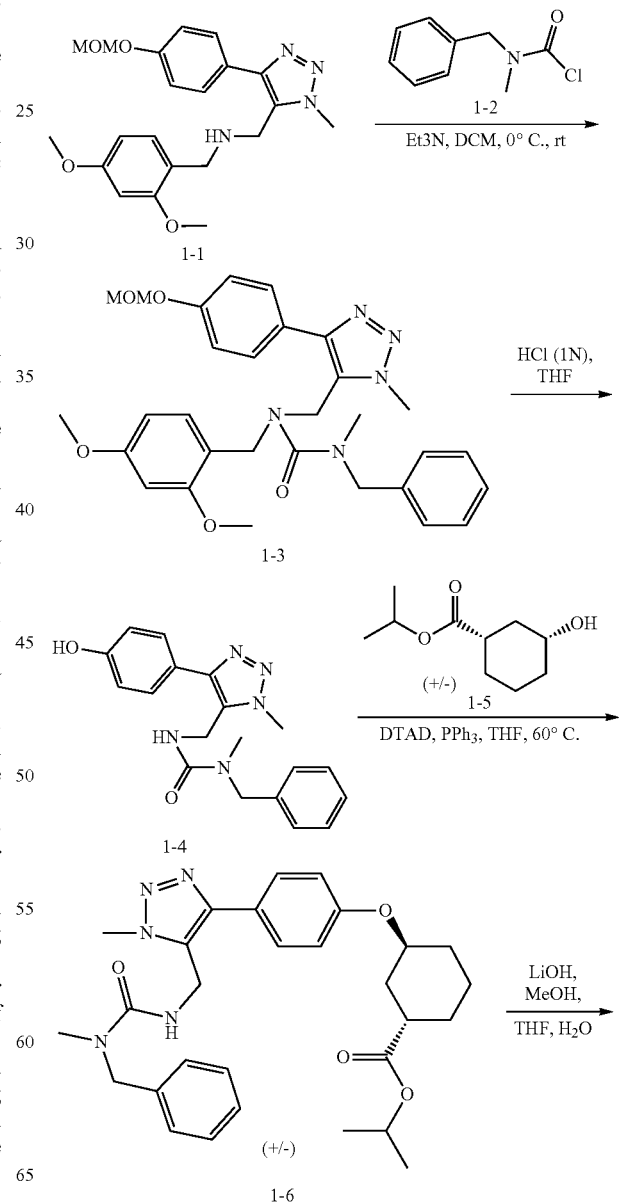

-continued

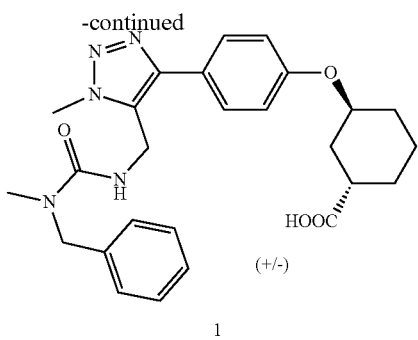

1 (+/-)

Step (1): Preparation of 1-benzyl-3-(2,4-dimethoxy-benzyl)-3-((4-(4-(methoxymethoxy)phenyl)-1-methyl-1H-1,2,3-triazol-5-yl)methyl)-1-methylurea

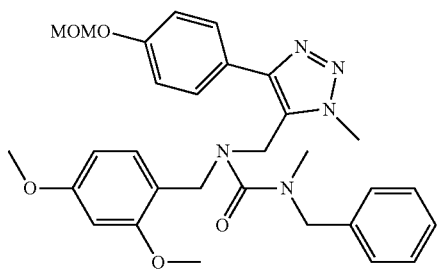

1-3

Compound 1-1 (340 mg, 0.82 mmol) was dissolved in dichloromethane (20 mL), and then triethylamine (165 mg, 1.63 mmol) was added. The reaction system was cooled to 0° C., added with benzyl(methyl)carbamic chloride (184 mg, 0.977 mmol), and then slowly warmed to room temperature and reacted for 16 h. Then the reaction system was quenched with water (10 mL), washed with saturated brine (20 mL), dried over anhydrous sodium sulfate and concentrated, and the residue was separated by column chromatography (DCM/MeOH=30/1) to give Compound 1-3 (190 mg, 42% yield) in the form of a yellow solid. LC-MS [M+H]$^+$: 546.1.

Step (2): Preparation of 1-benzyl-3-((4-(4-hydroxyphenyl)-1-methyl-1H-1,2,3-triazol-5-yl)methyl)-1-methylurea

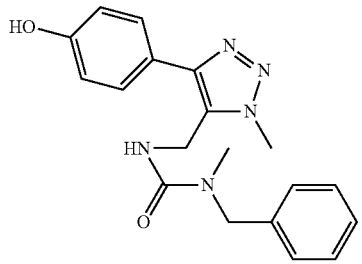

1-4

Compound 1-3 (190 mg, 0.35 mmol) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=20/1) to give Compound 1-4 (93 mg, 74% yield) in the form of a yellow solid. LC-MS [M+H]$^+$: 352.4.

Step (3): Preparation of (+/−)-isopropyl (1S,3S)-3-(4-(5-((3-phenyl-3-methylureido)methyl)-1-methyl-1H-1,2,3-triazol-4-yl)-phenoxy)cyclohexane-1-carboxylate

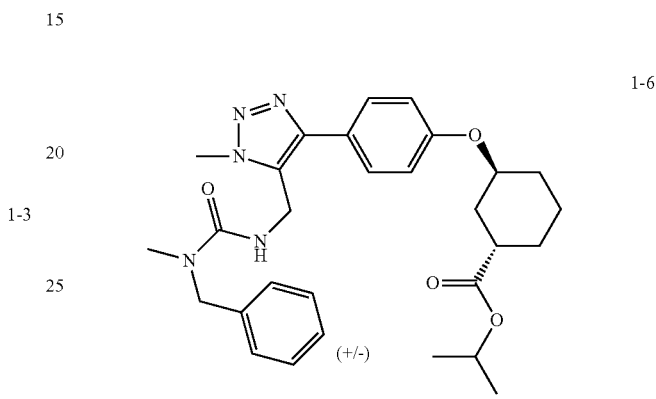

1-6 (+/-)

Compound 1-4 (50 mg, 0.14 mmol), isopropyl 3-hydroxy-cyclohexane-1-carboxylate (109 mg, 0.57 mmol), DTAD (131 mg, 0.57 mmol) and PPh$_3$ (150 mg, 0.57 mmol) were dissolved in THF (10 mL), and the reaction system was stirred overnight at 60° C. under nitrogen atmosphere. Then the reaction system was purified by silica gel column chromatography (DCM/EA=50/1) to give Compound 1-6 (130 mg) in the form of a yellow solid. LC-MS [M+H]$^+$: 520.2.

Step (4): Preparation of (+/−)-(1S,3S)-3-(4-(5-((3-phenyl-3-methylureido)methyl)-1-methyl-1H-1,2,3-triazol-4-yl)-phenoxy)cyclohexane-1-carboxylic acid

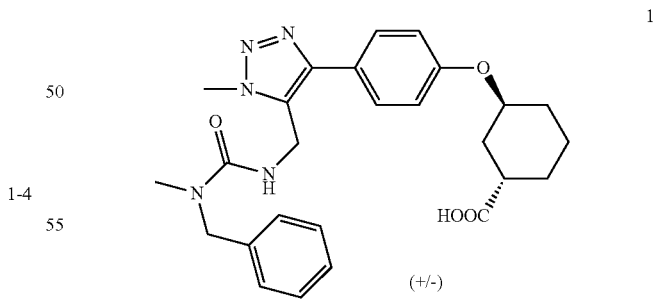

1 (+/-)

Compound 1-6 (130 mg, crude product) was dissolved in THF (9 mL), and MeOH (3 mL), H$_2$O (3 mL) and lithium hydroxide (42 mg, 1.0 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation. The residue was purified by silica gel column chromatography (DCM/MeOH=20/1) and then lyophilized to give Compound 1 (38 mg) in the form of a white solid.

LC-MS [M+H]⁺: 478.2. ¹H NMR (400 MHz, MeOD) δ 7.64-7.56 (m, 2H), 7.37-7.20 (m, 3H), 7.16 (d, J=7.1 Hz, 2H), 7.08-7.01 (m, 2H), 4.69-4.67 (m, 1H), 4.64 (s, 2H), 4.47 (s, 2H), 4.11 (s, 3H), 2.82-2.73 (m, 1H), 2.76 (s, 3H), 2.06-2.04 (m, 1H), 1.92-1.78 (m, 3H), 1.74-1.44 (m, 4H).

Example 2

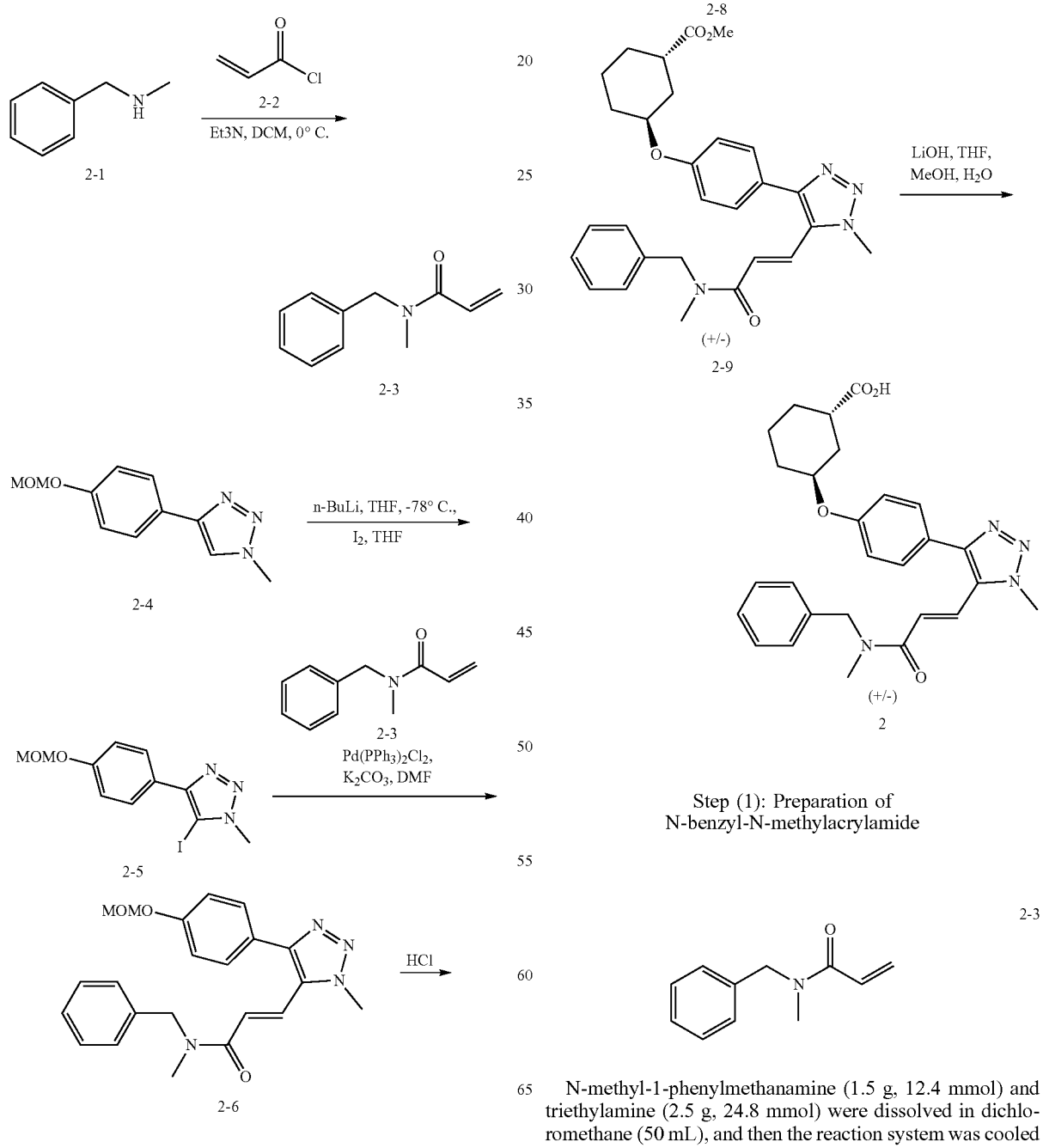

Step (1): Preparation of N-benzyl-N-methylacrylamide

N-methyl-1-phenylmethanamine (1.5 g, 12.4 mmol) and triethylamine (2.5 g, 24.8 mmol) were dissolved in dichloromethane (50 mL), and then the reaction system was cooled to 0° C., added with acryloyl chloride (126 mL, 2.4 M) dropwise, and then reacted at 0° C. for 2 h. Then the reaction system was slowly warmed to room temperature, washed successively with water (20 mL) and saturated brine (20 mL), dried over anhydrous sodium sulfate and concentrated to give Compound 2-3 (1.7 g, 78% yield) in the form of a yellow solid. LC-MS [M+H]⁺: 176.2.

Step (2): Preparation of 5-iodo-4-(4-(methoxymethoxy)phenyl)-1-methyl-1H-1,2,3-triazole

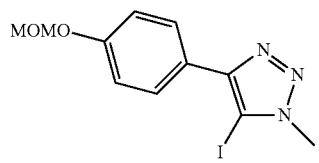

2-5

Compound 2-4 (800 mg, 3.65 mmol) was dissolved in tetrahydrofuran (30 mL), and then the reaction system was cooled to −78° C. and added with n-butyl lithium (1.82 mL, 2.4 M) dropwise. After reaction at −78° C. for 1 h, the reaction system was added with a solution of iodine (1.4 g, 5.47 mmol) in tetrahydrofuran (5 mL) dropwise, and then reacted at −78° C. for 1 h. Then the reaction system was quenched with saturated ammonium chloride (20 mL), and extracted with ethyl acetate (30 mL×2). The organic phase was washed with saturated brine (50 mL), dried over anhydrous sodium sulfate and concentrated, and the residue was separated by column chromatography (DCM/EA=4/1) to give Compound 2-5 (1.2 g, 90% yield) in the form of a white solid. LC-MS [M+H]⁺: 346.4.

Step (3): Preparation of (E)-N-benzyl-3-(4-(4-(methoxymethoxy)phenyl)-1-methyl-1H-1,2,3-triazol-5-yl)-N-methylacrylamide

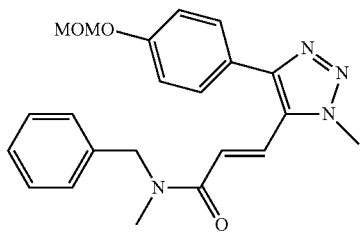

2-6

Compound 2-5 (518 mg, 1.5 mmol), Compound 2-3 (290 mg, 1.65 mmol), [1,1'-bis(diphenylphosphino)ferrocene]dichloropalladium(II) (105 mg, 0.15 mmol) and potassium carbonate (105 mg, 0.15 mmol) were added to anhydrous N,N-dimethylformamide (10 mL), and the reaction system was heated to 120° C. and reacted for 2 h under nitrogen atmosphere. Then the reaction system was quenched with water (30 mL), and extracted with ethyl acetate (30 mL×3).

The organic phases were combined, washed with saturated brine (30 mL×2), dried over anhydrous sodium sulfate, filtered and concentrated, and the residue was separated by column chromatography (DCM/MeOH=40/1) to give Compound 2-6 (470 mg, 79% yield) in the form of a white solid. LC-MS [M+H]⁺: 393.2.

Step (4): Preparation of (E)-N-benzyl-3-(4-(4-hydroxyphenyl)-1-methyl-1H-1,2,3-triazol-5-yl)—N-methylacrylamide

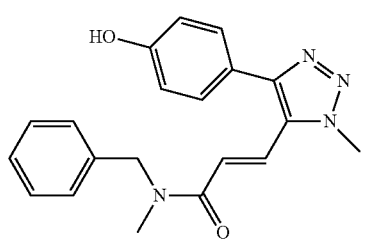

2-7

Compound 2-6 (470 mg, 1.2 mmol) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate, and concentrated to give Compound 2-7 (400 mg, 95% yield) in the form of a yellow solid. LC-MS [M+H]⁺: 349.2.

Step (5): Preparation of (+/−)-methyl (1S,3S)-3-((4-(5-((((E)-benzyl(methyl)carbamoyl)-1-en-1-yl)methyl)-1-methyl-1H-1,2,3-triazol-4-yl)-phenoxy)cyclohexane-1-carboxylate

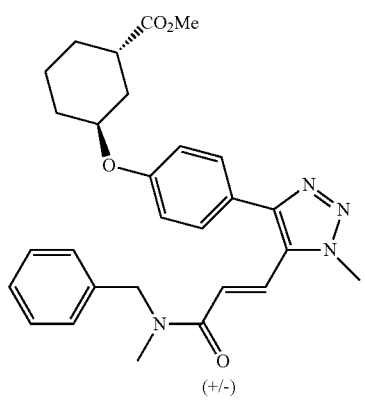

2-9

Compound 2-7 (300 mg, 0.31 mmol), methyl (3S)-3-hydroxycyclohexane-1-carboxylate (272 mg, 0.63 mmol), DIAD (142 mg, 63 mmol) and PPh₃ (162 mg, 0.63 mmol) were dissolved in THF (10 mL), and the reaction system was stirred overnight at room temperature under nitrogen atmosphere.

Then the reaction system was purified by silica gel column chromatography (DCM/EA=5/1) to give Compound 2-9 (300 mg) in the form of a yellow solid. LC-MS [M+H]⁺: 489.1.

Step (6): Preparation of (+/−)-(1S,3S)-3-((4-(5-((((E)-benzyl(methyl)carbamoyl)-1-en-1-yl)methyl)-1-methyl-1H-1,2,3-triazol-4-yl)-phenoxy)cyclohexane-1-carboxylic acid

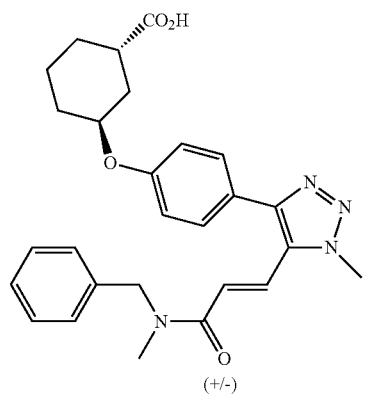

Compound 2-9 (300 mg, crude product) was dissolved in THF (9 mL), and MeOH (3 mL), H₂O (3 mL) and lithium hydroxide (42 mg, 1.0 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation. The residue was purified by silica gel column chromatography (DCM/MeOH=20/1) and then lyophilized to give Compound 2 (20 mg) in the form of a white solid. LC-MS [M+H]⁺: 475.4.

Example 3

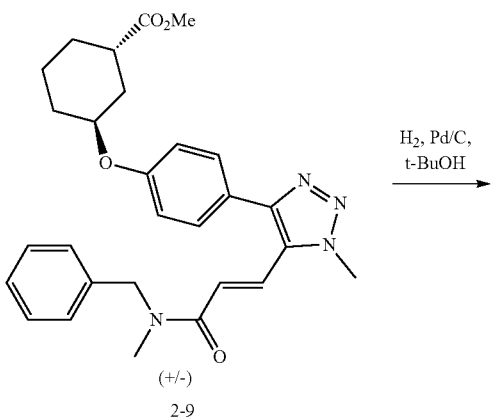

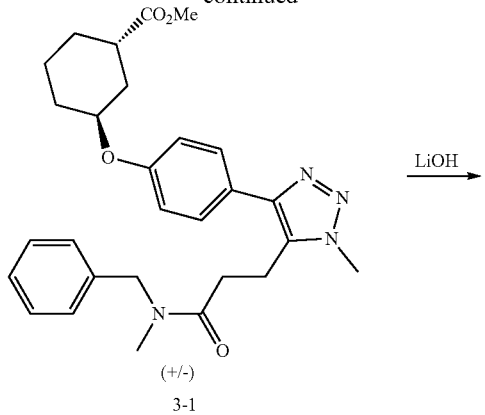

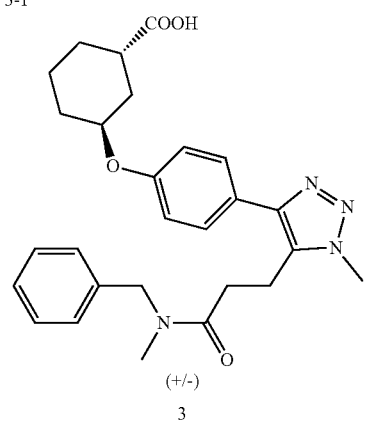

Step (1): Preparation of (+/−)-methyl (1S,3S)-3-((4-(5-(3-(benzyl(methyl)amino)-3-carbonylpropyl)-1-methyl-1H-1,2,3-triazol-4-yl)-phenoxy)cyclohexane-1-carboxylate

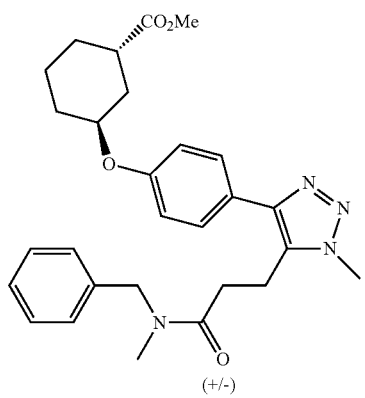

Compound 2-9 (610 mg, crude product) was dissolved in tert-butanol (20 mL), and then palladium on carbon (61 mg) was added. Hydrogen gas was introduced, and the reaction system was reacted at room temperature for 2 h. Palladium on carbon was filtered out, and the filtrate was concentrated to give Compound 3-1 (510 mg) in the form of a yellow solid. LC-MS [M+H]⁺: 491.8.

Step (2): Preparation of (+/−)-(1S,3S)-3-((4-(5-(3-(benzyl(methyl)amino)-3-carbonylpropyl)-1-methyl-1H-1,2,3-triazol-4-yl)-phenoxy)cyclohexane-1-carboxylic acid

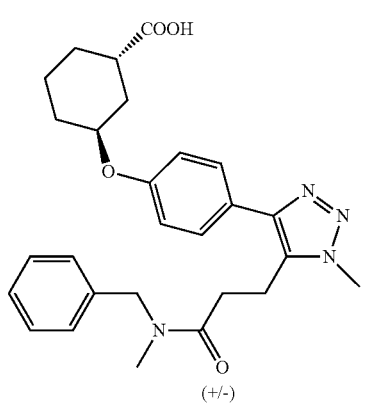

Compound 3-1 (510 mg, crude product) was dissolved in THF (9 mL), and MeOH (3 mL), H₂O (3 mL) and lithium hydroxide (42 mg, 1.0 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation.

The residue was purified by silica gel column chromatography (DCM/MeOH=20/1) and then lyophilized to give Compound 3 (20 mg) in the form of a white solid.

LC-MS [M+H]⁺: 477.2. ¹H NMR (400 MHz, DMSO) δ 12.20 (s, 1H), 7.60-7.50 (m, 2H), 7.33-7.26 (m, 3H), 7.15-6.99 (m, 4H), 4.69 (s, 1H), 4.48 (s, 1.4H), 4.46 (s, 0.7H), 4.04 (s, 2H), 3.98 (s, 1H), 3.12 (dd, J=17.0, 9.0 Hz, 2H), 2.80 (s, 1H), 2.79 (s, 2H), 2.74-2.61 (m, 3H), 1.98-1.46 (m, 8H).

Example 4

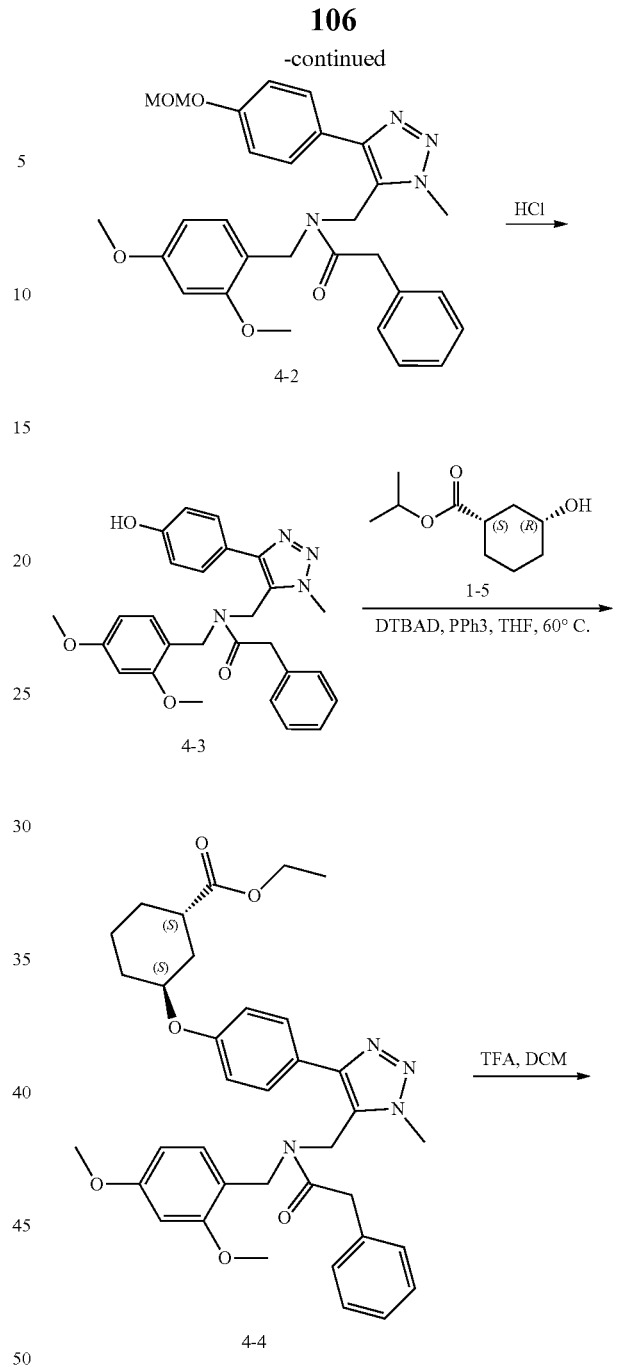

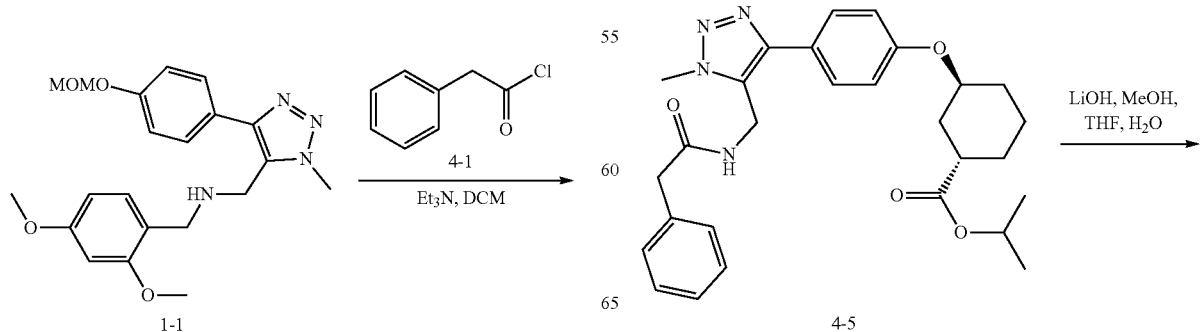

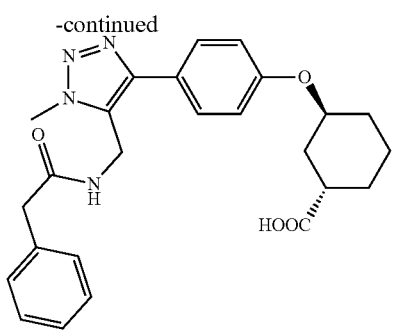

4

Step (1): Preparation of N-(2,4-dimethoxybenzyl)-N-((4-(4-(methoxymethoxy)phenyl)-1-methyl-1H-1,2,3-triazol-5-yl)methyl)-2-phenylacetamide

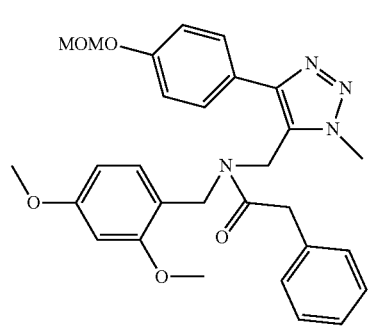

4-2

Compound 1-1 (1.3 g, 3.25 mmol) and triethylamine (0.7 g, 6.50 mmol) were dissolved in dichloromethane (25 mL), and then the reaction system was put in an ice water bath, added with phenylacetyl chloride (172 mg, 0.98 mmol) dropwise and then stirred overnight at room temperature. Then the reaction system was diluted with dichloromethane (25 mL), washed with saturated brine (25 mL), dried over anhydrous sodium sulfate, filtered and concentrated, and the residue was separated by column chromatography (PE/EA=4//1) to give Compound 4-2 (0.86 g, 50% yield) in the form of a white solid. LC-MS [M+H]⁺: 517.2.

Step (2): Preparation of N-(2,4-dimethoxybenzyl)-N-((4-(4-hydroxyphenyl)-1-methyl-1H-1,2,3-triazol-5-yl)methyl)-2-phenylacetamide

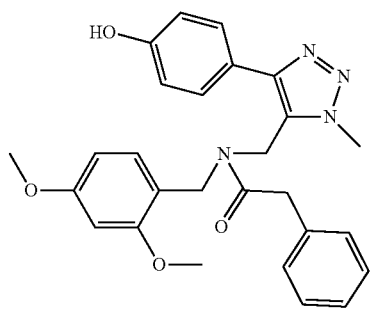

4-3

Compound 4-2 (800 mg, 1.55 mmol) was dissolved in tetrahydrofuran (5 mL), and then HCl (1 N, 5 mL) was added, and the reaction system was stirred overnight at room temperature. Then the reaction system was diluted with $H_2O$ (20 mL) and extracted with ethyl acetate (15 mL×2). The organic phases were combined, washed with saturated brine (15 mL), dried over anhydrous sodium sulfate, filtered and concentrated, and the residue was separated by column chromatography (PE/EA=1/1) to give Compound 4-3 (550 mg, 75% yield) in the form of a white solid.

LC-MS [M+H]⁺: 473.2.

Step (3): isopropyl (1S,3S)-3-(4-(5-((N-(2,4-dimethoxybenzyl)-2-N-phenylacetamido)methyl)-1-methyl-1H-1,2,3-triazol-4-yl)phenoxy)cyclohexane-1-carboxylate

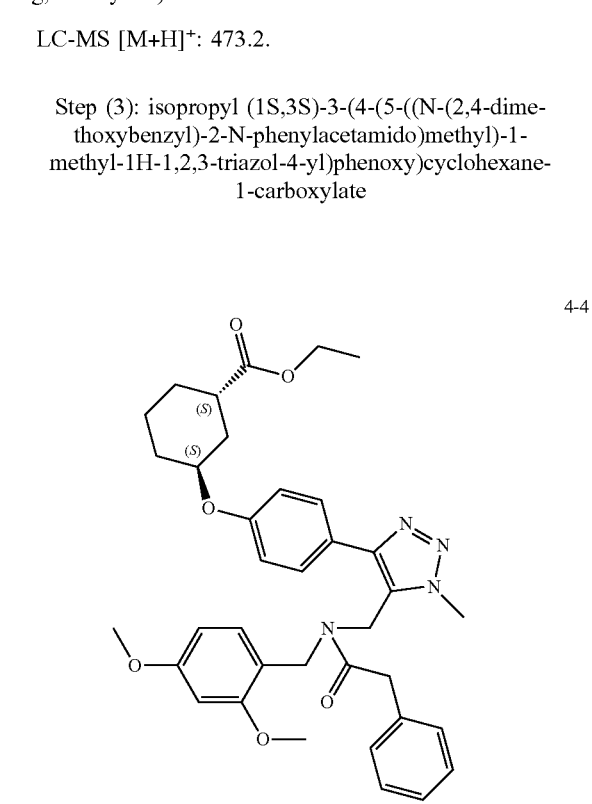

4-4

Compound 4-3 (260 mg, 0.55 mmol) was dissolved in tetrahydrofuran solution (15 mL), and then triphenylphosphonium (444 mg, 1.65 mmol), di-tert-butyl azodicarboxylate (380 mg, 1.65 mmol) and Compound 1-5 (307 mg, 1.65 mmol) were added under nitrogen atmosphere. Then the reaction system was warmed to 60° C. and stirred overnight. The reaction system was quenched with water (50 mL), and extracted with ethyl acetate (30 mL×2). The organic phases were combined, washed with saturated brine (20 mL×2), dried over anhydrous sodium sulfate, filtered and concentrated, and the residue was separated by column chromatography (PE/EA=2/1) to give Compound 4-4 (160 mg, 45% yield) in the form of a pale yellow oil. LC-MS [M+H]⁺: 627.3.

Step (4): Preparation of isopropyl (1S,3S)-3-((4-(5-(2-N-phenylacetamido))-1-methyl-1H-1,2,3-triazol-4-yl)-phenoxy)cyclohexane-1-carboxylate

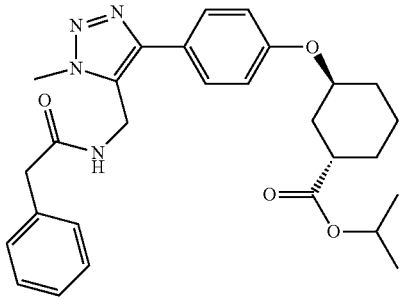

4-5

Compound 4-4 (160 mg, 0.25 mmol) was dissolved in dichloromethane (5 mL), and then trifluoroacetic acid (5 mL) was added dropwise, and the reaction system was stirred overnight at room temperature. After concentration under reduced pressure, the reaction system was diluted with H$_2$O (20 mL) and extracted with dichloromethane (15 mL×2). The organic phase was washed with saturated brine (15 mL), dried over anhydrous sodium sulfate, filtered and concentrated, and the residue was separated by column chromatography (PE/EA=1/1) to give Compound 4-5 (120 mg, 97% yield) in the form of a white solid. LC-MS [M+H]$^+$: 491.2.

Step (5): Preparation of (1S,3S)-3-((4-(5-(2-N-phenylacetamido))-1-methyl-1H-1,2,3-triazol-4-yl)-phenoxy)cyclohexane-1-carboxylic acid

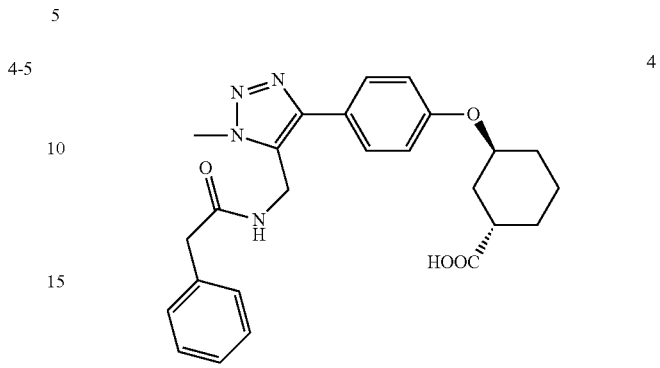

4

Compound 4-5 (120 mg, 0.24 mmol) was dissolved in a mixed solvent of tetrahydrofuran (6 mL), methanol (2 mL) and water (2 mL), and then lithium hydroxide hydrate (30 mg, 0.72 mmol) was added, and the reaction system was stirred at room temperature for 15 h. Then the reaction system was concentrated, diluted with H$_2$O (10 mL), adjusted to pH 2-3 with diluted HCl (1 N), and then extracted with ethyl acetate (10 mL×2). The organic phases were combined, washed with saturated brine (10 mL), dried over anhydrous sodium sulfate, filtered and concentrated, and the residue was purified by thin layer chromatography (DCM/MeOH=30/1) and lyophilized to give Compound 4 (90 mg, 84% yield) in the form of a white solid.

LC-MS [M+H]$^+$: 449.2. $^1$H NMR (400 MHz, CDCl$_3$) δ 7.38 (d, J=8.7 Hz, 2H), 7.33-7.28 (m, 3H), 7.18 (dd, J=7.5, 1.7 Hz, 2H), 6.93 (d, J=8.7 Hz, 2H), 6.38 (brs, 1H), 4.67-4.62 (m, 1H), 4.56 (d, J=5.3 Hz, 2H), 3.92 (s, 3H), 3.57 (s, 2H), 2.97-2.84 (m, 1H), 2.14-2.06 (m, 1H), 2.02-1.58 (m, 7H).

Example 5

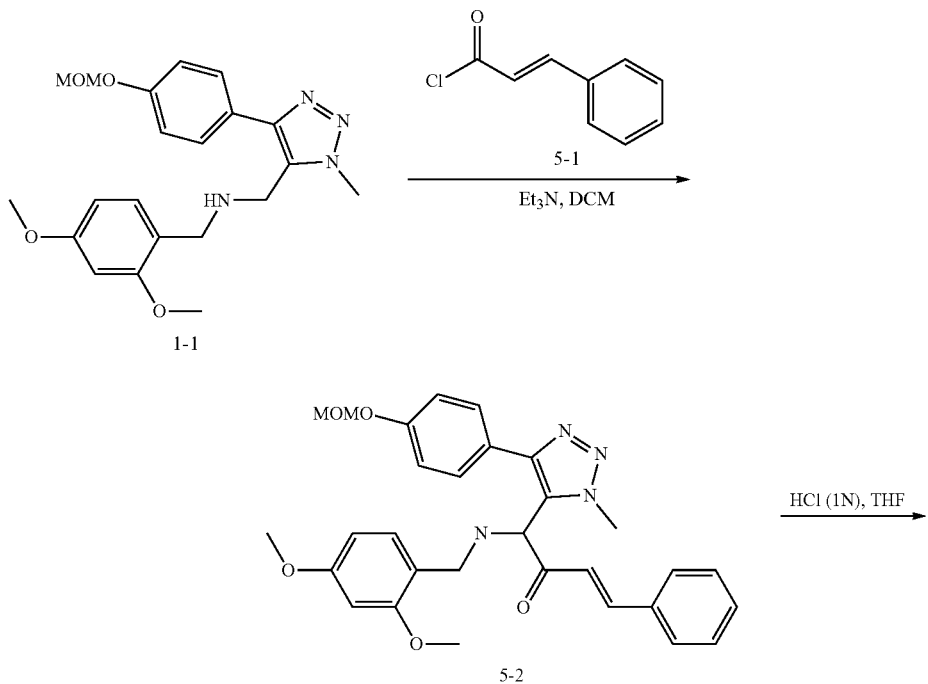

111
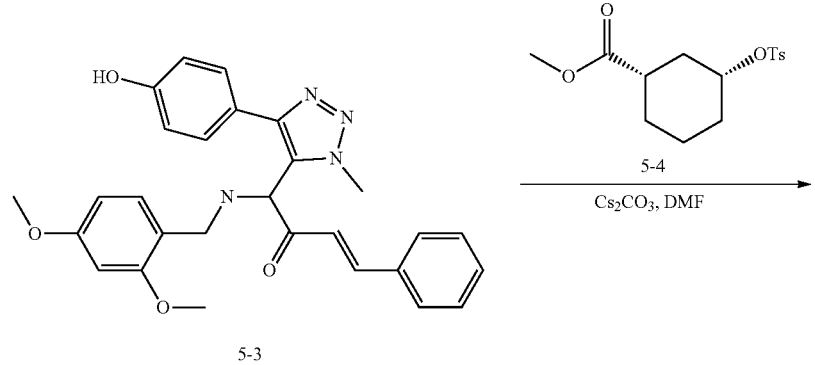
112
-continued
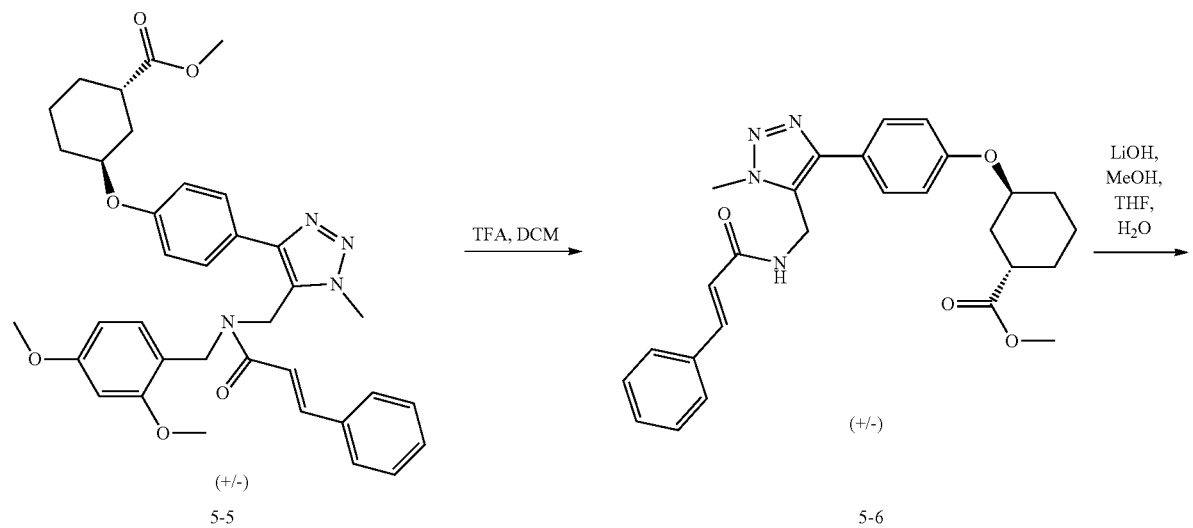
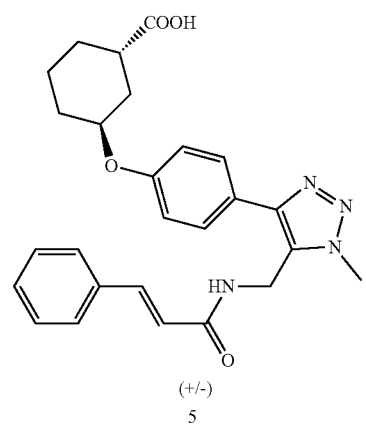 [SMILES: Cn1nnc(-c2ccc(O[C@H]3CCC[C@H](C(=O)O)C3)cc2)c1CNC(=O)/C=C/c1ccccc1]

Step (1): Preparation of N-(2,4-dimethoxybenzyl)-
N-((4-(4-(methoxymethoxy)phenyl)-1-methyl-1H-1,
2,3-triazol-5-yl)methyl)-cinnamamide

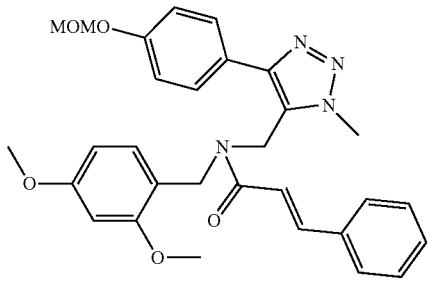

5-2

Compound 1-1 (324 mg, 0.814 mmol) was dissolved in dichloromethane (20 mL), and then triethylamine (165 mg, 1.63 mmol) was added. The reaction system was cooled to 0° C., added with cinnamoyl chloride (163 mg, 0.977 mmol), and then slowly warmed to room temperature and reacted for 16 h. Then the reaction system was quenched with water (10 mL), washed with saturated brine (20 mL), dried over anhydrous sodium sulfate and concentrated, and the residue was separated by column chromatography (DCM/MeOH=30/1) to give Compound 5-2 (320 mg, 76% yield) in the form of a yellow solid. LC-MS [M+H]⁺: 529.1.

Step (2): Preparation of N-(2,4-dimethoxybenzyl)-
N-((4-(4-hydroxyphenyl)-1-methyl-1H-1,2,3-triazol-
5-yl)methyl)-cinnamamide

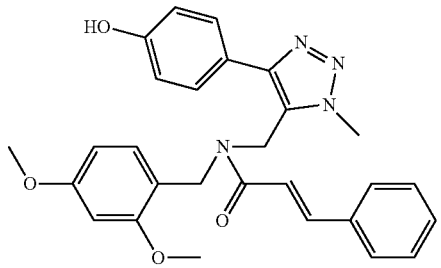

5-3

Compound 5-2 (320 mg, 0.605 mmol) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=20/1) to give Compound 5-3 (170 mg, 58% yield) in the form of a yellow solid. LC-MS [M+H]⁺: 485.2.

Step (3): Preparation of (+/−)-methyl (1S,3S)-3-(4-
(5-((N-(2,4-dimethoxybenzyl)cinnamamido)
methyl)-1-methyl-1H-1,2,3-triazol-4-yl)phenoxy)
cyclohexane-1-carboxylate

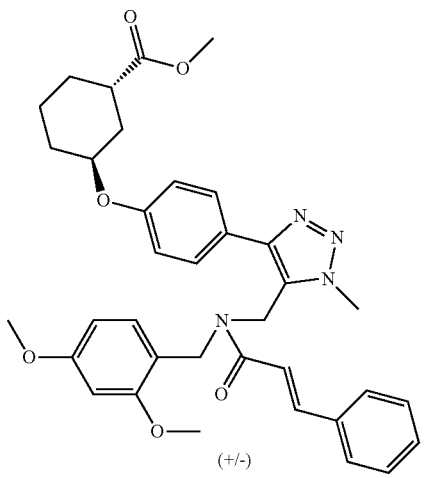

5-5

(+/−)

Compound 5-3 (170 mg, 0.35 mmol), Compound 5-4 (219 mg, 0.7 mmol) and cesium carbonate (286 mg, 0.875 mmol) were dissolved in DMF (10 mL), and then the reaction system was heated to 100° C. and reacted for 7 h under nitrogen atmosphere. Then the reaction system was diluted with ethyl acetate (20 mL), washed successively with water (10 mL×2) and saturated brine (10 mL), dried over anhydrous sodium sulfate and concentrated, and the residue was separated by column chromatography (DCM/MeOH=50/1) to give Compound 5-5 (190 mg, 86% yield) in the form of a yellow solid. LC-MS [M+H]⁺: 625.4.

Step (4): Preparation of (+/−)-methyl (1S,3S)-3-(4-
(5-(cinnamidomethyl)-1-methyl-1H-1,2,3-triazol-4-
yl)phenoxy)cyclohexane-1-carboxylate

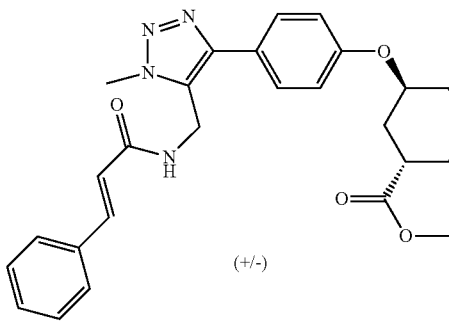

5-6

(+/−)

Compound 5-5 (190 mg, 0.3 mmol) was dissolved in dichloromethane (10 mL), and then trifluoroacetic acid (10 mL) was added, and the reaction system was stirred overnight at room temperature. Then the reaction system was concentrated, and the residue was diluted with ethyl acetate (20 mL), washed successively with saturated sodium bicarbonate (20 mL) and saturated brine (20 mL), dried over anhydrous sodium sulfate and concentrated, and the residue was separated by column chromatography (DCM/MeOH=30/1) to give Compound 5-6 (75 mg, 53% yield) in the form of a yellow solid. LC-MS [M+H]+: 475.3.

Step (5): Preparation of (+/−)-(1S,3S)-3-((4-(5-((((E)-benzyl(methyl)carbamoyl)-1-en-1-yl)methyl)-1-methyl-1H-1,2,3-triazol-4-yl)-phenoxy)cyclohexane-1-carboxylic acid

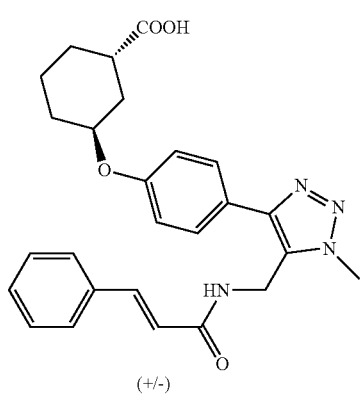

Compound 5-6 (75 mg, 0.157 mmol) was dissolved in THF (9 mL), and MeOH (3 mL), H$_2$O (3 mL) and lithium hydroxide (42 mg, 1.0 mmol) were added successively, and the reaction system was stirred overnight at room temperature. Then the reaction system was diluted with water (10 mL) and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation. The residue was purified by silica gel column chromatography (DCM/MeOH=20/1), separated by preparative chromatography, and then lyophilized to give Compound 5 (30 mg, 41% yield) in the form of a white solid.

LC-MS [M+H]+: 461.2. $^1$H NMR (400 MHz, MeOD) δ 7.66-7.52 (m, 5H), 7.46-7.35 (m, 3H), 7.09 (d, J=8.8 Hz, 2H), 6.59 (d, J=15.8 Hz, 1H), 4.76 (s, 2H), 4.74-4.75 (s, 1H), 4.17 (s, 3H), 2.79-2.76 (m, 1H), 2.08-2.06 (m, 1H), 2.00-1.85 (m, 3H), 1.84-1.56 (m, 4H).

Example 6

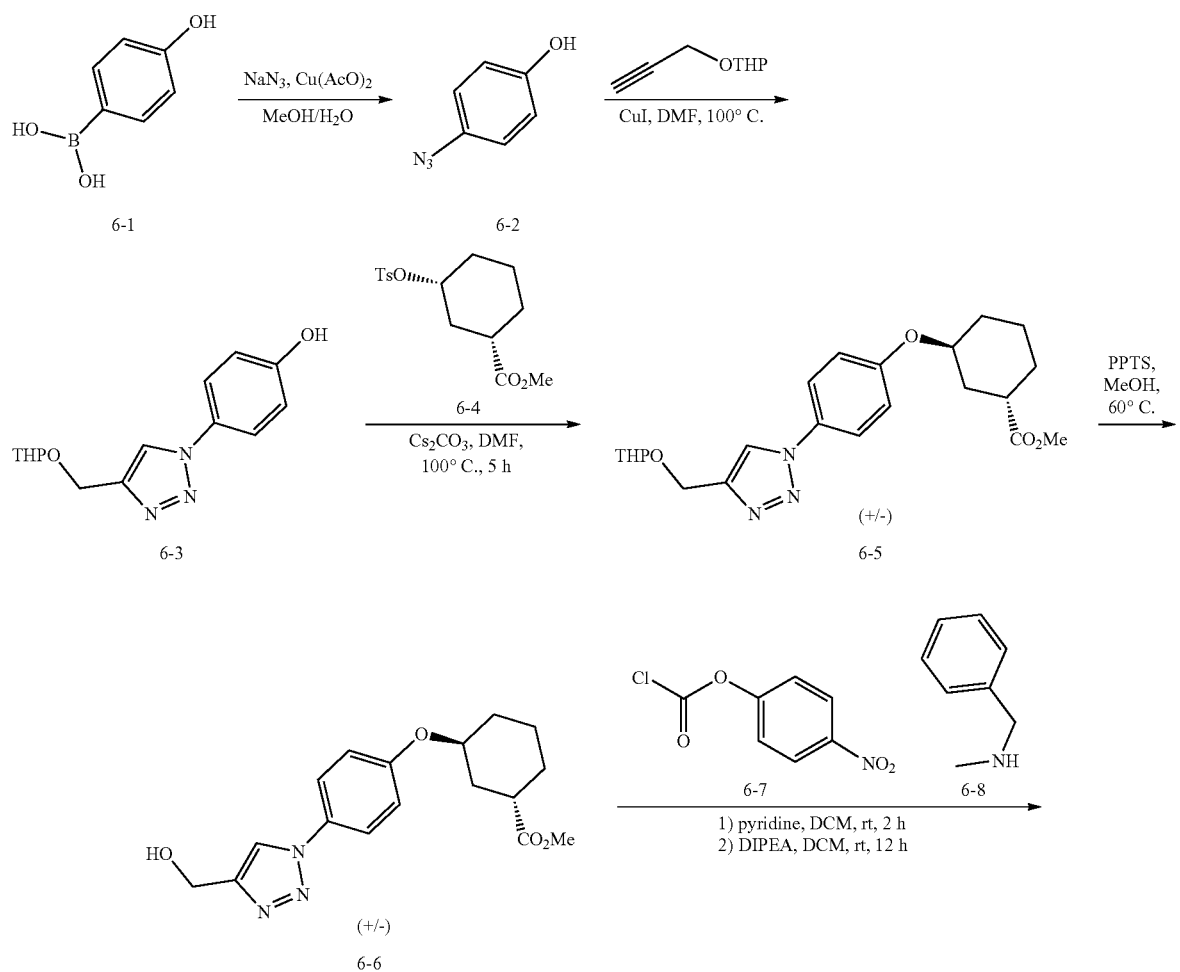

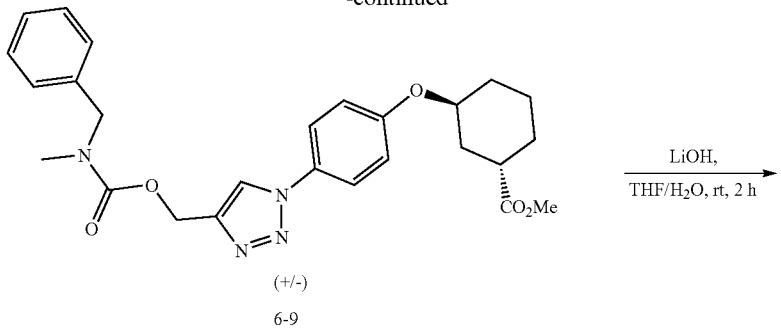

(+/-)
6-9

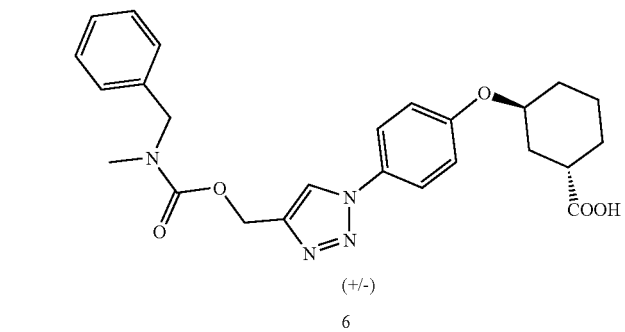

(+/-)
6

Step (1): Preparation of 4-azidophenol

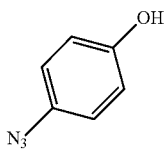

6-2

(4-hydroxyphenyl)boronic acid (4.96 g, 35.96 mmol) was dissolved in acetonitrile (25 mL) and water (25 mL), and then sodium azide (3.5 g, 53.94 mmol) and copper acetate (1.3 g, 7.192 mmol) were added, and the reaction system was reacted overnight at room temperature. After the reaction was completed, the reaction system was added with water (100 mL) and extracted with ethyl acetate (50 mL×3). The organic phases were combined, washed with saturated brine (100 mL×1), dried over anhydrous sodium sulfate, and filtered, and the filtrate was dried by rotary evaporation to give Compound 6-2 (3.59 g, 72% yield) in the form of a brown oil.

Step (2): Preparation of 4-(4-(((tetrahydro-2H-pyran-2-yl)oxo)methyl)-1H-1,2,3-triazol-1-yl)phenol 6-3

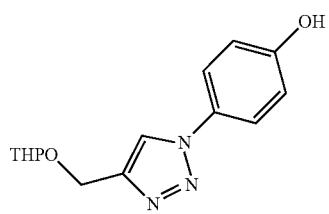

Compound 6-2 (3.59 g, 26.569 mmol) and copper(I) iodide (1.01 g, 5.314 mmol) were added to N,N-dimethylformamide (20 mL), and then 2-(prop-2-yn-1-oxy)tetrahydro-2H-pyran (4.47 g, 31.883 mmol) was added, and the reaction system was reacted at 100° C. for 15 h under nitrogen atmosphere. After the reaction was completed, the reaction system was cooled to room temperature, diluted with water (100 mL) and extracted with ethyl acetate (50 mL×3). The organic phases were combined, washed with saturated brine (150 mL×3), dried over anhydrous sodium sulfate and concentrated, and the residue was separated by column chromatography (PE/EA=10/1-3/1) to give Compound 6-3 (4 g, 54% yield) in the form of a purple oil. MS [M−H]⁻: 274.1.

Step (3): Preparation of (+/−)-methyl (1S,3S)-3-(4-(4-(((tetrahydro-2H-pyran-2-yl)oxo)methyl)-1H-1,2,3-triazol-1-yl)phenoxy)cyclohexane-carboxylate 6-5

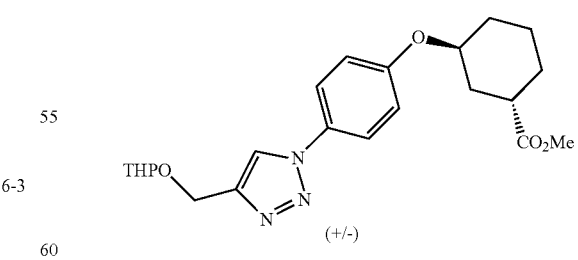

(+/-)

Compound 6-3 (260 mg, 0.94 mmol) and cesium carbonate (923 mg, 2.33 mmol) were dissolved in anhydrous DMF (5 mL), and then Compound 6-4 (354 mg, 1.13 mmol) was added. After reaction at 100° C. for 5 h, the reaction system was cooled to room temperature, added with water (20 mL) and extracted with ethyl acetate (10 mL×3). The organic phases were combined, washed with saturated brine (40 mL×3), dried over anhydrous sodium sulfate and filtered, and the filtrate was dried by rotary evaporation to give a crude product, which was separated by column chromatography (PE/EA=1/1) to give Compound 6-5 (118 mg, 30% yield) in the form of a yellow oil.

MS [M+H]$^+$: 416.8.

Step (4): Preparation of (+/−)-methyl (1S,3S)-3-(4-(4-(hydroxymethyl)-1H-1,2,3-triazol-1-yl) phenoxy) cyclohexane-carboxylate

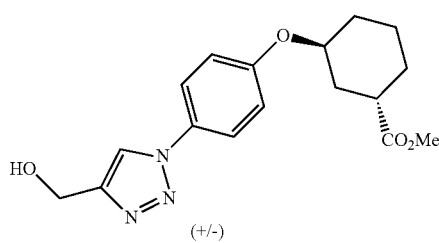

6-6

Compound 6-5 (118 mg, 0.28 mmol) was added to absolute methanol (5 mL), and then pyridinium p-toluenesulfonate (72 mg, 0.28 mmol) was added, and the reaction system was stirred at 60° C. for 3 h under nitrogen atmosphere. Then the reaction system was concentrated, and the residue was separated by thin layer chromatography (PE/EA=2/1) to give Compound 6-6 (60 mg, 63.7% yield) in the form of a yellow oil. LC-MS [M+H]$^+$: 332.8.

Step (5): Preparation of (+/−)-methyl (1S,3S)-3-(4-(4-(((benzyl(methyl)carbamoyl)oxo)methyl)-1H-1,2,3-triazol-1-yl)phenoxy)cyclohexane-carboxylate

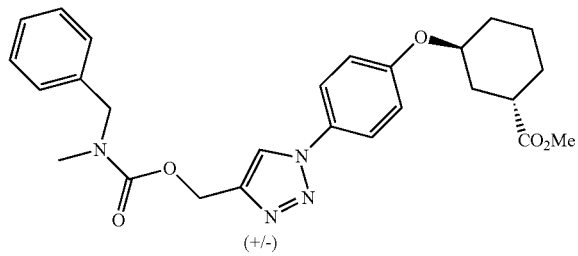

6-9

Compound 6-6 (60 mg, 0.18 mmol) and pyridine (72 mg, 0.91 mmol) were dissolved in dichloromethane (5 mL) under nitrogen atmosphere, and then the reaction system was cooled to 0° C., added with 4-nitrophenyl chloroformate (112 mg, 0.55 mmol), and then warmed to room temperature and stirred for 2 h. Then the reaction system was added with N-methylbenzylamine (134 mg, 1.1047 mmol) and diisopropylethylamine (47 mg, 0.36 mmol) and stirred overnight at room temperature. The reaction system was then washed with saturated brine, and the organic phase was dried over anhydrous sodium sulfate and concentrated, and the residue was separated by thin layer chromatography (PE/EA=2/1) to give Compound 6-9 (60 mg, 69% yield) in the form of a yellow oil. LC-MS [M+H]$^+$: 479.7.

Step (6): Preparation of (+/−)-(1S,3S)-3-(4-(4-(((benzyl(methyl)carbamoyl)oxo)methyl)-1H-1,2,3-triazol-1-yl)phenoxy)cyclohexane-1-carboxylic acid

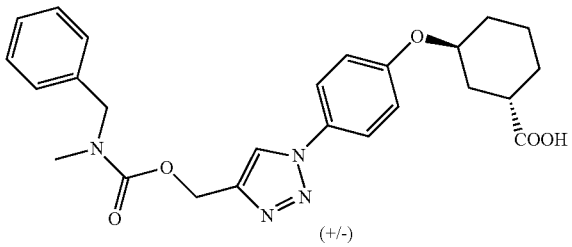

6

Compound 6-6 (60 mg, 0.1462 mmol) and lithium hydroxide (18 mg, 0.4386 mmol) were dissolved in methanol (3 mL) and water (3 mL). After reaction at room temperature for 10 h, the reaction system was concentrated, adjusted to pH 5 with diluted HCl (1 N), and then extracted with ethyl acetate (10 mL×3). The organic phases were combined, dried over anhydrous sodium sulfate and concentrated, and the residue was separated by chiral HPLC to give Compound 6 (4 mg, 7% yield) in the form of a white solid.

Compound 6: LC-MS [M−H]$^-$: 463.9. $^1$H NMR (400 MHz, CDCl$_3$) δ 8.00 (d, J=51.9 Hz, 1H), 7.63 (t, 2H), 7.33 (m, 2H), 7.28 (m, 2H), 7.21 (s, 1H), 7.06 (d, J=8.0 Hz, 2H), 5.37 (s, 2H), 4.71 (s, 1H), 4.50 (d, J=8.8 Hz, 2H), 2.90 (d, J=23.7 Hz, 3H), 2.15 (d, J=14.0 Hz, 1H), 2.07-1.53 (m, 8H).

Example 7

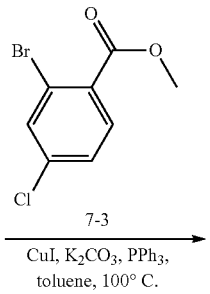

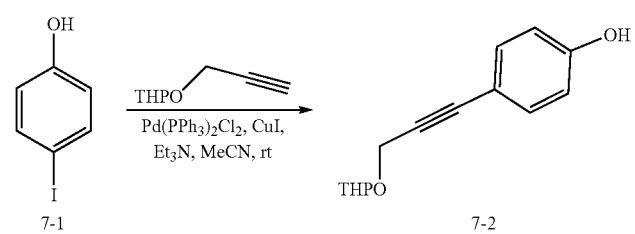

7-1    7-2

121

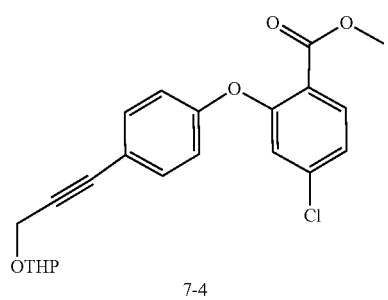

7-4

122

-continued

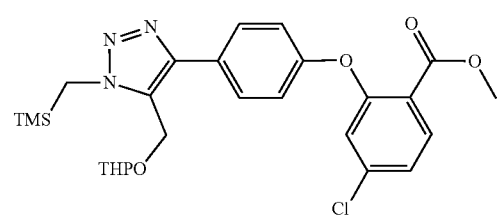

7-5

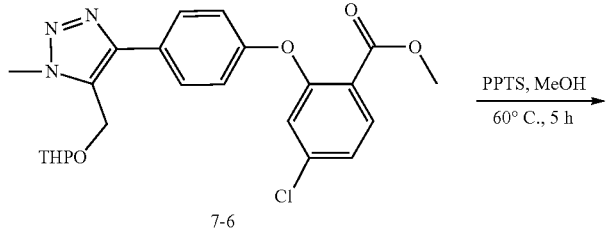

7-6

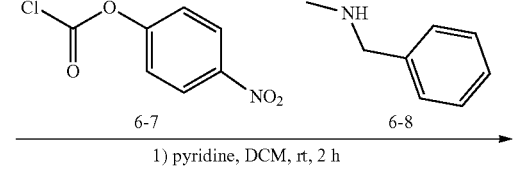

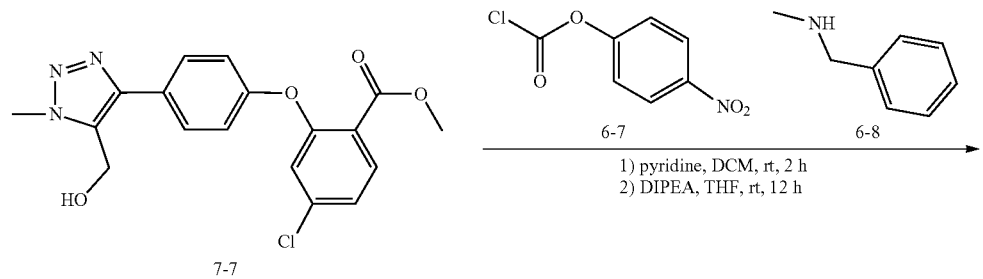

7-7

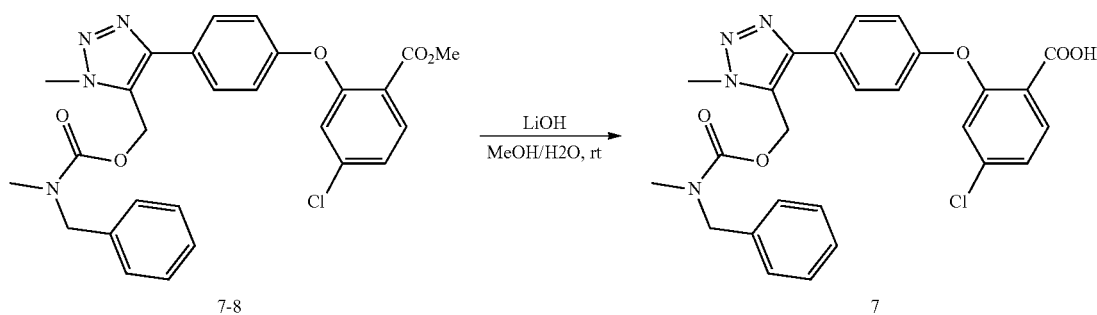

7-8 → 7

Step (1): Preparation of 4-(3-((tetrahydro-2H-pyran-2-yl)oxo)prop-1-yn-1-yl)phenol

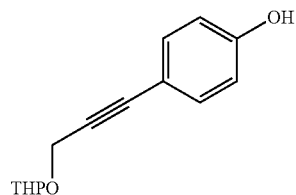

7-2

4-iodophenol (10 g, 45.45 mmol) and 2-(prop-2-yn-1-yloxy)tetrahydro-2H-pyran (9.56 g, 68.18 mmol) were dissolved in acetonitrile (20 mL), and then bis(triphenylphosphine)palladium(II) chloride (1.6 g, 2.273 mmol), triethylamine (13.8 g, 136.35 mmol) and copper(I) iodide (433 mg, 2.273 mmol) were added, and the reaction system was reacted overnight at room temperature. After the reaction was completed, the reaction system was filtered, concentrated, added with water (100 mL) and extracted with ethyl acetate (50 mL×3). The organic phases were combined, washed with saturated brine (100 mL×1), dried over anhydrous sodium sulfate and filtered, and the filtrate was dried by rotary evaporation, and the residue was purified by column chromatography (PE/EA=10/1-3/1) to give Compound 7-2 (8.5 g, 80% yield) in the form of a yellow oil. MS [M−H]⁻: 231.1.

Step (2): Preparation of methyl 4-chloro-2-(4-(3-
((tetrahydro-2H-pyran-2-yl)oxo)prop-1-yn-1-yl)
phenoxy)benzoate

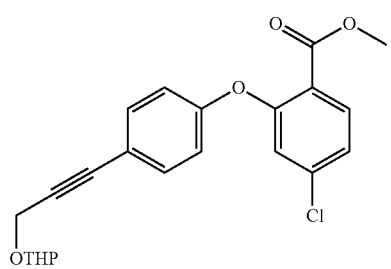

7-4

Compound 7-2 (6.4 g, 27.6564 an methyl 2-bromo-4-chlorobenzoate (4.6 g, 18.4376 mmol) were added to anhydrous toluene (100 mL), and then triphenylphosphine (242 mg, 0.9219 mmol), copper(I) iodide (176 mg, 0.9219 mmol) and potassium carbonate (5.1 g, 36.8752 mmol) were added, and the reaction system was reacted at 100° C. for 24 h under nitrogen atmosphere. After the reaction was completed, the reaction system was filtered. The filtrate was concentrated, diluted with water (100 mL) and extracted with ethyl acetate (50 mL×3). The organic phases were combined, washed with saturated brine (150 mL×3), dried over anhydrous sodium sulfate and concentrated, and the residue was separated by column chromatography (PE/EA=20/1-5/1) to give Compound 7-4 (2.5 g, 33.7% yield) in the form of a yellow oil. MS [M+H]$^+$: 401.0.

Step (3): Preparation of methyl 4-chloro-2-(4-(5-
(((tetrahydro-2H-pyran-2-yl)oxo)methyl)-1-((trimethylsilyl)methyl)-1H-1,2,3-triazol-4-yl)phenoxy)
benzoate

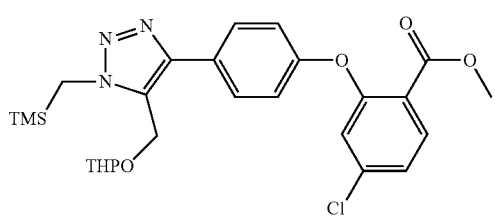

7-5

Compound 7-4 (1.9 g, 4.74 mmol), trimethylsilylmethyl azide (1.84 g, 14.22 mmol) and anhydrous DMF (20 mL) were added into a sealed tube. After reaction at 100° C. for a week, the reaction system was concentrated to remove the DMF, added with water (30 mL) and extracted with ethyl acetate (15 mL×3). The organic phases were combined, washed with saturated brine (40 mL×3), dried over anhydrous sodium sulfate and filtered, and the filtrate was dried by rotary evaporation to give a crude product, which was separated by column chromatography (PE/EA=30/1-5/1) to give Compound 7-5 (510 mg, 20% yield) in the form of a yellow oil. MS [M+H]$^+$: 530.1.

Step (4): methyl 4-chloro-2-(4-(1-methyl-5-(((tetrahydro-2H-pyran-2-yl)oxo)methyl)-1H-1,2,3-triazol-4-yl)phenoxy)benzoate

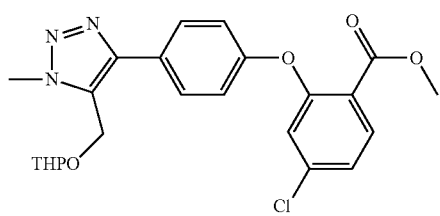

7-6

Compound 7-5 (510 mg, 0.9621 mmol) was added to anhydrous tetrahydrofuran (5 mL), and then tetrabutylammonium fluoride (1 mL, 1 M) was added, and the reaction system was stirred overnight at room temperature. The reaction system was then concentrated and the residue was separated by column chromatography (PE/EA=3/1-EA) to give Compound 7-6 (350 mg, 79% yield) in the form of a yellow oil. LC-MS [M+H]$^+$: 458.6.

Step (5): Preparation of methyl 4-chloro-2-(4-(5-
(hydroxymethyl)-1-methyl-1H-1,2,3-triazol-4-yl)
phenoxy)benzoate

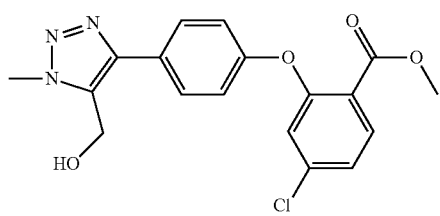

7-7

Compound 7-6 (300 mg, 0.6552 mmol) and pyridinium p-toluenesulfonate (165 mg, 0.6552 mmol) were dissolved in absolute methanol (5 mL), and the reaction system was stirred overnight at 60° C. Then the reaction system was concentrated to remove methanol, diluted with water (15 mL), and extracted with ethyl acetate (10 mL×3). The organic phases were combined, washed with saturated brine, dried over anhydrous sodium sulfate and concentrated, and the residue was separated by column chromatography (PE/EA=1/1) to give Compound 7-7 (213 mg) in the form of a white solid.

LC-MS [M+H]$^+$: 374.7.

Step (6): Preparation of methyl 4-chloro-2-(4-(5-(((benzyl(methyl)carbamoyl)oxo)methyl)-1-methyl-1H-12,3-triazol-4-yl)phenoxy)benzoate

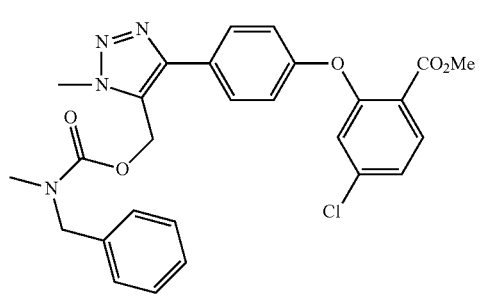

7-8

Compound 7-7 (169 mg, 0.4521 mmol) and pyridine (179 mg, 2.2605 mmol) were dissolved in dichloromethane (10 mL) under nitrogen atmosphere, and then the reaction system was cooled to 0° C., added with 4-nitrophenyl chloroformate (274 mg, 1.3563 mmol), and then warmed to room temperature and stirred for 2 h. Then the reaction system was added with N-methylbenzylamine (329 mg, 2.7126 mmol) and diisopropylethylamine (117 mg, 0.9042 mmol) and stirred overnight at room temperature. The reaction system was then washed with saturated brine, and the organic phase was dried over anhydrous sodium sulfate and concentrated, and the residue was separated by thin layer chromatography (PE/EA=1/1) to give Compound 7-8 (130 mg, 55% yield) in the form of a yellow oil. LC-MS [M+H]$^+$: 521.7.

Step (7): Preparation of 4-chloro-2-(4-(5-(((benzyl(methyl)carbamoyl)oxo)methyl)-1-methyl-1H-1,2,3-triazol-4-yl)phenoxy)benzoic acid

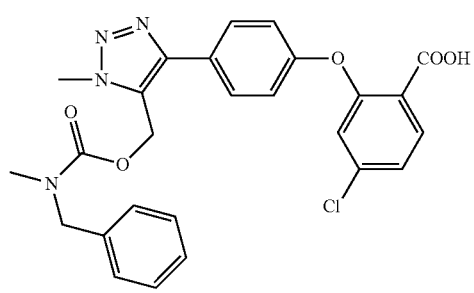

7

Compound 7-8 (130 mg, 0.2495 mmol) and lithium hydroxide (32 mg, 0.7486 mmol) were dissolved in methanol (3 mL) and water (3 mL). After reaction at room temperature for 10 h, the reaction system was concentrated, adjusted to pH 5 with diluted HCl (1 N), and then extracted with ethyl acetate (10 mL×3). The organic phases were combined, dried over anhydrous sodium sulfate and concentrated, and the residue was separated by thin layer chromatography (PE/EA=1/1) to give Compound 7 (70 mg, 44% yield) in the form of a white solid.

LC-MS [M−H]$^-$: 505.8. $^1$H NMR (400 MHz, DMSO) δ 13.16 (s, 1H), 7.89 (d, J=8.4 Hz, 1H), 7.73 (dd, J=26.3, 7.9 Hz, 2H), 7.39 (d, J=8.3 Hz, 1H), 7.36–7.04 (m, 6H), 7.00 (d, J=8.2 Hz, 1H), 5.35 (d, J=26.2 Hz, 2H), 4.41 (s, 2H), 4.09 (d, J=45.6 Hz, 3H), 2.79 (d, J=36.7 Hz, 3H).

Example 8

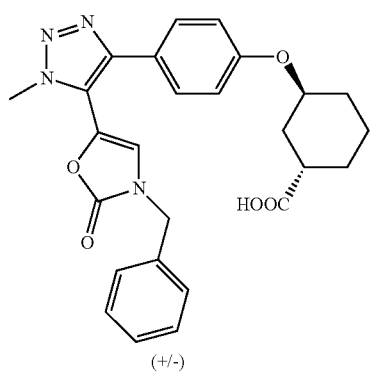

8

(+/-)

Refer to the synthesis procedures in Example 9 below, LC-MS [M−H]$^-$: 473.6.

Example 9

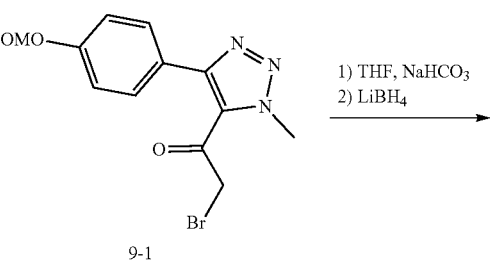

9-1

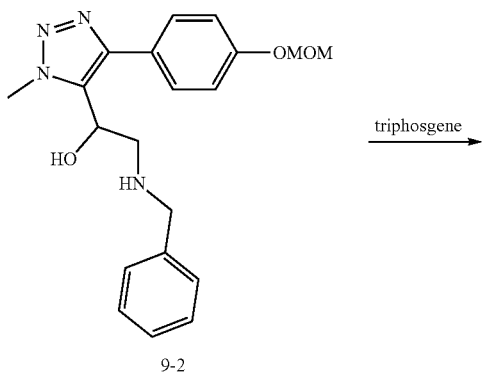

9-2

-continued

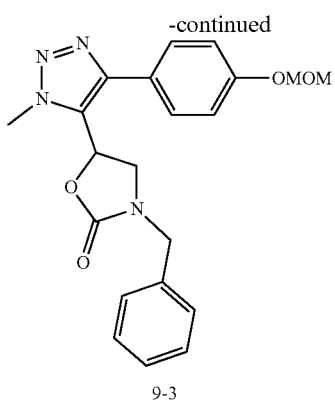

9-3

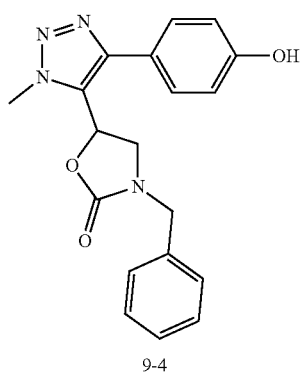

9-4

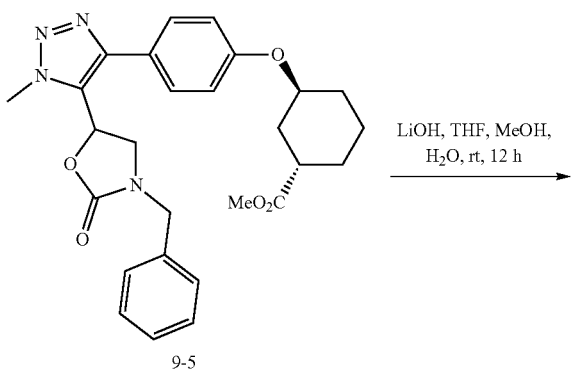

9-5

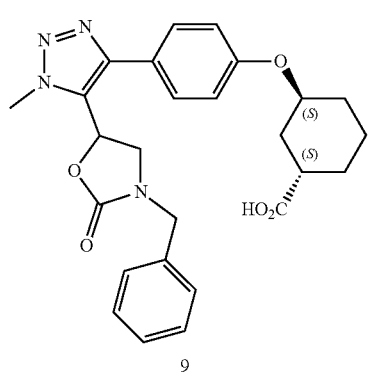

9

HCl →

Cs₂CO₃, DMF →

LiOH, THF, MeOH, H₂O, rt, 12 h →

Step (1): 2-(benzylamino)-1-(4-(4-(methoxymethoxy)phenyl)-1-methyl-1H-1,2,3-triazol-5-yl) ethan-1-ol

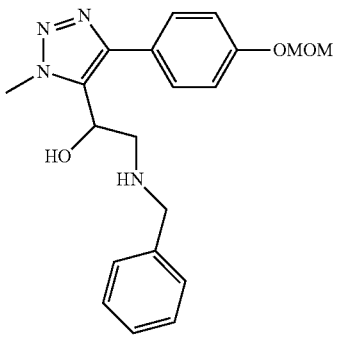

9-2

Compound 9-1 (190 mg, 0.56 mmol) was dissolved in tetrahydrofuran (10 mL), and then saturated sodium bicarbonate (0.5 mL) was added. The reaction system was cooled to 0° C. and then added with benzylamine (73 mg, 0.67 mmol). After reaction at 0° C. for 20 min, the reaction system was added with lithium borohydride (36 mg, 1.68 mmol), and then slowly warmed to room temperature and reacted for 1 h. Then the reaction system was quenched with water (10 mL) and extracted with ethyl acetate (10 mL×2). The organic phase was washed with saturated brine (20 mL), dried over anhydrous sodium sulfate and concentrated, and the residue was separated by column chromatography (DCM/MeOH=20/1) to give Compound 9-2 (65 mg, 31% yield) in the form of a yellow solid. LC-MS [M+H]⁺: 369.2.

Step (2): Preparation of 3-benzyl-5-(4-(4-(methoxymethoxy)phenyl)-1-methyl-1H-1,2,3-triazol-5-yl) oxazolidin-2-one

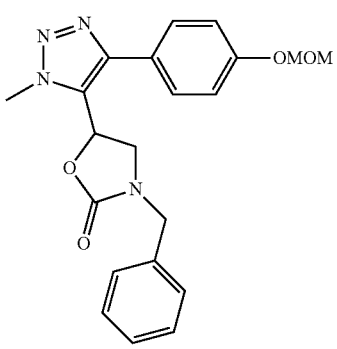

9-3

Compound 9-2 (65 mg, 0.177 mmol) was dissolved in tetrahydrofuran (5 mL), and then diisopropylethylamine (91 mg, 0.7 mmol) was added. The reaction system was cooled to 0° C., added with a solution of triphosgene (26 mg, 0.088 mmol) in tetrahydrofuran (5 mL), and then slowly warmed to room temperature and reacted for 1 h. Then the reaction system was quenched with saturated ammonium chloride (10 mL), and extracted with ethyl acetate (20 mL×2). The organic phase was washed with saturated brine (20 mL), dried over anhydrous sodium sulfate and concentrated, and the residue was separated by column chromatography (DCM/MeOH=50/1) to give Compound 9-3 (51 mg, 74% yield) in the form of a yellow solid. LC-MS [M+H]⁺: 395.3.

Step (3): Preparation of 3-benzyl-5-(4-(4-hydroxyphenyl)-1-methyl-1H-1,2,3-triazol-5-yl) oxazolidin-2-one

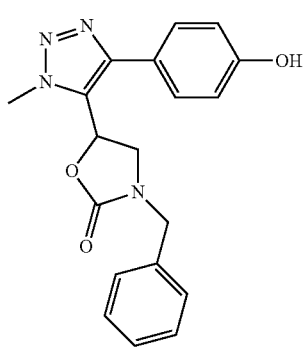

9-4

Compound 9-3 (51 mg, 0.13 mmol) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=20/1) to give Compound 9-4 (35 mg, 78% yield) in the form of a yellow solid. LC-MS [M+H]⁺: 351.2.

Step (4): Preparation of methyl (1S,3S)-3-(4-(5-(3-benzyl-2-carbonyloxazolidin-5-yl)-1-methyl-1H-1,2,3-triazol-4-yl)phenoxy)cyclohexane-1-carboxylate

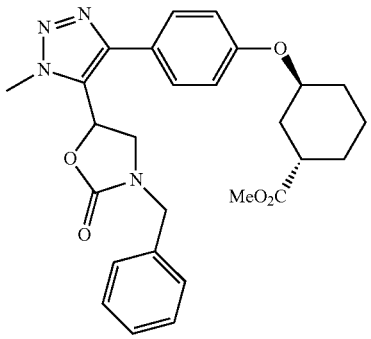

9-5

Compound 9-4 (35 mg, 0.1 mmol), methyl (1S,3R)-3-(tosyloxy) cyclohexane-1-carboxylate (42 mg, 0.12 mmol) and cesium carbonate (65 mg, 0.2 mmol) were dissolved in DMF (5 mL), and then the reaction system was heated to 100° C. and reacted for 7 h under nitrogen atmosphere. Then the reaction system was diluted with ethyl acetate (20 mL), washed successively with water (10 mL×2) and saturated brine (10 mL), dried over anhydrous sodium sulfate and concentrated, and the residue was separated by column chromatography (DCM/MeOH=20/1) to give Compound 9-5 (32 mg, 65% yield) in the form of a yellow solid. LC-MS [M+H]⁺: 491.2.

Step (5): Preparation of (1S,3S)-3-(4-(5-(3-benzyl-2-carbonyloxazolidin-5-yl)-1-methyl-1H-1,2,3-triazol-4-yl)phenoxy)cyclohexane-1-carboxylic acid

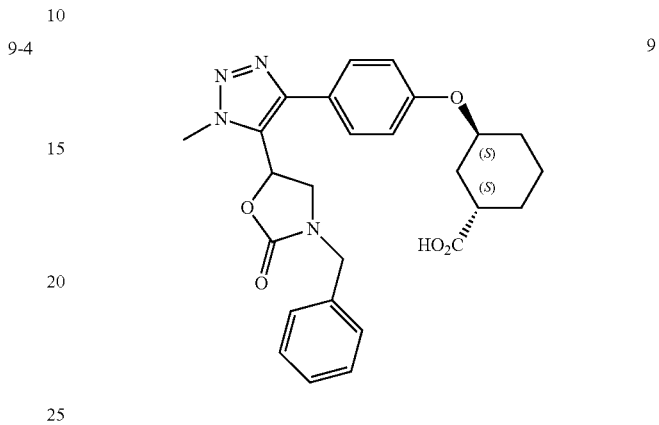

9

Compound 9-5 (32 mg, 0.065 mmol) was dissolved in THF (9 mL), and MeOH (3 mL), H₂O (3 mL) and lithium hydroxide (42 mg, 1.0 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate and filtered, and the filtrate was dried by rotary evaporation. The residue was purified by silica gel column chromatography (DCM/MeOH=20/1) and then lyophilized to give Compound 9 (4.5 mg, 15% yield) in the form of a white solid.

LC-MS [M+H]⁺: 477.2. ¹H NMR (400 MHz, MeOD) δ 7.43-7.29 (m, 5H), 7.25-7.23 (m, 2H), 7.08-7.01 (m, 2H), 6.01 (dd, J=9.5, 8.4 Hz, 1H), 4.77 (m, 1H), 4.39 (m, 2H), 4.11 (s, 3H), 3.81 (t, J=9.6 Hz, 1H), 3.44 (dd, J=9.3, 8.3 Hz, 1H), 2.81-2.83 (m, 1H), 2.09-2.11 (m, 1H), 2.00-1.86 (m, 3H), 1.83-1.58 (m, 4H).

Example 10

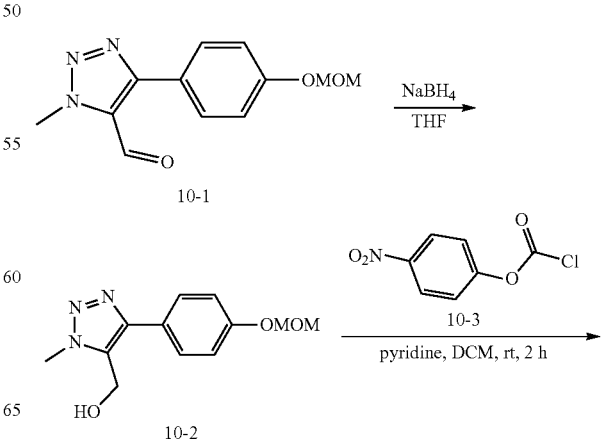

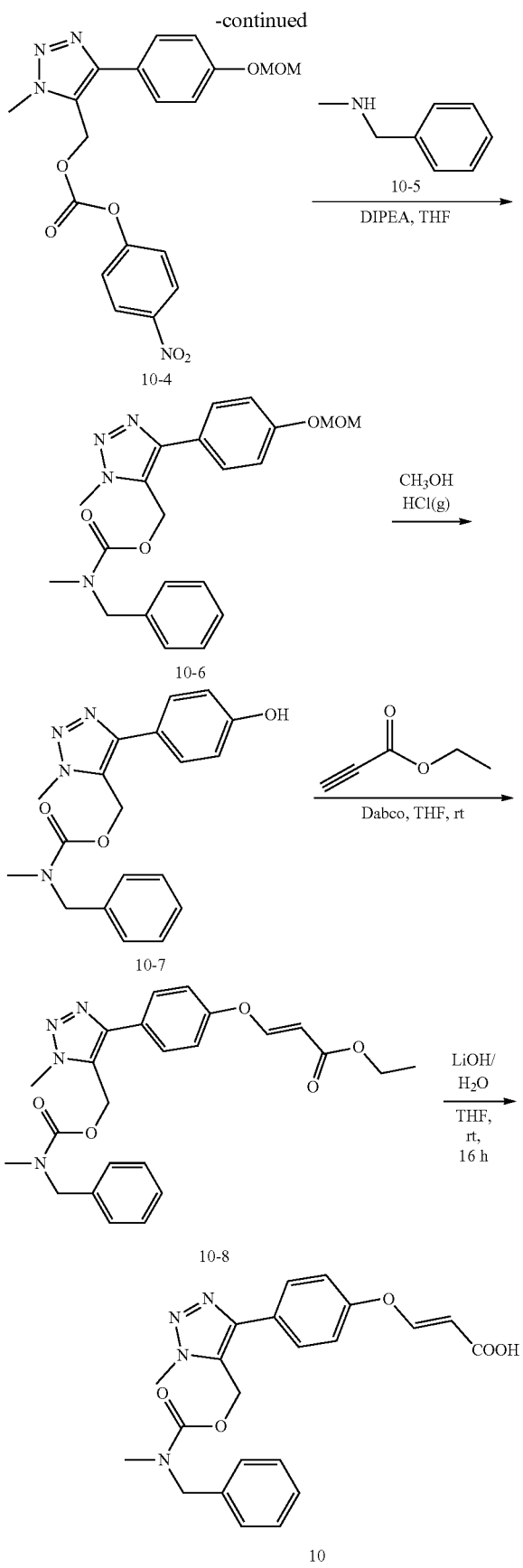

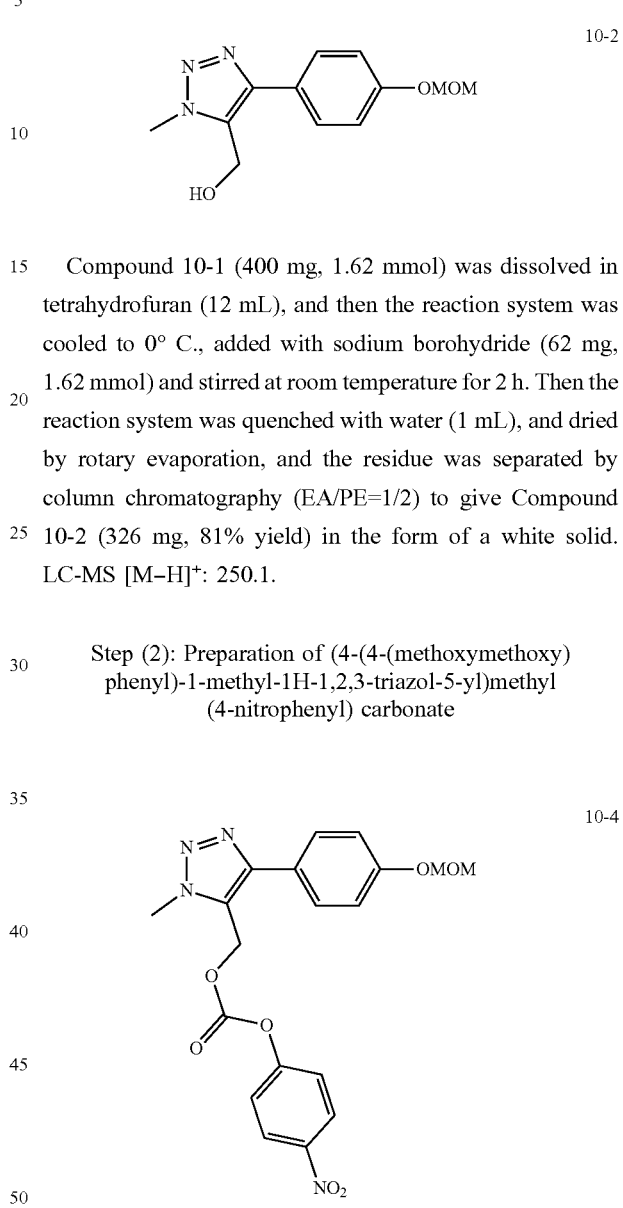

Step (1): Preparation of (4-(4-(methoxymethoxy)phenyl)-1-methyl-1H-1,2,3-triazol-5-yl)methanol Compound 10-1 (400 mg, 1.62 mmol) was dissolved in tetrahydrofuran (12 mL), and then the reaction system was cooled to 0° C., added with sodium borohydride (62 mg, 1.62 mmol) and stirred at room temperature for 2 h. Then the reaction system was quenched with water (1 mL), and dried by rotary evaporation, and the residue was separated by column chromatography (EA/PE=1/2) to give Compound 10-2 (326 mg, 81% yield) in the form of a white solid. LC-MS [M−H]$^+$: 250.1.

Step (2): Preparation of (4-(4-(methoxymethoxy)phenyl)-1-methyl-1H-1,2,3-triazol-5-yl)methyl (4-nitrophenyl) carbonate Compound 10-2 (326 mg, 1.31 mmol) and pyridine (310 mg, 3.92 mmol) were dissolved in dichloromethane (10 mL), and 4-nitrophenyl chloroformate (398 mg, 1.97 mmol) at 0° C. was added, and the reaction system was stirred overnight at room temperature. Then the reaction system was extracted with dichloromethane (20 mL×2), and the organic phases were combined, washed with saturated brine (20 mL) and concentrated, and the residue was separated by column chromatography (wet loading, PE/EA=5/1) to give Compound 10-4 (380 mg, 70% yield) in the form of a pale yellow solid. LC-MS [M+H]$^+$: 415.2.

Step (3): Preparation of (4-(4-(methoxymethoxy) phenyl)-1-methyl-1H-1,2,3-triazol-5-yl) methylbenzyl(methyl)carbamate

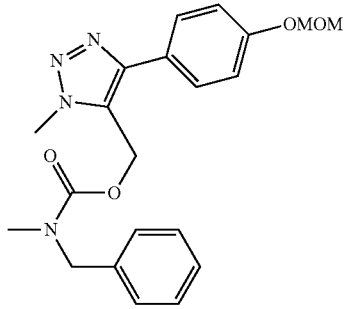

10-6

Compound 10-4 (380 mg, 0.92 mmol) and N,N-diisopropylethylamine (356 mg, 2.76 mmol) were added to anhydrous tetrahydrofuran (10 mL), and then N-methylbenzylamine (167 mg, 1.38 mmol) was added. The reaction system was reacted at room temperature overnight and extracted with ethyl acetate (30 mL×2). The organic phase was washed with saturated brine (30 mL), dried over anhydrous sodium sulfate and concentrated, and the residue was separated by column chromatography (PE/EA=1/1) to give Compound 10-6 (300 mg, 82% yield) in the form of a colorless oil. LC-MS [M+H]$^+$: 397.2.

Step (4): Preparation of(4-(4-hydroxyphenyl)-1-methyl-1H-1,2,3-triazol-5-yl)methylbenzyl(methyl) carbamate

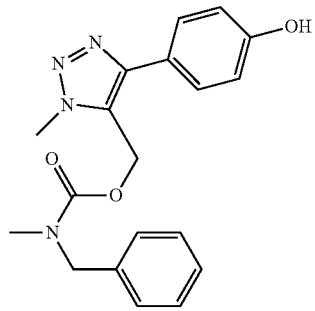

10-7

Compound 10-6 (300 mg, 0.76 mmol) was dissolved in dichloromethane (8 mL), and then a solution of HCl in methanol (1 mL) was added dropwise at room temperature. The reaction system was stirred at room temperature for 2 h and then concentrated to give Compound 10-7 (200 mg, 75% yield) in the form of a colorless oil. LC-MS [M+H]$^+$: 353.2.

Step (5): Preparation of ethyl (E)-3-(4-(5-(((benzyl (methyl)carbamoyl)oxo)methyl)-1-methyl-1H-1,2,3-triazol-4-yl)phenoxy)acrylate

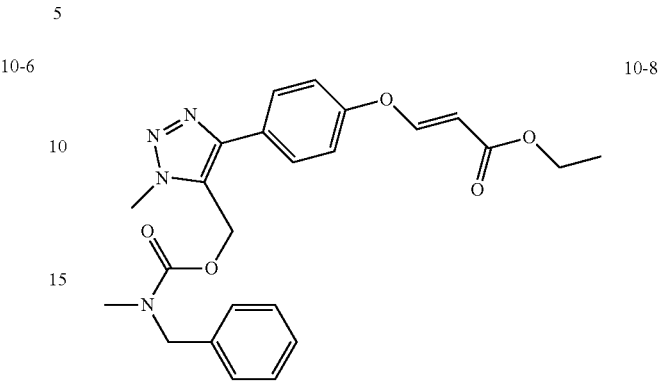

10-8

Compound 10-7 (70 mg, 0.20 mmol) and triethylenediamine (34 mg, 0.30 mmol) were dissolved in anhydrous tetrahydrofuran (5 mL), and then ethyl propiolate (39 mg, 0.40 mmol) was added, and the reaction system was stirred overnight at room temperature. Then the reaction system was extracted with ethyl acetate (20 mL×2). The organic phases were combined, washed with saturated brine (10 mL), dried over anhydrous sodium sulfate, filtered and concentrated, and the residue was separated by column chromatography (EA/PE=1/1) to give Compound 10-8 (55 mg, 62% yield) in the form of a colorless oil. LC-MS [M+H]$^+$: 451.2.

Step (6): Preparation of (E)-3-(4-(5-(((benzyl (methyl)carbamoyl)oxo)methyl)-1-methyl-1H-1,2,3-triazol-4-yl)phenoxy)acrylic acid

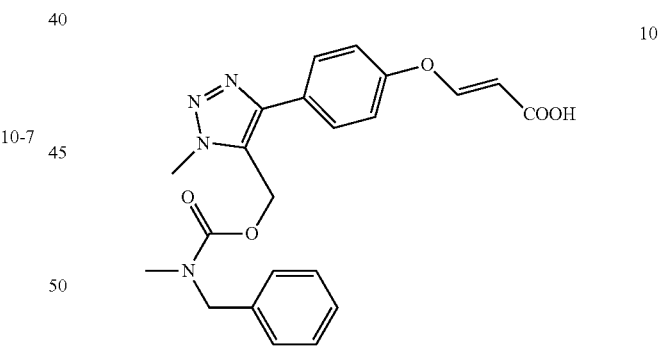

10

Compound 10-8 (55 mg, 0.12 mmol) was dissolved in tetrahydrofuran (2 mL), and then the reaction system was cooled to 0° C., added with aqueous lithium hydroxide solution (0.15 mL, 3 mol/L) dropwise, and stirred overnight at room temperature. The reaction system was then concentrated under reduced pressure, adjusted to pH 3 with diluted HCl (0.5 mL, 1 mol/L) and extracted with ethyl acetate (20 mL×2). After concentration, the residue was separated by preparative reverse phase chromatography (CH$_3$CN (0.1% FA)-H$_2$O (0.1% FA)) to give Compound 10 (23 mg, 45% yield) in the form of a white solid.

LC-MS [M+H]$^+$: 423.1. $^1$H NMR (400 MHz, MeOD) δ 7.96-7.79 (m, 2H), 7.75 (d, J=7.8 Hz, 1H), 7.24 (ddd, J=56.9, 31.0, 18.4 Hz, 7H), 5.58 (d, J=12.1 Hz, 1H), 5.43 (d, J=24.0 Hz, 2H), 4.48 (s, 2H), 4.17 (d, J=58.6 Hz, 3H), 2.88 (d, J=55.3 Hz, 3H).

Example 11

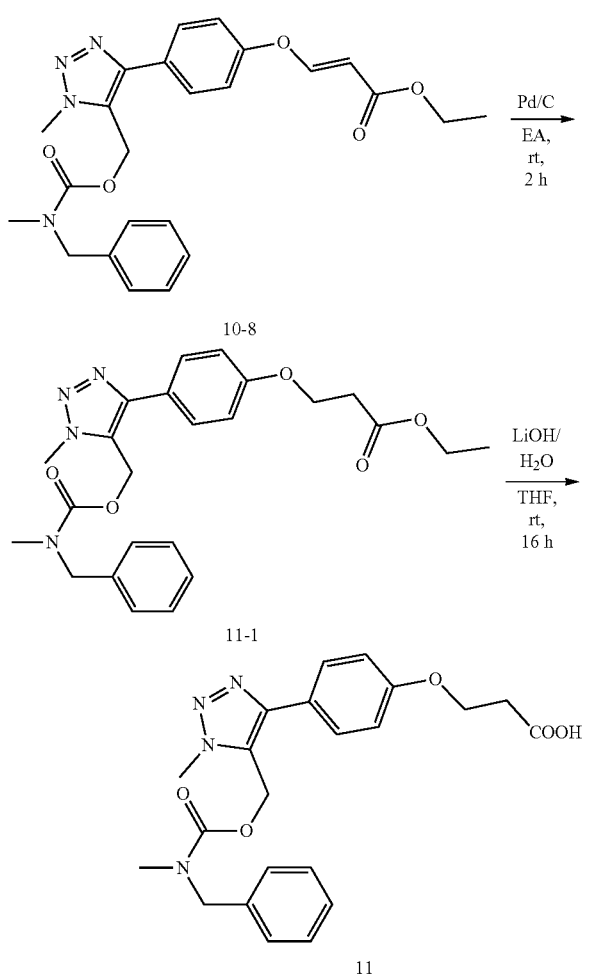

Step (1): Preparation of ethyl 3-(4-(5-(((benzyl (methyl)carbamoyl)oxo)methyl)-1-methyl-1H-1,2,3-triazol-4-yl)phenoxy)propionate

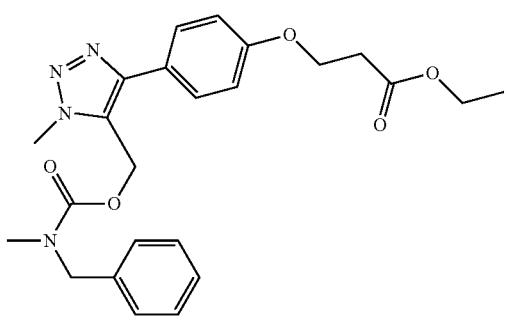

Compound 10-8 (200 mg, 0.44 mmol) was dissolved in ethyl acetate (8 mL), then palladium on carbon (20 mg) was added. Hydrogen was introduced, and then the reaction system was stirred at room temperature for 2 h, and filtered, and the filtrate was concentrated to give Compound 11-1 (190 mg, 94% yield) in the form of a colorless oil. LC-MS [M−H]+: 453.3.

Step (2): Preparation of 3-(4-(5-(((benzyl(methyl) carbamoyl)oxo)methyl)-1-methyl-1H-1,2,3-triazol-4-yl)phenoxy)propionic acid

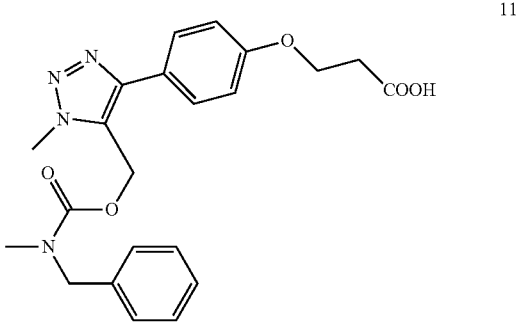 [SMILES: CN(Cc1ccccc1)C(=O)OCc1c(-c2ccc(OCCC(=O)O)cc2)nnn1C]

Compound 11-1 (190 mg, 0.42 mmol) was dissolved in tetrahydrofuran (5 mL), and then the reaction system was cooled to 0° C., added with aqueous lithium hydroxide solution (0.4 mL, 3 mol/L) dropwise, and stirred overnight at room temperature. The reaction system was then concentrated under reduced pressure, adjusted to pH 3 with diluted HCl (1.5 mL, 1 mol/L) and extracted with ethyl acetate (30 mL×2). After concentration, the residue was separated by preparative reverse phase chromatography (CH$_3$CN (0.1% FA)-H$_2$O (0.1% FA)) to give Compound 11 (42 mg, 23% yield) in the form of a white solid.

LC-MS [M+H]+: 425.2. $^1$H NMR (400 MHz, MeOD) δ 7.72-7.53 (m, 2H), 7.28 (t, J=16.7 Hz, 4H), 7.16-6.92 (m, 3H), 5.40 (d, J=22.2 Hz, 2H), 4.47 (d, J=8.3 Hz, 2H), 4.28 (s, 2H), 4.14 (d, J=61.5 Hz, 3H), 2.84 (dd, J=36.3, 30.5 Hz, 5H).

Example 12

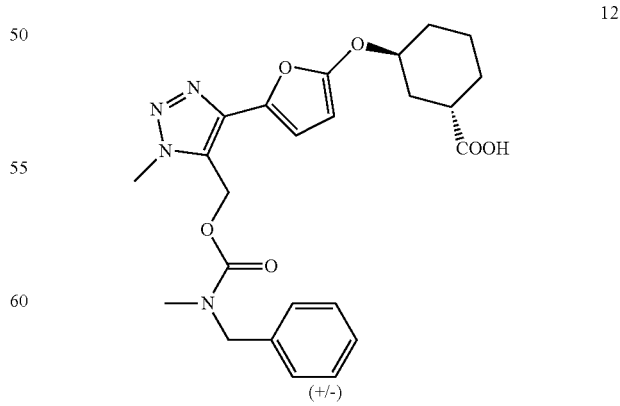

Refer to the synthesis procedures in Example 13 below, LC-MS [M+H]+: 469.4.

Example 13
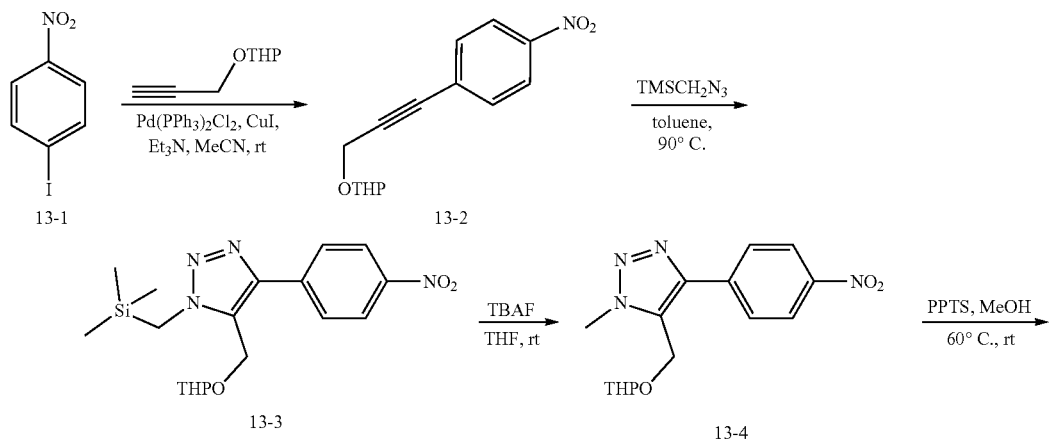
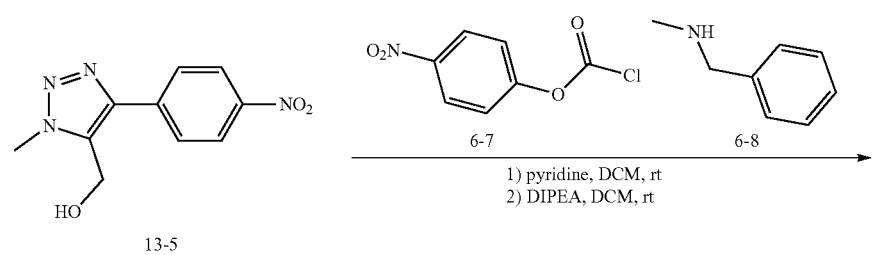
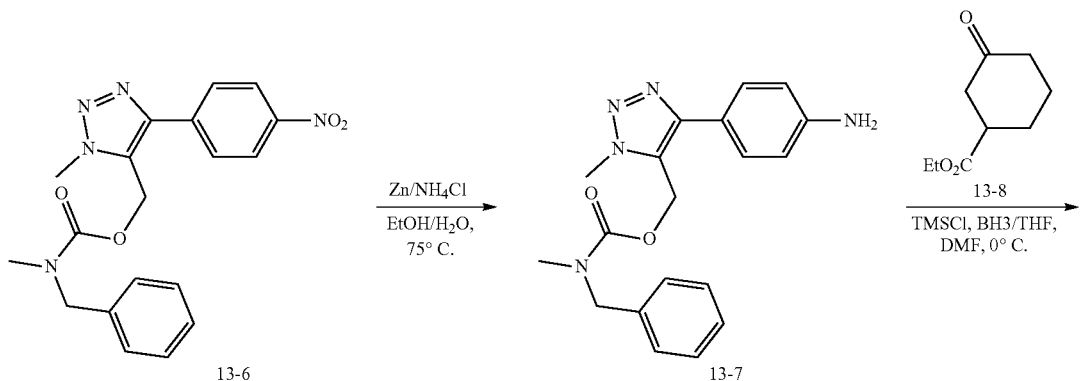
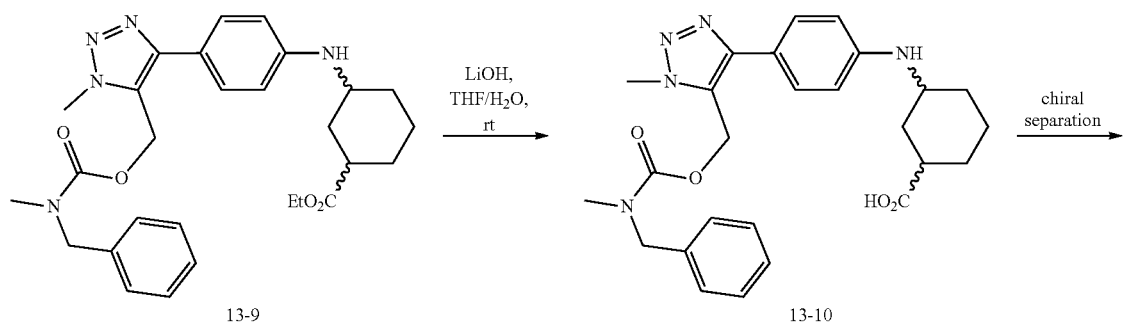

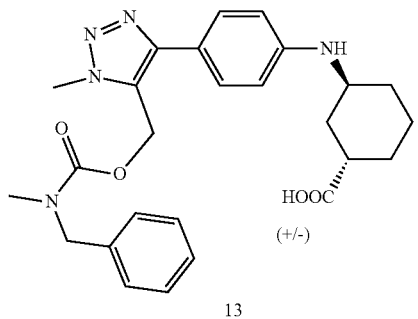

13

Step (1): Preparation of 2-((3-(4-nitrophenyl)prop-2-yn-1-yl)oxo)tetrahydro-2H-pyran

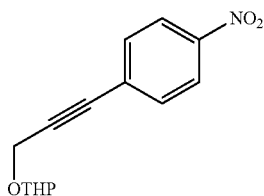

13-2

1-iodo-4-nitrobenzene (5 g, 20 mmol) and 2-(prop-2-yn-1-oxy)tetrahydro-2H-pyran (4.2 g, 30 mmol) were dissolved in acetonitrile (10 mL), and then bis(triphenylphosphine)palladium(II) chloride (702 g, 1 mmol), triethylamine (4.2 g, 60 mmol) and copper(I) iodide (191 mg, 1 mmol) were added, and the reaction system was reacted overnight at room temperature. After the reaction was completed, the reaction system was filtered, concentrated, added with water (50 mL) and extracted with ethyl acetate (30 mL×3). The organic phases were combined, washed with saturated brine (100 mL×1), dried over anhydrous sodium sulfate and filtered, and the filtrate was dried by rotary evaporation, and the residue was purified by column chromatography (PE/EA=20/1) to give Compound 13-2 (3.6 g, 68% yield) in the form of a yellow oil. MS [M+H]$^+$: 262.4.

Step (2): Preparation of 4-(4-nitrophenyl)-5-(((tetrahydro-2H-pyran-2-yl)oxo)methyl)-1-((trimethylsilyl)methyl)-1H-1,2,3-triazole

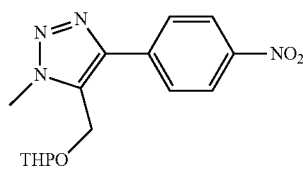

13-3

Compound 13-2 (3.1 g, 11.865 mmol) and trimethylsilylmethyl azide (4.6 g, 36.595 mmol) were dissolved in anhydrous toluene (50 mL). After reaction at 90° C. for 4 days, the reaction system was concentrated to remove the toluene, added with water (60 mL) and extracted with ethyl acetate (40 mL×3). The organic phases were combined, washed with saturated brine (150 mL), dried over anhydrous sodium sulfate and filtered, and the filtrate was dried by rotary evaporation to give a crude product, which was separated by column chromatography (PE/EA=40/1) to give Compound 13-3 (1 g, 21% yield) in the form of a white solid. MS [M+H]$^+$: 390.8.

Step (3): Preparation of 1-methyl-4-(4-nitrophenyl)-5-(((tetrahydro-2H-pyran-2-yl)oxo)methyl)-1H-1,2,3-triazole

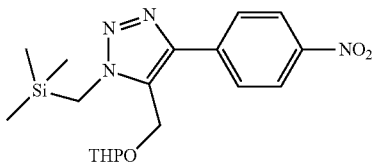

13-4

Compound 13-3 (960 mg, 2.4583 mmol) was added to anhydrous tetrahydrofuran (10 mL), and then tetrabutylammonium fluoride (2.5 mL, 1 M) was added, and the reaction system was stirred at room temperature for 1 h. The reaction system was then diluted with water (30 mL) and extracted with ethyl acetate (15 mL×3). The organic phases were combined, dried over anhydrous sodium sulfate and concentrated, and the residue was separated by column chromatography (PE/EA=3/1) to give Compound 13-4 (530 mg, 67% yield) in the form of a yellow solid. LC-MS [M+H]$^+$: 318.8.

Step (4): (1-methyl-4-(4-nitrophenyl)-1H-1,2,3-triazol-5-yl)methanol

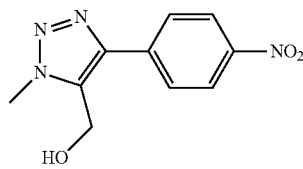

13-5

Compound 13-4 (500 mg, 1.57 mmol) and pyridinium p-toluenesulfonate (395 mg, 1.57 mmol) were dissolved in absolute methanol (10 mL), and the reaction system was stirred overnight at 60° C.

Then the reaction system was concentrated to remove methanol, diluted with water (15 mL), and extracted with ethyl acetate (10 mL×3). The organic phases were combined, washed with saturated brine, dried over anhydrous sodium sulfate and concentrated, and the residue was separated by column chromatography (PE/EA=10/1-3/1) to give Compound 13-5 (300 mg) in the form of a yellow oil. LC-MS [M+H]⁺: 234.8.

Step (5): Preparation of (1-methyl-4-(4-nitrophenyl)-1H-1,2,3-triazol-5-yl)methylbenzyl(methyl)carbamate

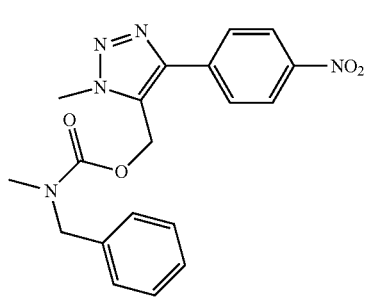

13-6

Compound 13-5 (290 mg, 1.2382 mmol) and pyridine (489 mg, 6.1910 mmol) were dissolved in dichloromethane (5 mL) under nitrogen atmosphere, and then the reaction system was cooled to 0° C., added with 4-nitrophenyl chloroformate (345 mg, 1.7146 mmol), and then warmed to room temperature and stirred for 2 h. Then the reaction system was added with N-methylbenzylamine (900 mg, 7.4292 mmol) and diisopropylethylamine (320 mg, 2.4764 mmol) and stirred overnight at room temperature. The reaction system was then washed with saturated brine, and the organic phase was dried over anhydrous sodium sulfate and concentrated, and the residue was separated by thin layer chromatography (PE/EA=1/1) to give Compound 13-6 (208 mg, 44% yield) in the form of a yellow oil. LC-MS [M+H]⁺: 382.8.

Step (6): Preparation of (4-(4-aminophenyl)-1-methyl-1H-1,2,3-triazol-5-yl)methylbenzyl(methyl)carbamate

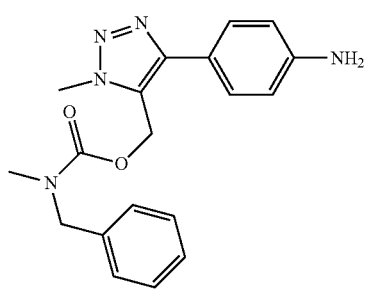

13-7

Compound 13-6 (180 mg, 0.472 mmol) was dissolved in ethanol (5 mL) and water (1 mL), and then zinc powder (309 mg, 4.72 mmol) and ammonium chloride (76 mg, 1.416 mmol) were added, and the reaction system was stirred under reflux for 6 h. The reaction system was then cooled to room temperature, diluted with water (20 mL), and extracted with ethyl acetate (10 mL×3). The organic phases combined, washed with saturated brine, dried over anhydrous sodium sulfate and concentrated, and the residue was separated by column chromatography (PE/EA=2/1-1/1) to give Compound 13-7 (140 mg, 84% yield) in the form of a yellow solid. LC-MS [M+H]⁺: 352.8.

Step (7): Preparation of ethyl 3-((4-(5-(((benzyl(methyl)carbamoyl)oxo)methyl)-1-methyl-1H-1,2,3-triazol-4-yl)phenyl)amino)cyclohexanecarboxylate

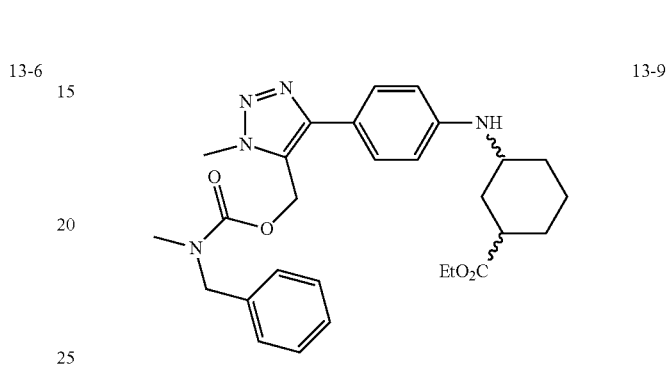

13-9

Compound 13-7 (110 mg, 0.313 mmol), trimethylchlorosilane (85 mg, 0.7825 mmol) and ethyl 3-carbonylcyclohexanecarboxylate (59 mg, 0.344 mmol) were added to anhydrous DMF (5 mL), and under nitrogen atmosphere, the reaction system was cooled to 0° C., slowly added with a solution of borane in tetrahydrofuran (0.3 mL, 1 M), and reacted at 0° C. for 1 h. Then the reaction system was quenched with saturated aqueous sodium carbonate solution (15 mL), stirred for 10 min, and then extracted with ethyl acetate (10 mL×3). The organic phases were combined, dried over anhydrous sodium sulfate and concentrated, and the residue was separated by thin layer chromatography (PE/EA=1/1) to give Compound 13-9 (100 mg, 63% yield) in the form of a yellow oil. LC-MS [M−H]⁺: 506.9.

Step (8): Preparation of (+/−)-3-((4-(5-(((benzyl(methyl)carbamoyl)oxo)methyl)-1-methyl-1H-1,2,3-triazol-4-yl)phenyl)amino)cyclohexanecarboxylic acid

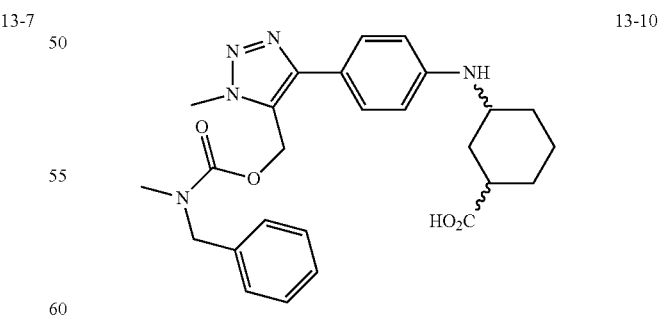

13-10

Compound 13-9 (100 mg, 0.1978 mmol) and lithium hydroxide (25 mg, 0.5934 mmol) were dissolved in tetrahydrofuran (3 mL) and water (3 mL). After reaction at room temperature for 10 h, the reaction system was concentrated, adjusted to pH 3 with diluted HCl (1 N), and then extracted with ethyl acetate (10 mL×3). The organic phases were combined, dried over anhydrous sodium sulfate and concentrated, and the residue was separated by preparative HPLC to give Compound 13-10 (80 mg, 70% yield) in the form of a white solid. LC-MS [M−H]⁻: 476.7.

Step (9)

3-((4-(5-(((benzyl(methyl)carbamoyl)oxo)methyl)-1-methyl-1H-1,2,3-triazol-4-yl)phenyl)amino)cyclohexanecarboxylic acid was separated by chiral HPLC to give Compound 13 (50.1 mg).

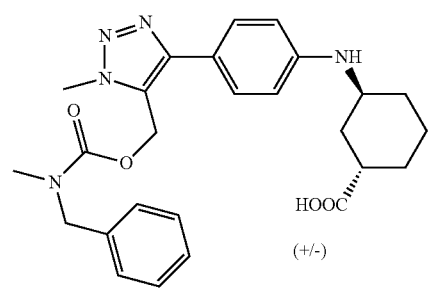

¹H NMR (400 MHz, CDCl₃) δ 7.57 (dd, J=26.4, 8.0 Hz, 2H), 7.34 (dd, J=15.7, 7.0 Hz, 3H), 7.27 (d, J=7.3 Hz, 1H), 7.14 (d, J=6.5 Hz, 1H), 6.65 (dd, J=23.9, 7.8 Hz, 2H), 5.33 (d, J=22.1 Hz, 2H), 4.48 (d, J=29.8 Hz, 2H), 4.10 (d, J=66.0 Hz, 3H), 3.34 (s, 1H), 2.92 (d, J=55.8 Hz, 3H), 2.49 (dd, J=25.8, 13.7 Hz, 2H), 2.16 (d, J=12.1 Hz, 1H), 2.11-2.01 (m, 1H), 1.95 (dd, J=9.8, 2.8 Hz, 1H), 1.45 (dd, J=20.3, 11.5 Hz, 2H), 1.33 (t, J=8.2 Hz, 1H), 1.14 (d, J=11.6 Hz, 1H).

Example 14

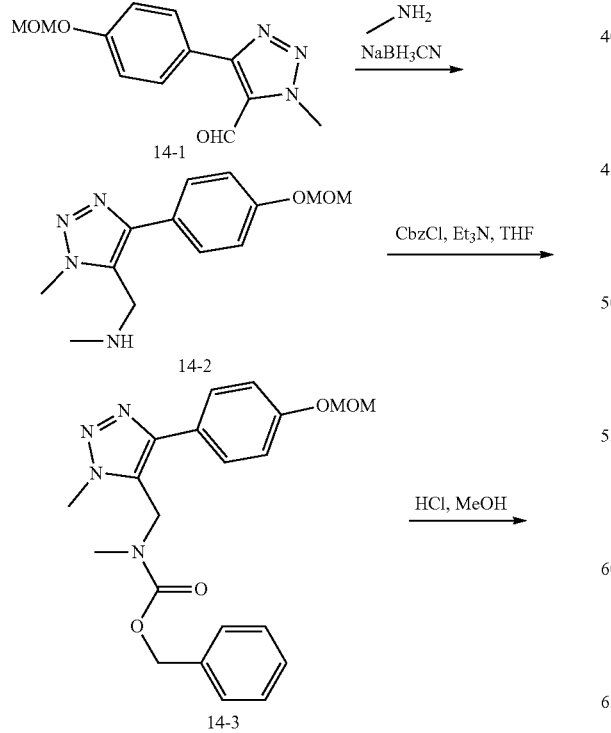

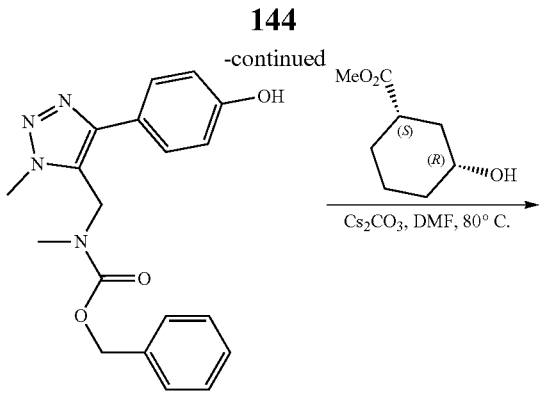

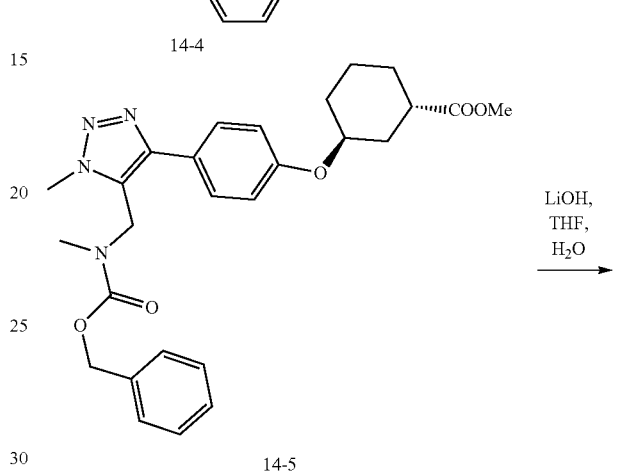

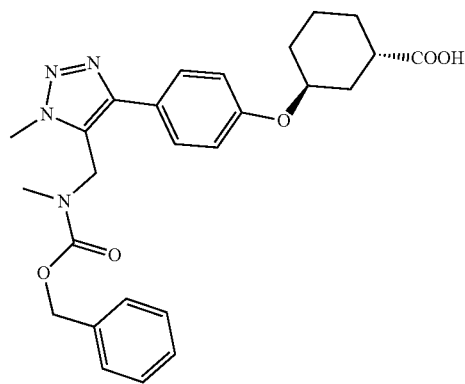

Step (1): Preparation of 1-(4-(4-(methoxymethoxy)phenyl)-1-methyl-1H-1,2,3-triazol-5-yl)-N-methylmethylamine

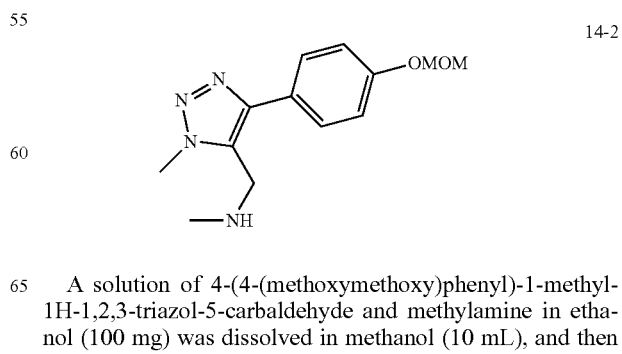

A solution of 4-(4-(methoxymethoxy)phenyl)-1-methyl-1H-1,2,3-triazol-5-carbaldehyde and methylamine in ethanol (100 mg) was dissolved in methanol (10 mL), and then the reaction system was stirred at room temperature for 2 h, added successively with sodium cyanoborohydride and saturated sodium bicarbonate (48 mg, 0.75 mmol), and reacted at room temperature for 10 h. Then the reaction system was concentrated, and the residue was separated by column chromatography (DCM/MeOH=40/1) to give Compound 14-2 (120 mg, 90% yield) in the form of a yellow solid. LC-MS [M+H]$^+$: 263.6.

Step (2): Preparation of benzyl ((4-(4-(methoxymethoxy)phenyl)-1-methyl-1H-1,2,3-triazol-5-yl) methyl)(methyl)carbamate

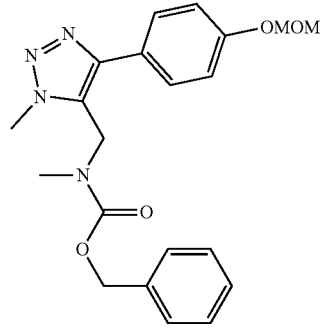

14-3

Compound 14-2 (120 mg, 0.46 mmol) and diisopropylethylamine (89 mg, 0.69 mmol) were dissolved in tetrahydrofuran (5 mL), and then benzyl chloroformate (86 mg, 0.5 mmol) was added, and the reaction system was heated to reflux and reacted for 16 h. Then the reaction system was concentrated, and the residue was separated by column chromatography (DCM/MeOH=30/1) to give Compound 14-3 (160 mg, 95% yield) in the form of a yellow solid. LC-MS [M+H]$^+$: 397.2.

Step (3): Preparation of benzyl ((4-(4-hydroxyphenyl)-1-methyl-1H-1,2,3-triazol-5-yl)methyl) (methyl)carbamate

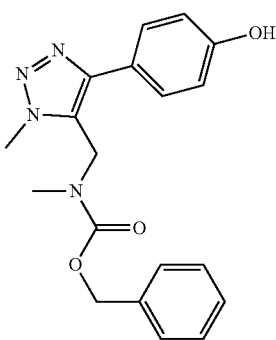

14-4

Compound 14-3 (160 mg, 0.45 mmol) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=20/1) to give Compound 14-4 (140 mg, 87% yield) in the form of a yellow solid. LC-MS [M+H]$^+$: 353.3.

Step (4): Preparation of methyl (1S,3S)-3-(4-(5-((((benzyloxy)carbonyl)(methyl)amino)methyl)-1-methyl-1H-1,2,3-triazol-4-yl)phenoxy)cyclohexane-1-carboxylate

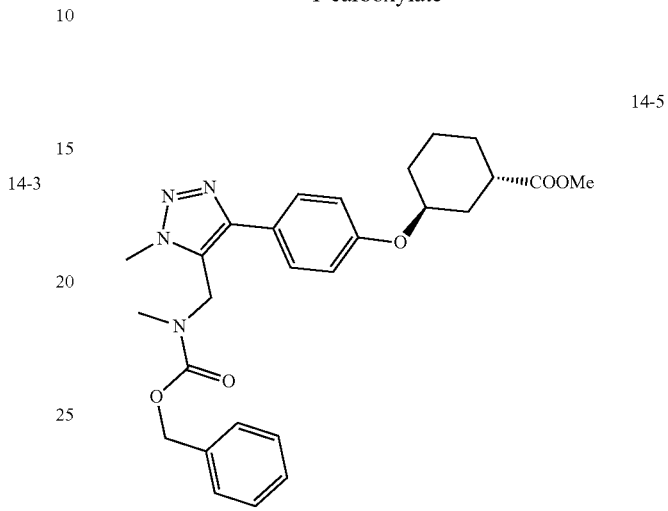

14-5

Compound 14-4 (110 mg, 0.31 mmol), methyl (1S,3R)-3-(tosyloxy)cyclohexane-1-carboxylate (198 mg, 1.25 mmol), DTAD (288 mg, 1.25 mmol) and PPh$_3$ (328 mg, 1.25 mmol) were dissolved in THF (15 mL), and the reaction system was stirred overnight at room temperature under nitrogen atmosphere. Then the reaction system was purified by silica gel column chromatography (DCM/EA=5/1) to give Compound 14-5 (260 mg) in the form of a yellow solid. LC-MS [M+H]$^+$: 521.5.

Step (5): Preparation of (1S,3S)-3-(4-(5-((((benzyloxy)carbonyl)(methyl)amino)methyl)-1-methyl-1H-1,2,3-triazol-4-yl)phenoxy)cyclohexane-1-carboxylic acid

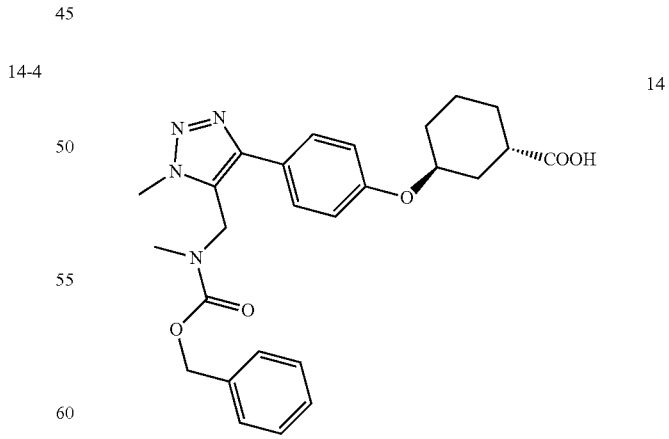

14

Compound 14-5 (260 mg, crude product) was dissolved in THF (9 mL), and MeOH (3 mL), H$_2$O (3 mL) and lithium hydroxide (42 mg, 1.0 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation. The residue was purified by silica gel column chromatography (DCM/MeOH=20/1) and then lyophilized to give Compound 14 (20 mg) in the form of a white solid.

LC-MS [M+H]$^+$: 479.4. $^1$H NMR (400 MHz, MeOD) δ 7.49-7.47 (m, 2H), 7.38-7.34 (m, 5H), 7.03 (d, J=8.3 Hz, 2H), 5.12 (s, 2H), 4.84 (s, 2H), 4.72 (s, 1H), 4.03 (s, 3H), 2.79-2.77 (m, 1H), 2.66 (s, 3H), 2.07-2.05 (m, 1H), 1.98-1.85 (m, 3H), 1.82-1.53 (m, 4H).

Example 15

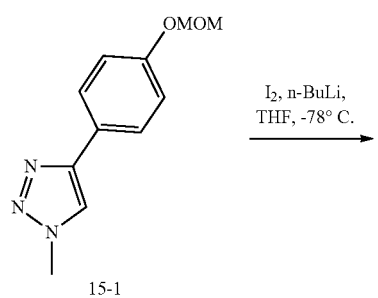
15-1

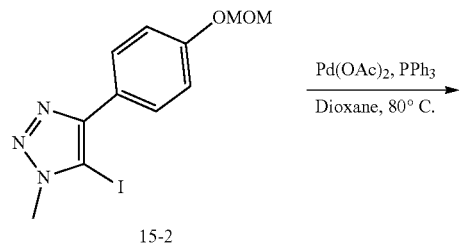
15-2

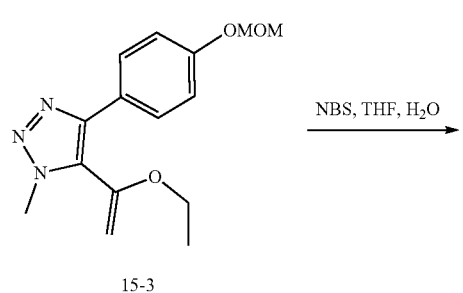
15-3

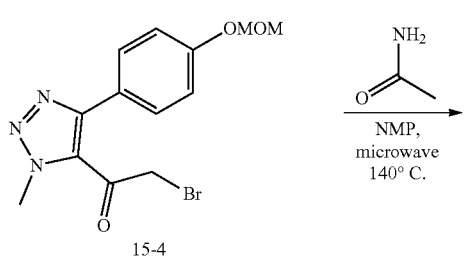
15-4

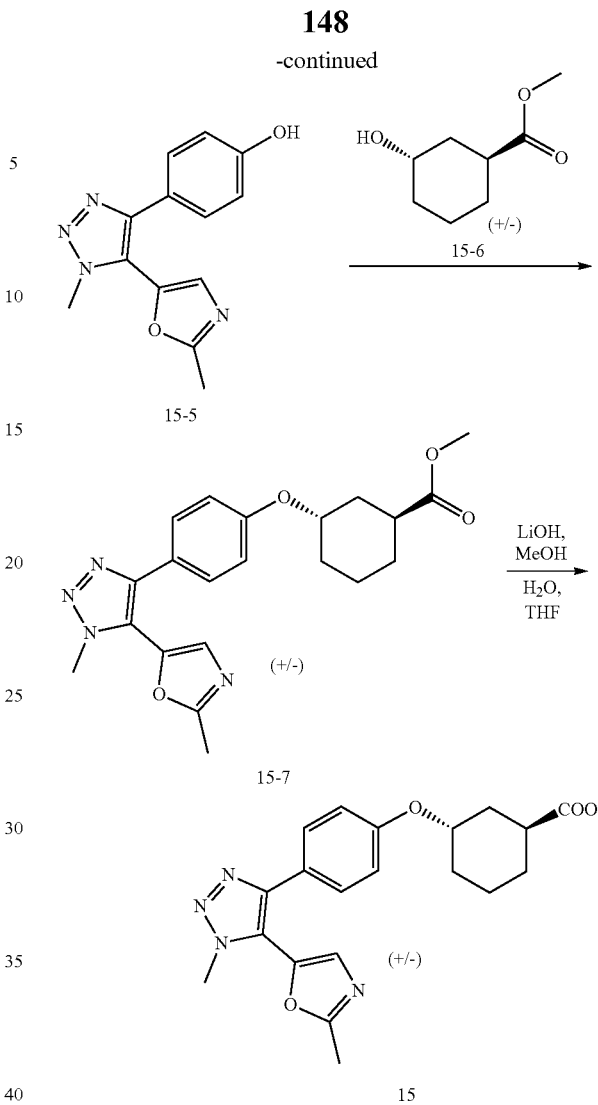

Step (1): Preparation of 5-iodo-4-(4-(methoxymethoxy)phenyl)-1-methyl-1H-1,2,3-triazole

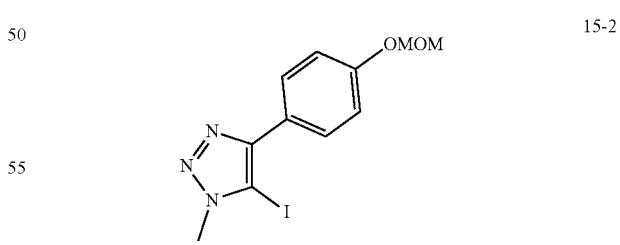
15-2

Compound 15-1 (2 g, 9.1 mmol) was dissolved in tetrahydrofuran (25 mL), and then the reaction system was cooled to −78° C., added with n-butyl lithium (2.4 N, 5.7 mL, 13.7 mmol) under nitrogen atmosphere and stirred at this temperature for 10 min. the reaction system was then added with iodine (3.5 g, 13.7 mmol) and stirred overnight at this temperature. Then the reaction system was quenched with water (50 mL), extracted with ethyl acetate (25 mL×3), and washed with saturated sodium chloride solution (20 mL×2). The organic phase was dried over anhydrous sodium sulfate and filtered. The filtrate was dried by rotary evaporation, and the residue was purified by silica gel column chromatography (PE/EA=3/1) to give Compound 15-2 (1.3 g, 41.41% yield) in the form of a white solid. LC-MS [M+H]+: 346.8.

Step (2): Preparation of 5-(1-ethoxyvinyl)-4-(4-(methoxymethoxy)phenyl)-1-methyl-1H-1,2,3-triazole

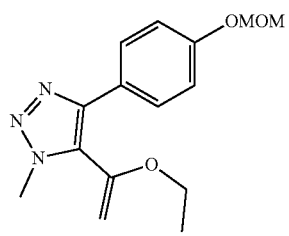

Compound 15-2 (1.3 g, 3.76 mmol), tributyl(1-ethoxyvinyl)tin (1.5 g, 4.14 mmol), palladium acetate (42 mg, 0.19 mmol) and triphenylphosphine (197 mg, 0.75 mmol) were dissolved in 1,4-dioxane (25 mL), and then the reaction system was stirred overnight at 80° C., quenched with water (30 mL), and extracted with ethyl acetate (20 mL×3). The organic phase was washed with saturated brine (20 mL), dried over anhydrous sodium sulfate and filtered, and the filtrate was dried by rotary evaporation. The residue was purified by silica gel column chromatography (PE/EA=5/1) to give Compound 15-3 (1 g, 83.57% yield) in the form of a white solid. LC-MS [M+H]+: 290.9.

Step (3): 2-bromo-1-(4-(4-(methoxymethoxy)phenyl)-1-methyl-1H-1,2,3-triazol-5-yl)ethan-1-ol

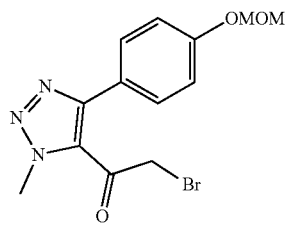

Compound 15-3 (1 g, 3.46 mmol) and N-bromosuccinimide (677 mg, 3.81 mmol) were dissolved in a mixed solvent of tetrahydrofuran (25 mL) and water (5 mL) under nitrogen atmosphere, and then the reaction system was stirred at room temperature for 1 h, diluted with water (20 mL) and extracted with ethyl acetate (15 mL×3). The organic phases were combined, washed with saturated brine (20 mL), dried over anhydrous sodium sulfate and filtered, and the filtrate was dried by rotary evaporation The crude product was purified by silica gel column chromatography (PE/EA=5/1) to give Compound 15-4 (480 mg, 47.31% yield) in the form of a brown solid. LC-MS [M+H]+: 339.6, 341.6.

Step (4): Preparation of 4-(1-methyl-5-(2-methyloxazol-5-yl)-1H-1,2,3-triazol-4-yl)phenol

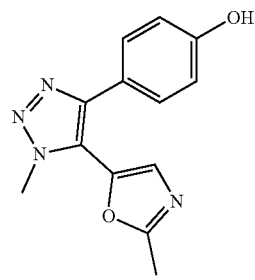

Compound 15-4 (230 mg, 0.68 mmol) and acetamide (828 mg, 14.02 mmol) were added to a microwave tube, and then the reaction system was heated in microwave at 160° C. for 30 min, cooled to room temperature, quenched with water (10 mL), and extracted with ethyl acetate (5 mL×3). The organic phase was dried over anhydrous sodium sulfate and filtered, and the filtrate was dried by rotary evaporation. The residue was purified by silica gel column chromatography (DCM/EA=2/1) to give Compound 15-5 (130 mg, 74.68% yield) in the form of a brown solid. LC-MS [M+H]+: 257.9.

Step (5): (+/−)-methyl (1S,3S)-3-(4-(1-methyl-5-(2-methyloxazol-5-yl)-1H-1,2,3-triazol-4-yl) phenoxy) cyclohexane-1-carboxylate

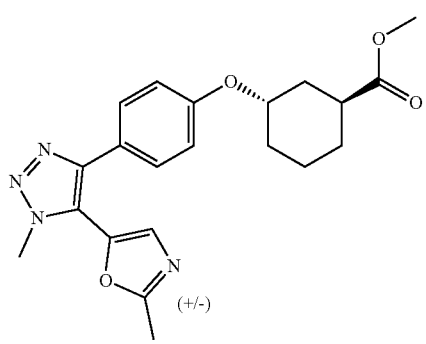

Compound 15-5 (100 mg, 0.51 mmol), methyl (3S)-3-hydroxycyclohexane-1-carboxylate (320 mg, 2.03 mmol), DTAD (466 mg, 2.03 mmol) and triphenylphosphine (532 mg, 2.03 mmol) were dissolved in tetrahydrofuran (20 mL), and then the reaction system was stirred overnight at room temperature, quenched with water (20 mL), extracted with ethyl acetate (15 mL×3), and washed with saturated sodium chloride solution (20 mL). The organic phase was dried over anhydrous sodium sulfate and filtered. The filtrate was dried by rotary evaporation, and the residue was purified by silica gel column chromatography (DCM/EA=5/1) to give Compound 15-7 (178 mg, 88.14% yield) in the form of a white solid. LC-MS [M+H]+: 397.8.

Step (7): (+/−)-(1S,3S)-3-(4-(1-methyl-5-(2-methyl-oxazol-5-yl)-1H-1,2,3-triazol-4-yl)phenoxy) cyclohexane-1-carboxylic acid

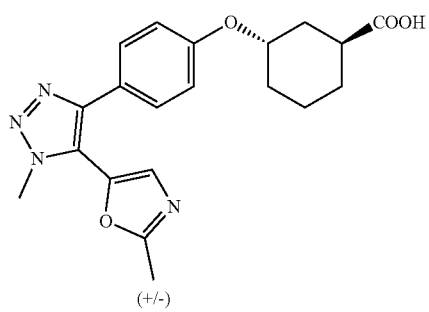

(+/−)

Compound 15-7 (178 mg, 0.45 mmol) was dissolved in a mixed solution of tetrahydrofuran (3 mL), methanol (1 mL) and water (1 mL), and then an aqueous lithium hydroxide solution was added, and the reaction system was stirred overnight at room temperature. Water (10 mL) was added to quench the reaction, and the organic solvent was removed by rotary evaporation. The reaction system was then adjusted to pH 2-3 with diluted HCl (1 N) and extracted with ethyl acetate (20 mL×3). The organic phase was dried over anhydrous sodium sulfate and filtered, and the filtrate was dried by rotary evaporation. The residue was purified by silica gel column chromatography (DCM/EA=1/1) and lyophilized to give Compound 15 (10 mg, 36.95% yield) in the form of a white solid.

LC-MS [M+H]$^+$: 383.7.

$^1$H NMR (400 MHz, MeOD) δ 8.04 (s, 1H), 7.53 (d, 2H), 7.01 (d, J=8.8 Hz, 2H), 4.74-4.70 (m, 1H), 4.12 (s, 3H), 2.82-2.77 (m, J=9.5 Hz, 1H), 2.56 (s, 3H), 2.09-2.04 (m, J=13.1 Hz, 1H), 1.94-1.87 (m, J=10.4 Hz, 3H), 1.81-1.74 (m, J=12.0 Hz, 1H), 1.69-1.59 (m, 3H).

Example 16

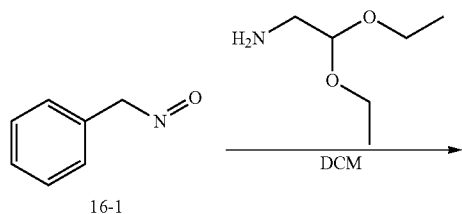

16-1

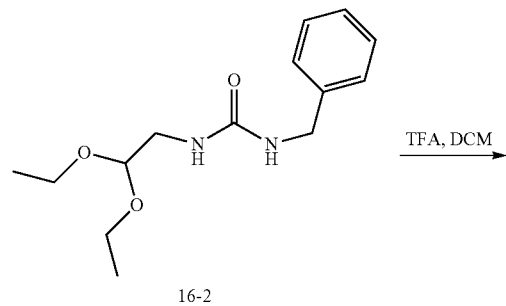

16-2

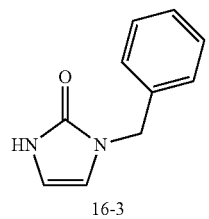

16-3

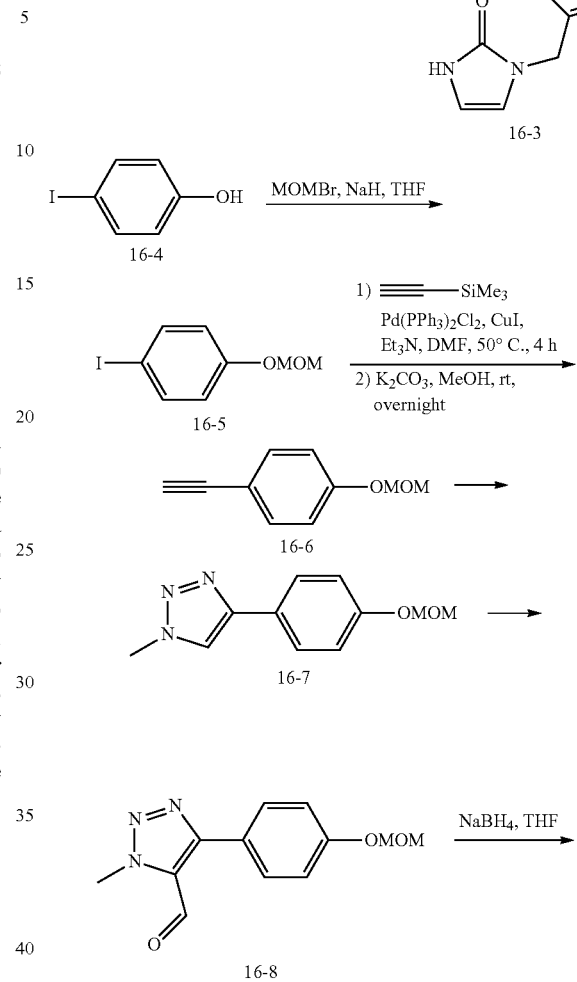

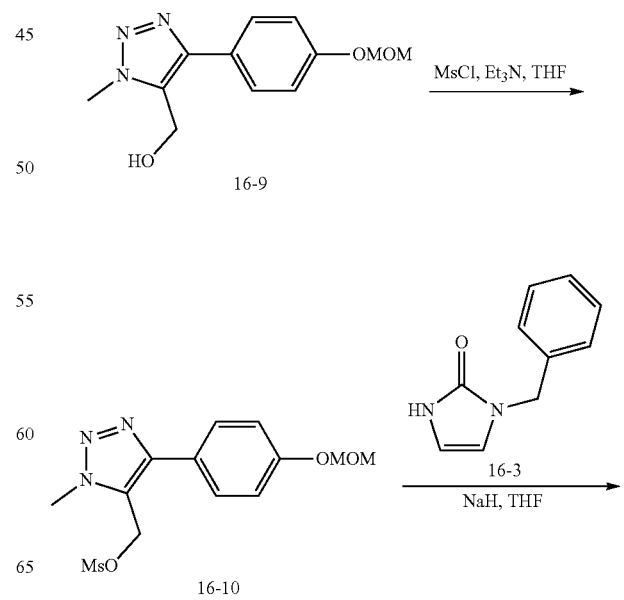

153
-continued

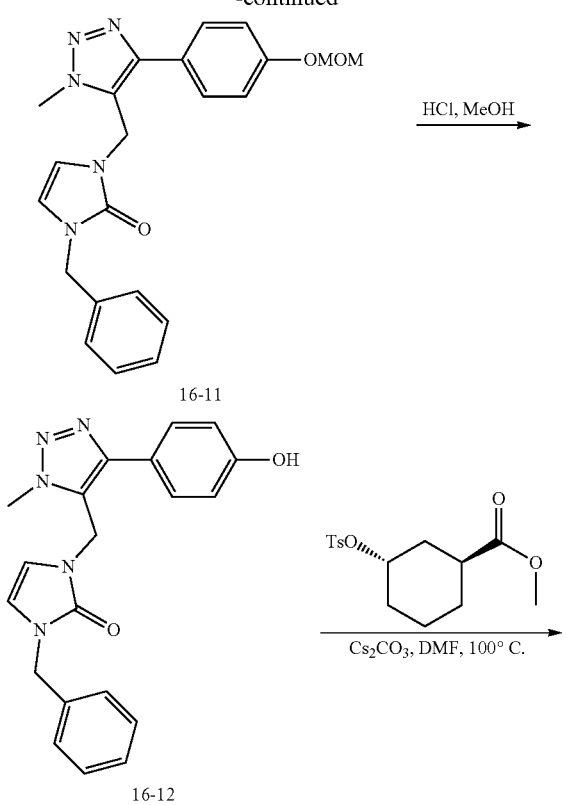

16-11

16-12

16-13

16

154

Step (1): Preparation of
1-benzyl-1,3-dihydro-2H-imidazol-2-one

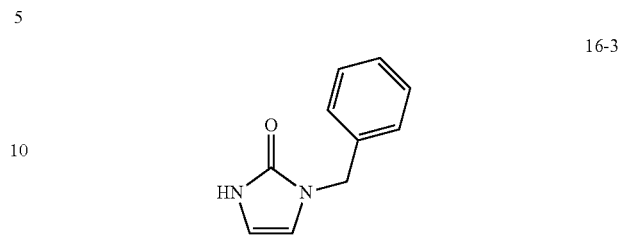

16-3

(isocyanatomethyl)benzene (2.0 g, 15 mmol) and 2,2-diethoxyethan-1-amine (2.0 g, 15 mmol) were dissolved in dichloromethane (20 mL). After reaction for 3 h, the reaction system was added dropwise with trifluoroacetic acid (2 mL) and then reacted at room temperature for another 3 h. The reaction system was then quenched with water (20 mL), and extracted with ethyl acetate (25 mL×3). The organic phases were combined, washed with saturated brine (20 mL), dried over anhydrous sodium sulfate and concentrated, and the residue was separated by column chromatography (PE/EA=5/1) to give Compound 16-3 (180 mg, 57.7% yield) in the form of a white solid. LC-MS [M+H]$^+$: 349.4.

Step (2): Preparation of
1-iodo-4-(methoxymethoxy)benzene

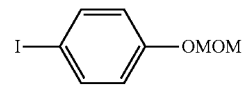

16-5 p-iodophenol (30.0 g, 136.4 mmol) was dissolved in tetrahydrofuran (300 mL), and then the reaction system was cooled to 0° C., added with sodium hydride (9.8 g, 163.6 mmol) in portions, and maintained at this temperature. After reaction for 20 min, the reaction system was added dropwise with bromomethyl methyl ether (17.8 g, 143.2 mmol) and then reacted for 2 h. The reaction system was then quenched with ammonium chloride solution (200 mL), and extracted with ethyl acetate (250 mL×3). The organic phases were combined, washed with saturated brine (200 mL), dried over anhydrous sodium sulfate, and concentrated to give Compound 16-5 (30.0 g) in the form of a yellow oil.

Step (3): Preparation of
1-ethynyl-4-(methoxymethoxy)benzene

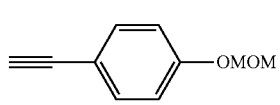

16-6

Compound 16-5 (30 g, 113.7 mmol), trimethylsilylacetylene (13.4 g, 136.3 mmol), Pd(PPh$_3$)Cl$_2$ (2.5 g, 3.5 mmol), copper(I) iodide (1.3 g, 6.8 mmol) and triethylamine (45.8 g, 544.7 mmol) were dissolved in DMF (30 mL), and then the reaction system was reacted at 50° C. for 4 h, quenched with water (30 mL), and extracted with ethyl acetate (45 mL×3).

The organic phases were combined, washed with saturated brine (20 mL), dried over anhydrous sodium sulfate and concentrated. The resulting solid was dissolved in methanol (30 mL), and then potassium carbonate (24.4 g, 176.7 mmol) was added. The reaction system was reacted overnight at room temperature, quenched with water (30 mL), and extracted with ethyl acetate (45 mL×3). The organic phases were combined, washed with saturated brine (20 mL), dried over anhydrous sodium sulfate and concentrated, and the residue was separated by column chromatography (PE/EA=5/1) to give Compound 16-6 (15 g, 81.1% yield over two steps) in the form of a white solid.

Step (4): Preparation of 4-(4-(methoxymethoxy)phenyl)-1-methyl-1H-1,2,3-triazole

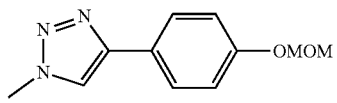

16-7

Compound 16-6 (15.0 g, 92.2 mmol), sodium azide (18 g, 276.8 mmol), iodomethane (39 g, 267.8 mmol), copper sulfate pentahydrate (4.7 g, 18.8 mmol), sodium vitamin C (7.3 g, 36.8 mmol) and potassium carbonate (46.5 g, 461.25 mmol) were dissolved in water and tert-butanol (1/1, 40 mL), and then the reaction system was reacted at room temperature for 24 h, quenched with water (40 mL), and extracted with ethyl acetate (45 mL×3). The organic phases were combined, washed with saturated brine (40 mL), dried over anhydrous sodium sulfate and concentrated, and the residue was separated by column chromatography (PE/EA=5/1) to give Compound 16-7 (25.0 g, 83.3% yield) in the form of a white solid. LC-MS [M+H]$^+$: 220.6.

Step (5): 4-(4-(methoxymethoxy)phenyl)-1-methyl-1H-1,2,3-triazole-5-carbaldehyde

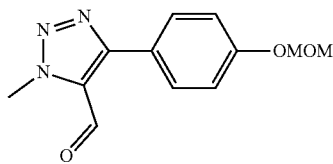

16-8

Compound 16-7 (25.0 g, 114 mmol) was dissolved in tetrahydrofuran (40 mL), and then the reaction system was cooled to −78° C. and slowly added with n-butyl lithium (71.3 mL, 171 mmol) dropwise. After reaction at this temperature for 1 h, the reaction system was added with DMF (12.5 g, 171 mmol) and reacted for 2 h. The reaction system was then quenched with water (40 mL), and extracted with ethyl acetate (45 mL×3). The organic phases were combined, washed with saturated brine (40 mL), dried over anhydrous sodium sulfate and concentrated, and the residue was separated by column chromatography (PE/EA=3/1) to give Compound 16-8 (20.0 g, 71.4% yield) in the form of a white solid. LC-MS [M+H]$^+$: 248.2.

Step (6): Preparation of (4-(4-(methoxymethoxy)phenyl)-1-methyl-1H-1,2,3-triazol-5-yl)methanol

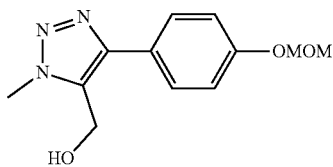

16-9

Compound 16-8 (2.0 g, 8.1 mmol) and sodium borohydride (367 mg, 9.7 mmol) were dissolved in tetrahydrofuran (20 mL), and then the reaction system was reacted overnight at room temperature, quenched with water (20 mL), and extracted with ethyl acetate (30 mL×3). The organic phases were combined, washed with saturated brine (20 mL), dried over anhydrous sodium sulfate and concentrated, and the residue was separated by column chromatography (DCM/MeOH=30/1) to give Compound 16-9 (2.0 g) in the form of a yellow oil.

LC-MS [M+H]$^+$: 250.4.

Step (7): Preparation of (4-(4-(methoxymethoxy)phenyl)-1-methyl-1H-1,2,3-triazol-5-yl)methyl methanesulfonate

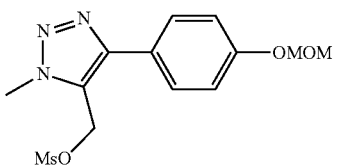

16-10

Compound 16-9 (2.0 g, 8.0 mmol) and triethylamine (2.4 g, 24 mmol) were dissolved in tetrahydrofuran (20 mL), and then the reaction system was cooled to 0° C. and added with methylsulfonyl chloride (2.7 g, 24 mmol) dropwise. The reaction system was then warmed to room temperature, reacted over overnight at room temperature, quenched with water, and extracted with ethyl acetate (30 mL×3). The organic phases were combined, washed with saturated brine (20 mL), dried over anhydrous sodium sulfate, and concentrated to give Compound 16-10 (2.0 g) in the form of a yellow oil. LC-MS [M+H]$^+$: 328.4.

Step (8): 1-benzyl-3-((4-(4-(methoxymethoxy)phenyl)-1-methyl-1H-1,2,3-triazol-5-yl)methyl)-1,3-dihydro-2H-imidazol-2-one

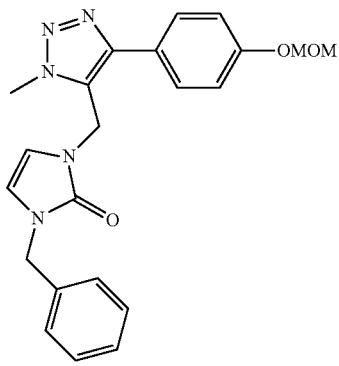

16-11

Compound 16-10 (500 mg, 1.53 mmol) was dissolved in tetrahydrofuran (5 mL), and then the reaction system was cooled to 0° C., slowly added with sodium hydride (180 mg, 4.6 mmol), and maintained at this temperature. After reaction for 20 min, the reaction system was added with 1-benzyl-1,3-dihydro-2H-imidazol-2-one (320 mg, 1.84 mmol) and warmed to room temperature. The reaction system was then reacted overnight at room temperature, quenched with water, and extracted with ethyl acetate (15 mL×3). The organic phase was washed with saturated brine (15 mL), dried over anhydrous sodium sulfate, and concentrated to give Compound 16-11 (500 mg) in the form of a yellow oil. LC-MS [M+H]$^+$: 406.4.

Step (9): Preparation of 1-benzyl-3-((4-(4-hydroxyphenyl)-1-methyl-1H-1,2,3-triazol-5-yl)methyl)-1,3-dihydro-2H-imidazol-2-one

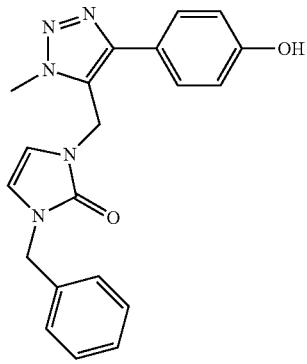

16-12

Compound 16-11 (500 mg, 1.2 mmol) was dissolved in a solution of HCl in methanol (5 mL), and then the reaction system was stirred at room temperature for 2 h and concentrated. The residue was separated by column chromatography (PE/MA=4/1) to give Compound 16-12 (150 mg, 34.6% yield) in the form of a white solid.

Step (10): Preparation of (+/−)-methyl (1S,3S)-3-(4-(5-((3-benzyl-2-carbonyl-2,3-dihydro-1H-imidazol-1-yl)methyl)-1-methyl-1H-1,2,3-triazol-4-yl)phenoxy)cyclohexane-1-carboxylate

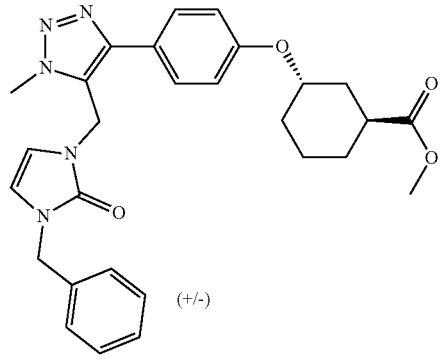

16-13

Compound 16-12 (150 mg, 0.42 mmol), methyl (1S,3S)-3-(tosyloxy)cyclohexane-1-carboxylate (262 mg, 0.84 mmol) and cesium carbonate (273 mg, 0.84 mmol) were dissolved in anhydrous DMF (5 mL), and then the reaction system was warmed to 100° C., reacted for 3 h under nitrogen atmosphere, quenched with water, and extracted with ethyl acetate (15 mL×3). The organic phase was washed with saturated brine (15 mL), dried over anhydrous sodium sulfate and concentrated, and the residue was separated by column chromatography (PE/EA=1/1) to give Compound 16-13 (55 mg, 26.2% yield) in the form of a yellow oil.
LC-MS [M+H]$^+$: 502.2.

Step (11): Preparation of (+/−)-(1S,3S)-3-(4-(5-((3-benzyl-2-carbonyl-2,3-dihydro-1H-imidazol-1-yl)methyl)-1-methyl-1H-1,2,3-triazol-4-yl)phenoxy)cyclohexane-1-carboxylic acid

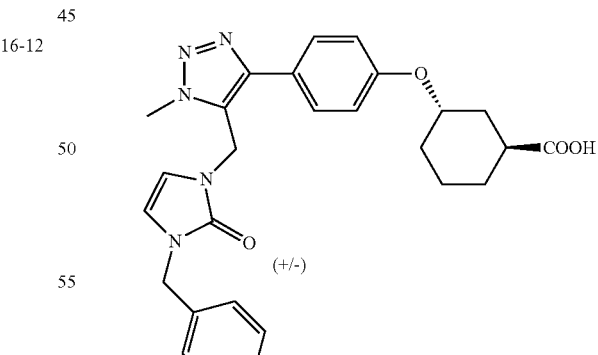

16

Compound 16-13 (55 mg, 0.1 mmol) and lithium hydroxide (21 mg, 0.5 mmol) were dissolved in a mixed solvent of THF (3 mL), MeOH (1 mL) and H$_2$O (1 mL), and then the reaction system was stirred overnight at room temperature, quenched with water (10 mL), and extracted with ethyl acetate (5 mL×3). The organic phase was dried over Na$_2$SO$_4$ and filtered, and the filtrate was dried by rotary evaporation and concentrated. The residue was separated by column chromatography (DCM/MeOH=40/1) and lyophilized to give Compound 16 (10 mg, 27.8% yield) in the form of a white solid.

$^1$H NMR (400 MHz, MeOD) δ 7.55-7.51 (m, 2H), 7.37-7.28 (m, 3H), 7.24-7.20 (m, 2H), 7.07-7.03 (m, 2H), 6.38 (d, J=3.0 Hz, 1H), 6.16 (d, J=3.0 Hz, 1H), 5.15 (s, 2H), 4.78 (s, 2H), 4.74 (s, 1H), 4.17 (s, 3H), 2.84-2.78 (m, 1H), 2.08-2.12 (m, 1H), 1.91-1.97 (m, 3H), 1.77-1.60 (m, 4H).

Example 17

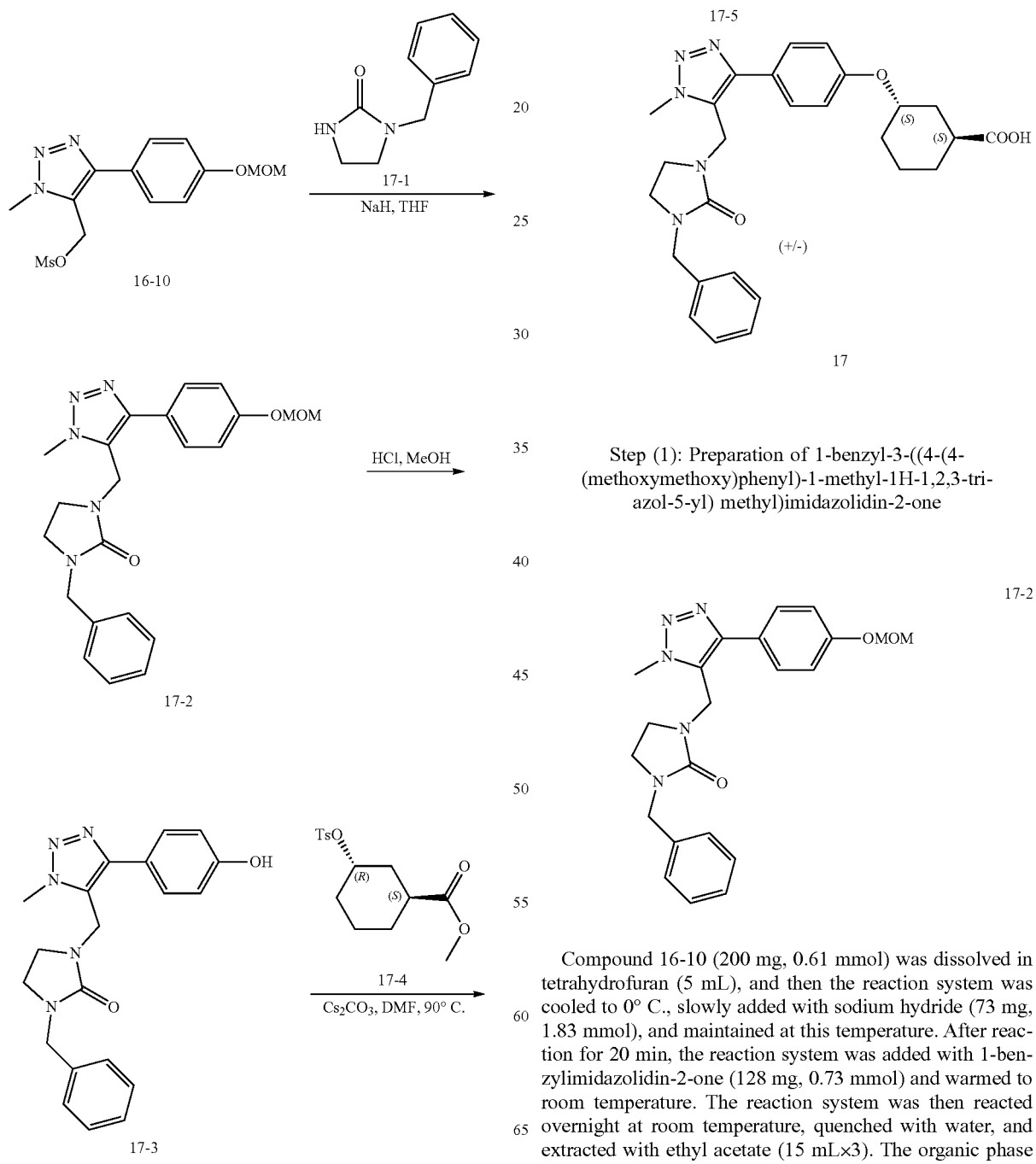

Step (1): Preparation of 1-benzyl-3-((4-(4-(methoxymethoxy)phenyl)-1-methyl-1H-1,2,3-triazol-5-yl) methyl)imidazolidin-2-one Compound 16-10 (200 mg, 0.61 mmol) was dissolved in tetrahydrofuran (5 mL), and then the reaction system was cooled to 0° C., slowly added with sodium hydride (73 mg, 1.83 mmol), and maintained at this temperature. After reaction for 20 min, the reaction system was added with 1-benzylimidazolidin-2-one (128 mg, 0.73 mmol) and warmed to room temperature. The reaction system was then reacted overnight at room temperature, quenched with water, and extracted with ethyl acetate (15 mL×3). The organic phase was washed with saturated brine (15 mL), dried over anhydrous sodium sulfate, and concentrated to give Compound 17-2 (200 mg) in the form of a yellow oil. LC-MS [M+H]⁺: =408.2.

Step (2): Preparation of 1-benzyl-3-((4-(4-hydroxyphenyl)-1-methyl-1H-1,2,3-triazol-5-yl)methyl) imidazolidin-2-one

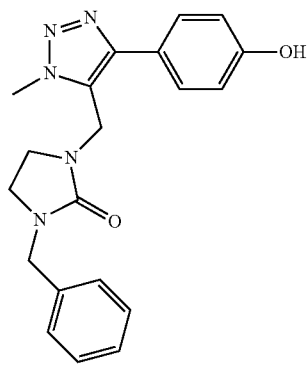

17-3

Compound 17-2 (200 mg, 0.49 mmol) was dissolved in a solution of HCl in methanol (5 mL), and then the reaction system was stirred at room temperature for 2 h and concentrated. The residue was separated by column chromatography (PE/MA=4/1) to give Compound 17-3 (100 mg) in the form of a white solid. LC-MS [M+H]⁺: 364.2.

Step (3): Preparation of (+/−)-methyl (1S,3S)-3-(4-(5-((3-benzyl-2-carbonylimidazolidin-1-yl) methyl)-1-methyl-1H-1,2,3-triazol-4-yl)phenoxy)cyclohexane-1-carboxylate

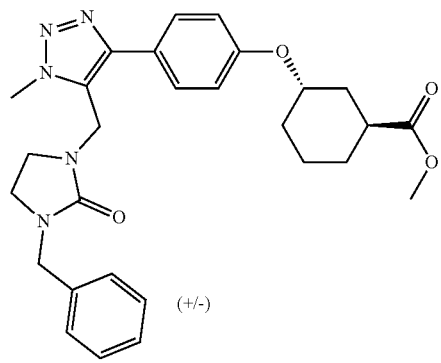

17-5

Compound 17-3 (100 mg, 0.28 mmol), methyl (1S,3R)-3-(tosyloxy)cyclohexane-1-carboxylate (175 mg, 0.56 mmol) and cesium carbonate (273 mg, 0.84 mmol) were dissolved in anhydrous DMF (5 mL), and then the reaction system was warmed to 90° C., reacted for 3 h under nitrogen atmosphere, quenched with water, and extracted with ethyl acetate (15 mL×3). The organic phase was washed with saturated brine (15 mL), dried over anhydrous sodium sulfate and concentrated, and the residue was separated by column chromatography (PE/EA=1/1) to give Compound 17-5 (100 mg, 70.9% yield) in the form of a yellow oil.

LC-MS [M+H]⁺: 504.2.

Step (4): Preparation of (+/−)-(1S,3S)-3-(4-(5-((3-benzyl-2-carbonylimidazolidin-1-yl)methyl)-1-methyl-1H-1,2,3-triazol-4-yl)phenoxy)cyclohexane-1-carboxylic acid

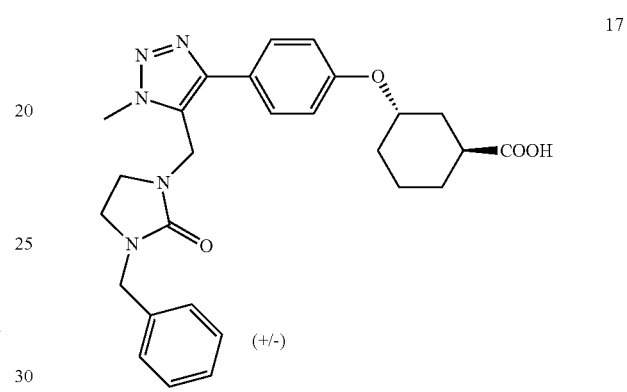

17

Compound 17-5 (100 mg, 0.19 mmol) and lithium hydroxide (40 mg, 0.95 mmol) were dissolved in a mixed solvent of THF (3 mL), MeOH (1 mL) and H₂O (1 mL), and then the reaction system was stirred overnight at room temperature, quenched with water (10 mL), and extracted with ethyl acetate (5 mL×3). The organic phase was dried over Na₂SO₄ and filtered, and the filtrate was dried by rotary evaporation and concentrated. The residue was separated by column chromatography (DCM/MeOH=40/1) and lyophilized to give Compound 17 (20 mg, 27.8% yield) in the form of a white solid.

¹H NMR (400 MHz, MeOD) δ 7.60-7.54 (m, 2H), 7.34-7.37 (m, 2H), 7.31-7.22 (m, 3H), 7.10-7.03 (m, 2H), 4.73 (s, 3H), 4.37 (s, 2H), 4.14 (s, 3H), 3.18-3.04 (m, 4H), 2.83-2.76 (m, J=9.8 Hz, 1H), 2.13-2.05 (m, 1H), 1.98-1.87 (m, 3H), 1.80-1.58 (m, 4H).

Example 18

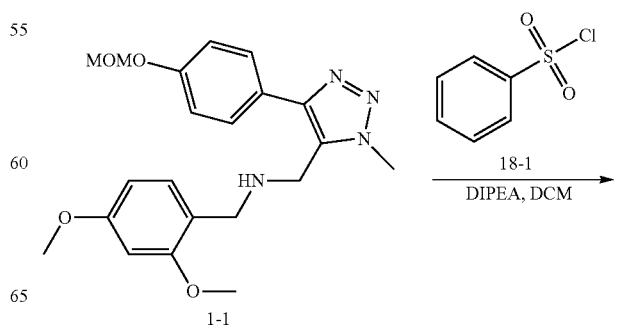

163
-continued

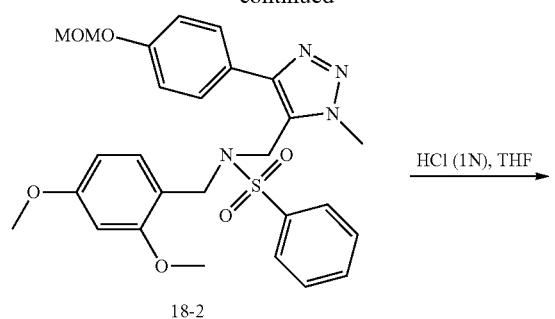

18-2

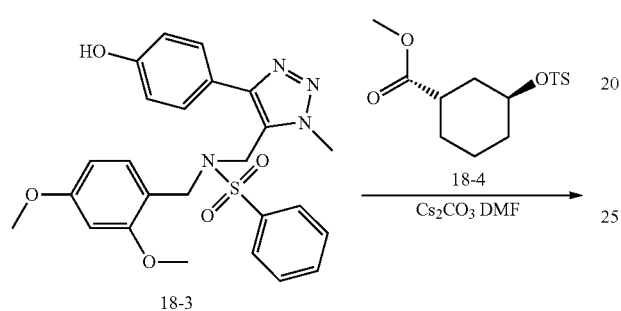

18-3

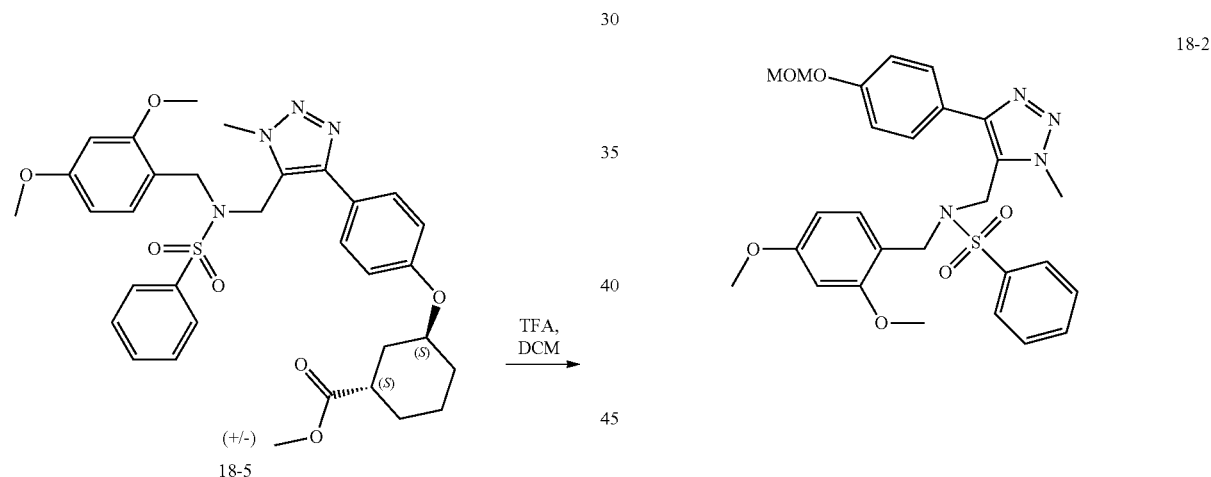

18-5

18-6

164
-continued

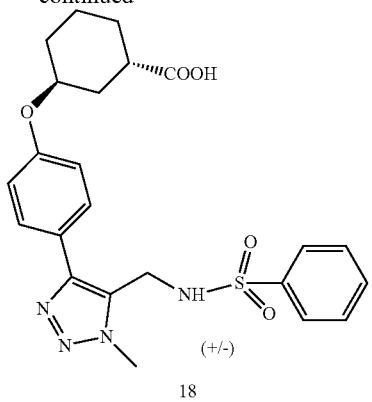

18

Step (1): Preparation of N-(2,4-dimethoxybenzyl)-N-((4-(4-(methoxymethoxy)phenyl)-1-methyl-1H-1,2,3-triazol-5-yl)methyl)-benzenesulfonamide

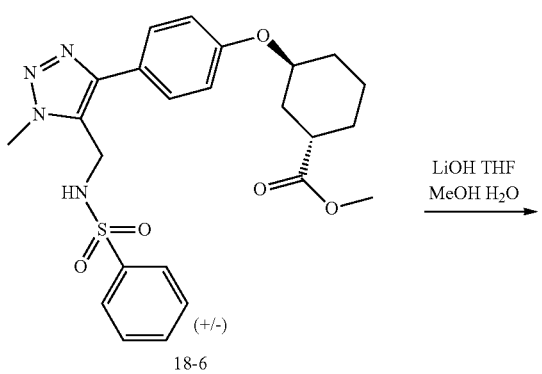

18-2

Compound 1-1 (324 mg, 0.814 mmol) and N,N-diisopropylethylamine (210 mg, 1.63 mmol) were dissolved in dichloromethane (10 mL), and then benzenesulfonyl chloride (172 mg, 0.98 mmol) was added, and the reaction system was stirred overnight at room temperature. The reaction system was then quenched with water (15 mL) and extracted with dichloromethane (15 mL×2). The organic phases were combined, washed with saturated brine (15 mL), dried over anhydrous sodium sulfate, filtered and concentrated, and the residue was separated by column chromatography (DCM/CH$_3$OH=25/1) to give Compound 18-2 (370 mg, 85% yield) in the form of a colorless oil. LC-MS [M+H]$^+$: 539.2.

Step (2): Preparation of N-(2,4-dimethoxybenzyl)-N-((4-(4-hydroxyphenyl)-1-methyl-1H-1,2,3-triazol-5-yl)methyl)-benzenesulfonamide

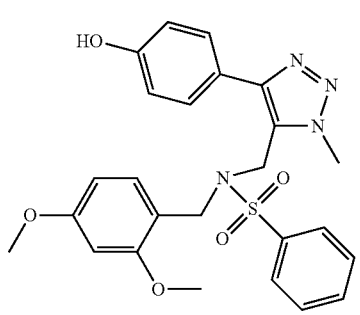

Compound 18-2 (370 mg, 0.69 mmol) was dissolved in tetrahydrofuran (5 mL), and then HCl (5 mL, 1 N) was added, and the reaction system was stirred overnight at room temperature. Then the reaction system was diluted with $H_2O$ (20 mL) and extracted with ethyl acetate (15 mL×2). The organic phases were combined, washed with saturated brine (15 mL), dried over anhydrous sodium sulfate, filtered and concentrated, and the residue was separated by column chromatography ($DCM/CH_3OH=100/1$) to give Compound 18-3 (277 mg, 81% yield) in the form of a colorless oil. LC-MS $[M+H]^+$: 495.1.

Step (3): Preparation of (+/−)-methyl (1S,3S)-3-(4-(5-((N-(2,4-dimethoxybenzyl)benzenesulfonamido)methyl)-1-methyl-1H-1,2,3-triazol-4-yl)phenoxy)cyclohexane-1-carboxylate

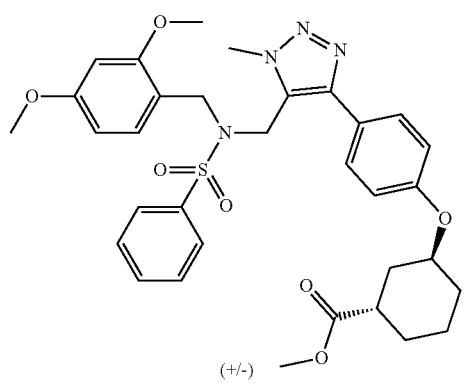

Compound 18-3 (277 mg, 0.56 mmol) was dissolved in N,N-dimethylformamide (10 mL), and then methyl (1S,3S)-3-(tosyloxy)cyclohexane-1-carboxylate (300 mg, 1.1 mmol) and cesium carbonate (454 mg, 1.4 mmol) were added, and the reaction system was warmed to 100° C. and stirred overnight. Then the reaction system was cooled to room temperature, quenched with water (50 mL) and extracted with ethyl acetate (20 mL×2). The organic phases were combined, washed with saturated brine (20 mL), dried over anhydrous sodium sulfate, filtered and concentrated, and the residue was separated by column chromatography (DCM/$CH_3OH=100/1$) to give Compound 18-5 (210 mg, 59% yield) in the form of a colorless oil. LC-MS $[M+H]^+$: 635.4.

Step (4): Preparation of (+/−)-methyl (1S,3S)-3-(4-(1-methyl-5-(benzenesulfonamidomethyl)-1H-1,2,3-triazol-4-yl)phenoxy)cyclohexane-1-carboxylate

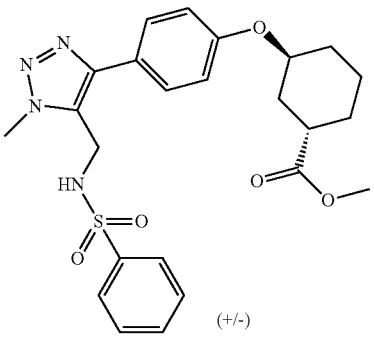

Compound 18-5 (210 mg, 0.3 mmol) was dissolved in dichloromethane (5 mL), and then trifluoroacetic acid (5 mL) was added dropwise, and the reaction system was stirred overnight at room temperature. After concentration under reduced pressure, the reaction system was then diluted with $H_2O$ (20 mL) and extracted with dichloromethane (15 mL×2). The organic phase was washed with saturated brine (15 mL), dried over anhydrous sodium sulfate, filtered and concentrated, and the residue was separated by column chromatography ($DCM/CH_3OH=100/1$) to give Compound 18-6 (140 mg, 93% yield) in the form of a white solid. LC-MS $[M+H]^+$: 485.2.

Step (5): Preparation of (+/−)-(1S,3S)-3-(4-(1-methyl-5-(benzenesulfonamidomethyl)-1H-1,2,3-triazol-4-yl)phenoxy)cyclohexane-1-carboxylic acid

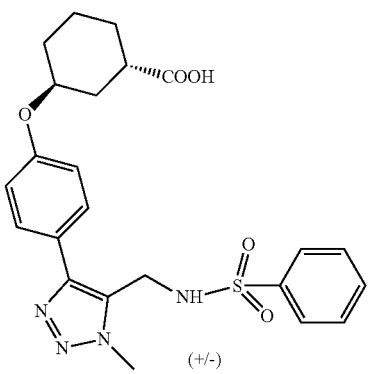

Compound 18-6 (140 mg, 0.29 mmol) was dissolved in a mixed solvent of tetrahydrofuran (3 mL), methanol (1 mL) and water (1 mL), and then lithium hydroxide hydrate (42 mg, 0.87 mmol) was added, and the reaction system was stirred at room temperature for 5 h. Then the reaction system was concentrated, diluted with $H_2O$ (10 mL), adjusted to pH 2-3 with diluted HCl (1 N), and then extracted with ethyl acetate (10 mL×2). The organic phases were combined, washed with saturated brine (10 mL), dried over anhydrous sodium sulfate, filtered and concentrated, and the crude product was purified by preparative reverse phase chromatography and lyophilized to give Compound 18 (52 mg, 38% yield) in the form of a white solid.

LC-MS [M+H]$^+$: 471.4. $^1$H NMR (400 MHz, MeOD) δ7.79 (d, J=7.7 Hz, 2H), 7.67 (t, J=7.5 Hz, 1H) 7.56 (t, J=7.7 Hz, 2H), 7.40 (d, J=8.8 Hz, 2H), 6.98 (d, J=8.8 Hz, 2H), 4.75-4.70 (m, 1H), 4.28 (s, 2H), 4.08 (s, 3H), 2.82-2.78 (m, 1H) 2.06-1.97 (m, 1H), 1.95-1.92 (m, 3H), 1.80-1.63 (m, 4H).

Example 19

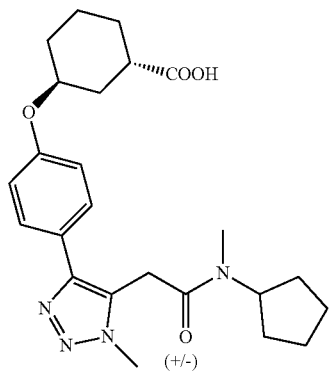

Refer to the synthesis procedures in Example 20 below, LC-MS [M+H]$^+$: 441.2.

Example 20

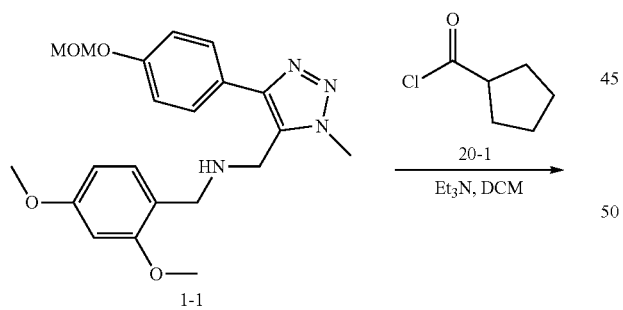

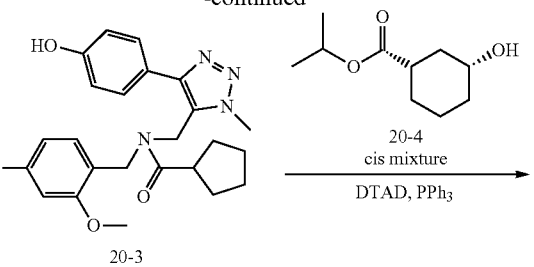

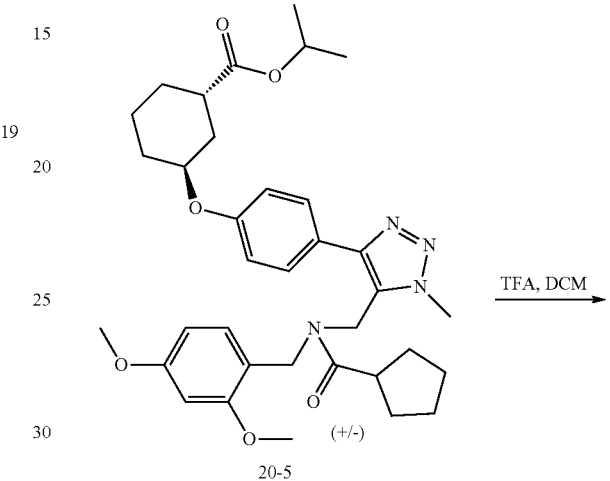

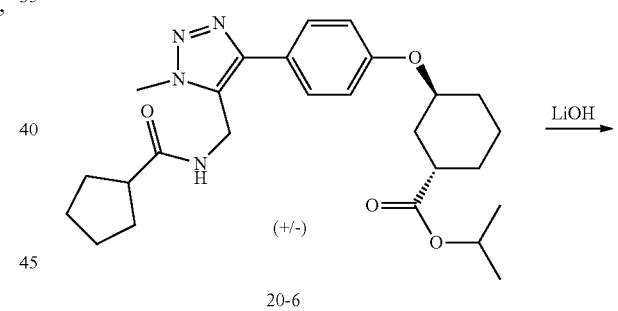

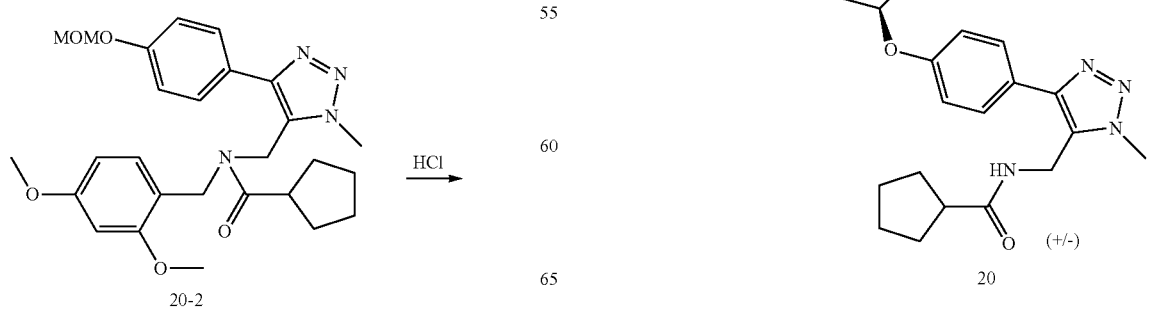

Step (1): Preparation of N-(2,4-dimethoxybenzyl)-N-((4-(4-(methoxymethoxy)phenyl)-1-methyl-1H-1,2,3-triazol-5-yl)methyl)-cyclopentanecarboxamide

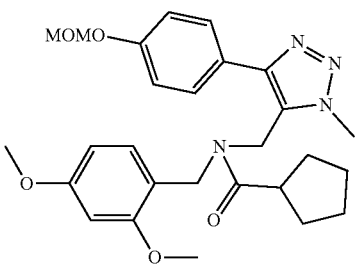

20-2

Compound 1-1 (320 mg, 0.806 mmol) was dissolved in dichloromethane (20 mL), and then triethylamine (165 mg, 1.63 mmol) was added. The reaction system was cooled to 0° C., added with cyclopentanylcarbonyl chloride (127 mg, 0.96 mmol), and then slowly warmed to room temperature and reacted for 16 h. Then the reaction system was quenched with water (10 mL), washed with saturated brine (20 mL), dried over anhydrous sodium sulfate and concentrated, and the residue was separated by column chromatography (DCM/MeOH=30/1) to give Compound 20-2 (300 mg, 75% yield) in the form of a yellow solid. LC-MS [M+H]$^+$: 495.4.

Step (2): Preparation of N-(2,4-dimethoxybenzyl)-N-((4-(4-hydroxyphenyl)-1-methyl-1H-1,2,3-triazol-5-yl)methyl)-cyclopentanecarboxamide

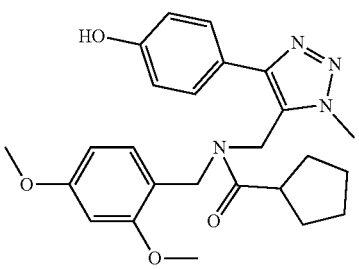

20-3

Compound 20-2 (300 mg, 0.605 mmol) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=20/1) to give Compound 20-3 (130 mg, 48% yield) in the form of a yellow solid. LC-MS [M+H]$^+$: 451.2.

Step (3): Preparation of (+/−)-isopropyl (1S,3S)-3-(4-(5-((N-(2,4-dimethoxybenzyl)cyclopentanecarboxamido<oxalylamino>)methyl)-1-methyl-1H-1,2,3-triazol-4-yl)phenoxy)cyclohexane-1-carboxylate

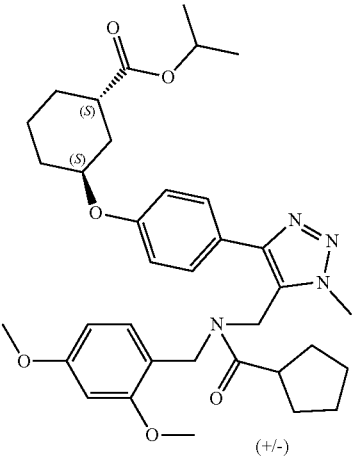

20-5

Compound 20-3 (130 mg, 0.29 mmol), (+/−)-isopropyl 3-hydroxycyclohexane-1-carboxylate (219 mg, 1.15 mmol), DTAD (265 mg, 1.15 mmol) and PPh$_3$ (301 mg, 1.15 mmol) were dissolved in THF (10 mL), and the reaction system was stirred overnight at 60° C. under nitrogen atmosphere. Then the reaction system was purified by silica gel column chromatography (DCM/EA=50/1) to give Compound 20-5 (370 mg) in the form of a yellow solid. LC-MS [M+H]$^+$: 619.4.

Step (4): Preparation of (+/−)-isopropyl (1S,3S)-3-(4-(5-(cyclopentanecarboxamido<oxalylamino>methyl)-1-methyl-1H-1,2,3-triazol-4-yl)phenoxy)cyclohexane-1-carboxylate

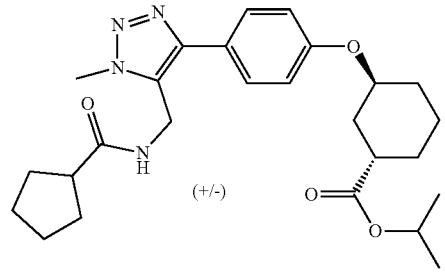

20-6

Compound 20-5 (370 mg, crude product) was dissolved in dichloromethane (10 mL), and then trifluoroacetic acid (10 mL) was added, and the reaction system was stirred overnight at room temperature. Then the reaction system was concentrated, and the residue was diluted with ethyl acetate (20 mL), washed successively with saturated sodium bicarbonate (20 mL) and saturated brine (20 mL), dried over anhydrous sodium sulfate and concentrated, and the residue was separated by column chromatography (DCM/

MeOH=30/1) to give Compound 20-6 (220 mg) in the form of a yellow solid. LC-MS [M+H]⁺: 469.2.

Step (5): Preparation of (+/−)-(1S,3S)-3-(4-(5-(cyclopentanecarboxamido<oxalylamino>methyl)-1-methyl-1H-1,2,3-triazol-4-yl)phenoxy)cyclohexane-1-carboxylate

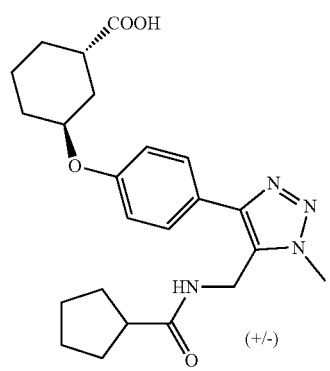

Compound 20-6 (220 mg, crude product) was dissolved in THF (9 mL), and MeOH (3 mL), H₂O (3 mL) and lithium hydroxide (42 mg, 1.0 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation.

The residue was purified by silica gel column chromatography (DCM/MeOH=30/1), separated by preparative chromatography, and then lyophilized to give Compound 20 (50 mg) in the form of a white solid.

LC-MS [M+H]⁺: 427.2. ¹H NMR (400 MHz, MeOD) δ 7.68-7.54 (m, 2H), 7.15-7.02 (m, 2H), 4.85-4.64 (m, 1H), 4.63 (s, 2H), 4.12 (s, 3H), 2.81-2.68 (m, 1H), 2.61-2.58 (m, 1H), 2.07-2.05 (m, 1H), 2.02-1.91 (m, 3H), 1.91-1.44 (m, 12H).

Example 21

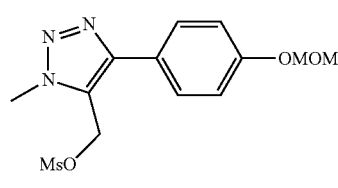

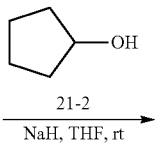

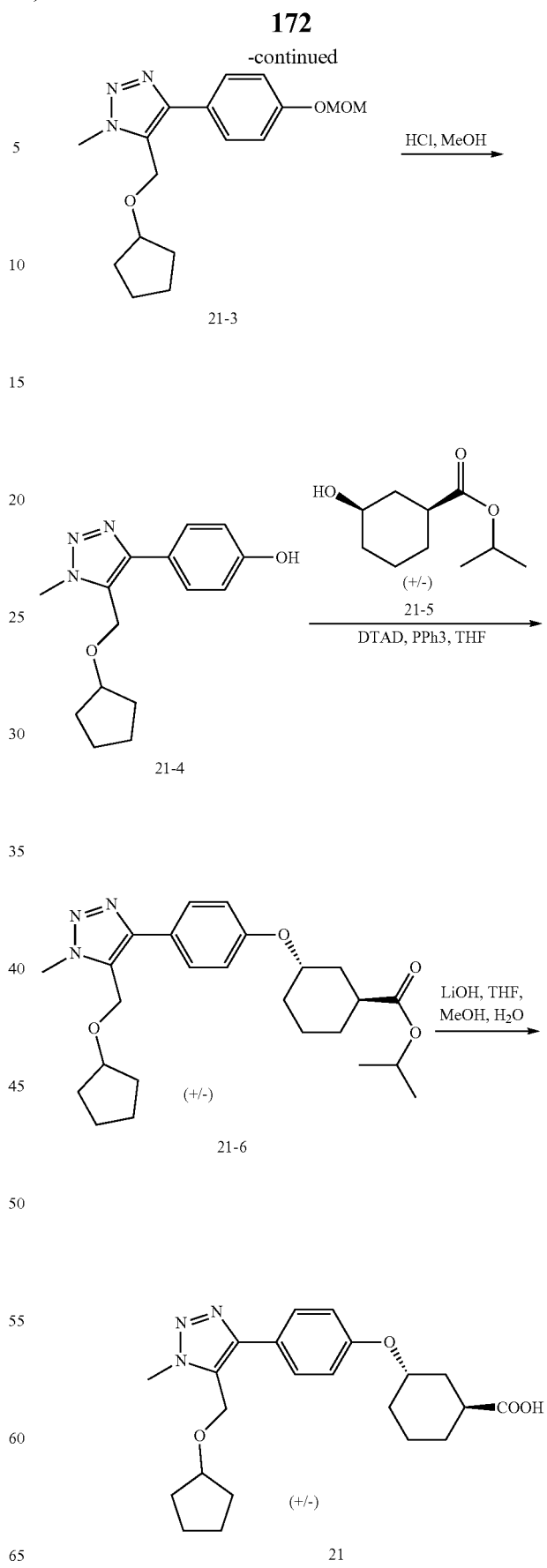

Step (1): Preparation of 5-((cyclopentyloxy)methyl)-4-(4-(methoxymethoxy)phenyl)-1-methyl-1H-1,2,3-triazole

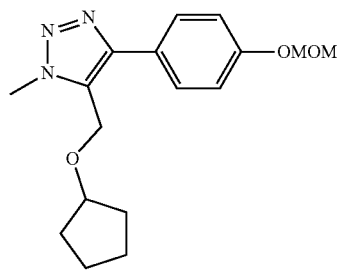

21-3

Compound 21-1 (300 mg, 1.12 mmol) was dissolved in tetrahydrofuran (5 mL), and then the reaction system was cooled to 0° C., slowly added with sodium hydride (224 mg, 5.6 mmol), and maintained at this temperature. After reaction for 20 min, the reaction system was added with cyclopentanol (280 mg, 3.36 mmol) and warmed to room temperature. The reaction system was then reacted overnight at room temperature, quenched with water, and extracted with ethyl acetate (15 mL×3). The organic phase was washed with saturated brine (15 mL), dried over anhydrous sodium sulfate, and concentrated to give Compound 21-3 (1200 mg) in the form of a yellow oil. LC-MS [M+H]$^+$: 318.2.

Step (2): Preparation of 4-(5-((cyclopentyloxy)methyl)-1-methyl-1H-1,2,3-triazol-4-yl)phenol

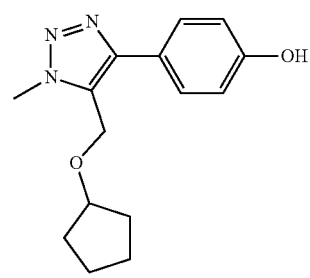

21-4

Compound 21-3 (120 mg, 0.38 mmol) was dissolved in a solution of HCl in methanol (5 mL), and then the reaction system was stirred at room temperature for 2 h and concentrated. The residue was separated by column chromatography (PE/MA=4/1) to give Compound 21-4 (100 mg) in the form of a white solid. LC-MS [M+H]$^+$: 274.4.

Step (3): Preparation of (+/−)-isopropyl (1S,3S)-3-(4-(5-((cyclopentyloxy)methyl)-1-methyl-1H-1,2,3-triazol-4-yl)phenoxy)cyclohexane-1-carboxylate

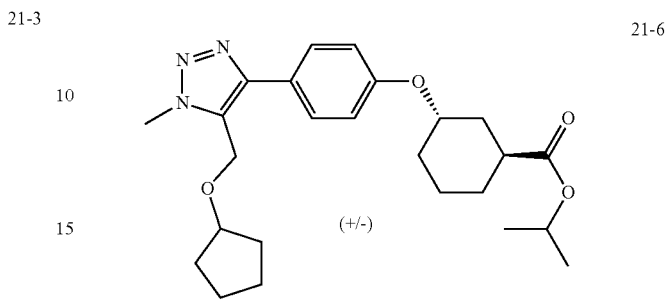

21-6

Compound 21-4 (216 mg, 1.12 mmol), di-tert-butyl azodicarboxylate (267 mg, 1.12 mmol) and triphenylphosphine (304 mg, 1.12 mmol) were dissolved in tetrahydrofuran (5 mL), and then the reaction system was reacted at 60° C. for 12 h under nitrogen atmosphere, quenched with water, and extracted with ethyl acetate (15 mL×3). The organic phases were combined, washed with saturated brine (15 mL), dried over anhydrous sodium sulfate and concentrated, and the residue was separated by column chromatography (PE/EA=2/1) to give Compound 21-6 (100 mg) in the form of a yellow oil. LC-MS [M+H]$^+$: 442.4.

Step (4): Preparation of (+/−)-(1S,3S)-3-(4-(5-((cyclopentyloxy)methyl)-1-methyl-1H-1,2,3-triazol-4-yl) phenoxy)cyclohexane-1-carboxylic acid

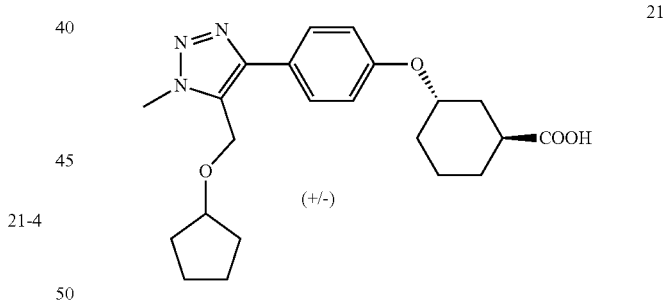

21

Compound 21-6 (200 mg, 0.46 mmol) and lithium hydroxide (96 mg, 0.23 mmol) were dissolved in a mixed solvent of THF (3 mL), MeOH (1 mL) and H$_2$O (1 mL), and then the reaction system was stirred overnight at room temperature, quenched with water (10 mL), and extracted with ethyl acetate (5 mL×3). The organic phase was dried over Na$_2$SO$_4$ and filtered, and the filtrate was dried by rotary evaporation and concentrated. The residue was separated by column chromatography (DCM/MeOH=40/1) and lyophilized to give Compound 21 (40 mg, 21.7% yield) in the form of a white solid. LC-MS [M+H]$^+$: 400.4.

$^1$H NMR (400 MHz, MeOD) δ 7.57 (d, J=8.8 Hz, 2H), 7.09 (d, J=8.8 Hz, 2H), 4.78-4.73 (m, 1H), 4.65 (s, 2H), 4.14 (s, 3H), 4.11-4.05 (m, 1H), 2.86-2.77 (m, 1H), 2.08-2.12 (d, J=13.4 Hz, 1H), 1.99-1.88 (m, 3H), 1.84-1.55 (m, 12H).

Example 22

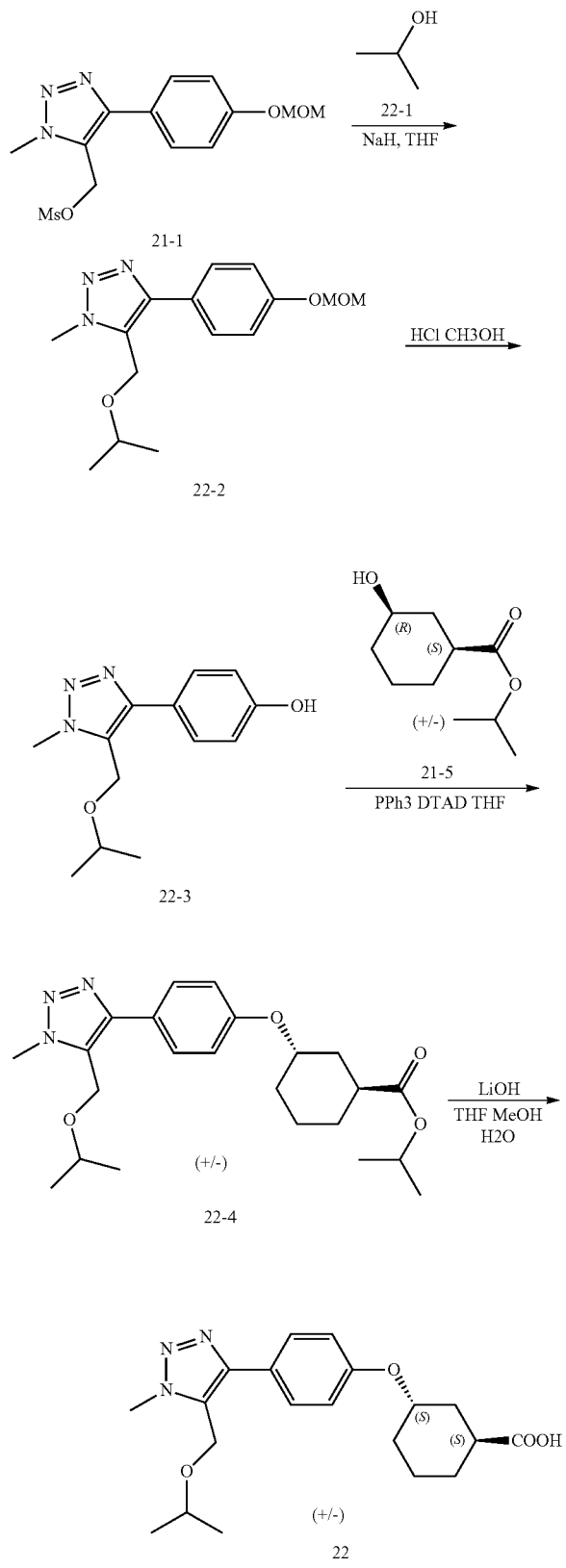

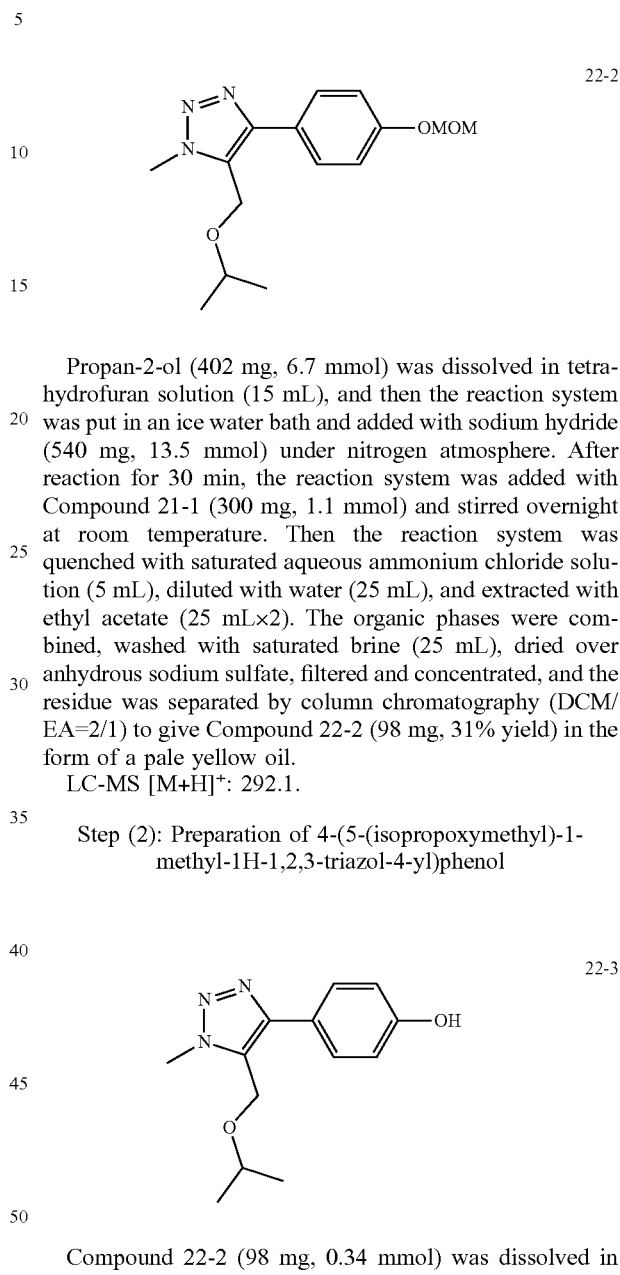

Step (1): Preparation of 5-(isopropoxymethyl)-4-(4-(methoxymethoxy)phenyl)-1-methyl-1H-1,2,3-triazole Propan-2-ol (402 mg, 6.7 mmol) was dissolved in tetrahydrofuran solution (15 mL), and then the reaction system was put in an ice water bath and added with sodium hydride (540 mg, 13.5 mmol) under nitrogen atmosphere. After reaction for 30 min, the reaction system was added with Compound 21-1 (300 mg, 1.1 mmol) and stirred overnight at room temperature. Then the reaction system was quenched with saturated aqueous ammonium chloride solution (5 mL), diluted with water (25 mL), and extracted with ethyl acetate (25 mL×2). The organic phases were combined, washed with saturated brine (25 mL), dried over anhydrous sodium sulfate, filtered and concentrated, and the residue was separated by column chromatography (DCM/EA=2/1) to give Compound 22-2 (98 mg, 31% yield) in the form of a pale yellow oil.
LC-MS [M+H]$^+$: 292.1.

Step (2): Preparation of 4-(5-(isopropoxymethyl)-1-methyl-1H-1,2,3-triazol-4-yl)phenol Compound 22-2 (98 mg, 0.34 mmol) was dissolved in methanol (5 mL), and then a solution of hydrogen chloride in methanol (2 mL, 4 N) was added, and the reaction system was reacted at room temperature for 2 h. Then the reaction system was dried by rotary evaporation, diluted with H$_2$O (10 mL) and extracted with ethyl acetate (10 mL×2). The organic phases were combined, washed with saturated brine (10 mL), dried over anhydrous sodium sulfate, filtered and concentrated, and the residue was separated by column chromatography (DCM/EA=3/1) to give Compound 22-3 (62 mg, 74% yield) in the form of a pale yellow oil. LC-MS [M+H]$^+$: 248.1.

Step (3): Preparation of (+/−)-isopropyl (1S,3S)-3-(4-(5-(isopropoxymethyl)-1-methyl-1H-1,2,3-triazol-4-yl)phenoxy)cyclohexane-1-carboxylate

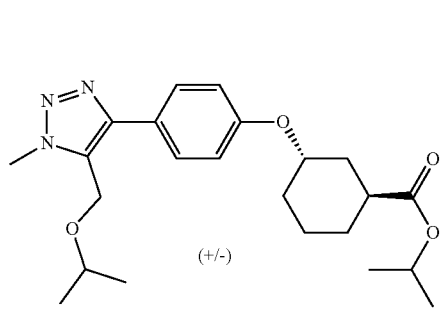

22-4

Compound 22-3 (10 mL) was added with triphenylphosphonium (262 mg, 1.0 mmol), di-tert-butyl azodicarboxylate (230 mg, 1.0 mmol) and isopropyl (1S,3R)-3-hydroxycyclohexane-1-carboxylate (186 mg, 1.0 mmol) under nitrogen atmosphere, and then the reaction system was warmed to 60° C. and stirred overnight. The reaction system was then quenched with water (25 mL), and extracted with ethyl acetate (20 mL×2). The organic phases were combined, washed with saturated brine (20 mL×2), dried over anhydrous sodium sulfate, filtered and concentrated, and the residue was separated by column chromatography (DCM/EA=8/1) to give Compound 22-4 (37 mg, 36% yield) in the form of a pale yellow oil. LC-MS [M+H]⁺: 416.2.

Step (4): Preparation of (+/−)-(1S,3S)-3-(4-(5-(isopropoxymethyl)-1-methyl-1H-1,2,3-triazol-4-yl)phenoxy)cyclohexane-1-carboxylic acid

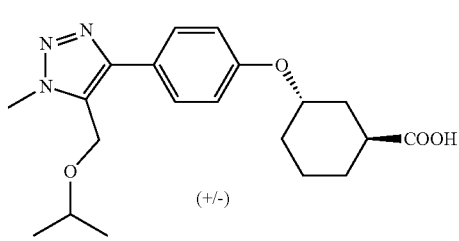

22

Compound 22-4 (37 mg, 0.089 mmol) was dissolved in a mixed solvent of tetrahydrofuran (3 mL), methanol (1 mL) and water (1 mL), and then lithium hydroxide hydrate (18.7 mg, 0.44 mmol) was added, and the reaction system was stirred at room temperature for 5 h. The reaction system was concentrated, diluted with water (10 mL), adjusted to pH 2-3 with diluted HCl (1 N), and then extracted with ethyl acetate (10 mL×2). The organic phases were combined, washed with saturated brine (10 mL), dried over anhydrous sodium sulfate, filtered and concentrated, and the crude product was purified by preparative reverse phase chromatography and lyophilized to give Compound 22 (5.9 mg, 14% yield) in the form of a white solid.

LC-MS [M+Na]: 396.2. ¹H NMR (400 MHz, MeOD) δ 7.57 (d, J=8.7 Hz, 2H), 7.09 (d, J=8.7 Hz, 2H), 4.78-4.74 (m, 1H), 4.69 (s, 2H), 4.14 (s, 3H), 3.79-3.74 (m, 1H), 2.79-2.75 (m, 1H), 1.96-1.64 (m, 8H), 1.23 (d, J=6.1 Hz, 6H).

Example 23

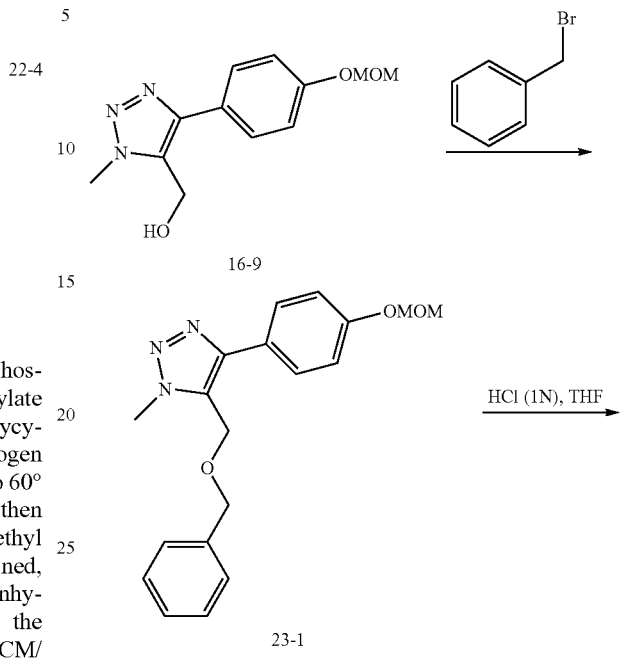

-continued

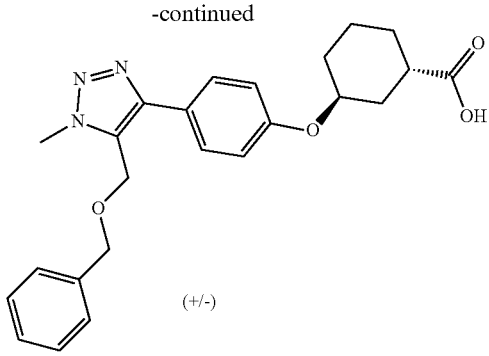

23 (+/-)

Step (1): Preparation of 5-((benzyloxy)methyl)-4-(4-(methoxymethoxy)phenyl)-1-methyl-1H-1,2,3-triazole 23-1

Compound 16-9 (200 mg, 0.8 mmol) was dissolved in DMF (20 mL), and then the reaction system was cooled to 0° C., added with sodium hydride (39 mg, 0.96 mmol), and reacted at room temperature for half an hour. The reaction system was then added with benzyl bromide (274 mg, 1.6 mmol), slowly warmed to room temperature and reacted for 16 h. Then the reaction system was quenched with water (10 mL), washed with saturated brine (20 mL), dried over anhydrous sodium sulfate and concentrated, and the residue was separated by column chromatography (DCM/MeOH=50/1) to give Compound 23-1 (240 mg) in the form of a yellow solid. LC-MS [M+H]$^+$: 340.2.

Step (2): Preparation of 4-(5-((benzyloxy)methyl)-1-methyl-1H-1,2,3-triazol-4-yl)phenol 23-2

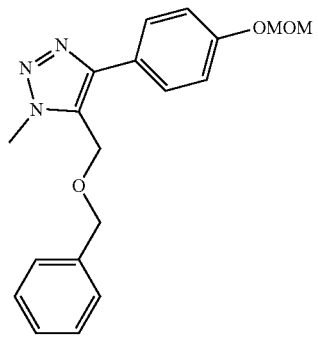

Compound 23-1 (220 mg, crude product) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=20/1) to give Compound 23-2 (140 mg) in the form of a yellow solid. LC-MS [M+H]$^+$: 296.2.

Step (3): Preparation of (+/−)-methyl (1S,3S)-3-(4-(5-((benzyloxy)methyl)-1-methyl-1H-1,2,3-triazol-4-yl)phenoxy)cyclohexane-1-carboxylate 23-3

Compound 23-2 (140 mg, 0.47 mmol), methyl (1S,3R)-3-(tosyloxy)cyclohexane-1-carboxylate (296 mg, 0.95 mmol) and cesium carbonate (337 mg, 1.03 mmol) were dissolved in DMF (10 mL), and then the reaction system was heated to 100° C. and reacted for 7 h under nitrogen atmosphere. Then the reaction system was diluted with ethyl acetate (20 mL), washed successively with water (10 mL×2) and saturated brine (10 mL), dried over anhydrous sodium sulfate and concentrated, and the residue was separated by column chromatography (DCM/MeOH=50/1) to give Compound 23-3 (160 mg, 78% yield) in the form of a yellow solid. LC-MS [M+H]$^+$: 436.2.

Step (4): Preparation of (+/−)-(1S,3S)-3-(4-(5-((benzyloxy)methyl)-1-methyl-1H-1,2,3-triazol-4-yl) phenoxy)cyclohexane-1-carboxylic acid

23

Compound 23-3 (160 mg, 0.367 mmol) was dissolved in THF (9 mL), and MeOH (3 mL), H₂O (3 mL) and lithium hydroxide (77 mg, 1.8 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate and filtered, and the filtrate was dried by rotary evaporation. The residue was purified by silica gel column chromatography (DCM/MeOH=20/1) and then lyophilized to give Compound 23 (33 mg, 21% yield) in the form of a white solid.

LC-MS [M+H]⁺: 422.4.

¹H NMR (400 MHz, MeOD) δ 7.66-7.45 (m, 2H), 7.45-7.30 (m, 5H), 7.10-6.99 (m, 2H), 4.89 (s, 1H), 4.71 (s, 2H), 4.60 (s, 2H), 4.11 (s, 3H), 2.83-2.81 (m, 1H), 2.09-2.08 (m, 1H), 1.86-1.81 (m, 3H), 1.72-1.49 (m, 4H).

Example 24

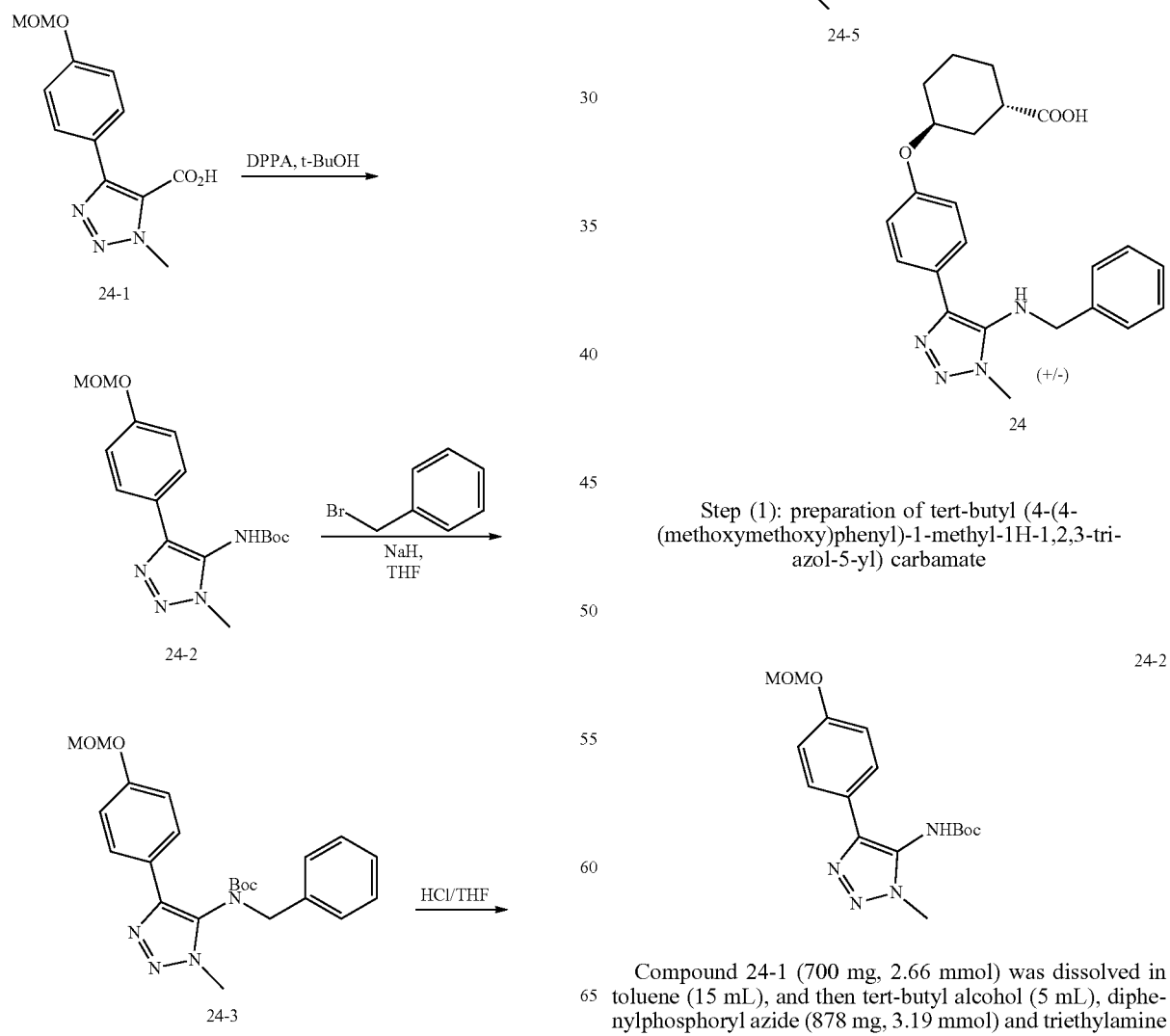

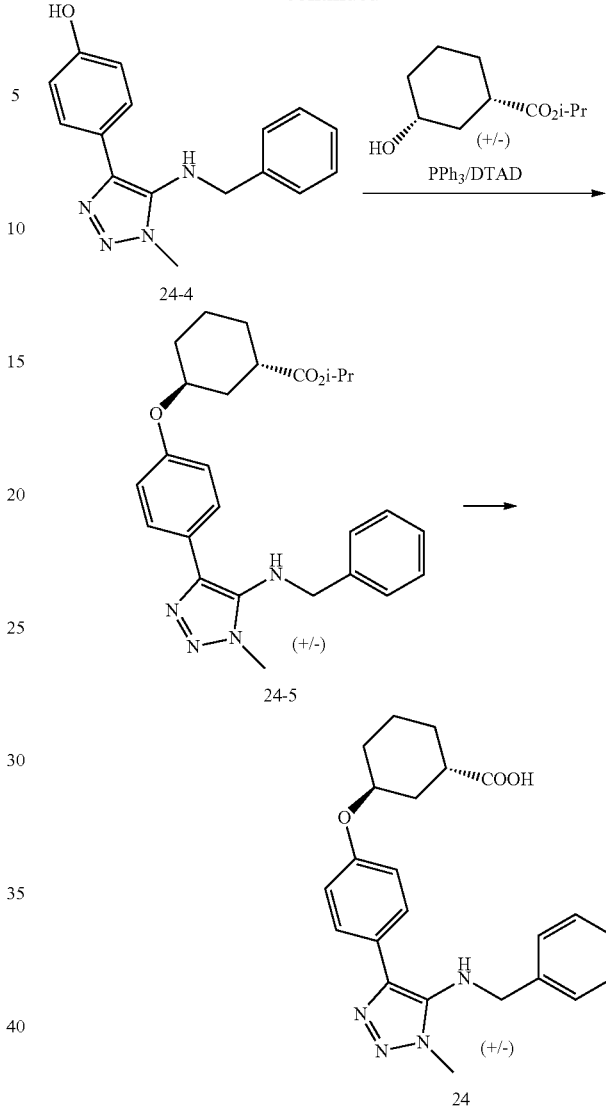

Step (1): preparation of tert-butyl (4-(4-(methoxymethoxy)phenyl)-1-methyl-1H-1,2,3-triazol-5-yl) carbamate Compound 24-1 (700 mg, 2.66 mmol) was dissolved in toluene (15 mL), and then tert-butyl alcohol (5 mL), diphenylphosphoryl azide (878 mg, 3.19 mmol) and triethylamine (537 mg, 5.32 mmol) were added, and then the reaction system was heated to reflux and reacted for 16 h under nitrogen atmosphere. The reaction system was concentrated, and the residue was separated by column chromatography (DCM/MeOH=50/1) to give Compound 24-2 (0.29 g, 32.5% yield) in the form of a white solid. LC-MS [M+H]$^+$: 335.4.

Step (2): Preparation of tert-butyl benzyl (4-(4-(methoxymethoxy)phenyl)-1-methyl-1H-1,2,3-triazol-5-yl)carbamate

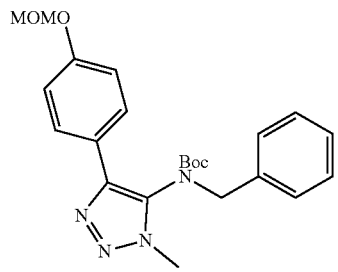

24-3

Compound 24-2 (0.29 g, 0.87 mmol) was dissolved in tetrahydrofuran (15 mL), and the reaction system was cooled to 0° C. and added with sodium hydride (35 mg, 0.86 mmol). The reaction system was then warmed to room temperature, reacted for 0.5 h, added with benzyl bromide (222 mg, 1.3 mmol) and reacted overnight at room temperature. Then the reaction system was quenched with saturated ammonium chloride (10 mL), and extracted with ethyl acetate (20 mL×2). The organic phase was washed with saturated brine (20 mL), dried over anhydrous sodium sulfate and concentrated, and the residue was separated by column chromatography (DCM/MeOH=50/1) to give Compound 24-3 (320 mg, 86% yield) in the form of a white solid. LC-MS [M+H]$^+$: 425.2.

Step (3): Preparation of 4-(5-(benzylamino)-1-methyl-1H-1,2,3-triazol-4-yl)phenol

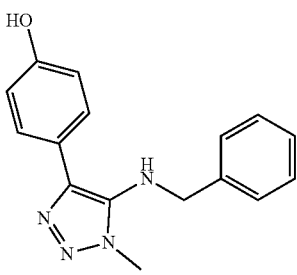

24-4

Compound 24-3 (320 mg, 0.75 mmol) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=30/1) to give Compound 24-4 (120 mg, 57% yield) in the form of a yellow solid. LC-MS [M+H]$^+$: 281.2.

Step (4): Preparation of (+/−)-isopropyl (1S,3S)-3-(4-(5-(benzylamino)-1-methyl-1H-1,2,3-triazol-4-yl)phenoxy)cyclohexane-1-carboxylate

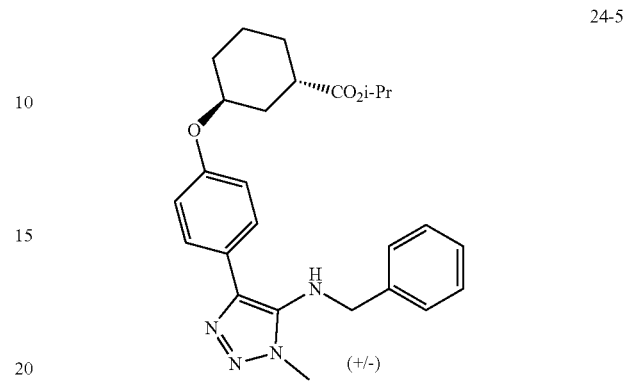

24-5

Compound 24-4 (90 mg, 0.32 mmol), (+/−)-isopropyl 3-hydroxycyclohexane-1-carboxylate (238 mg, 1.28 mmol), DTAD (295 mg, 1.28 mmol) and PPh$_3$ (335 mg, 1.28 mmol) were dissolved in THF (10 mL), and the reaction system was stirred overnight at 60° C. under nitrogen atmosphere. Then the reaction system was purified by silica gel column chromatography (DCM/EA=50/1) to give Compound 24-5 (290 mg, crude product) in the form of a yellow solid. LC-MS [M+H]$^+$: 449.2.

Step (5): Preparation of (+/−)-(1S,3S)-3-(4-(5-(benzylamino)-1-methyl-1H-1,2,3-triazol-4-yl)phenoxy)cyclohexane-1-carboxylate

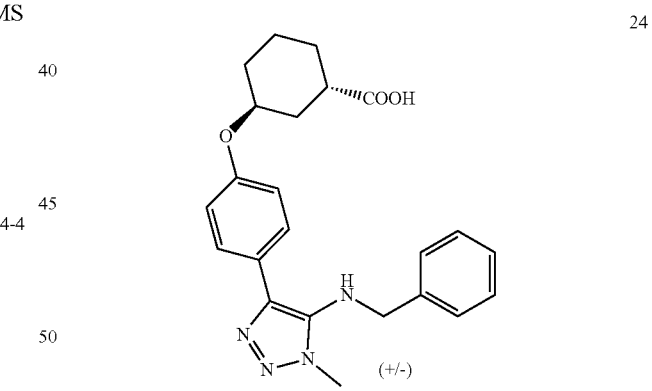

24

Compound 24-5 (290 mg, crude product) was dissolved in THF (18 mL), and MeOH (6 mL), H$_2$O (6 mL) and lithium hydroxide (52 mg, 1.25 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate and filtered, and the filtrate was dried by rotary evaporation. The residue was purified by silica gel column chromatography (DCM/MeOH=20/1) and then lyophilized to give Compound 24 (38 mg, 29% yield over two steps) in the form of a white solid. LC-MS [M+H]$^+$: 407.4.

¹H NMR (400 MHz, MeOD) δ 7.53-7.51 (m, 2H), 7.21-7.19 (m, 3H), 7.10-7.07 (m, 2H), 7.04-7.01 (m, 2H), 4.73-4.72 (m, 1H), 4.12 (s, 2H), 3.73 (s, 3H), 2.80-2.76 (m, 1H), 2.13-2.08 (m, 1H), 1.96-1.90 (m, 3H), 1.85-1.77 (m, 1H), 1.73-1.64 (m, 3H).

Example 25

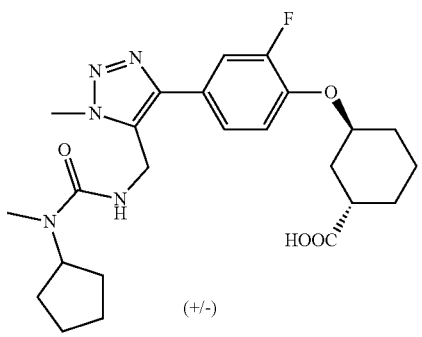

(+/-)

The synthetic route is similar to that in Example 1, LC-MS [M+H]⁺: 474.2.

Example 26

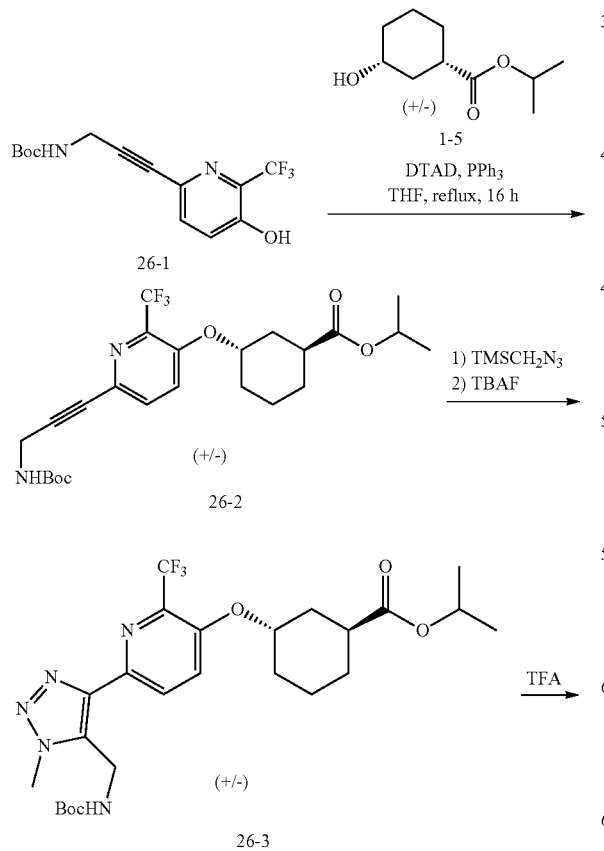

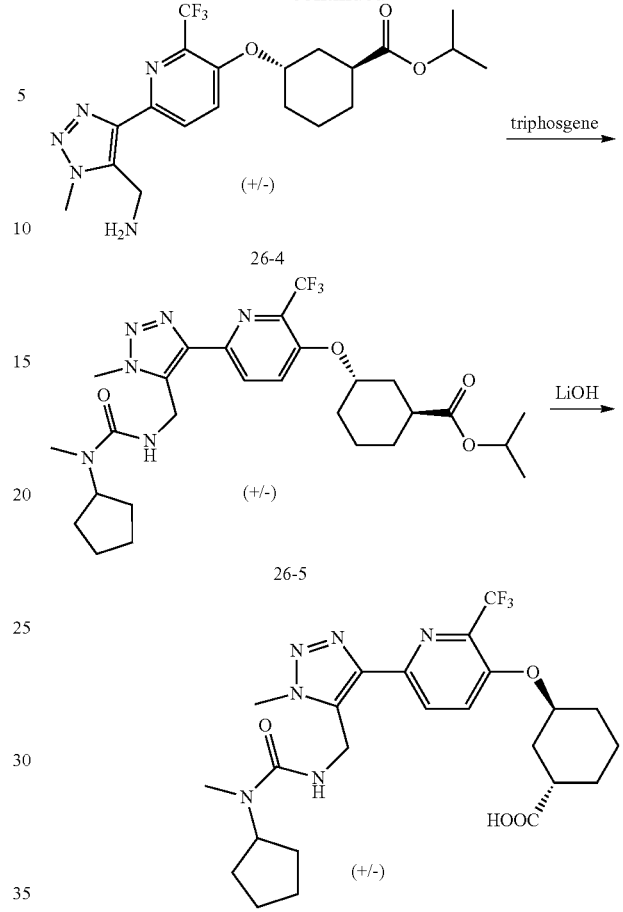

Step (1): Preparation of (+/−)-isopropyl (1S,3S)-3-((6-(3-((tert-butoxycarbonyl)amino)prop-1-yn-1-yl)-2-(trifluoromethyl)pyridin-3-yl)oxo)cyclohexane-1-carboxylate Compound 26-1 (3.3 g, 10.5 mmol), (+/−)-isopropyl 3-hydroxycyclohexane-1-carboxylate (3.64 g, 20 mmol), DTAD (4.6 g, 20 mmol) and PPh₃ (5.25 g, 2 mmol) were dissolved in THF (50 mL), and the reaction system was stirred overnight at 60° C. under nitrogen atmosphere. Then the reaction system was purified by silica gel column chromatography (PE/EA=5/1) to give Compound 26-2 (4.8 g, 95.3% yield) in the form of a yellow solid. LC-MS [M+H]⁺: 485.3.

Step (2): Preparation of (+/−)-isopropyl (1S,3S)-3-((6-(5-(((tert-butoxycarbonyl)amino)methyl)-1-methyl-1H-1,2,3-triazol-4-yl)-2-(trifluoromethyl)pyridin-3-yl)oxo)cyclohexane-1-carboxylate

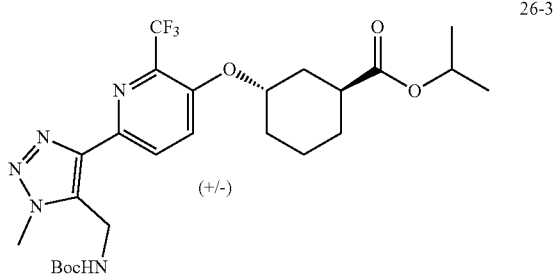 [SMILES: CC(C)OC(=O)[C@H]1CCC[C@H](Oc2ccc(-c3nnn(C)c3CNC(=O)OC(C)(C)C)nc2C(F)(F)F)C1]

26-3

Compound 26-2 (4.8 g, 10 mmol) was dissolved in DMF (20 mL), and then (azidomethyl)trimethylsilane (4.26 g, 33 mmol) was added, and the reaction system was heated to 90° C. and stirred for 96 h under nitrogen atmosphere. Then the reaction system was quenched with water (100 mL), extracted with ethyl acetate (10 mL×2) and washed with saturated brine (10 mL×2). The organic phase was dried over anhydrous sodium sulfate and filtered to remove solids, and the filtrate was dried by rotary evaporation. The residue was dissolved in tetrahydrofuran (20 mL), and then the reaction system was added with tetrabutylammonium fluoride (33 mL) and reacted at room temperature for 2 h. Then the reaction system was quenched with saturated ammonium chloride (50 mL), extracted with ethyl acetate (50 mL×2) and washed with saturated brine (30 mL×2). The organic phase was dried over anhydrous sodium sulfate and purified by silica gel column chromatography (PE/EA=4/1) to give Compound 26-3 (840 mg, 12% yield over two steps) in the form of a yellow solid. LC-MS [M+H]⁺: 542.5.

Step (3): Preparation of (+/−)-isopropyl (1S,3S)-3-((6-(5-(aminomethyl)-1-methyl-1H-1,2,3-triazol-4-yl)-2-(trifluoromethyl)pyridin-3-yl)oxo)cyclohexane-1-carboxylate

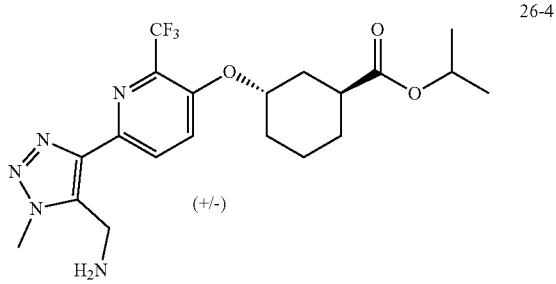 [SMILES: CC(C)OC(=O)[C@H]1CCC[C@H](Oc2ccc(-c3nnn(C)c3CN)nc2C(F)(F)F)C1]

26-4

Compound 26-3 (840 mg, 1.55 mmol) was dissolved in dichloromethane (10 mL), and then trifluoroacetic acid (5 mL) was added, and the reaction system was stirred overnight at room temperature. Then the reaction system was diluted with water (20 mL), adjusted to pH 8-9 with saturated sodium carbonate and extracted with dichloromethane (30 mL×2). The organic phase was washed successively with water (20 mL) and saturated brine (20 mL), dried over anhydrous sodium sulfate and concentrated, and the residue was separated by column chromatography (DCM/MeOH=20/1) to give Compound 26-4 (580 mg, 84.5% yield) in the form of a yellow solid. LC-MS [M+H]⁺: 442.3.

Step (4): Preparation of (+/−)-isopropyl (1S,3S)-3-((6-(5-((3-cyclopentyl-3-methylureido)methyl)-1-methyl-1H-1,2,3-triazol-4-yl)-2-(trifluoromethyl)pyridin-3-yl)oxo)cyclohexane-1-carboxylate

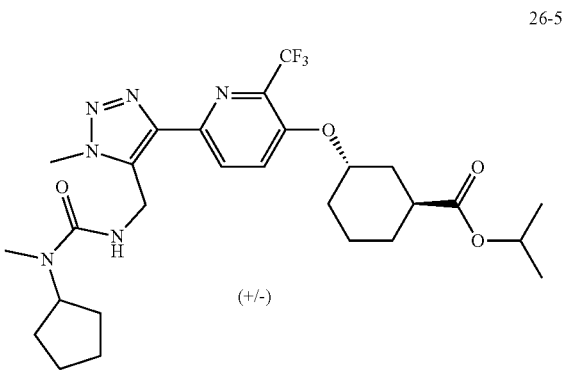 [SMILES: CC(C)OC(=O)[C@H]1CCC[C@H](Oc2ccc(-c3nnn(C)c3CNC(=O)N(C)C3CCCC3)nc2C(F)(F)F)C1]

26-5

Triphosgene (410 mg, 1.38 mmol) was dissolved in tetrahydrofuran (5 mL), and then the reaction system was cooled to 0° C. and slowly added with a solution of triethylamine (958 mg, 9.48 mmol) and N-methylcyclopentylamine (536 mg, 3.95 mmol) in tetrahydrofuran (10 mL) dropwise. After reaction at 0° C. for 1 h, the reaction system was added with Compound 26-4 (350 mg, 0.79 mmol), slowly warmed to room temperature and reacted for 16 h. Then the reaction system was quenched with water (10 mL) and extracted with ethyl acetate (30 mL). The organic phase was washed with saturated brine (20 mL), dried over anhydrous sodium sulfate and concentrated, and the residue was separated by column chromatography (DCM/MeOH=30/1) to give Compound 26-5 (600 mg, crude product) in the form of a yellow solid.

LC-MS [M+H]⁺: 567.4.

Step (5): Preparation of (+/−)-(1S,3S)-3-((6-(5-((3-cyclopentyl-3-methylureido)methyl)-1-methyl-1H-1,2,3-triazol-4-yl)-2-(trifluoromethyl)pyridin-3-yl)oxo)cyclohexane-1-carboxylic acid

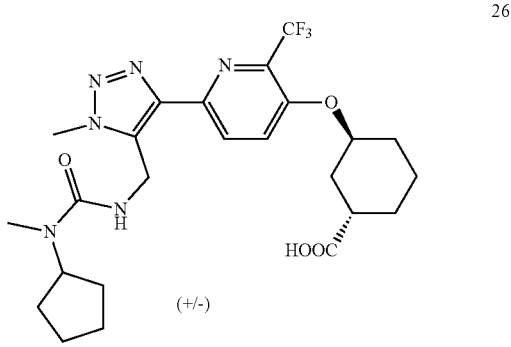 [SMILES: CN(C(=O)NCc1c(-c2ccc(O[C@H]3CCC[C@H](C(=O)O)C3)c(C(F)(F)F)n2)nnn1C)C1CCCC1]

26

Compound 26-5 (600 mg, crude product) was dissolved in THF (18 mL), and MeOH (6 mL), H₂O (6 mL) and lithium hydroxide (218 mg, 5.3 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation. The residue was purified by silica gel column chromatography (DCM/MeOH=20/1), subjected to chiral resolution, and then lyophilized to give Compound 26 (34 mg) in the form of a white solid. LC-MS [M+H]⁺: 525.4.

¹H NMR (400 MHz, MeOD) δ 8.35 (d, J=8.8 Hz, 1H), 7.91 (d, J=8.9 Hz, 1H), 5.02-4.97 (m, 1H), 4.69 (s, 2H), 4.45-4.34 (m, 1H), 4.24 (s, 2H), 2.79-2.68 (m, 1H), 2.68 (s, 3H), 2.17-2.13 (m, 1H), 1.97-1.92 (m, 3H), 1.75-1.45 (m, 12H).

Example 27

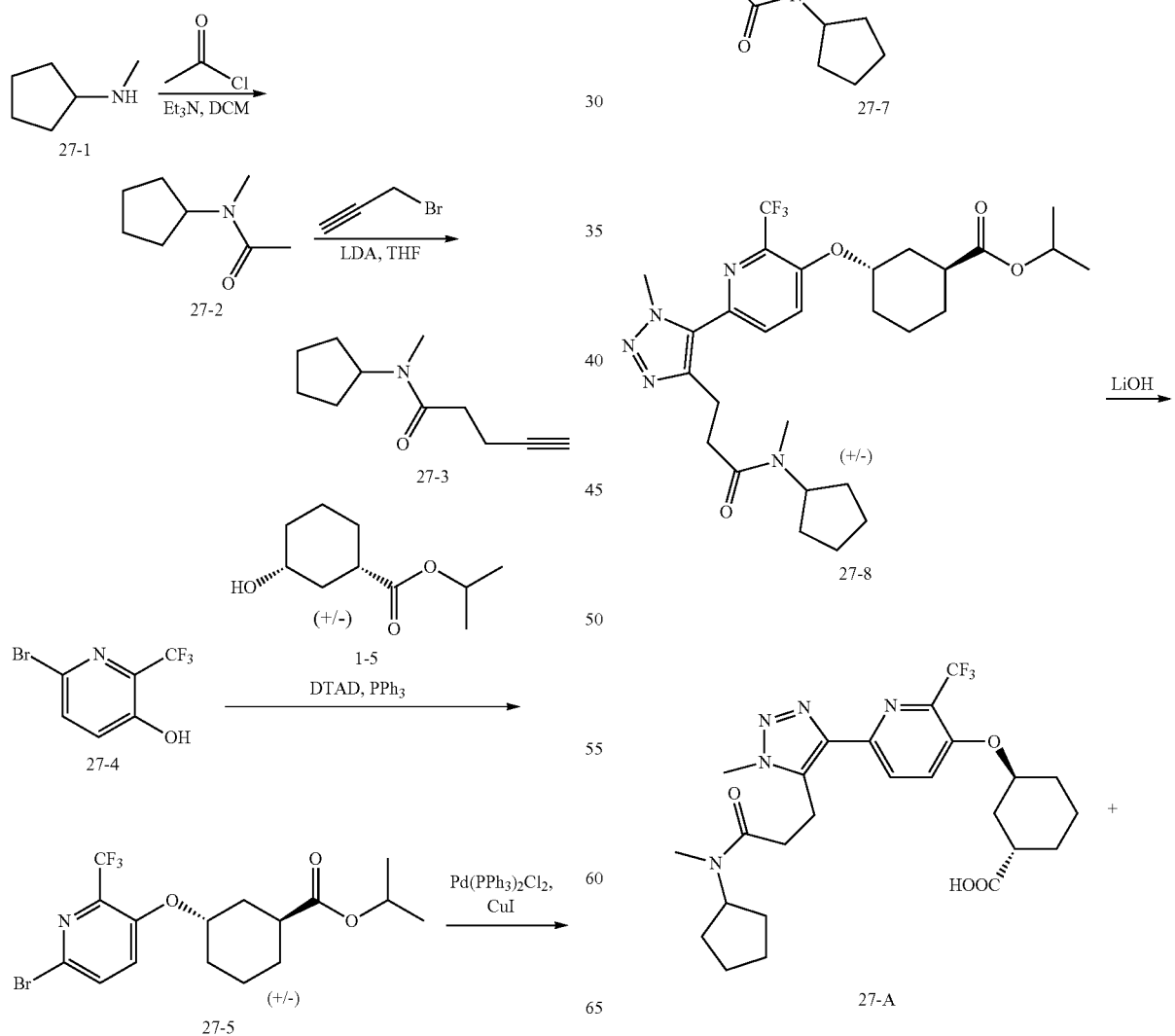

-continued

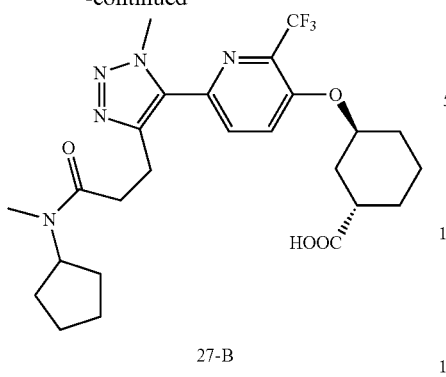

27-B

Step (1): Preparation of
N-cyclopentyl-N-methylpent-acetamide

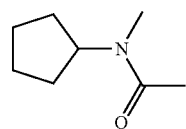

27-2

N-methylcyclopentylamine (1.0 g, 7.4 mmol) was dissolved in dichloromethane (20 mL), and then the reaction system was cooled to 0° C., added with acetyl chloride (0.7 g, 8.9 mmol), and stirred overnight at room temperature. Then the reaction system was diluted with dichloromethane (50 mL), washed with saturated sodium carbonate (30 mL×2) and washed with saturated brine (30 mL×2). The organic phase was dried over anhydrous sodium sulfate and concentrated to give Compound 27-2 (0.74 g, crude product) in the form of a yellow oil. LC-MS [M+H]$^+$: 142.6.

Step (2): Preparation of
N-cyclopentyl-N-methylpent-4-ynamide

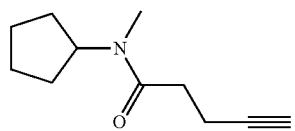

27-3

Compound 27-2 (0.74 g, 5.2 mmol) was dissolved in tetrahydrofuran (20 mL), and then the reaction system was cooled to −78° C. and added with lithium diisopropylamide (3.9 mL, 7.8 mmol). After reaction at −78° C. for 1 h, the reaction system was added with propargyl bromide (1.24 g, 10.4 mmol) and reacted for 1 h. Then the reaction system was quenched with saturated ammonium chloride (20 mL), extracted with ethyl acetate (50 mL×2) and washed with saturated sodium carbonate (30 mL×2). The organic phase was dried over anhydrous sodium sulfate and concentrated to give Compound 27-3 (0.54 g, crude product) in the form of a yellow oil. LC-MS [M+H]$^+$: 180.3.

Step (3): preparation of (+/−)-isopropyl (1S,3S)-3-((6-bromo-2-(trifluoromethyl)pyridin-3-yl)oxo) cyclohexane-1-carboxylate

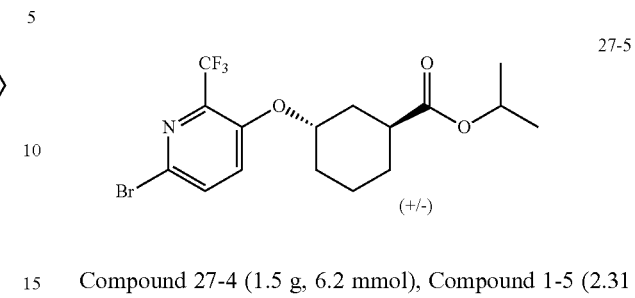

27-5

Compound 27-4 (1.5 g, 6.2 mmol), Compound 1-5 (2.31 g, 12.4 mmol), DTAD (2.86 g, 12.4 mmol) and PPh$_3$ (3.25 g, 12.4 mmol) were dissolved in THF (50 mL), and the reaction system was stirred overnight at 60° C. under nitrogen atmosphere. Then the reaction system was purified by silica gel column chromatography (DCM/EA=50/1) to give Compound 27-5 (1.7 g, 68% yield) in the form of a yellow solid. LC-MS [M+H]$^+$: 410.4.

Step (4): Preparation of (+/−)-isopropyl (1S,3S)-3-((6-(5-(cyclopentyl(methyl)amino)-5-carbonylpent-1-yn-1-yl)-2-(trifluoromethyl)pyridin-3-yl)oxo)cyclohexane-1-carboxylate

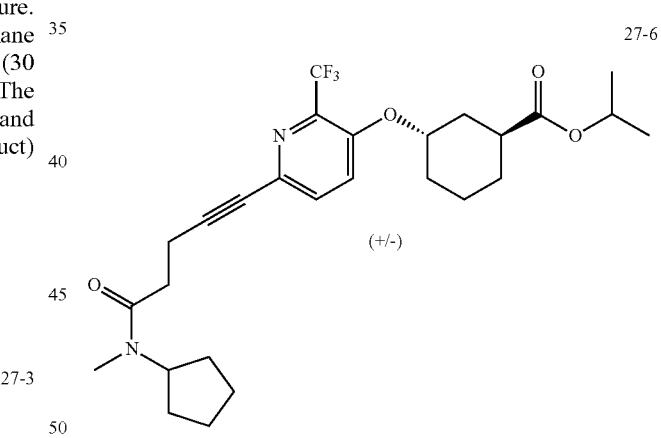

27-6

Compound 27-5 (641 mg, 1.56 mmol) was dissolved in DMF (15 mL), and then N-cyclopentyl-N-methylpent-4-ynamide (280 mg, 1.56 mmol), copper(I) iodide (18 mg, 0.09 mmol), bis(triphenylphosphine)palladium(II) chloride (33 mg, 0.047 mmol) and triethylamine (643 mg, 4.68 mmol) were added successively, and the reaction system was stirred overnight at 80° C. under nitrogen atmosphere. Then the reaction system was purified by silica gel column chromatography (PE/EA=4/1) to give Compound 27-6 (0.63 g, 75.6% yield) in the form of a yellow solid.

LC-MS [M+H]$^+$: 509.2.

193

Step (5): Preparation of (+/−)-isopropyl (1S,3S)-3-((6-(5-(3-(cyclopentyl(methyl)amino)-3-carbonylpropyl)-1-methyl-1H-1,2,3-triazol-4-yl)-2-(trifluoromethyl)pyridin-3-yl)oxo)cyclohexane-1-carboxylate and (+/−)-isopropyl (1S,3S)-3-((6-(4-(3-(cyclopentyl(methyl)amino)-3-carbonylpropyl)-1-methyl-1H-1,2,3-triazol-5-yl)-2-(trifluoromethyl)pyridin-3-yl)oxo)cyclohexane-1-carboxylate

194

Step (6): Preparation of (+/−)-(1S,3S)-3-((6-(5-(3-(cyclopentyl(methyl)amino)-3-carbonylpropyl)-1-methyl-1H-1,2,3-triazol-4-yl)-2-(trifluoromethyl)pyridin-3-yl)oxo)cyclohexane-1-carboxylic acid and (+/−)-(1S,3S)-3-((6-(4-(3-(cyclopentyl(methyl)amino)-3-carbonylpropyl)-1-methyl-1H-1,2,3-triazol-5-yl)-2-(trifluoromethyl)pyridin-3-yl)oxo)cyclohexane-1-carboxylic acid

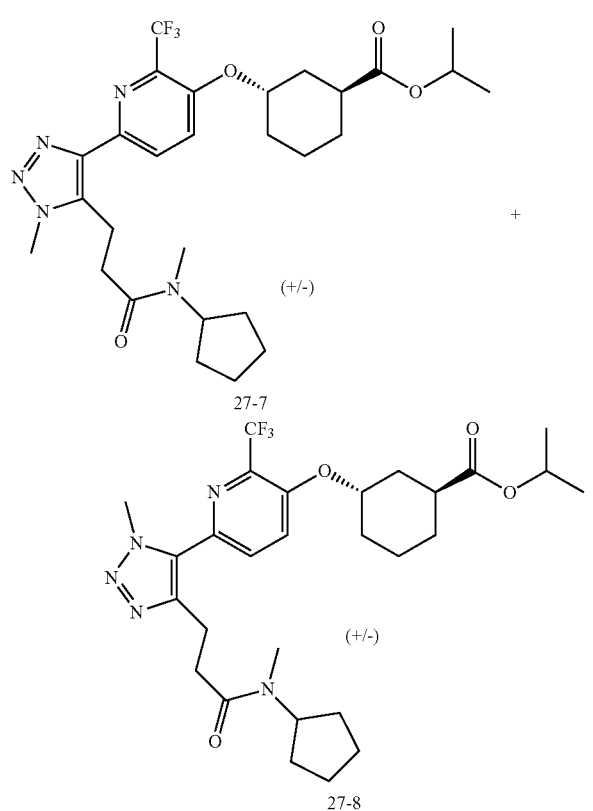

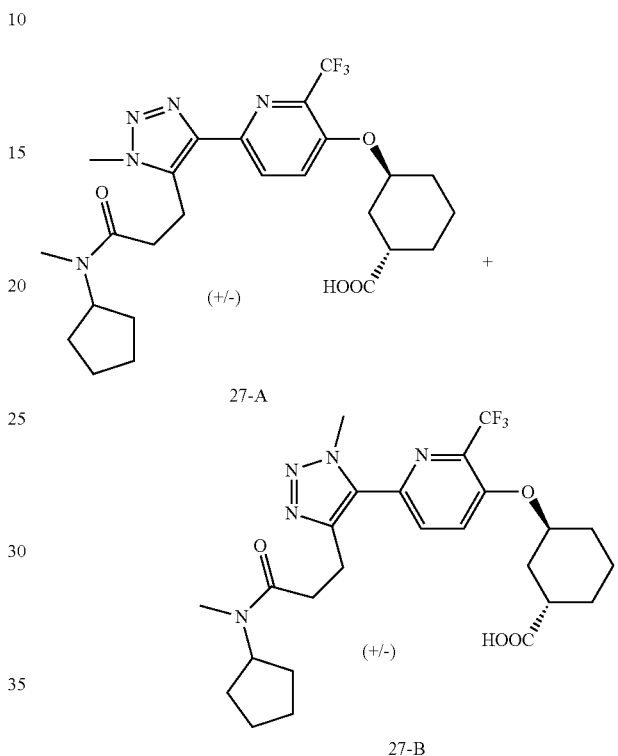

Compound 27-6 (0.74 g, 1.46 mmol) was dissolved in DMF (10 mL), and then (azidomethyl)trimethylsilane (567 mg, 4.38 mmol) was added, and the reaction system was heated to 90° C. and stirred for 48 h under nitrogen atmosphere. Then the reaction system was quenched with water (50 mL), extracted with ethyl acetate (40 mL×2) and washed with saturated brine (30 mL×2). The organic phase was dried over anhydrous sodium sulfate and filtered to remove solids, and the filtrate was dried by rotary evaporation. The residue was dissolved in tetrahydrofuran (20 mL), and then the reaction system was added with tetrabutylammonium fluoride (1 mL) and reacted at room temperature for 2 h. Then the reaction system was quenched with saturated ammonium chloride (20 mL), extracted with ethyl acetate (20 mL×2) and washed with saturated brine (20 mL×2). The organic phase was dried over anhydrous sodium sulfate and purified by silica gel column chromatography (PE/EA=4/1) to give a crude compound (a mixture of two isomers, 220 mg, 13% yield over two steps) in the form of a yellow solid. LC-MS [M+H]$^+$: 566.4.

The product of the last step (220 mg, mixture) was dissolved in THF (18 mL), and then MeOH (6 mL), H$_2$O (6 mL) and lithium hydroxide (63 mg, 1.5 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation. The residue was purified by silica gel column chromatography (DCM/MeOH=15/1), separated by preparative chromatography, and then lyophilized to give a white solid.

Compound 27-A: white solid, 29 mg, LC-MS [M+H]$^+$: 524.6.

$^1$H NMR (400 MHz, MeOD) δ 8.26-8.23 (m, 1H), 7.93-7.77 (m, 1H), 4.97-4.95 (m, 1H), 4.84-4.52 (m, 1H), 4.13-4.12 (d, 3H), 3.31-3.30 (m, 2H), 3.08 (t, J=7.1 Hz, 1H), 2.93 (t, J=7.3 Hz, 1H), 2.76-2.73 (m, 4H), 2.16-2.12 (m, 1H), 1.93-1.71 (m, 3H), 1.82-1.34 (m, 12H).

Compound 27-B: white solid, 34 mg, LC-MS [M+H]$^+$: 524.6.

$^1$H NMR (400 MHz, MeOD) δ 8.01-7.96 (m, 1H), 7.92-7.87 (m, 1H), 5.02-4.98 (m, 0.6H), 4.84-4.57 (m, 1H), 4.33-4.19 (m, 0.4H), 4.16 (d, 3H), 3.11-3.06 (m, 2H), 2.98-2.68 (m, 6H), 2.20-2.13 (m, 1H), 1.98-1.92 (m, 3H), 1.84-1.38 (m, 12H).

Example 28

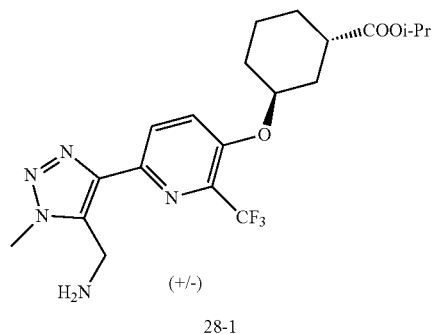

28-1 triphosgene →

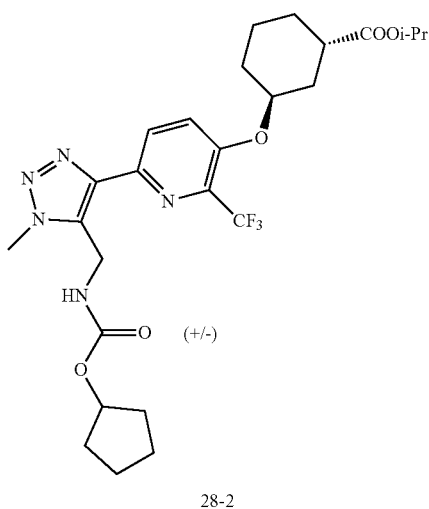

28-2

LiOH →

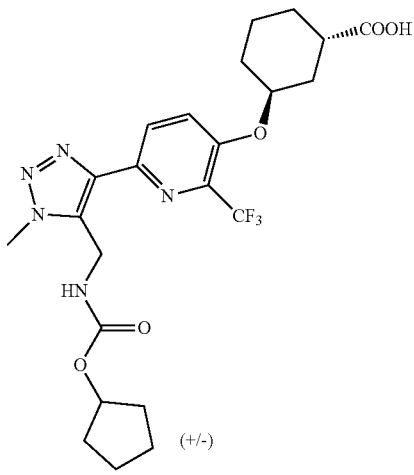

28

Step (1): Preparation of (+/−)-isopropyl (1S,3S)-3-((6-(5-((((cyclopentyloxy)carbonyl)amino)methyl)-1-methyl-1H-1,2,3-triazol-4-yl)-2-(trifluoromethyl)pyridin-3-yl)oxo)cyclohexane-1-carboxylate

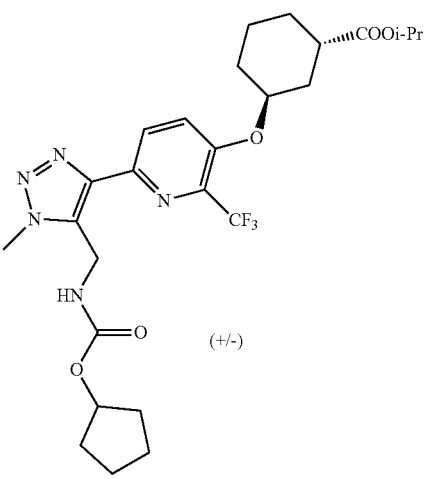

28-2

Triphosgene (120 mg, 0.42 mmol) was dissolved in tetrahydrofuran (5 mL), and then the reaction system was cooled to 0° C. and slowly added with a solution of triethylamine (158 mg, 1.56 mmol) and cyclopentylmethylamine (103 mg, 1.2 mmol) in tetrahydrofuran (5 mL) dropwise. After reaction at 0° C. for 1 h, the reaction system was added with Compound 28-1 (50 mg, 0.12 mmol), slowly warmed to room temperature and reacted for 16 h. Then the reaction system was quenched with water (10 mL) and extracted with ethyl acetate (20 mL). The organic phase was washed with saturated brine (20 mL), dried over anhydrous sodium sulfate and concentrated, and the residue was separated by column chromatography (DCM/MeOH=30/1) to give Compound 28-2 (60 mg, 85% yield) in the form of a yellow solid. LC-MS [M+H]⁺: 554.2.

Step (2): Preparation of (+/−)-(1S,3S)-3-((6-(5-(((((cyclopentyloxy)carbonyl)amino)methyl)-1-methyl-1H-1,2,3-triazol-4-yl)-2-(trifluoromethyl)pyridin-3-yl)oxo)cyclohexane-1-carboxylic acid

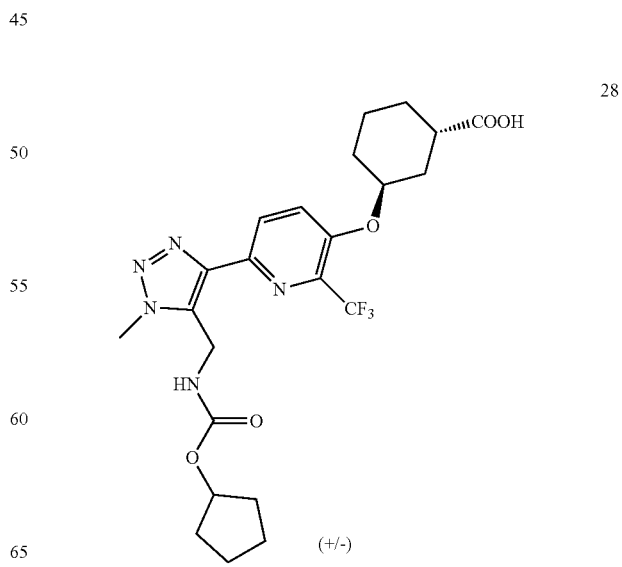

28

Compound 28-2 (60 mg, 0.11 mmol) was dissolved in THF (9 mL), and MeOH (3 mL), H₂O (3 mL) and lithium hydroxide (23 mg, 0.55 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation. The residue was purified by silica gel column chromatography (DCM/MeOH=20/1), separated by preparative chromatography, and then lyophilized to give Compound 28 (25 mg, 45.4% yield) in the form of a white solid.

LC-MS [M+H]⁺: 512.6. ¹H NMR (400 MHz, MeOD) δ 8.29 (d, J=8.9 Hz, 1H), 7.87 (d, J=9.0 Hz, 1H), 5.03-5.01 (m, 2H), 4.76 (s, 2H), 4.21 (s, 3H), 2.80-2.74 (m, 1H), 2.17-2.15 (m, 1H), 2.03-1.88 (m, 3H), 1.72-1.44 (m, 12H).

Example 29

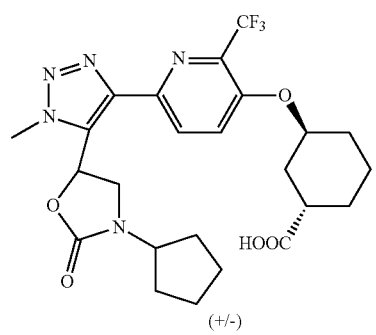

29

The preparation process is similar to that in Example 9, LC-MS [M+H]⁺: 524.5.

Example 30

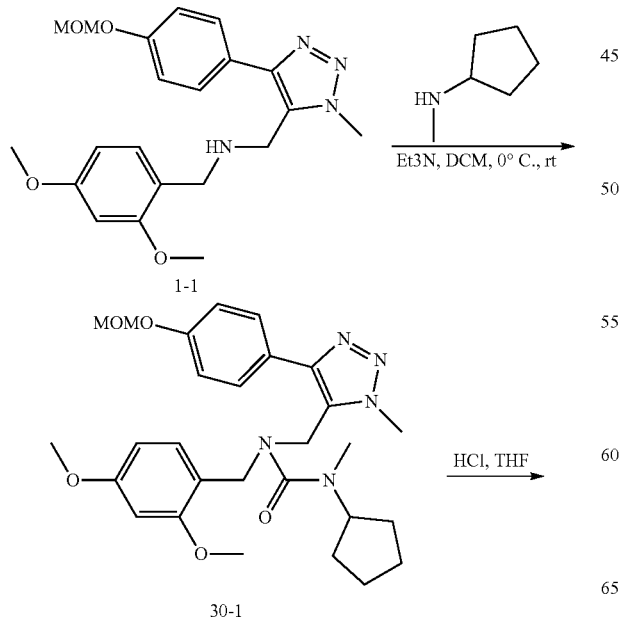

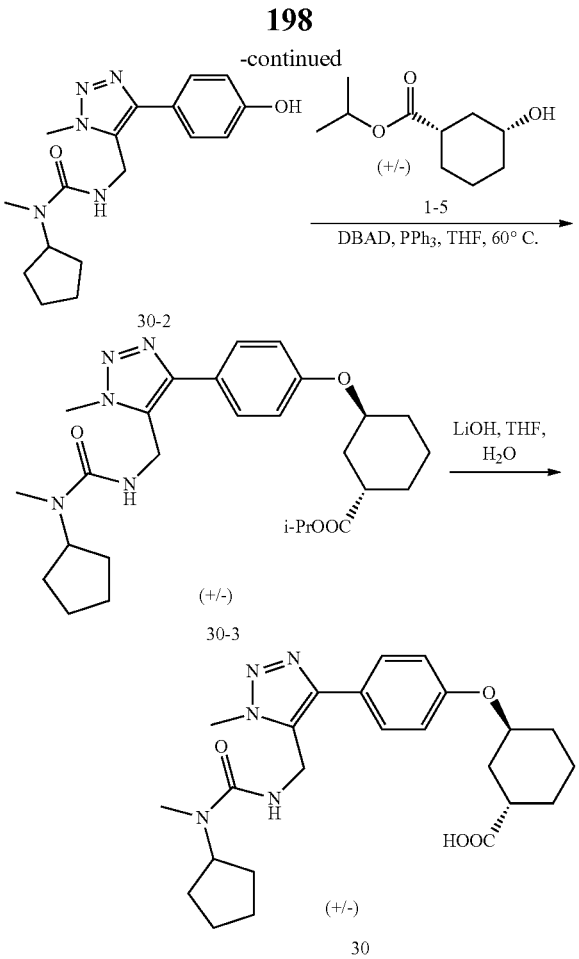

Step (1): Preparation of 3-(2,4-dimethoxybenzyl)-3-((4-(4-(methoxymethoxy)phenyl)-1-methyl-1H-1,2,3-triazol-5-yl)methyl)-1-cyclopentyl-1-methylurea

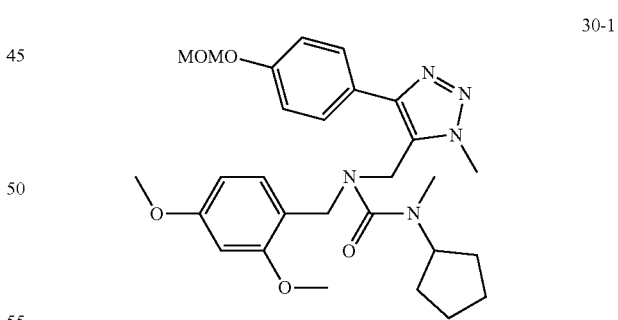

Triphosgene (232 mg, 0.78 mmol) was dissolved in dichloromethane (10 mL), and then the reaction system was cooled to 0° C. and slowly added with a solution of triethylamine (394 mg, 3.91 mmol) and cyclopentylmethylamine (318 mg, 2.34 mmol) in dichloromethane (10 mL) dropwise. After reaction at 0° C. for 1 h, the reaction system was added with Compound 1-1 (300 mg, 0.78 mmol), slowly warmed to room temperature and reacted for 16 h. Then the reaction system was quenched with water (10 mL), washed with saturated brine (20 mL), dried over anhydrous sodium sulfate and concentrated, and the residue was separated by column chromatography (DCM/MeOH=30/1) to give Compound 30-1 (400 mg, crude product).

LC-MS [M+H]⁺: 524.2.

Step (2): Preparation of 3-((4-(4-hydroxyphenyl)-1-methyl-1H-1,2,3-triazol-5-yl)methyl)-1-cyclopentyl-1-methylurea

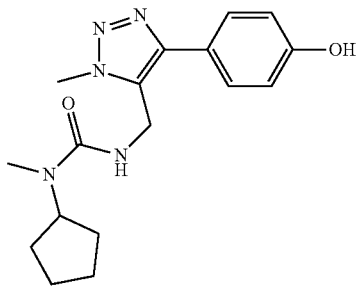

30-2

Compound 30-1 (400 mg, crude product) was dissolved in tetrahydrofuran (10 mL), and then HCl (5 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=15/1) to give Compound 30-2 (60 mg) in the form of a yellow solid. LC-MS [M+H]⁺: 330.4.

Step (3): Preparation of (+/−)-isopropyl (1S,3S)-3-(4-(5-((3-cyclopentyl-3-methylureido)methyl)-1-methyl-1H-1,2,3-triazol-4-yl)phenoxy)cyclohexane-1-carboxylate

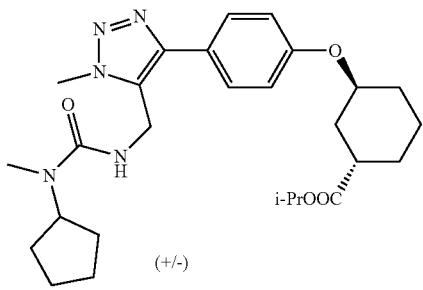

30-3

Compound 30-2 (60 mg, 0.18 mmol), (+/−)-isopropyl 3-hydroxycyclohexane-1-carboxylate (135 mg, 0.73 mmol), DTAD (168 mg, 0.73 mmol) and PPh₃ (192 mg, 0.73 mmol) were dissolved in THF (10 mL), and the reaction system was stirred overnight at 60° C. under nitrogen atmosphere. Then the reaction system was purified by silica gel column chromatography (DCM/EA=50/1) to give Compound 30-3 (85 mg, crude product) in the form of a yellow solid. LC-MS [M+H]⁺: 498.2.

Step (4): Preparation of (+/−)-(1S,3S)-3-(4-(5-((3-cyclopentyl-3-methylureido)methyl)-1-methyl-1H-1,2,3-triazol-4-yl)phenoxy)cyclohexane-1-carboxylic acid

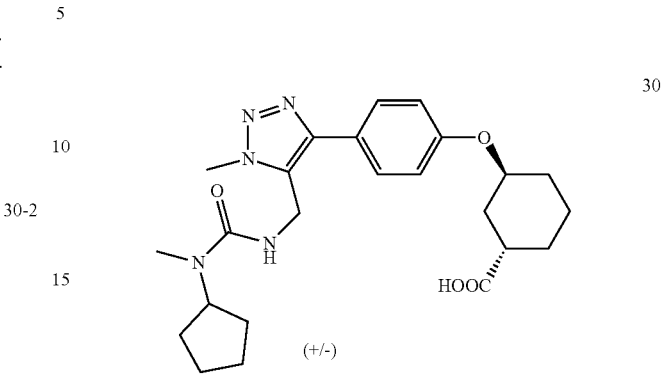

30

Compound 30-3 (85 mg, crude product) was dissolved in THF (9 mL), and MeOH (3 mL), H₂O (3 mL) and lithium hydroxide (42 mg, 1.0 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate, and filtered, and the filtrate was dried by rotary evaporation.

The residue was purified by silica gel column chromatography (DCM/MeOH=20/1) and then lyophilized to give Compound 30 (35 mg) in the form of a white solid.

LC-MS [M+H]⁺: 456.2. ¹H NMR (400 MHz, DMSO) δ 12.19 (s, 1H), 7.69 (d, J=8.8 Hz, 2H), 7.03 (d, J=8.8 Hz, 2H), 6.76 (t, J=4.8 Hz, 1H), 4.72-4.67 (m, 1H), 4.45-4.41 (m, 3H), 4.03 (s, 3H), 2.71-2.63 (m, 1H), 2.62 (s, 3H), 1.96-1.94 (m, 1H), 1.87-1.77 (m, 3H), 1.65-1.59 (m, 6H), 1.55-1.37 (m, 6H).

Example 31

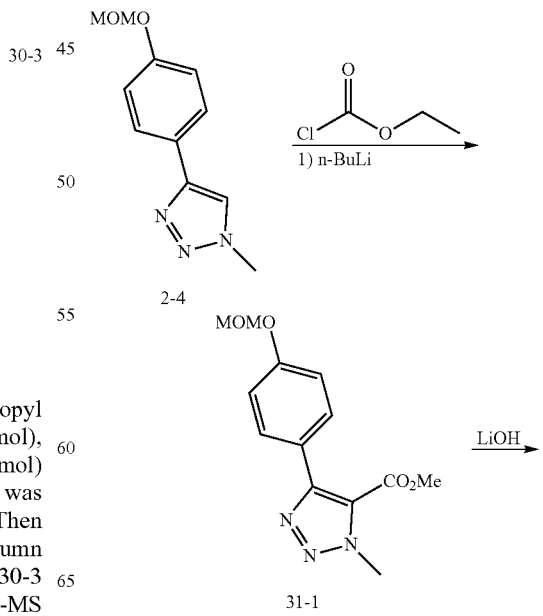

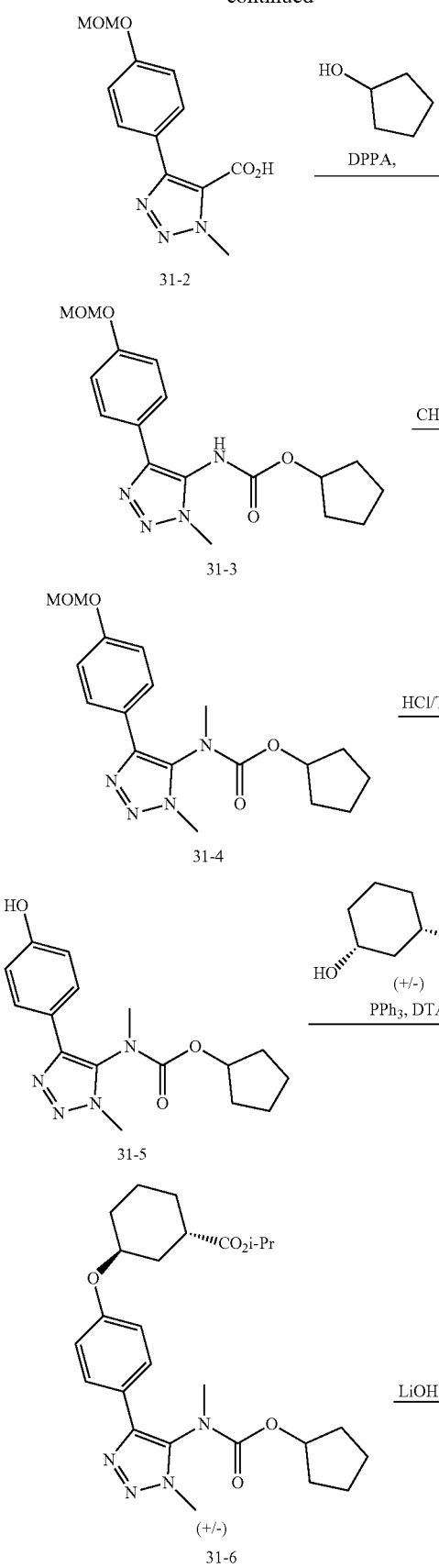

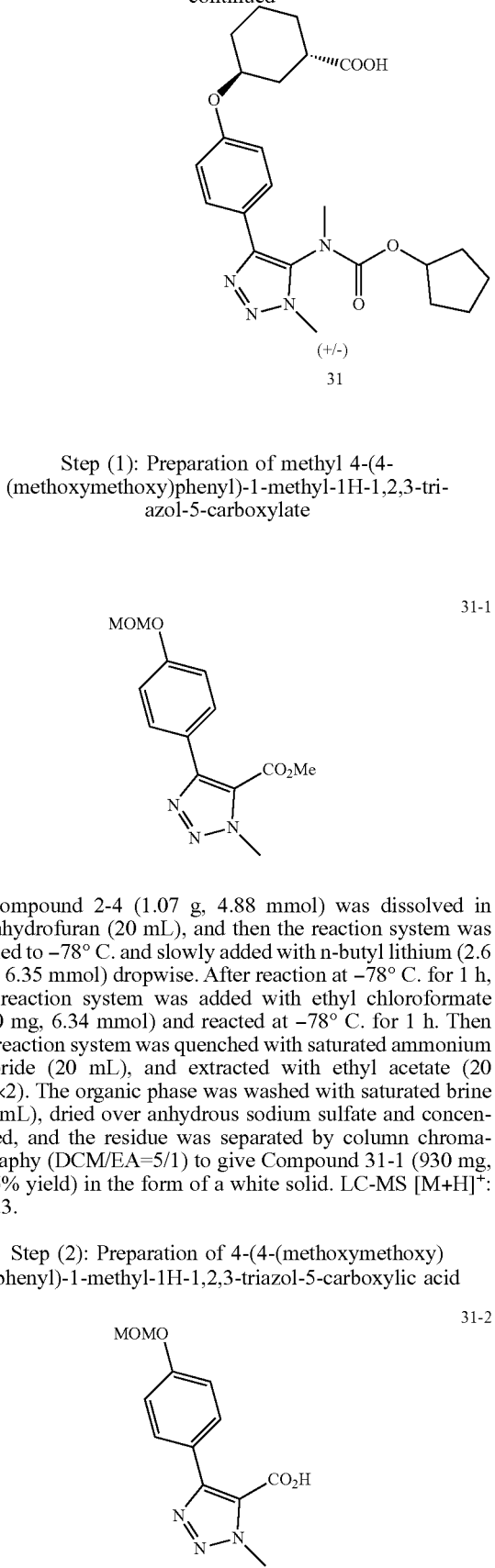

Step (1): Preparation of methyl 4-(4-(methoxymethoxy)phenyl)-1-methyl-1H-1,2,3-triazol-5-carboxylate Compound 2-4 (1.07 g, 4.88 mmol) was dissolved in tetrahydrofuran (20 mL), and then the reaction system was cooled to −78° C. and slowly added with n-butyl lithium (2.6 mL, 6.35 mmol) dropwise. After reaction at −78° C. for 1 h, the reaction system was added with ethyl chloroformate (600 mg, 6.34 mmol) and reacted at −78° C. for 1 h. Then the reaction system was quenched with saturated ammonium chloride (20 mL), and extracted with ethyl acetate (20 mL×2). The organic phase was washed with saturated brine (20 mL), dried over anhydrous sodium sulfate and concentrated, and the residue was separated by column chromatography (DCM/EA=5/1) to give Compound 31-1 (930 mg, 71.5% yield) in the form of a white solid. LC-MS [M+H]⁺: 278.3.

Step (2): Preparation of 4-(4-(methoxymethoxy)phenyl)-1-methyl-1H-1,2,3-triazol-5-carboxylic acid Compound 31-1 (930 mg, 3.35 mmol) was dissolved in tetrahydrofuran (20 mL), and MeOH (6 mL), $H_2O$ (6 mL) and lithium hydroxide (705 mg, 16.8 mmol) were added successively, and the reaction system was stirred overnight at room temperature. Then water (20 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate and filtered, and the filtrate was dried by rotary evaporation. The residue was purified by silica gel column chromatography (DCM/MeOH=30/1) to give Compound 31-2 (860 mg, 96% yield) in the form of a white solid. LC-MS [M+H]$^+$: 264.2.

Step (3): Preparation of cyclopentyl (4-(4-(methoxymethoxy)phenyl)-1-methyl-1H-1,2,3-triazol-5-yl) carbamate

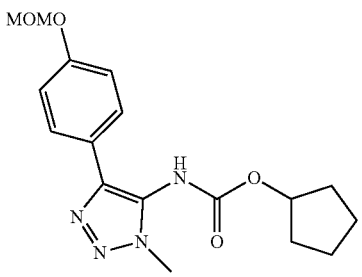

31-3

Compound 31-2 (160 mg, 0.61 mmol) was dissolved in toluene (10 mL), and then cyclopentanol (105 mg, 1.21 mmol), diphenylphosphoryl azide (201 mg, 0.73 mmol) and triethylamine (123 mg, 1.21 mmol) were added, and the reaction system was heated to reflux and reacted for 16 h under nitrogen atmosphere. The reaction system was concentrated, and the residue was separated by column chromatography (DCM/MeOH=50/1) to give Compound 31-3 (0.2 g, 94% yield) in the form of a white solid. LC-MS [M+H]$^+$: 347.2.

Step (4): Preparation of cyclopentyl (4-(4-(methoxymethoxy)phenyl)-1-methyl-1H-1,2,3-triazol-5-yl) (methyl)carbamate

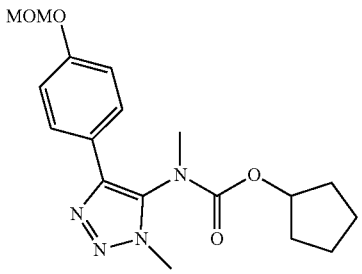

31-4

Compound 31-3 (0.2 g, 0.58 mmol) was dissolved in tetrahydrofuran (10 mL), and the reaction system was cooled to 0° C. and added with sodium hydride (35 mg, 0.86 mmol). The reaction system was then warmed to room temperature, reacted for 0.5 h, added with iodomethane (164 mg, 1.15 mmol) and reacted overnight at room temperature. Then the reaction system was quenched with saturated ammonium chloride (10 mL), and extracted with ethyl acetate (20 mL×2). The organic phase was washed with saturated brine (20 mL), dried over anhydrous sodium sulfate and concentrated, and the residue was separated by column chromatography (DCM/MeOH=50/1) to give Compound 31-4 (190 mg, 90% yield) in the form of a white solid. LC-MS [M+H]$^+$: 361.4.

Step (5): Preparation of cyclopentyl (4-(4-hydroxyphenyl)-1-methyl-1H-1,2,3-triazol-5-yl)(methyl) carbamate

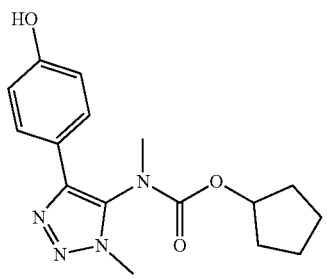

31-5

Compound 31-4 (190 mg, 0.53 mmol) was dissolved in tetrahydrofuran (10 mL), and then HCl (2 N, 5 mL) was added, and the reaction system was stirred overnight at room temperature. Then the reaction system was diluted with ethyl acetate (20 mL), washed successively with water (20 mL) and saturated brine (20 mL), dried over anhydrous sodium sulfate and concentrated, and the residue was separated by column chromatography (DCM/MeOH=15/1) to give Compound 31-5 (120 mg, 71% yield) in the form of a yellow solid. LC-MS [M+H]$^+$: 317.4.

Step (6): Preparation of (+/−)-isopropyl (1S,3S)-3-(4-(5-(((cyclopentyloxy)carbonyl)(methyl)amino)-1-methyl-1H-1,2,3-triazol-4-yl)phenoxy)cyclohexane-1-carboxylate

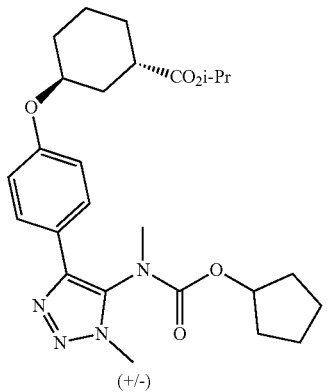

31-6

(+/−)

Compound 31-5 (120 mg, 0.38 mmol), (+/−)-isopropyl 3-hydroxycyclohexane-1-carboxylate (283 mg, 1.52 mmol), DTAD (350 mg, 1.52 mmol) and $PPh_3$ (398 mg, 1.52 mmol)

were dissolved in THF (10 mL), and the reaction system was stirred overnight at 60° C. under nitrogen atmosphere.

Then the reaction system was purified by silica gel column chromatography (DCM/EA=50/1) to give Compound 31-6 (260 mg) in the form of a yellow solid. LC-MS [M+H]$^+$: 485.2.

Step (7): Preparation of (+/−)-(1S,3S)-3-(4-(5-(((cyclopentyloxy)carbonyl)(methyl)amino)-1-methyl-1H-1,2,3-triazol-4-yl)phenoxy)cyclohexane-1-carboxylic acid

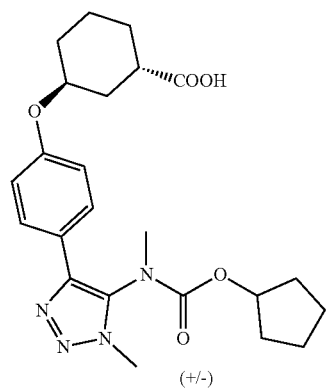

31

Compound 31-6 (260 mg, crude product) was dissolved in THF (18 mL), and MeOH (6 mL), H$_2$O (6 mL) and lithium hydroxide (52 mg, 1.25 mmol) were added successively, and the reaction system was stirred overnight at room temperature. Then water (10 mL) was added for dilution, and the organic solvent was removed by rotary evaporation under reduced pressure. The aqueous phase was adjusted to pH 5-6 with HCl (1 N), and extracted with dichloromethane (10 mL×2). The organic phase was dried over anhydrous sodium sulfate and filtered, and the filtrate was dried by rotary evaporation. The residue was purified by silica gel column chromatography (DCM/MeOH=20/1) and then lyophilized to give Compound 31 (40 mg, 38% yield over two steps) in the form of a white solid.

LC-MS [M+H]$^+$: 443.6. $^1$H NMR (400 MHz, MeOD) δ 7.54 (d, J=8.8 Hz, 2H), 7.06 (d, J=8.8 Hz, 2H), 5.22-5.09 (m, 1H), 4.75-4.73 (m, 1H), 3.93 (s, 3H), 3.16-3.13 (m, 3H), 2.79-2.76 (m, 1H), 1.91-1.79 (m, 1H), 1.76-1.71 (m, 4H), 1.64-1.19 (m, 11H).

Example 32

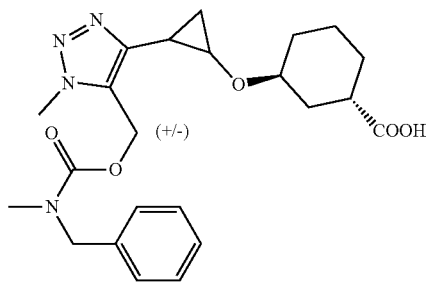

32

Refer to the method in Example 1, LC-MS [M+H]$^+$: =443.21.

Example 33

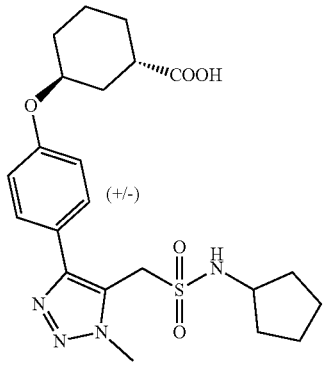

33

Refer to the method in Example 18, LC-MS [M+H]$^+$: 463.17.

Example 34

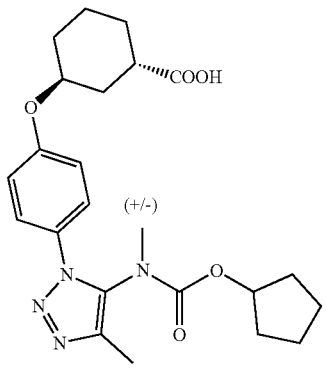

34

Refer to the method in Example 31, LC-MS [M+H]$^+$: 443.20.

Example 35

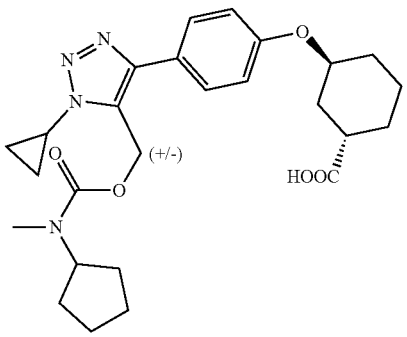

35

Refer to the method in Example 31, LC-MS [M+H]+: 483.21.

Example 36

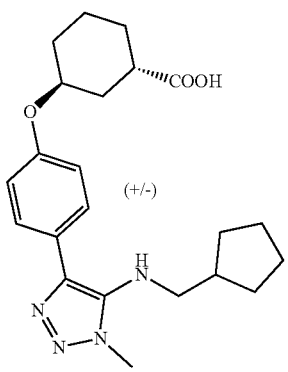

36

Refer to the method in Example 31, LC-MS [M+H]+: 399.20.

Example 37

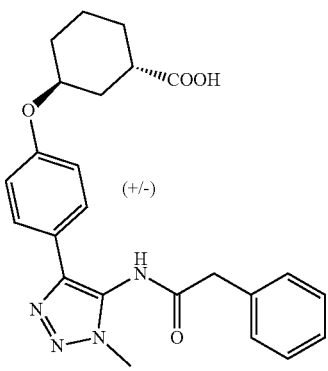

37

Refer to the method in Example 31, LC-MS [M+H]+: 435.19.

Example 38

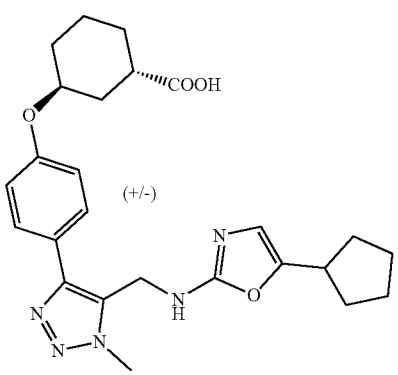

38

Refer to the method in Example 31, LC-MS [M+H]+: 466.17.

Example 39

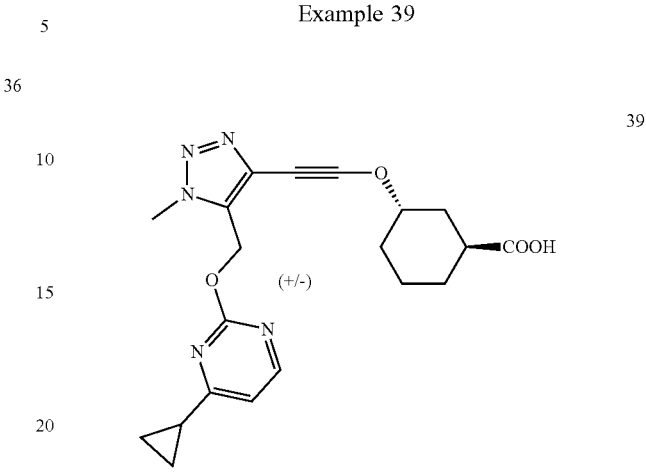

39

Refer to the method in Example 1, LC-MS [M+H]+: 398.12.

Biological Experiments

Example A: In Vitro Evaluation of Biological Activity

The antagonist property of the compounds disclosed herein was determined using the FLIPR (fluorescence imaging plate reader) method, wherein the compounds are inhibitors for the intracellular calcium increase induced by activation of hLPAR1 (human lysophosphatidic acid receptor 1, accession No. NM_001401.4) expressed in CHO-K1 cells (Chinese hamster ovary cells K1, ATCC).

CHO-K1 cells stably expressing hLPAR1 were cultured in F-12 medium containing 10% FBS (fetal bovine serum, Gibco, 10099-141), 1% penicillin-streptomycin (Gibco, 15140-122) and 0.4 mg/mL hygromycin B (Gibco, 10687010) in a cell incubator (37° C., 5% humidity). During 18-24 h prior to the FLIPR experiment, cells at 250,000 cells/mL were seeded into a 96-well plate (25,000 cells/well) and incubated overnight in the cell incubator. On the day of the experiment, the medium was discarded and the cells were washed in a FLIPR buffer (0.3 mL of probenecid (Thermo, P36400), 0.6 mL of 1 M HEPES (Invitrogen, 15630080) and 29.1 mL of HBSS (Invitrogen, 14065056) per 30 mL of buffer). Each well was added with 75 μL of 1 mM Fluo-4 AM fluorescent dye (Thermo, F14202) and then the cells were subjected to dye-loading incubation at 37° C. for 1.0 h. The 96-well plate was then washed once with buffer, added with a buffer containing a test compound or vehicle at 50 μL per well and then incubated for 30 min at room temperature. The cell plate was then placed in the FLIPR for baseline fluorescence measurements (excitation at 485 nm and emission at 525-535 nm). An agonist (oleoyl-L-α-lysophosphatidic acid sodium salt (Sigma, L7260) at a final concentration of 1 μM) or a vehicle (ultrapure water) was then added at 50 μL/well, fluorescence values were measured for 2 min at 1-second intervals, and finally the output fluorescence counts were analyzed.

$IC_{50}$ values obtained using the above method are shown in Table 1.

TABLE 1

IC$_{50}$ values of compounds of Examples 1-39 for LPAR1 receptor

| Compound | Example No. | LPAR1 IC$_{50}$ (μM) |
|---|---|---|
| Compound 1 | Example 1 | B |
| Compound 2 | Example 2 | B |
| Compound 3 | Example 3 | B |
| Compound 4 | Example 4 | B |
| Compound 5 | Example 5 | C |
| Compound 6 | Example 6 | B |
| Compound 7 | Example 7 | C |
| Compound 8 | Example 8 | B |
| Compound 9 | Example 9 | B |
| Compound 10 | Example 10 | B |
| Compound 11 | Example 11 | B |
| Compound 12 | Example 12 | C |
| Compound 13 | Example 13 | B |
| Compound 14 | Example 14 | B |
| Compound 15 | Example 15 | C |
| Compound 16 | Example 16 | C |
| Compound 17 | Example 17 | B |
| Compound 18 | Example 18 | B |
| Compound 19 | Example 19 | B |
| Compound 20 | Example 20 | B |
| Compound 21 | Example 21 | B |
| Compound 22 | Example 22 | B |
| Compound 23 | Example 23 | B |
| Compound 24 | Example 24 | C |
| Compound 25 | Example 25 | B |
| Compound 26 | Example 26 | A |
| Compound 27-A | Example 27 | A |
| Compound 27-B | Example 27 | C |
| Compound 28 | Example 28 | B |
| Compound 29 | Example 29 | C |
| Compound 30 | Example 30 | B |
| Compound 31 | Example 31 | B |
| Compound 32 | Example 32 | C |
| Compound 33 | Example 33 | C |
| Compound 34 | Example 34 | C |
| Compound 35 | Example 35 | C |
| Compound 36 | Example 36 | C |
| Compound 37 | Example 37 | C |
| Compound 38 | Example 38 | C |
| Compound 39 | Example 39 | A |

A: IC$_{50}$ ≤ 50 nM;
B: 50 < IC$_{50}$ ≤ 300 nM;
C: 300 < IC$_{50}$ ≤ 10,000 nM.

The results show that the above compounds have good inhibitory activity against LPAR1. The IC$_{50}$ value of some of the compounds was 10,000 nM or less, 300 nM or less, or even 50 nM or less. In view of such excellent inhibitory activity, application thereof as LPAR1 inhibitors to treat the diseases or disorders described above is promising.

Example B: In Vitro Evaluation of Biological Activity (Cell Activity)

The activity of the compounds disclosed herein at the cell level in vitro is evaluated by A2058 (human melanoma cells, Beina Bio, BNCC341099) cell scratch assay. The inhibitory activity of the compounds against LPAR1 can be reflected by inhibition of cell scratch healing.

A2058 cells in a T75 cm$^2$ cell culture flask were digested and gently pipetted into single cells, adjusted to a cell density of 4×10$^5$ cells/mL, and then seeded into a 24-well plate. After the cell confluence reached 80%, the cell culture plate was taken out and the original medium was discarded. Serum-free medium was then added, and the cells were starved overnight in an incubator (37° C., 5% CO$_2$). The cell culture plate was then taken out, and cell scratches were made along the diameter of the wells using a 200 μL pipette tip. The cell culture plate was then added with 500 μL of serum-free medium and then shaken gently to wash away the residual cells on the scratched surface, and this was repeated twice. The medium was discarded and 500 μL of 1% FBS medium containing the compound was then added, and the mixture was incubated at 37° C. for 30 min. The medium was discarded, and 500 μL of 1% FBS medium containing 10 μM compound and 10 μM LPA was added. Olympus CKX53 was used to observe the scratches, and MShot image analysis system was used to take pictures and measure the scratch area at 0 h. Then the cell culture plate was incubated in the incubator (37° C., 5% CO$_2$). 24 h later, the scratches were observed again with Olympus CKX53, and MShot image analysis system was used to take pictures and measure the scratch area at 24 h. Cell migration inhibition rate was calculated according to the following formula:

$$\text{Cell migration inhibition rate}(\%) = 1 - \frac{\text{scratch area of compound group at 0 h} - \text{scratch area of compound group at 24 h}}{\text{scratch area of control group at 0 h} - \text{scratch area of control group at 24 h}}$$

TABLE 2

Inhibition rate of some of the compounds against scratch migration of A2058 cells

| Compound | Example No. | Cell migration inhibition rate (% 20 μM) |
|---|---|---|
| Compound 1 | Example 1 | B |
| Compound 2 | Example 2 | C |
| Compound 3 | Example 3 | B |
| Compound 4 | Example 4 | B |
| Compound 5 | Example 5 | C |
| Compound 6 | Example 6 | B |
| Compound 7 | Example 7 | C |
| Compound 8 | Example 8 | C |
| Compound 9 | Example 9 | B |
| Compound 10 | Example 10 | B |
| Compound 11 | Example 11 | C |
| Compound 12 | Example 12 | C |
| Compound 13 | Example 13 | C |
| Compound 14 | Example 14 | B |
| Compound 15 | Example 15 | B |
| Compound 16 | Example 16 | B |
| Compound 17 | Example 17 | C |
| Compound 18 | Example 18 | B |
| Compound 19 | Example 19 | C |
| Compound 20 | Example 20 | B |
| Compound 21 | Example 21 | B |
| Compound 22 | Example 22 | B |
| Compound 23 | Example 23 | B |
| Compound 24 | Example 24 | C |
| Compound 25 | Example 25 | B |
| Compound 26 | Example 26 | B |
| Compound 27-A | Example 27 | A |
| Compound 27-B | Example 27 | C |
| Compound 28 | Example 28 | A |
| Compound 29 | Example 29 | C |
| Compound 30 | Example 30 | B |
| Compound 31 | Example 31 | B |

A: 50-70%;
B: 30-50%;
C: 0-30%.

It can be seen from the data in Table 2 that the above-mentioned compounds of the present invention have relatively good inhibitory activity against LPAR1, wherein some compounds have an inhibitory rate of 30-50% against A2058 cell migration, some compounds have an inhibitory rate of 50-70%, and cell migration is remarkably inhibited.

Example C: In Vitro Cytotoxicity Assay

In vitro cytotoxicity assay for the compounds disclosed herein was performed in HepG2 cells using the CCK-8 method. HepG2 cells (Beina Bio) in the logarithmic growth phase were collected, the concentration of cell suspension was adjusted, and then the cells were plated on a 96-well cell culture plate at 50,000 cells/well.

The cells were then incubated overnight in a cell incubator (5% $CO_2$, 37° C.), and after 80-90% cell confluence was achieved, test compounds or vehicle (DMSO) at various concentration gradients were added after medium change. The resulting mixture was incubated in the cell incubator (5% $CO_2$, 37° C.) for 48 h. After the treatment, the medium in the plate was discarded. The plate was washed twice with PBS, added with CCK-8 working solution (Beyotime) at 100 μL per well, and then incubated at 37° C. for 1.5 h in the dark. Absorbance at $OD_{450nm}$ was measured for each well on a microplate reader, and $CC_{50}$ value of each compound was analyzed and calculated. $CC_{50}$ values obtained using the above method are shown in Table 3.

TABLE 3

$CC_{50}$ values obtained for some of the compounds

| Compound | Example No. | HepG2 $CC_{50}$ (μM) |
|---|---|---|
| Compound 1 | Example 1 | >200 |
| Compound 2 | Example 2 | >200 |
| Compound 3 | Example 3 | >200 |
| Compound 4 | Example 4 | >200 |
| Compound 5 | Example 5 | >200 |
| Compound 6 | Example 6 | >200 |
| Compound 7 | Example 7 | >200 |
| Compound 8 | Example 8 | >200 |
| Compound 9 | Example 9 | >200 |
| Compound 10 | Example 10 | >200 |
| Compound 11 | Example 11 | >200 |
| Compound 12 | Example 12 | >200 |
| Compound 13 | Example 13 | >200 |
| Compound 14 | Example 14 | >200 |
| Compound 15 | Example 15 | >200 |
| Compound 16 | Example 16 | >200 |
| Compound 17 | Example 17 | >200 |
| Compound 18 | Example 18 | >200 |
| Compound 19 | Example 19 | >200 |
| Compound 20 | Example 20 | >200 |
| Compound 21 | Example 21 | >200 |
| Compound 22 | Example 22 | >200 |
| Compound 23 | Example 23 | >200 |
| Compound 24 | Example 24 | >200 |
| Compound 25 | Example 25 | >200 |
| Compound 26 | Example 26 | >200 |
| Compound 27-A | Example 27 | >200 |
| Compound 27-B | Example 27 | >200 |
| Compound 28 | Example 28 | >200 |
| Compound 29 | Example 29 | >200 |
| Compound 30 | Example 30 | >200 |
| Compound 31 | Example 31 | >200 |

It can be seen from the data in Table 3 that the compounds disclosed herein all have good safety, and the $CC_{50}$ values of the compounds are all greater than 200 μM.

Example D: Test of In Vitro Metabolic Stability

The in vitro metabolic stability of the compounds disclosed herein was determined through incubation of liver microsomes of various species. A proper amount of test compound was added into a liver microsome reaction system (1 mg/mL liver microsome protein, 25 U/mL glucose-6 phosphate dehydrogenase, 1 mM NADP, 6 mM D-glucose 6-phosphate and 5 mM $MgCl_2$), and then the mixture was incubated in a water bath kettle at 37° C. to start reaction. At each time point, 100 μL of the reaction system was added into a centrifuge tube containing 400 μL of internal standard working solution (containing a 200 ng/mL solution of dexamethasone, diclofenac, tolbutamide and labetalol in acetonitrile) precooled at 0° C. so as to stop the reaction, and the mixture was then centrifuged at 10,000 g for 10 min at 4° C. The supernatant was collected for LC-MS assay so as to obtain the values of in vitro metabolic half-life of the test compounds in liver microsomes of various species.

The metabolic half-life data obtained using the above method are shown in Table 4.

TABLE 4

Metabolic half-life values obtained for some the compounds

| Compound | Example No. | Metabolic half-life in human liver microsome min | Metabolic half-life in rat liver microsome min | Metabolic half-life in mouse liver microsome min | Compound | Example No. | Metabolic half-life in human liver microsome min | Metabolic half-life in rat liver microsome min | Metabolic half-life in mouse liver microsome min |
|---|---|---|---|---|---|---|---|---|---|
| Compound 2 | Example 2 | >30 | >30 | >30 | Compound 3 | Example 3 | >30 | >30 | >30 |
| Compound 7 | Example 7 | >30 | <30 | >30 | Compound 25 | Example 25 | >30 | >30 | >30 |
| Compound 26 | Example 26 | >30 | >30 | >30 | Compound 27-A | Example 27 | 231.83 | 57.05 | 192.02 |
| Compound 31 | Example 31 | >30 | >30 | >30 | | | | | |

The results show that the compounds disclosed herein have relatively good metabolic stability in human, rat, and mouse liver microsomes, wherein the $T_{1/2}$ of some of the compounds in human liver microsome is more than 30 min, or even more than 90 min.

Example E: Pharmacodynamic Evaluation on Bleomycin-Induced Lung Fibrosis Models of Mice Pharmacodynamic evaluation of the compounds disclosed herein was performed using bleomycin-induced lung fibrosis models of mice.

The bleomycin-induced pulmonary fibrosis models of C57BL/6 mice were established by administering 3 mg/kg of bleomycin in a single rapid spray (tracheal spray) with a nebulizer. For the normal control group, normal saline was used instead. Immediately after injection, the animals were erected at a 90-degree angle and rotated left and right for 2 min to allow the medical solution to be evenly distributed in the lungs. On day 0, the bleomycin induction group was randomly divided into a model group and an administration group (divided into low, medium, and high dosage groups) according to body weight. On days 0-20 of the experiment, animals in the normal control group and the model control group were intragastrically administered with vehicle (0.5% CMC-Na) once daily, and animals in the administration group was administered with a corresponding dosage of the compound. After 21 days of consecutive administration, the mice were anesthetized by intraperitoneal injection of 1% sodium pentobarbital (0.06 mL/10 g) and then put to death by bleeding at abdominal aorta. The thoracic cavity was cut open, the whole lungs of the mice were taken out, and the residual blood on the surface was washed away with normal saline. The left lung was soaked in 4% paraformaldehyde for use in the detection of pulmonary inflammation and fibrosis using HE and Masson staining. After the upper bronchus and blood vessels was removed as much as possible, the remaining lung was weighed, added with 1×Ripa lysis buffer (containing protease inhibitor cocktail and PMSF) at a ratio of 2 mL/100 mg, homogenized with a homogenizer, and then stored in a refrigerator at −80° C. for use in the detection of the levels of hydroxyproline, Collagen I and α-SMA in lung tissue.

The results show that the compounds disclosed herein can alleviate bleomycin-induced lung fibrosis in mice by inhibiting the fibrogenic mechanism mediated by LPAR1.

In this specification, terms such as "one embodiment", "some embodiments", "examples", "a specific example", or "some examples" means that a particular feature, structure, material or characteristic described in reference to the embodiment or example is included in at least one embodiment or example of the present invention. In this specification, the schematic descriptions of the terms described above do not necessarily refer to the same embodiment or example. Moreover, the specific features, materials, structures and other characteristics described may be combined in any one or more embodiments or examples in an appropriate manner. Moreover, various embodiments or examples and features of various embodiments or examples described in this specification can be combined by one skilled in the art to the extent that they do not contradict each other.

Although examples of the present invention are illustrated and described above, it will be appreciated that the above examples are exemplary and not to be construed as limiting the present invention, and that changes, modifications, substitutions and alterations can be made to the above examples by those of ordinary skill in the art within the scope of the present invention.

The invention claimed is:

1. A triazole compound of formula (I) or a stereoisomer, a tautomer, an isotopically labeled compound, a nitrogen oxide, a solvate, a polymorph, an ester, or a pharmaceutically acceptable salt thereof, Formula (I)
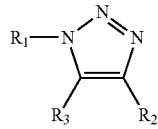

wherein, $R_1$ is selected from H and $CH_3$;

$R_2$ is selected from the following groups:

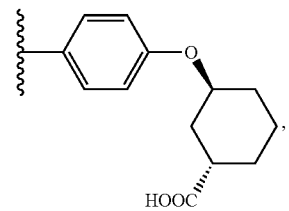

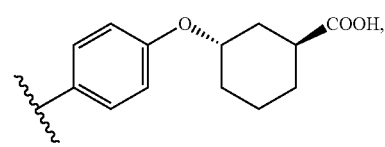

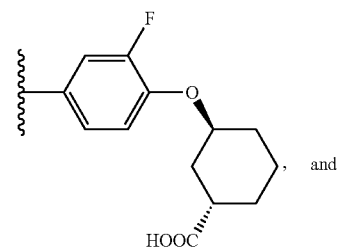, and

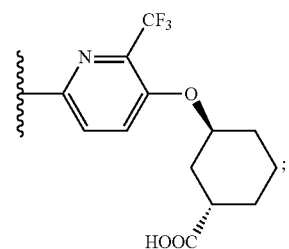;

R₃ is selected from H and the following groups:
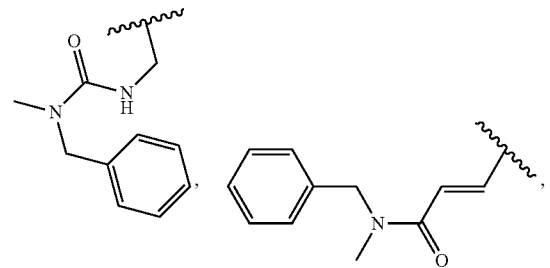
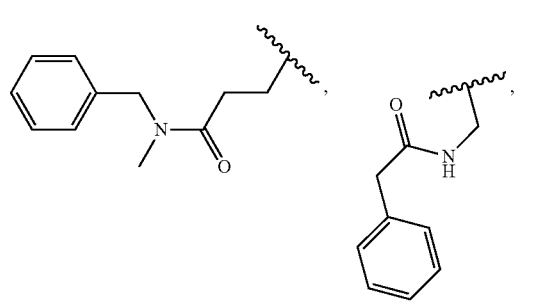
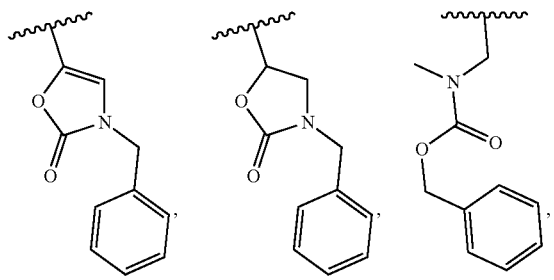
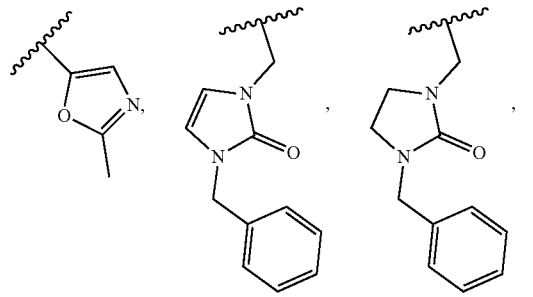
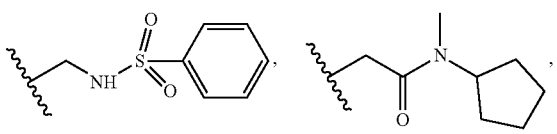
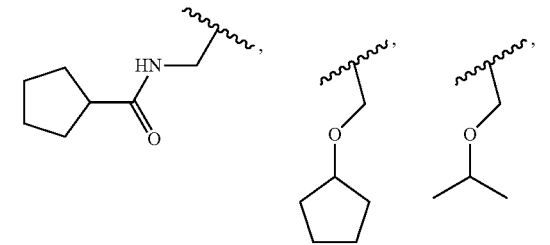
-continued
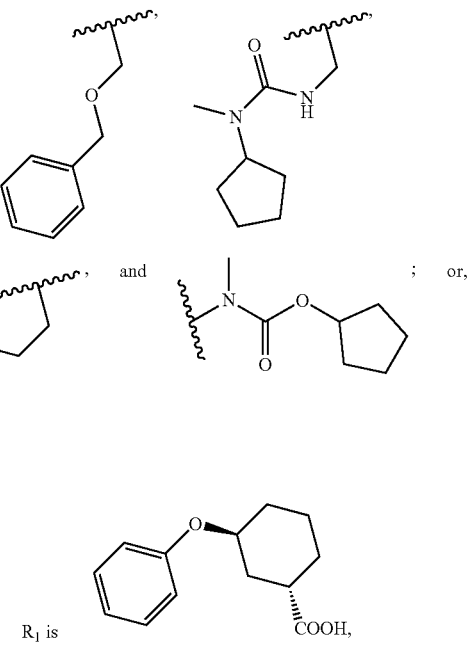
$R_1$ is
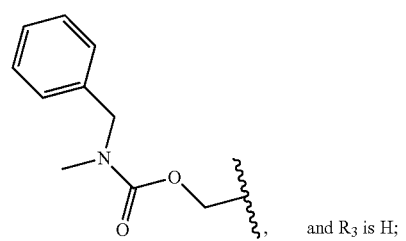
$R_2$ is 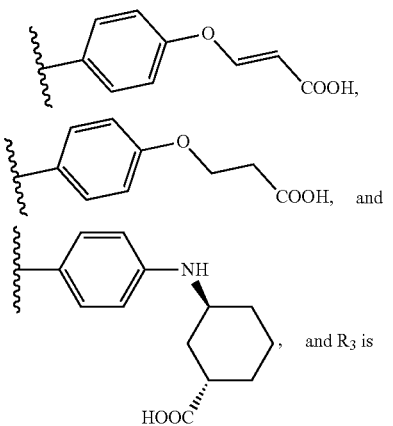 and $R_3$ is H;
or, $R_1$ is $CH_3$, $R_2$ is selected from the following groups:
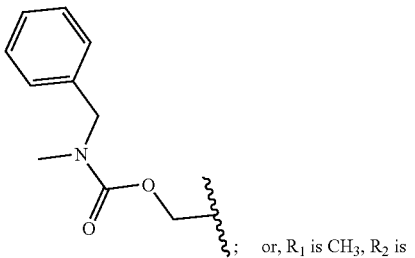
and $R_3$ is
; or, $R_1$ is $CH_3$, $R_2$ is 217
-continued
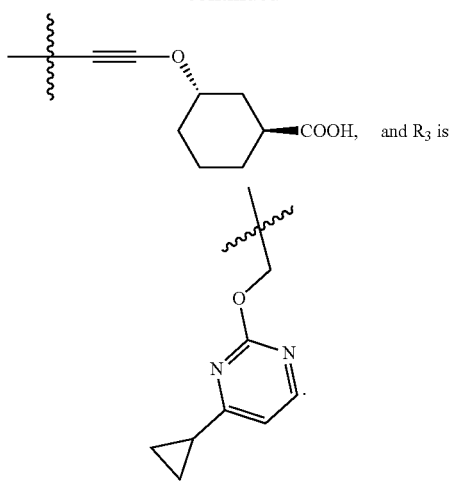
and R₃ is
2. A triazole compound or a stereoisomer, a tautomer, an isotopically labeled compound, a nitrogen oxide, a solvate, a polymorph, a ester, or a pharmaceutically acceptable salt thereof,
wherein the triazole compound is selected from
1
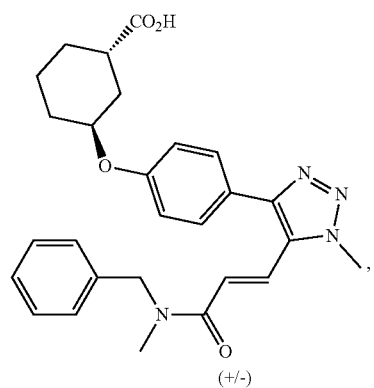
(+/-)
2
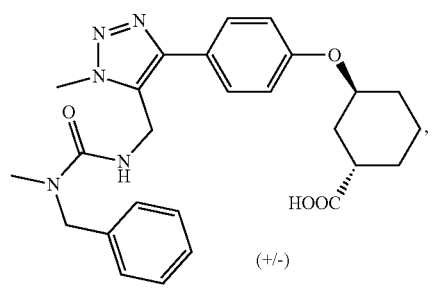
(+/-)
218
-continued
3
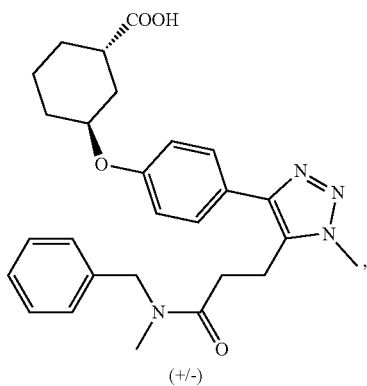
(+/-)
4
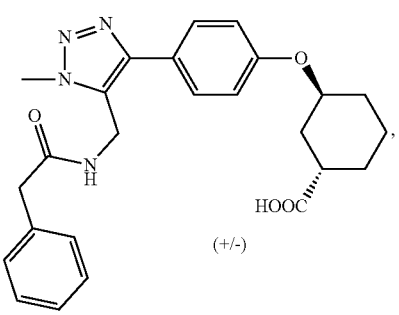
(+/-)
5
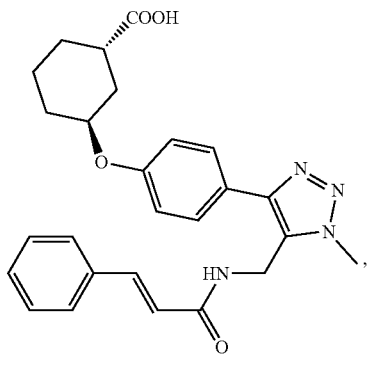
(+/-)
6
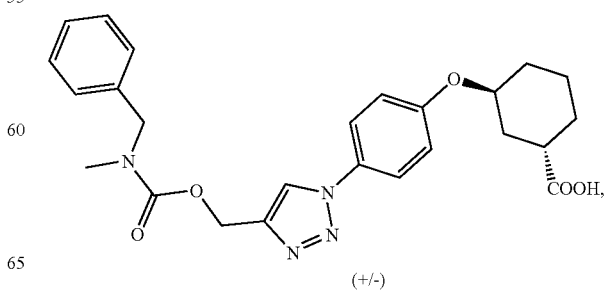
(+/-)

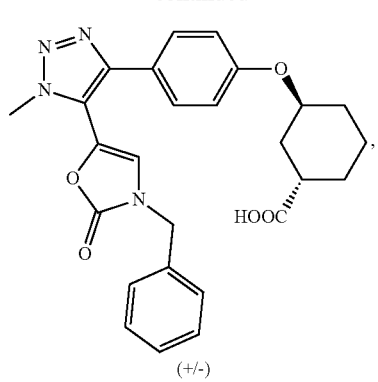
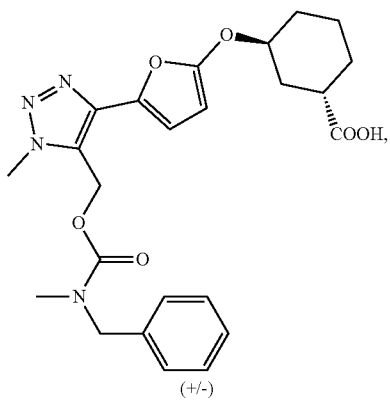
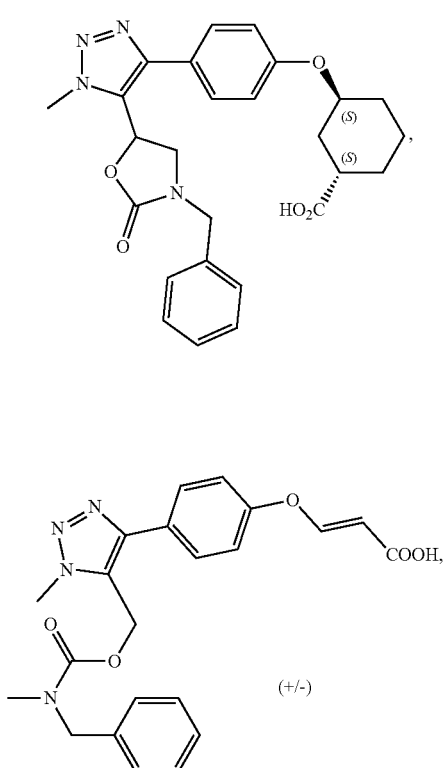
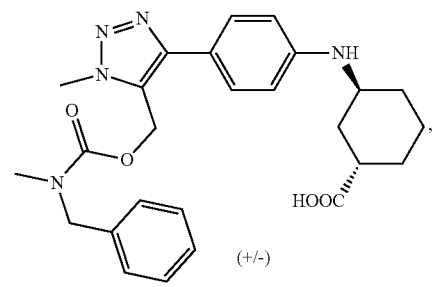
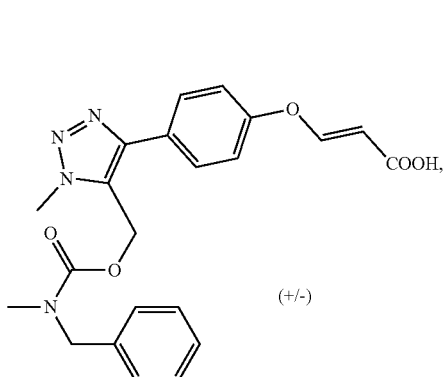
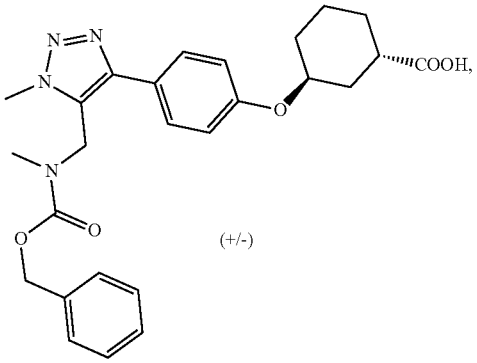
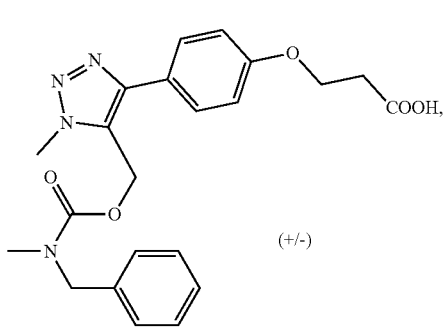
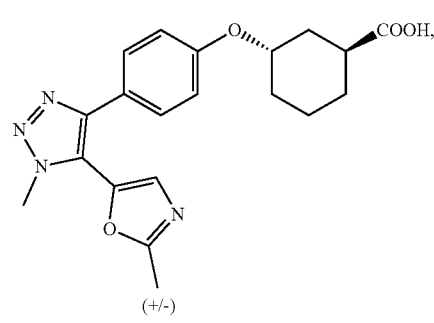

-continued
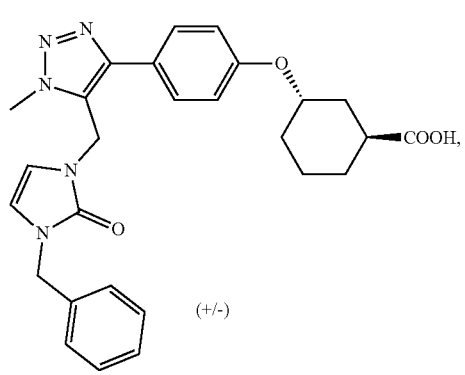
16
(+/-)
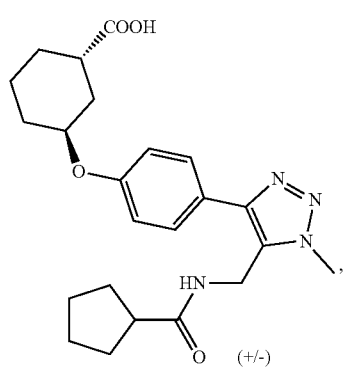
20
(+/-)
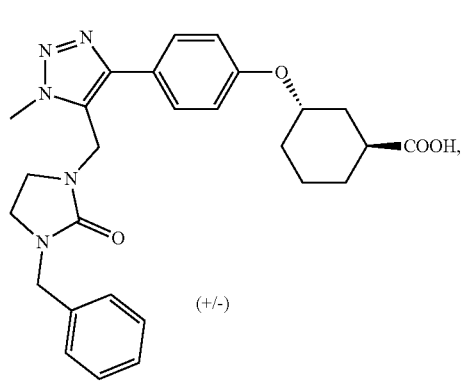
17
(+/-)
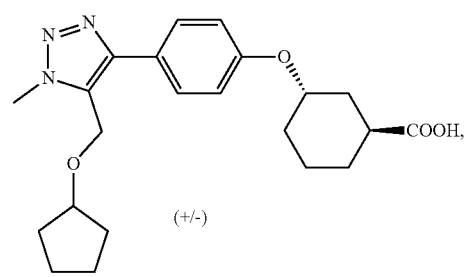
21
(+/-)
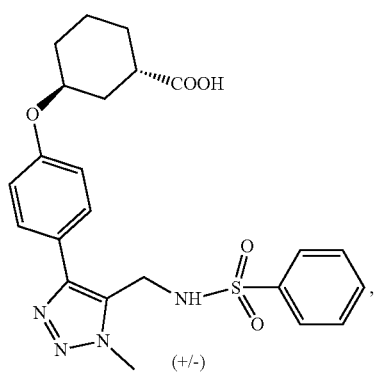
18
(+/-)
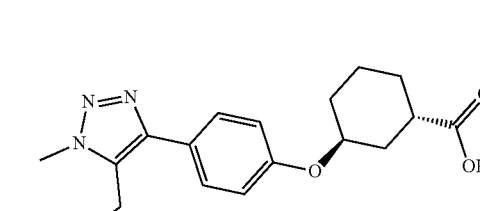
22
(+/-)
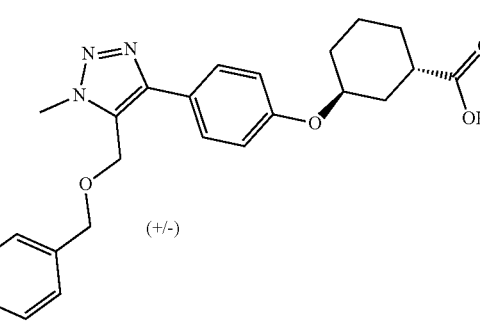
23
(+/-)
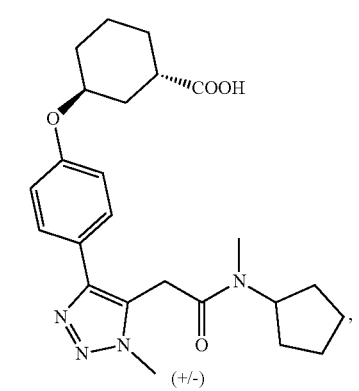
19
(+/-)
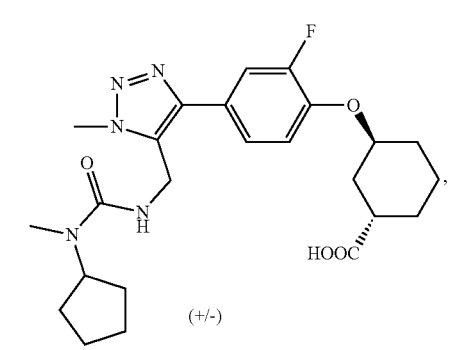
25
(+/-)

26
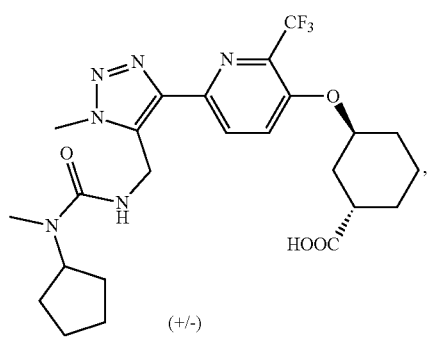
(+/-)
27-A
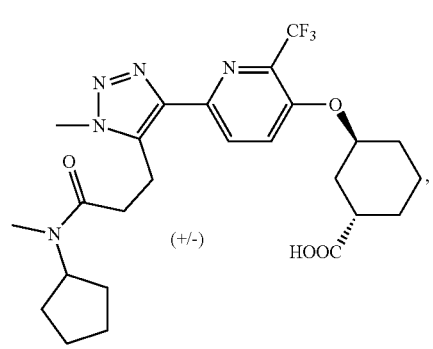
(+/-)
27-B
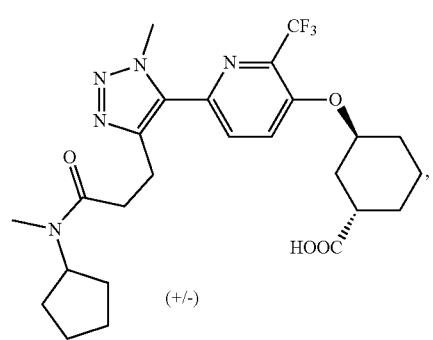
(+/-)
28
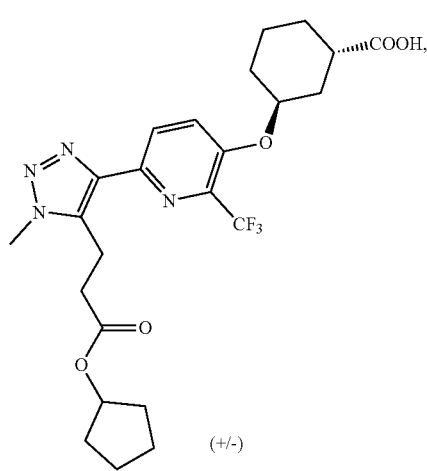
(+/-)
29
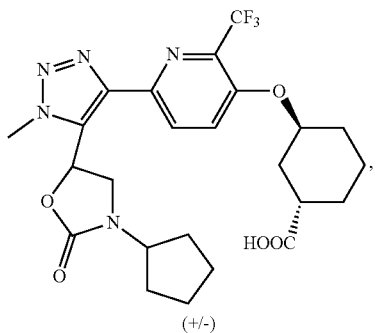
(+/-)
30
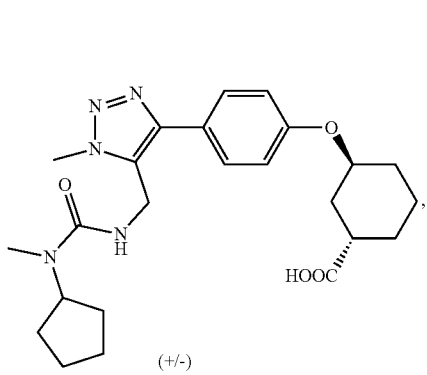
(+/-)
31
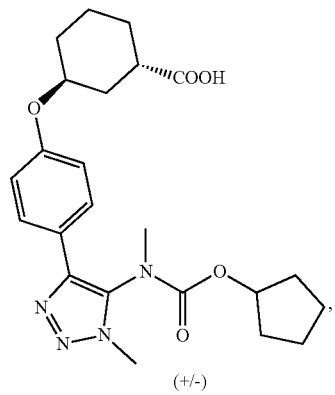
(+/-)
33
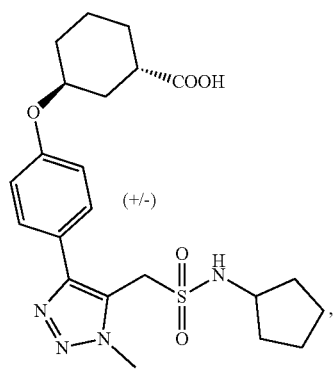
(+/-)

-continued

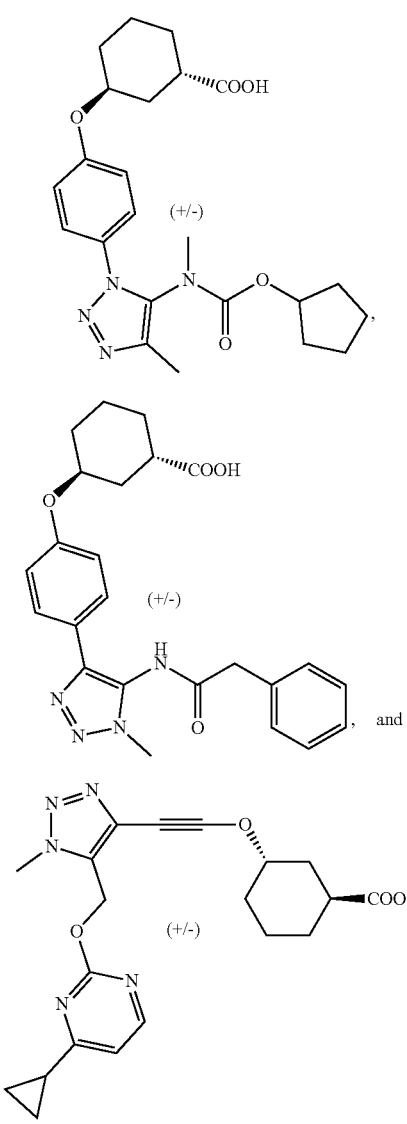

3. A preparation method for the triazole compound according to claim 1 is Scheme 9 or Scheme 12, wherein wherein Scheme 9 comprises: Compound 10-8A is reacted with H₂ in the presence of Pd/C to give Compound M-12; and Compound M-12 is reacted in the presence of a base to give the compound of formula (I);

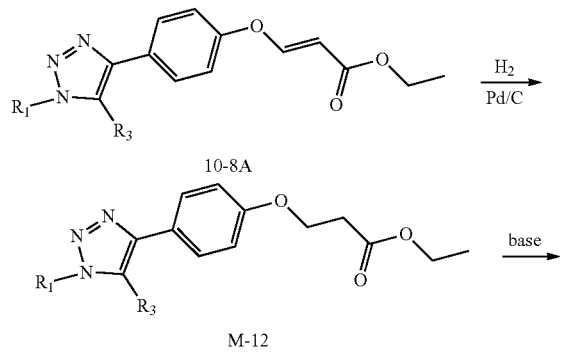

-continued

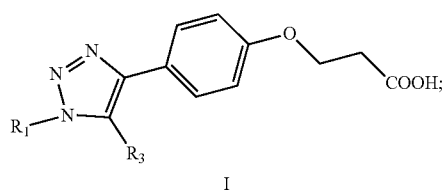

wherein Scheme 12 comprises:

Compound 15-1 is reacted with I₂ in the presence of n-butyl lithium to give Compound M-18;

Compound M-18 is reacted with Compound 1a in the presence of Pd(OAc)₂ and PPh₃ to give Compound M-19;

Compound M-19 is reacted with NBS to give Compound M-20; and

Compound M-20 is reacted with acetamide in the presence of NMP under microwave heating to give the compound of formula (I);

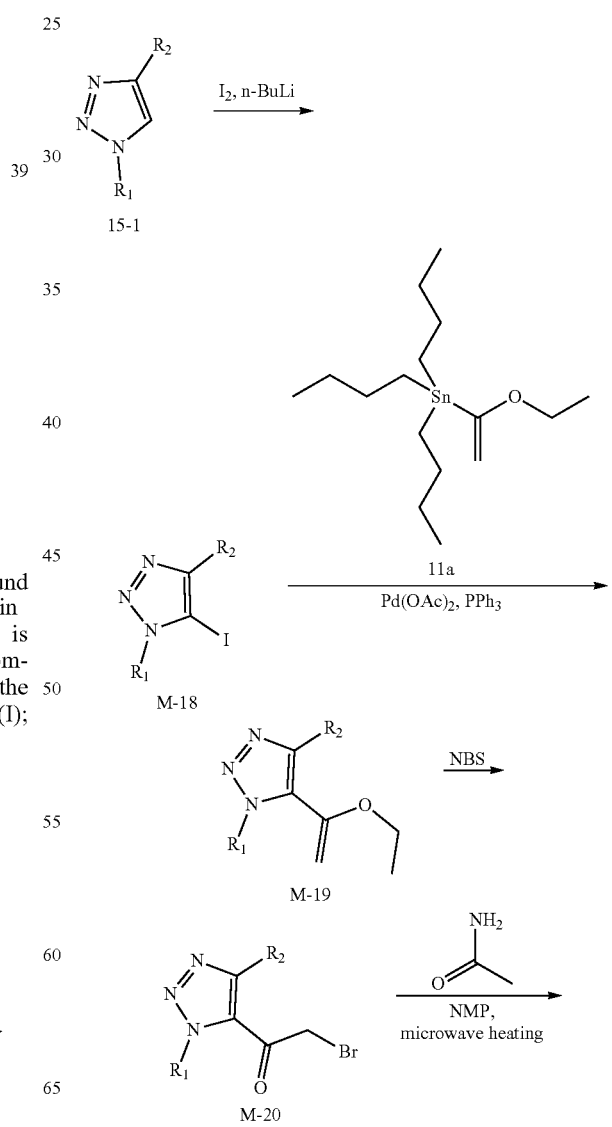

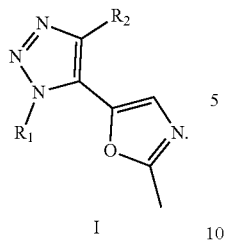

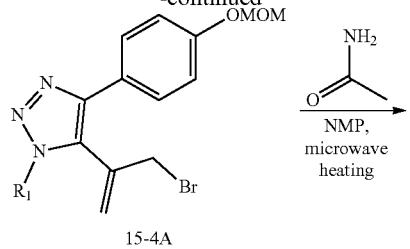

4. The preparation method according to claim 3 is Scheme 12A, which comprises:
   Compound 15-1a is reacted with I₂ in the presence of n-butyl lithium to give Compound 15-2A;
   Compound 15-2A is reacted with Compound 11a in the presence of Pd(OAc)₂ and PPh₃ to give Compound 15-3A;
   Compound 15-3A is reacted with NBS to give Compound 15-4A;
   Compound 15-4A is reacted with acetamide in the presence of NMP under microwave heating to give Compound 15-5A;
   Compound 15-5A is reacted with Compound 15-6 to give Compound 15-7A; and
   Compound 15-7A is reacted in the presence of a base to give the compound of formula (I);

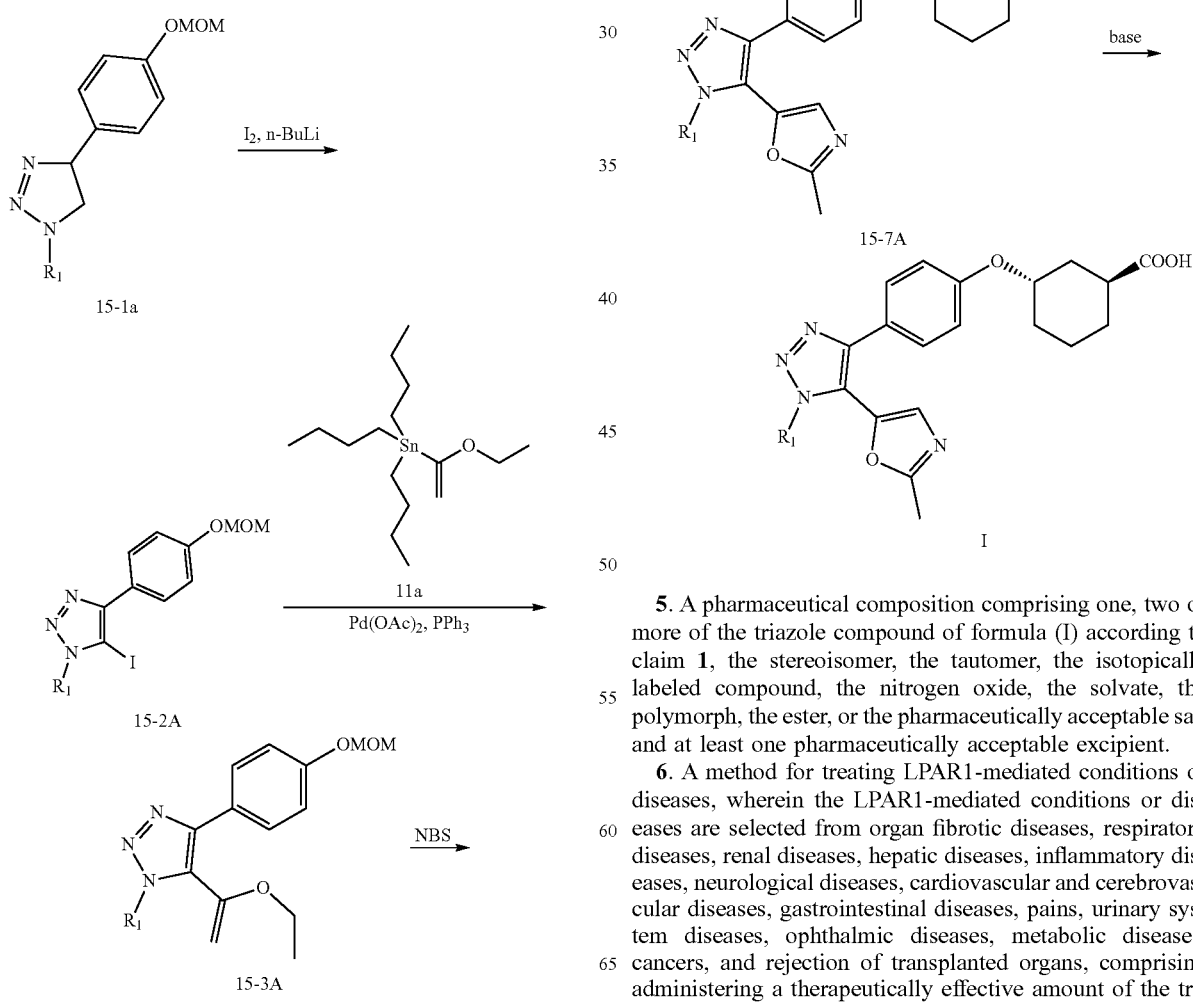

5. A pharmaceutical composition comprising one, two or more of the triazole compound of formula (I) according to claim 1, the stereoisomer, the tautomer, the isotopically labeled compound, the nitrogen oxide, the solvate, the polymorph, the ester, or the pharmaceutically acceptable salt and at least one pharmaceutically acceptable excipient.

6. A method for treating LPAR1-mediated conditions or diseases, wherein the LPAR1-mediated conditions or diseases are selected from organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers, and rejection of transplanted organs, comprising administering a therapeutically effective amount of the triazole compound of formula (I) according to claim 1, the stereoisomer, the tautomer, the isotopically labeled compound, the nitrogen oxide, the solvate, the polymorph, the ester, or the pharmaceutically acceptable salt thereof to a subject in need thereof.

7. A pharmaceutical composition comprising one, two or more of the triazole compound according to claim 2, the stereoisomer, the tautomer, the isotopically labeled compound, the nitrogen oxide, the solvate, the polymorph, the ester, or the pharmaceutically acceptable salt thereof, and at least one pharmaceutically acceptable excipient.

8. A method for treating LPAR1-mediated conditions or diseases, wherein the LPAR1-mediated conditions or diseases are selected from organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers, and rejection of transplanted organs, comprising administering a therapeutically effective amount of the compound according to claim 2, the stereoisomer, the tautomer, the isotopically labeled compound, the nitrogen oxide, the solvate, the polymorph, the ester, or the pharmaceutically acceptable salt thereof to a subject in need thereof.

* * * * *